(12) United States Patent
Bridgeman et al.

(10) Patent No.: US 12,187,778 B2
(45) Date of Patent: Jan. 7, 2025

(54) RECEPTORS PROVIDING TARGETED COSTIMULATION FOR ADOPTIVE CELL THERAPY

(71) Applicant: INSTIL BIO (UK) LIMITED, Manchester (GB)

(72) Inventors: John Bridgeman, Manchester (GB); Robert Hawkins, Manchester (GB); Ruben Rodriguez, Dallas, TX (US); Gray Kueberuwa, Manchester (GB)

(73) Assignee: INSTIL BIO (UK) LIMITED, Manchester (GB)

( * ) Notice: Subject to any disclaimer, the term of this patent is extended or adjusted under 35 U.S.C. 154(b) by 0 days.

(21) Appl. No.: 17/823,223

(22) Filed: Aug. 30, 2022

(65) Prior Publication Data
US 2023/0002470 A1    Jan. 5, 2023

Related U.S. Application Data

(63) Continuation of application No. 17/843,480, filed on Jun. 17, 2022, which is a continuation of application No. PCT/US2021/042075, filed on Jul. 16, 2021.

(60) Provisional application No. 63/053,494, filed on Jul. 17, 2020.

(51) Int. Cl.
| C07K 14/725 | (2006.01) |
| A61K 39/00 | (2006.01) |
| C07K 14/705 | (2006.01) |
| C12N 5/0783 | (2010.01) |
| C12N 15/62 | (2006.01) |
| C12N 15/86 | (2006.01) |

(52) U.S. Cl.
CPC ...... *C07K 14/7051* (2013.01); *A61K 39/4611* (2023.05); *A61K 39/4636* (2023.05); *A61K 39/464402* (2023.05); *A61K 39/464429* (2023.05); *A61K 39/464482* (2023.05); *C07K 14/70521* (2013.01); *C07K 14/70578* (2013.01); *C12N 5/0636* (2013.01); *C12N 15/625* (2013.01); *C12N 15/86* (2013.01); *A61K 2239/59* (2023.05); *C07K 2317/24* (2013.01); *C07K 2319/00* (2013.01); *C12N 2740/15043* (2013.01)

(58) Field of Classification Search
CPC .......... C07K 16/3007; C07K 14/70578; C07K 2317/565; C07K 2317/622; A61K 2039/505
See application file for complete search history.

(56) References Cited

U.S. PATENT DOCUMENTS

| 5,399,346 A | 3/1995 | Anderson et al. |
| 5,580,859 A | 12/1996 | Felgner et al. |
| 5,589,466 A | 12/1996 | Felgner et al. |
| 5,858,358 A | 1/1999 | June et al. |
| 5,883,223 A | 3/1999 | Gray |
| 6,326,193 B1 | 12/2001 | Liu et al. |
| 6,352,694 B1 | 3/2002 | June et al. |
| 6,534,055 B1 | 3/2003 | June et al. |
| 6,692,964 B1 | 2/2004 | June et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,067,318 B2 | 6/2006 | June et al. |
| 7,144,575 B2 | 12/2006 | June et al. |
| 7,172,869 B2 | 2/2007 | June et al. |
| 7,175,843 B2 | 2/2007 | June et al. |
| 7,232,566 B2 | 6/2007 | June et al. |
| 7,232,888 B2 | 6/2007 | Begent et al. |
| 7,446,190 B2 | 11/2008 | Sadelain et al. |
| 7,507,412 B2 | 3/2009 | Burger et al. |
| 7,626,011 B2 | 12/2009 | Begent et al. |
| 7,741,465 B1 | 6/2010 | Eshhar et al. |
| 9,598,489 B2 | 3/2017 | Powell, Jr. |
| 10,117,896 B2 | 11/2018 | Powell, Jr. et al. |
| 10,640,569 B2 | 5/2020 | Beatty et al. |
| 10,654,928 B2 | 5/2020 | Kloss et al. |
| 10,844,117 B2 | 11/2020 | Powell, Jr. |
| 10,881,688 B2 | 1/2021 | Leek et al. |

(Continued)

FOREIGN PATENT DOCUMENTS

| WO | WO 2001/029058 | 4/2001 |
| WO | WO 2001/096584 | 12/2001 |

(Continued)

OTHER PUBLICATIONS

Hashimoto et al. Biology and Pharmaceutical Bulletin. 22(10)1068-1072 (1999) Construction of the scFV from 196-14 antibody toward ovarian cancer associated antigen CA125. 1999. Of Record. (Year: 1999).*
Lee et al.Immunity. Aug. 18, 2015; 43(2): 227-239. doi:10.1016/j.immuni.2015.06.018.A mechanical switch couples T cell receptor triggering to the cytoplasmic juxtamembrane regions of CD3ζζ (Year: 2015).*
Levin et al .Potent Activation of Human T Cells by mRNA Encoding Constitutively Active CD40. The Journal of Immunology, 2018, 201: 2959-2968. (Year: 2018).*
Alvarez-Vallina et al., Antigen-Specific Targeting Of CD28-Mediated T Cell Co-Stimulation Using Chimeric Single-Chain Antibody Variable Fragment-CD28 Receptors. Euro J Immunol. Oct. 1, 1996; 26(10):2304-2309.

(Continued)

*Primary Examiner* — Amy E Juedes
*Assistant Examiner* — Brian Hartnett
(74) *Attorney, Agent, or Firm* — KNOBBE MARTENS OLSON & BEAR LLP

(57) ABSTRACT

The present invention relates to a chimeric costimulatory antigen receptor (CoStAR) useful in adoptive cell therapy (ACT), and cells comprising the CoStAR. The CoStAR can act as a modulator of cellular activity enhancing responses to defined antigens. The present invention also provides CoStAR proteins, nucleic acids encoding the CoStAR and therapeutic uses thereof.

13 Claims, 53 Drawing Sheets

Specification includes a Sequence Listing.

(56) References Cited

U.S. PATENT DOCUMENTS

| | | | |
|---|---|---|---|
| 10,981,969 | B2 | 4/2021 | June et al. |
| 11,697,677 | B2 | 7/2023 | Bridgeman et al. |
| 11,945,876 | B2 | 4/2024 | Bridgeman et al. |
| 2004/0043401 | A1 | 3/2004 | Sadelain et al. |
| 2004/0101519 | A1 | 5/2004 | June et al. |
| 2006/0034810 | A1 | 2/2006 | Riley et al. |
| 2006/0121005 | A1 | 6/2006 | Berenson et al. |
| 2007/0036773 | A1 | 2/2007 | Cooper et al. |
| 2012/0321667 | A1 | 12/2012 | Sentman |
| 2014/0050708 | A1 | 2/2014 | Powell, Jr. et al. |
| 2014/0099309 | A1 | 4/2014 | Powell, Jr. et al. |
| 2014/0286987 | A1 | 9/2014 | Spencer et al. |
| 2017/0209492 | A1 | 7/2017 | June et al. |
| 2017/0246278 | A1 | 8/2017 | Valdes et al. |
| 2018/0044404 | A1 | 2/2018 | Oda et al. |
| 2018/0125890 | A1 | 5/2018 | Anderson et al. |
| 2018/0273640 | A1 | 9/2018 | Liang et al. |
| 2018/0319862 | A1* | 11/2018 | Thompson .............. A61P 35/00 |
| 2019/0023764 | A1 | 1/2019 | Wu et al. |
| 2020/0009190 | A1 | 1/2020 | Oda et al. |
| 2020/0078402 | A1 | 3/2020 | Ostertag et al. |
| 2020/0115448 | A1 | 4/2020 | Liu et al. |
| 2022/0160760 | A1 | 5/2022 | Bridgeman et al. |
| 2022/0348631 | A1 | 11/2022 | Bridgeman et al. |
| 2023/0002504 | A1 | 1/2023 | Bridgeman et al. |
| 2023/0055694 | A1 | 2/2023 | Bridgeman et al. |
| 2023/0059511 | A1 | 2/2023 | Bridgeman et al. |
| 2023/0227576 | A1 | 7/2023 | Bridgeman et al. |
| 2023/0277670 | A1 | 9/2023 | Bridgeman et al. |
| 2023/0331808 | A1 | 10/2023 | Bridgeman et al. |
| 2024/0058447 | A1 | 2/2024 | Moon et al. |

FOREIGN PATENT DOCUMENTS

| | | |
|---|---|---|
| WO | WO 2015/112626 A9 | 7/2015 |
| WO | WO 2016/126608 A1 | 8/2016 |
| WO | WO 2016/141357 A1 | 9/2016 |
| WO | WO 2017/079705 A1 | 5/2017 |
| WO | WO 2018/156711 A1 | 8/2018 |
| WO | WO 2018/208849 A1 | 11/2018 |
| WO | WO 2020/016661 A2 | 1/2020 |
| WO | WO 2020/152451 A1 | 7/2020 |
| WO | WO 2021/048850 A1 | 3/2021 |
| WO | WO 2021/123832 A1 | 6/2021 |
| WO | WO 2022/016112 A1 | 1/2022 |
| WO | WO 2022/271881 A1 | 12/2022 |

OTHER PUBLICATIONS

Lanitis et al., Chimeric Antigen Receptor T Cells with Dissociated Signaling Domains Exhibit Focused Antitumor Activity with Reduced Potential for Toxicity In Vivo. Cancer Immun Res. Jul. 1, 2013; 1(1): 43-53.

Li et al., Chimeric Antigen Receptor-Engineered T Cells for Liver Cancers, Progress and Obstacles. Tumor Biol. Mar. 2017; 39(3): 1-8.

Levin-Piaeda O., CD40 Costimulation Enhances CAR-T Cell Activation—Joint Meeting of the Israeli Immunol. Society (IIS) and Israeli Society for Cancer Research (ISCR) 2019; pp. 1-2 (Sep. 25, 2019) Retrieved from the Internet: URL: https://program.eventact.com/lecture?id=204321&code=430912; 1 page.

Mata et al., Inducible Activation of MyD88 and CD40 in CAR T Cells Results in Controllable and Potent Antitumor Activity in Preclinical Solid Tumor. Cancer Disc. Nov. 1, 2017; 7(11): 1306-1319.

Weinkove et al., Selecting Costimulatory Domains for Chimeric Antigen Receptors: Functional and Clinical Considerations. Clin Transl Immunol. Jan. 1, 2019; 8(5): e1049.

International Search Report and Written Opinion issued in PCT/GB2020/050120 on Apr. 7, 2020; 11 pages.

International Search Report and Written Opinion issued in PCT/US2021/042075 on Oct. 27, 2021; 12 pages.

International Search Report and Written Opinion issued in PCT/US2021/042079 on Oct. 28, 2021; 12 pages.

Ahonen et al., The CD40-TRAF6 Axis Controls Affinity Maturation and the Generation of Long-lived Plasma Cells. Nat Immunol. May 2002;3(5): 451-456.

Altschul et al., Basic local alignment search tool. J Mol Biol. Oct. 5, 1990; 215(3): 405-410.

Ankri et al., Human T Cells Engineered to Express a Programmed Death 1/28 Costimulatory Retargeting Molecule Display Enhanced Antitumor Activity. J Immunol. Oct. 15, 2013;191(8): 4121-4129.

Barrangou et al., CRISPR provides acquired resistance against viruses in prokaryotes. Science. Mar. 23, 2007; 315(5819): 1709-1712.

Bridgeman et al., Building Better Chimeric Antigen Receptors for Adoptive T Cell Therapy. Curr Gene Ther. Apr. 1, 2010; 10(2): 77-90.

Chung et al., All TRAFs are not Created Equal: Common and Distinct Molecular Mechanisms of TRAF-mediated Signal Transduction. J Cell Science Feb. 15, 2002; 115(4): 679-688.

ClinicalTrials.gov: NCT00968760; "CD19-specific T Cell Infusion in Patients with B-Lineage Lymphoid Malignancies". Aug. 31, 2009. NIH U.S. National Library of Medicine; downloaded in 10 pages.

ClinicalTrials.gov: NCT01653717; "CD19-specific T-cell for Chronic Lymphocytic Leukemia (CLL)". Jul. 31, 2021. NIH U.S. National Library of Medicine; downloaded in 7 pages.

Coney et al., Cloning of a Tumor-associated Antigen: MOv18 and MOv19 Antibodies Recognize a Folate-binding Protein. Cancer Res. Nov. 15, 1991;51(22): 6125-3612.

Davis et al., T-cell Antigen Receptor Genes and T-cell Recognition. Nature Aug. 1, 1988; 334(6181):395-402.

Davis et al., Ligand Recognition by (alpha) (beta) T Cell Receptors. Annu Rev Immunol. (1998) 16: 523-544.

Garland et al., The Use of Teflon Cell Culture Bags to Expand Functionally Active CD8+ cytotoxic T Lymphocytes. J Immunol Meth. Jul. 30, 1999;227(1-2): 53-63.

Genbank accession No. X99993; dated Jul. 23, 2016; 1 page.

Genbank accession No. X99994; dated Jul. 23, 2016; 1 page.

GenBank accession No. NP_001241.1; provided by RefSeq Nov. 2014, 3 pages.

GenBank accession No. NP_001552.2; provided by RefSeq Jul. 2008, 3 pages.

GenBank accession No. NP_001758.2; provided by RefSeq Jun. 2016, 4 pages.

GenBank accession No. NP_003028.1; last updated Mar. 6, 2000, 3 pages.

GenBank accession No. NP_003318.1; provided by RefSeq Jul. 2008, 3 pages.

GenBank accession No. NP_004186.1; provided by RefSeq Feb. 2011, 3 pages.

GenBank accession No. NP_006130.1: provided by RefSeq Jul. 2011, 5 pages.

GenBank accession No. NP_036224.1; provided by RefSeq Jul. 2008, 4 pages.

GenBank accession No. NP_055081.1; provided by RefSeq Jul. 2008, 3 pages.

GenBank accession No. NP_596867; provided by RefSeq Jul. 2008, 5 pages.

GenBank accession No. NP_001139345.1; provided by RefSeq May 2020, 3 pages.

GenBank accession No. NP_001315538.1; provided by RefSeq Jun. 2016, 3 pages.

GenBank accession No. NP_001317683.1; last updated Sep. 3, 2016, 3 pages.

Govers et al., "TCRs Genetically Linked to CD28 and CD3ε do not mispair with endogenous TCR chains and mediate enhanced T cell persistence and anti-melanoma activity". J Immunol. Nov. 15, 2014;193(10): 5315-26.

Grissa et al., The CRISPRdb database and tools to display CRISPRs and to generate dictionaries of spacers and repeats. BMC Bioinformatics. May 23, 2007; 8(1): 172; 10 pages.

(56) References Cited

OTHER PUBLICATIONS

Grupp et al., Chimeric Antigen Receptor—Modified T Cells for Acute Lymphoid Leukemia. New Engl J Med. Apr. 18, 2013;368(16): 1509-1518.
Guedan et al., Enhancing Car T Cell Persistence through ICOS and 3-1BB Costimulation. JCI Insight. Jan. 11, 2018; 3(1): e96976 in 17 pages.
Guest et al., The role of extracellular spacer regions in the optimal design of chimeric immune receptors: evaluation of four different scFvs and antigens. J Immunother. May 1, 2005; 28(3): 203-211.
Haanen et al., Selective Expansion of Cross-reactive CD8+ Memory T Cells by Viral Variants. J Exp Med., Nov. 1, 1999;190(9): 1319-1328.
Hashimoto et al., Construction of the Single-Chain Fv from 196-14 Antibody Toward Ovarian Cancer-associated Antigen CA125. Biol Pharma Bulletin. Oct. 15, 1999;22(10): 1068-72.
Hudecek et al., Receptor affinity and extracellular domain modifications affect tumor recognition by ROR1-specific chimeric antigen receptor T cells. Clin Cancer Res. Jun. 15, 2013; 19(12): 3153-3164.
Hudecek et al., The nonsignalling extracellular spacer domain of chimeric antigen receptors is decisive for in vivo antitumor activity. Cancer Immunol Res. Feb. 2015; 3(2): 125-135.
Hurton et al., Tethered IL-15 Augments Antitumor Activity and Promotes a Stem-cell Memory Aubset in Tumor-specific T Cells. PNAS USA. Nov. 29, 2016;113(48): E7788-E7797.
Izumoto et al., Phase II Clinical Trial of Wilms Tumor 1 Peptide Vaccination for Patients with Recurrent Glioblastoma Multiforme. J Neurosurg. 2008. 108(5): 963-971.
Kochenderfer et al., Chemotherapy-refractory diffuse large B-cell lymphoma and indolent B-cell malignancies can be effectively treated with autologous T cells expressing an anti-CD19 chimeric antigen receptor. J Clin Oncol. Feb. 20, 2015; 33(6): 540-550.
Leo et al., Differential Requirements for Tumor Necrosis Factor Receptor-associated Factor Family Proteins in CD40-mediated Induction of NF-kappaB and Jun N-terminal Kinase Activation. J Biol Chem. Aug. 6, 1999:274(32): 22414-22422.
Li et al., Limited Cross-Linking of 4-1BB by 4-1BB Ligand and the Agonist Monoclonal Antibody Utomilumab. Cell Reports 2018; 25:909-920.
MacKey et al., Distinct Contributions of Different CD40 TRAF Binding Sites to CD154-induced Dendritic Cell Maturation and IL-12 Secretion. Eur J Immunol. Mar. 2003; 33(3): 779-789.
Manuri et al., piggyBac Transposon/Transposase System to Generate CD19-specific T Cells for the Treatment of B-lineage Malignancies. Hum Gene Ther. Apr. 1, 2010;21(4): 427-437.
Marraffini et al., CRISPR Interference Limits Horizontal Gene Transfer in *Staphylococci* by Targeting DNA. Science Dec. 19, 2008;322(5909): 1843-1845.
Mátés et al., Molecular Evolution of a Novel Hyperactive Sleeping Beauty Transposase Enables Robust Stable Gene Transfer in Vertebrates. Nat Genet. Jun. 2009;41(6): 753-761.
Monjezi et al., Enhanced CAR T-cell engineering using non-viral Sleeping Beauty transposition from minicircle vectors. Leukemia. Jan. 2017;31(1): 186-194.
Morgan et al., "Cancer Regression in Patients After Transfer of Genetically Engineered Lymphocytes". Science Oct. 6, 2006;314(5796): 126-129.
Morita et al., Enhanced Expression of Anti-CD19 Chimeric Antigen Receptor in piggyBac Transposon-engineered T Cells. Mol Ther Meth Clin Dev. Mar. 16, 2018;8: 131-140; online 2017.
Mukundan et al., TNF Receptor-associated Factor 6 is an Essential Mediator of CD40-activatedProinflammatory Pathways in Monocytes and Macrophages. J Immunol. Jan. 15, 2005; 174(2): 1081-1090.
Murphy K. Janeway's Immunobiology. (2011) x-xix, TOC in 12 pages.
Nakazawa et al, PiggyBac-mediated Cancer Immunotherapy Using EBV-specific Cytotoxic T-cells Expressing HER2-specific Chimeric Antigen Receptor. Mol Ther. Dec. 1, 2011;19(12): 2133-2143.
Park H.H., Structure of TRAF Family: Current Understanding of Receptor Recognition. Front Immunol. Aug. 30, 2018; 9: 1999 in 7 pages.
Pearson et al., Improved tools for biological sequence comparison. PNAS USA Apr. 1988; 85(8): 2444-2448.
Prosser et al., Tumor PD-L1 Co-stimulates Primary Human CD8+ Cytotoxic T Cells Modified to Express a PD1: CD28 Chimeric Receptor. Mol Immunol . . . Jul. 1, 2012;51(3-4): 263-272.
Rapoport et al., NY-ESO-1 Specific TCR Engineered T-cells Mediate Sustained Antigen-specific Antitumor Effects in Myeloma. Nat Med. Aug. 2015;21(8): 914-921.
Rosenberg et al., Use of Tumor-Infiltrating Lymphocytes and Interleukin-2 in the Immunotherapy of Patients with Metastatic Melanoma. New England J Med. Dec. 22, 1988;319(25): 1676-1680.
Rosenberg et al., Gene Transfer Into Humans—Immunotherapy of Patients with Advanced Melanoma, Using Tumor-infiltrating Lymphocytes Modified by Retroviral Gene Transduction. New England J Med. Aug. 30, 1990;323(9): 570-578.
Rosenberg et al., Durable Complete Responses in Heavily Pretreated Patients with Metastatic Melanoma Using T-cell Transfer Immunotherapy. Clin Cancer Res. 2011, 17(13): 4550-4557.
Sambrook et al., Molecular Cloning: A Laboratory Manual. Cold Spring Harbor Laboratory, New York; 2001, TOC; 18 pages.
Scholler et al., Decade-long Safety and Function of Retroviral-modified Chimeric Antigen Receptor T Cells. Sci Transl Med. May 2, 2012;4(132): 132ra53; in 16 pages.
Singh et al., Redirecting Specificity of T-cell Populations for CD19 Using the Sleeping Beauty System. Cancer Res. Apr. 15, 2008;68(8): 2961-2971.
Ten Berge et al., Selective Expansion of a Peripheral Blood CD8+ Memory T cell Subset ExpressingBoth Granzyme B and L-selectin During Primary Viral Infection in Renal Allograft Recipients. Transplant Proc. Dec. 1, 1998;30(8): 3975-3977.
Thokala et al., Redirecting Specificity of T Cells Using the Sleeping Beauty System to Express Chimeric Antigen Receptors by Mix-and-Matching of VL and VH Domains Targeting CD123+ Tumors. PLoS ONE. Aug. 22, 2016;11(8): e0159477 in 23 pages.
UniProtKB/Swiss-Prot: Accession No. P01861; "Nucleotide Sequence of a human immunoglobulin C gamma 4 gene". Dated: Jul. 21, 1986; Downloaded in 7 pages.
Wilkie et al., Retargeting of human T cells to tumor-associated MUC1: the evaluation of a chimeric antigen receptor. J Immunol. Apr. 1, 2008; 180(7): 4901-4909.
Ye et al., The Structural Basis for the Recognition of Diverse Receptor Sequences by TRAF2. Mol Cell. Sep. 1999; 4: 321-330.
U.S. Appl. No. 17/562,618, including its patent prosecution history, the cited references, and the Office Actions therein., filed Dec. 27, 2021, Bridgeman et al.
U.S. Appl. No. 17/822,251 including its patent prosecution history, the cited references, and the Office Actions therein., filed Aug. 25, 2022, Bridgeman et al.
U.S. Appl. No. 17/807,109 including its patent prosecution history, the cited references, and the Office Actions therein., filed Jun. 15, 2022, Bridgeman et al.
U.S. Appl. No. 17/936,102 including its patent prosecution history, the cited references, and the Office Actions therein., filed Sep. 28, 2022, Bridgeman et al.
ClinicalTrials.gov: NCT01653717; "CD19-specific T-cell for Chronic Lymphocytic Leukemia (CLL)". NIH U.S. National Library of Medicine; Jul. 31, 2012; downloaded in 7 pages.
International Search Report and Written Opinion issued in PCT/US2022/033580 on Nov. 7, 2022; 14 pages.
International Search Report and Written Opinion issued in PCT/US2022/073741 on Nov. 22, 2022; 12 pages.
Yu et al., Reducing affinity as a strategy to boost immunomodulatory antibody agonism. Nature. Feb. 2023;1:1-9.
U.S. Office Action dated Jan. 19, 2023 for U.S. Appl. No. 17/843,480.
GenBank accession No. S76526.1; last updated Jul. 27, 1995, accessible online: (https://www.ncbi.nlm.nih.gov/nuccore/S76526.1); 1 page.

(56) References Cited

OTHER PUBLICATIONS

GenBank accession No. S76530.1; last updated Jul. 26, 2016, accessible online: (https://www.ncbi.nlm.nih.gov/nuccore/S76530.1); 1 page.
Kanda et al., Construction and expression of chimeric antibodies by a simple replacement of heavy and light chain V genes into a single cassette vector. Hybridoma Oct. 1994;13(5): 359-366.
U.S. Appl. No. 18/316,548 including its patent prosecution history, the cited references, and the Office Actions therein., filed May 12, 2023, Bridgeman et al.
U.S. Appl. No. 18/323,342 including its patent prosecution history, the cited references, and the Office Actions therein., filed May 24, 2023, Moon et al.
Assaraf et al., The folate receptor as a rational therapeutic target for personalized cancer treatment. Drug Resist Updates. Oct. 1, 2014;17(4-6): 89-95.
Bagnoli et al., Downmodulation of caveolin-1 expression in human ovarian carcinoma is directly related to α-folate receptor overexpression. Oncogene. Sep. 2000;19(41): 4754-4763.
Barden et al., CAR and TCR form individual signaling synapses and do not cross-activate, however, can co-operate in T cell activation. Front Immunol. Feb. 1, 2023;14:1110482 in 13 pages.
Bridgeman et al., The optimal antigen response of chimeric antigen receptors harboring the CD3zeta transmembrane domain is dependent upon incorporation of the receptor into the endogenous TCR/CD3 complex. J Immunol. Jun. 15, 2010;184(12):6938-6949.
Bridgeman et al., CD3ζ-based chimeric antigen receptors mediate T cell activation via cis- and trans-signalling mechanisms: implications for optimization of receptor structure for adoptive cell therapy. Clin Exp Immunol. Feb. 2014;175(2):258-267.
ClinicalTrials.gov: NCT03585764; "MOv19-BBz CAR T Cells in aFR Expressing Recurrent High Grade Serous Ovarian, Fallopian Tube, or Primary Peritoneal Cancer". NIH U.S. National Library of Medicine; Jul. 13, 2018; downloaded in 9 pages.
Finney et al., Chimeric Receptors Providing Both Primary and Costimulatory Signaling in T Cells from a Single Gene Product. J Immunol. Sep. 15, 1998;161(6): 2791-2797.
Foster et al., Regulated Expansion and Survival of Chimeric Antigen Receptor-modified T Cells Using Small Molecule-dependent Inducible MyD88/CD40. Mol Ther. Sep. 6, 2017;25(9): 2176-2188.
Huang et al., A single peptide-major histocompatibility complex ligand triggers digital cytokine secretion in CD4(+) T cells. Immunity. Nov. 14, 2013;39(5):846-857.
James et al., Antigen sensitivity of CD22-specific chimeric TCR is modulated by target epitope distance from the cell membrane. J Immunol. May 15, 2008;180(10):7028-7038.
Kandalaft et al., A Phase I Clinical Trial of Adoptive Transfer of Folate Receptor-α Redirected Autologous T Cells for Recurrent Ovarian Cancer. J Transl Med. Dec. 2012;10: 157; in 10 pages.
Kelemen L.E., The role of folate receptor a in cancer development, progression and treatment: cause, consequence or innocent bystander?. Int J Cancer. Jul. 15, 2006;119(2): 243-250.
Kershaw et al., A Phase I Study on Adoptive Immunotherapy Using Gene-Modified T Cells for Ovarian Cancer. Clin Cancer Res. Oct. 15, 2006;12(20 Pt 1): 6106-6115.
Kloss et al., Combinatorial antigen recognition with balanced signaling promotes selective tumor eradication by engineered T cells. Nat Biotechnol. Jan. 2013; 31(1): 71-75.
Kurosaki et al., Serum folate receptor α as a biomarker for ovarian cancer: Implications for diagnosis, prognosis and predicting its local tumor expression. Int J Cancer. Apr. 15, 2016;138(8): 1994-2002.
Lim et al., The Principles of Engineering Immune Cells to Treat Cancer. Cell. Feb. 9, 2017;168(4): 724-740.
Liu et al., Systematic analysis of the aberrances and functional implications of ferroptosis in cancer. Iscience. Jul. 24, 2020;23(7): 101302 in 26 pages.
Maher et al., Human T-lymphocyte Cytotoxicity and Proliferation directed by a Single Chimeric Torz CD28 Receptor. Nature Biotech. Jan. 1, 2002;20(1): 70-75.
Mao et al., The affinity of antigen-binding domain on the antitumor efficacy of CAR T cells: Moderate is better. Front Immunol. Oct. 17, 2022;13:1032403.
Morgan et al., Case report of a serious adverse event following the administration of T cells transduced with a chimeric antigen receptor recognizing ERBB2. Mol Ther. Apr. 2010;18(4):843-851.
Munroe et al., A Costimulatory Function for T Cell CD40. J Immunol. Jan. 15, 2007;178(2): 671-682.
Parker et al., Folate receptor expression in carcinomas and normal tissues determined by a quantitative radioligand binding assay. Analy Biochem. Mar. 15, 2005;338(2): 284-293.
Ross et al., Differential regulation of folate receptor isoforms in normal and malignant tissues in vivo and in established cell lines. Physio Clin Impl Cancer. May 1, 1994;73(9): 2432-2443.
Salter et al., Comparative analysis of TCR and CAR signaling informs CAR designs with superior antigen sensitivity and in vivo function. Sci Signal. Aug. 24, 2021;14(697):eabe2606 in 35 pages.
Schmidt et al., Eradication of melanomas by targeted elimination of a minor subset of tumor cells. PNAS. Feb. 8, 2011; 108(6) 2474-2479.
Song et al., In vivo persistence, tumor localization, and antitumor activity of CAR-engineered T cells is enhanced by costimulatory signaling through CD137 (4-1BB). Cancer Res. Jul. 1, 2011;71(13):4617-4927.
Sykulev et al., Evidence that a single peptide-MHC complex on a target cell can elicit a cytolytic T cell response. Immunity. Jun. 1996;4(6):565-571.
Thistlethwaite et al., The clinical efficacy of first-generation carcinoembryonic antigen (CEACAM5)-specific CAR T cells is limited by poor persistence and transient pre-conditioning-dependent respiratory toxicity. Cancer Immunol Immunother. Nov. 2017;66(11):1425-1436.
Watanabe et al., Target antigen density governs the efficacy of anti-CD20-CD28-CD3 ζ chimeric antigen receptor-modified effector CD8+ T cells. J Immunol. Feb. 1, 2015;194(3):911-920.
Weitman et al., Distribution of the folate receptor GP38 in normal and malignant cell lines and tissues. Cancer Res. Jun. 15, 1992:52(12): 3396-3401.
Wilkie et al., Selective expansion of chimeric antigen receptor-targeted T-cells with potent effector function using interleukin-4. J Biol Chem. Aug. 13, 2010;285(33):25538-25544.
U.S. Office Action dated Jun. 2, 2023 for U.S. Appl. No. 17/843,480.
International Search Report and Written Opinion issued in PCT/US2023/067434 on Nov. 14, 2023; 24 pages.
U.S. Office Action dated Jan. 12, 2024 for U.S. Appl. No. 17/843,480.

* cited by examiner

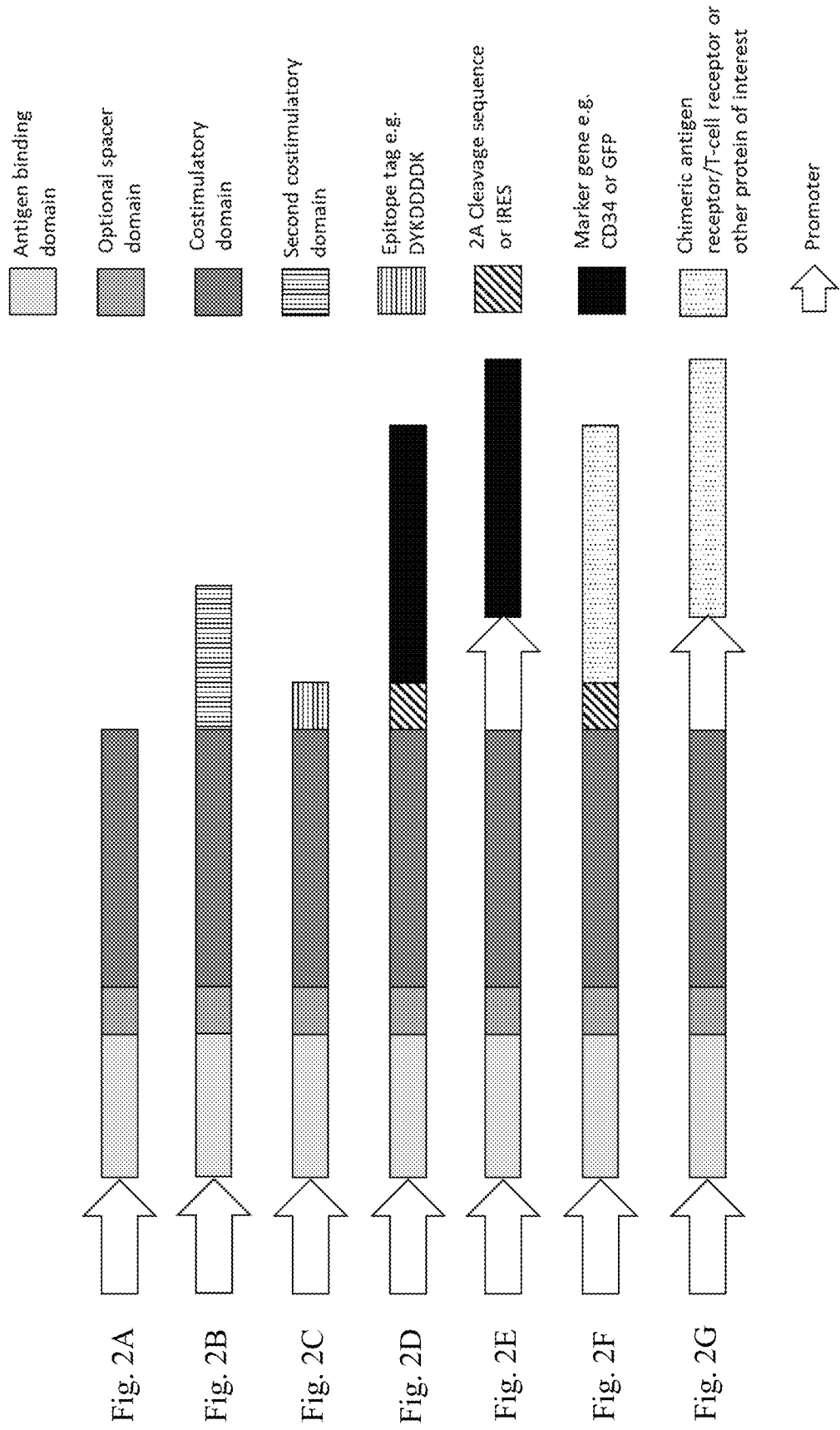

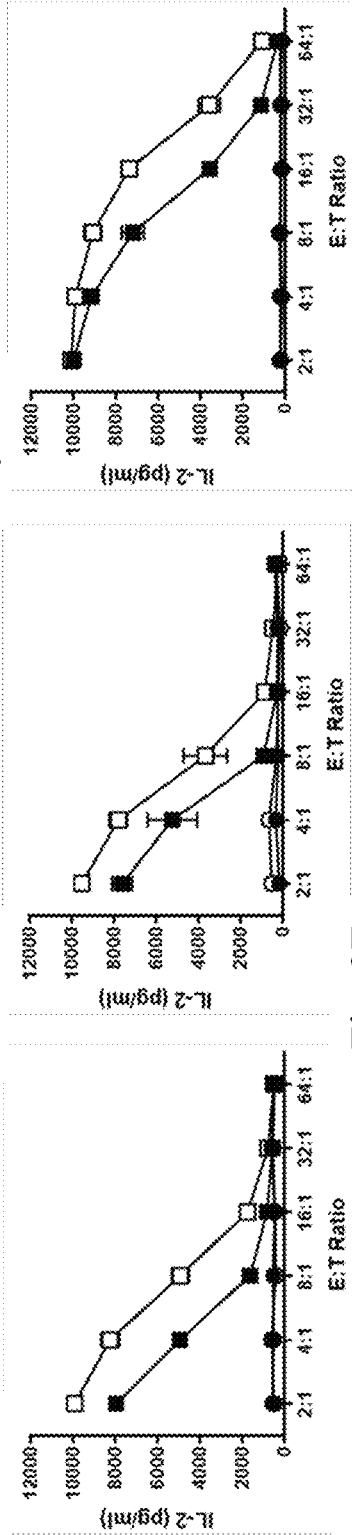

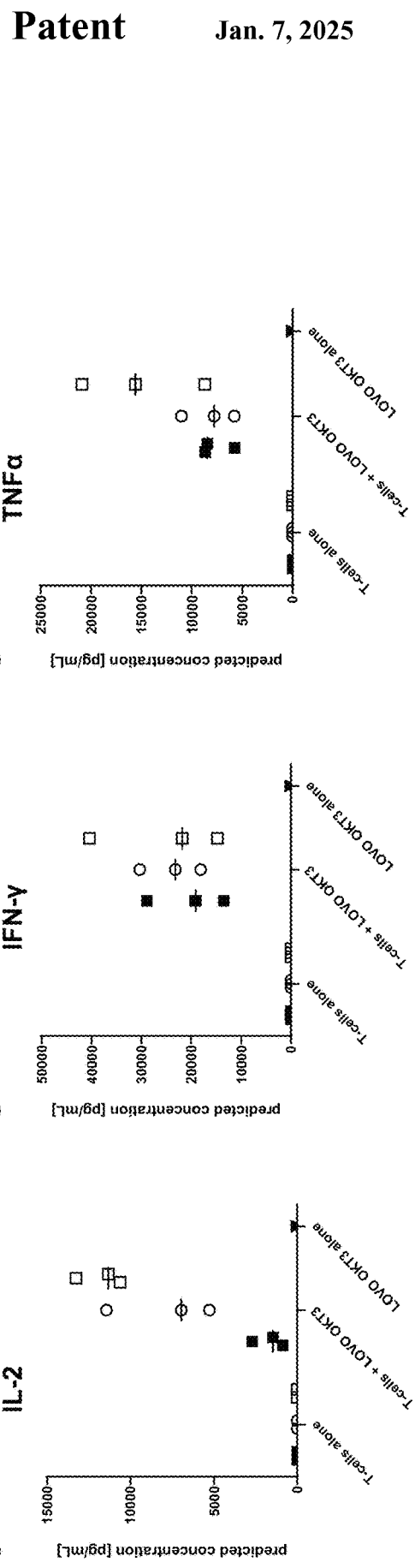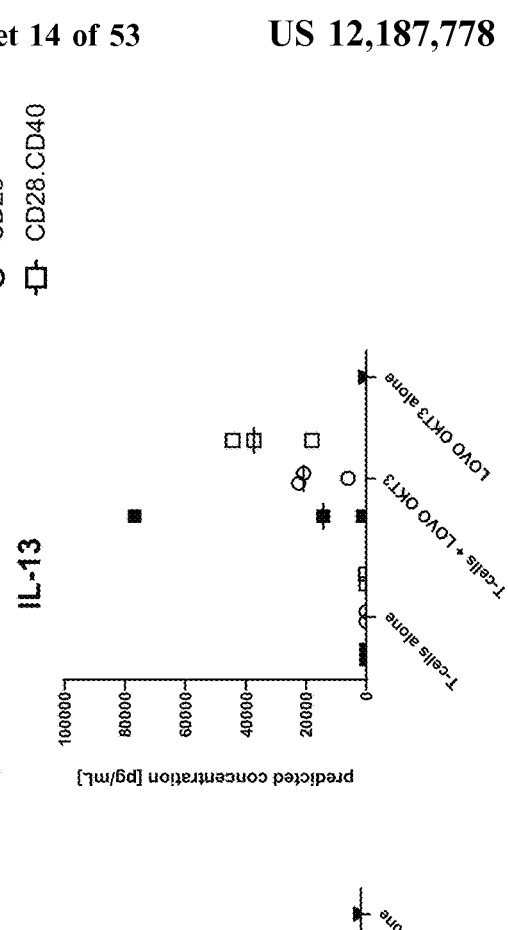

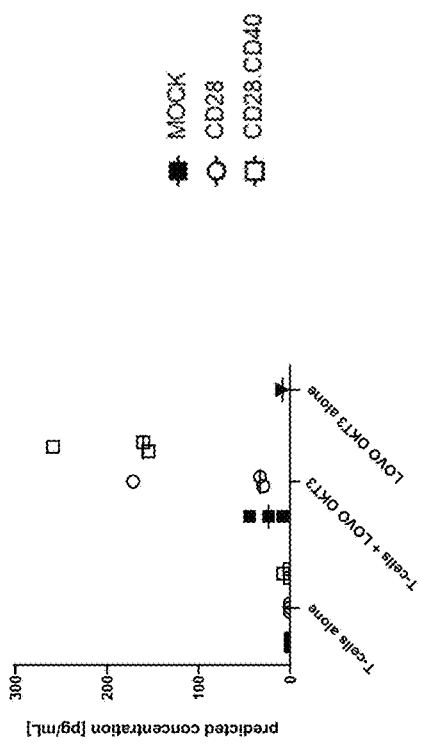
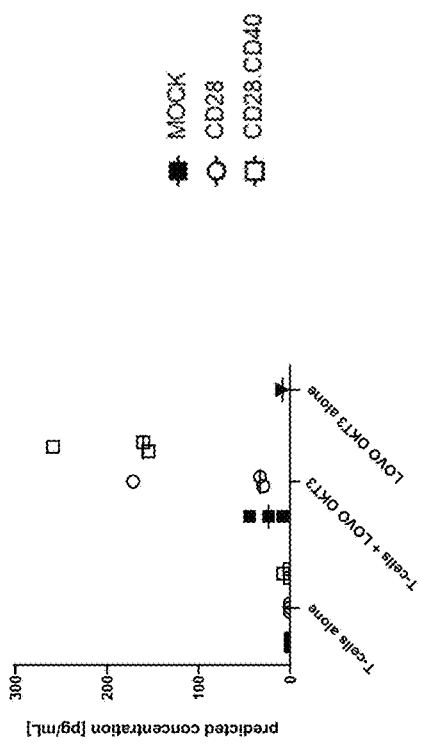
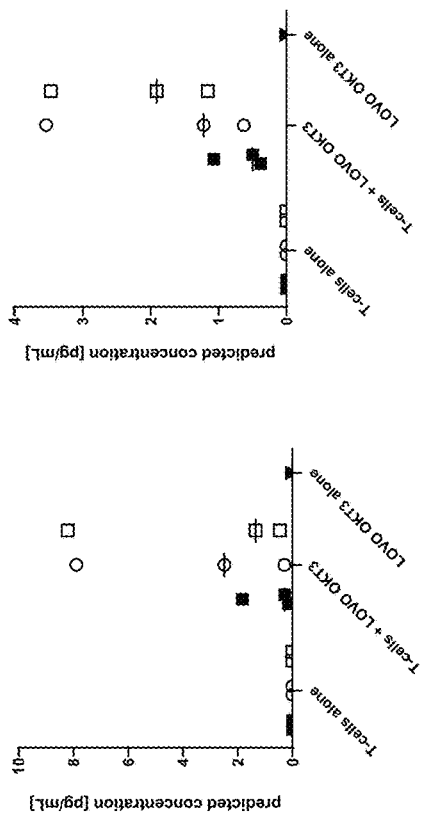
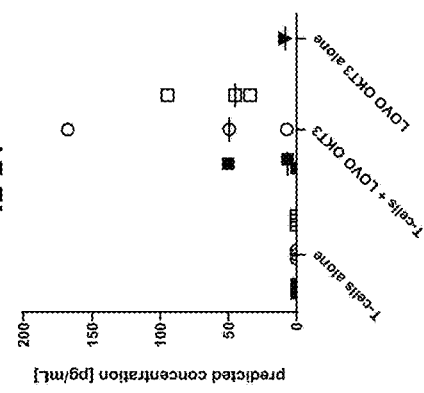
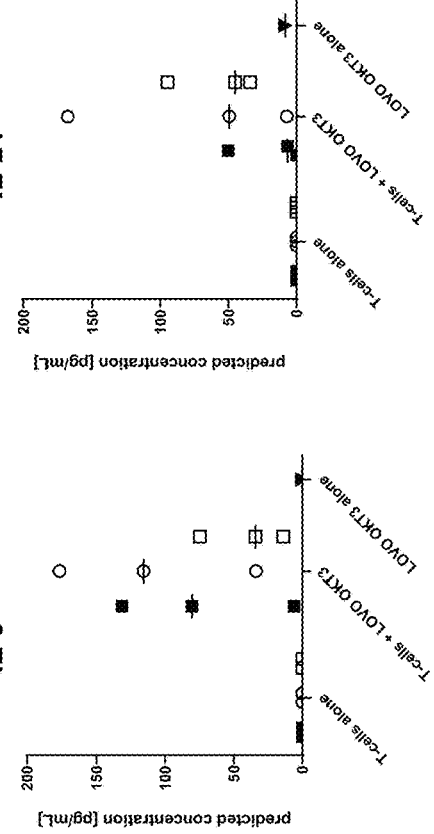
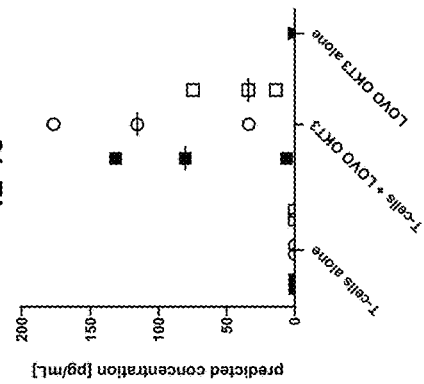
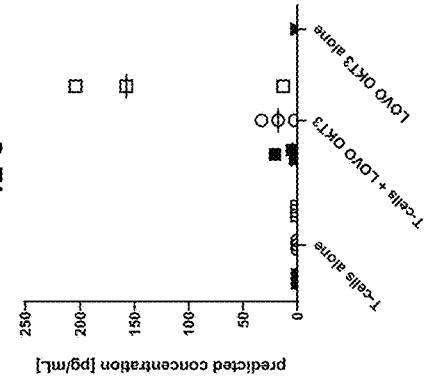

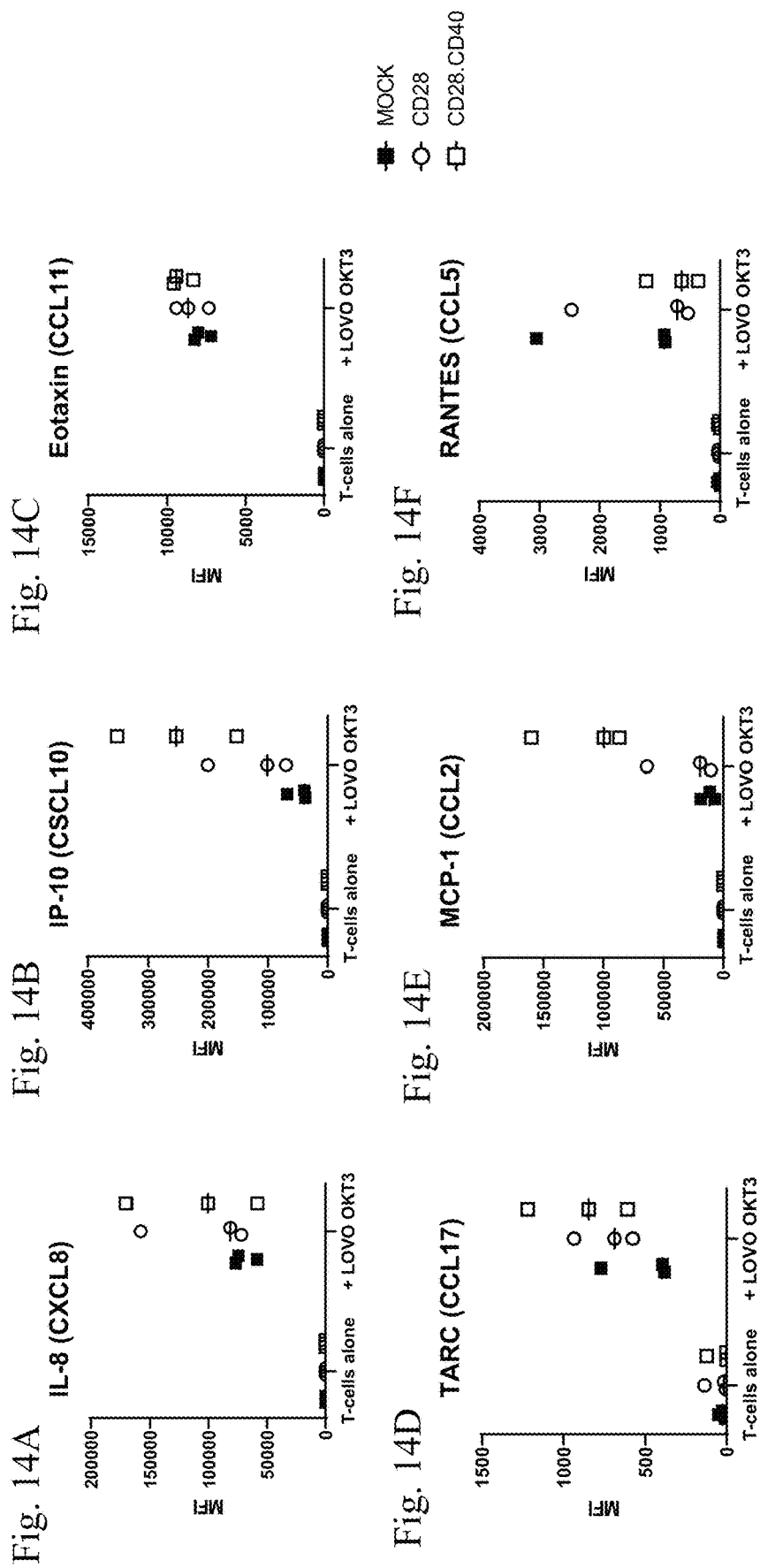

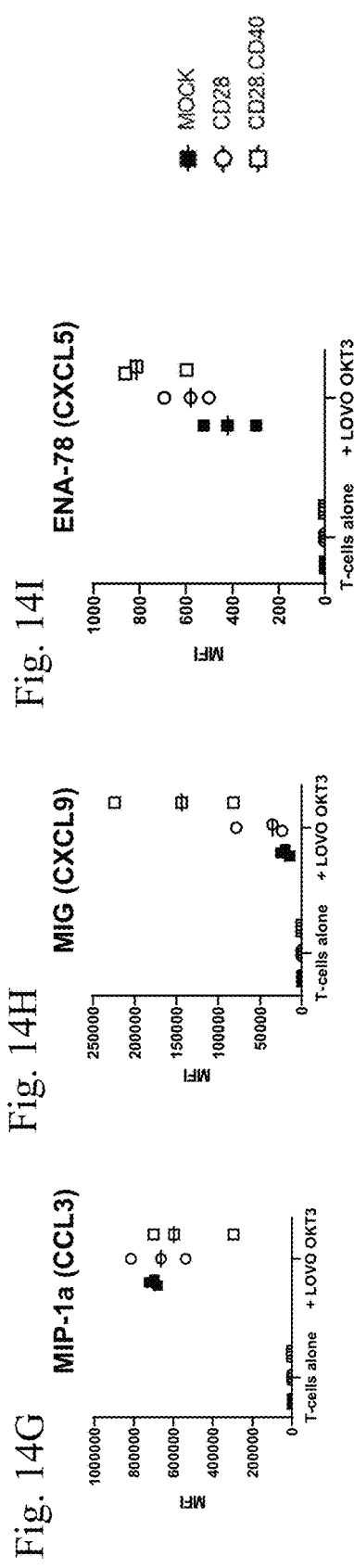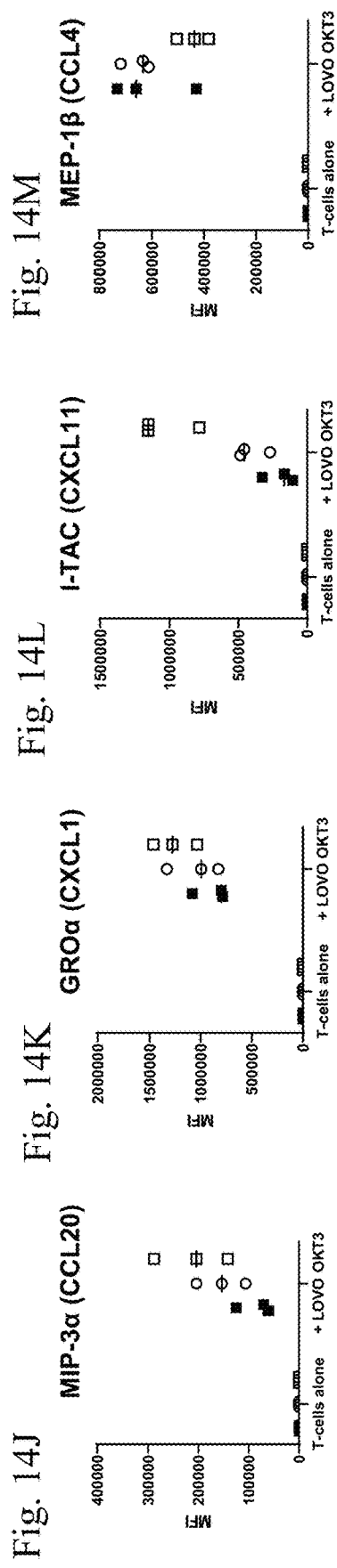

FolR expression in tumor

TIL + Autologous Tumor

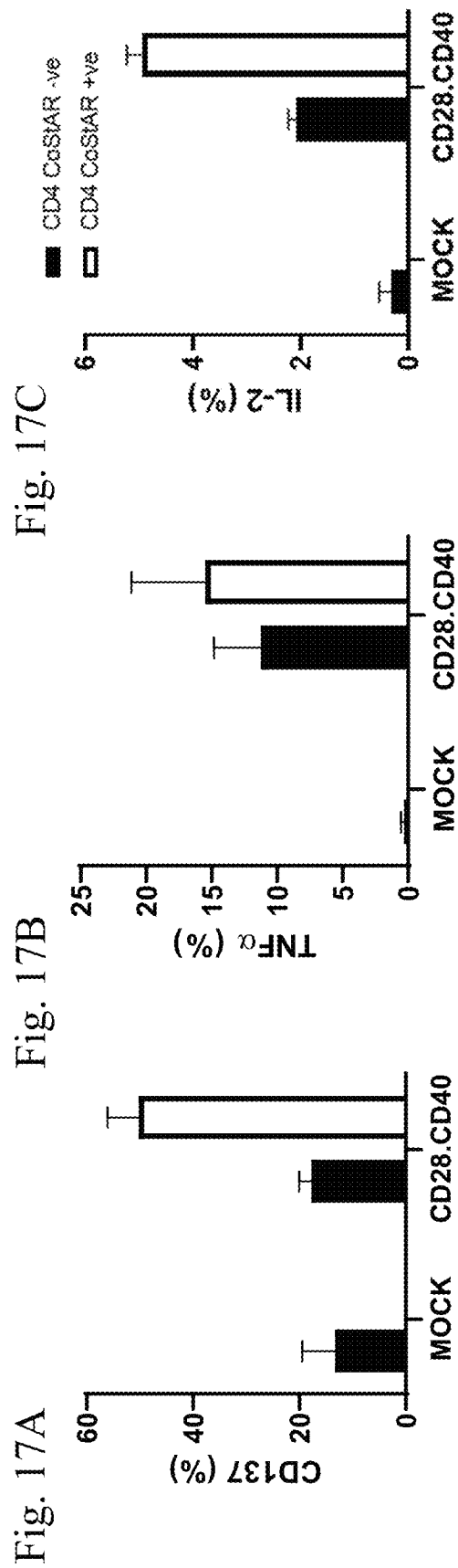

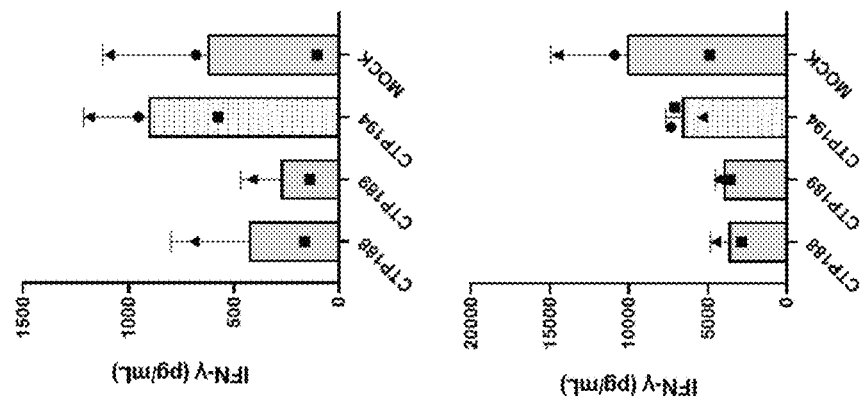
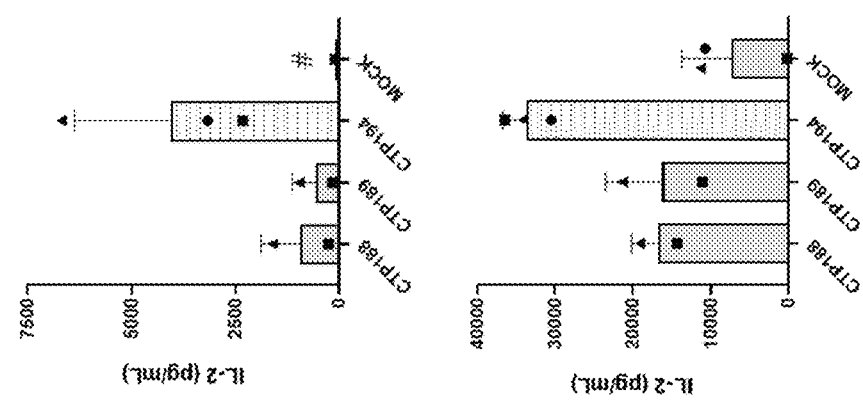
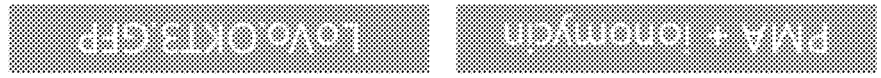
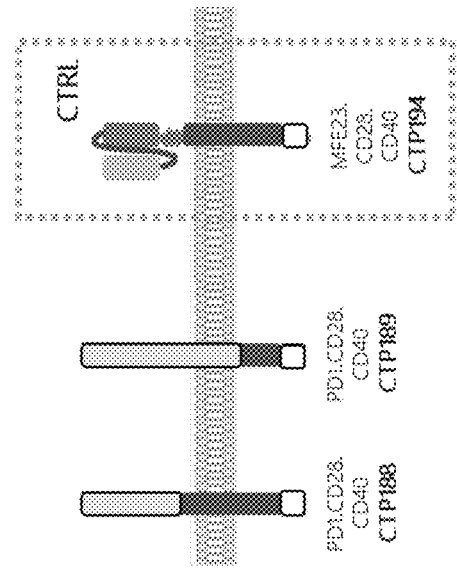
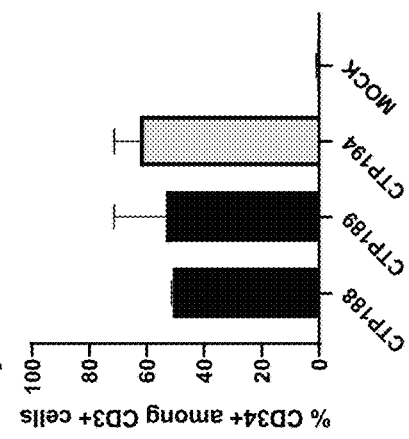
Fig. 21A
Fig. 21B
Fig. 21C

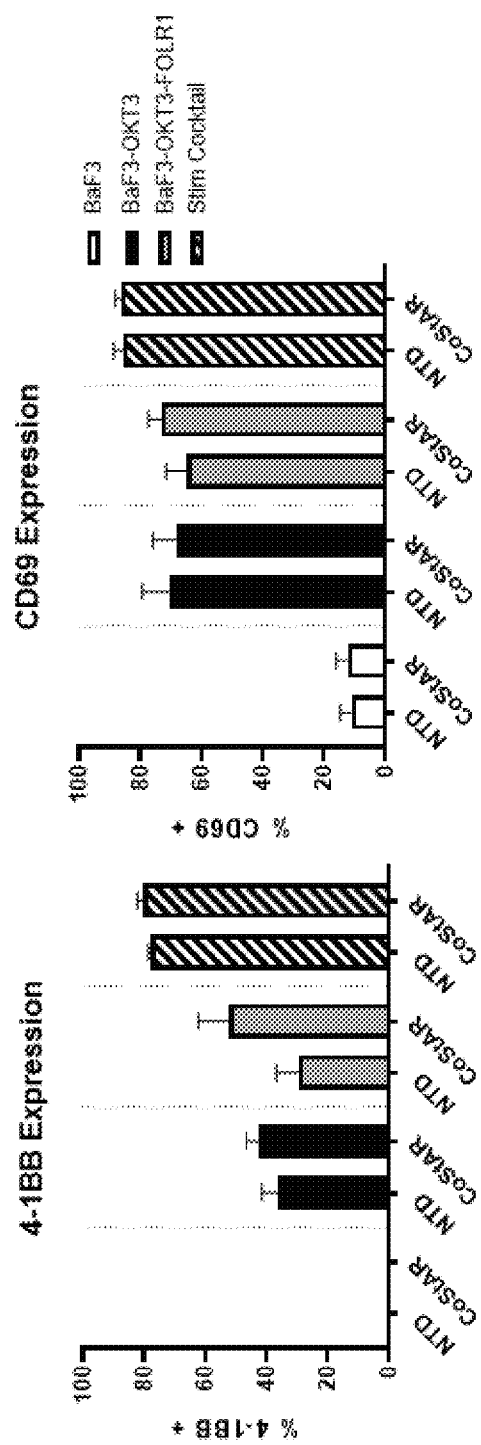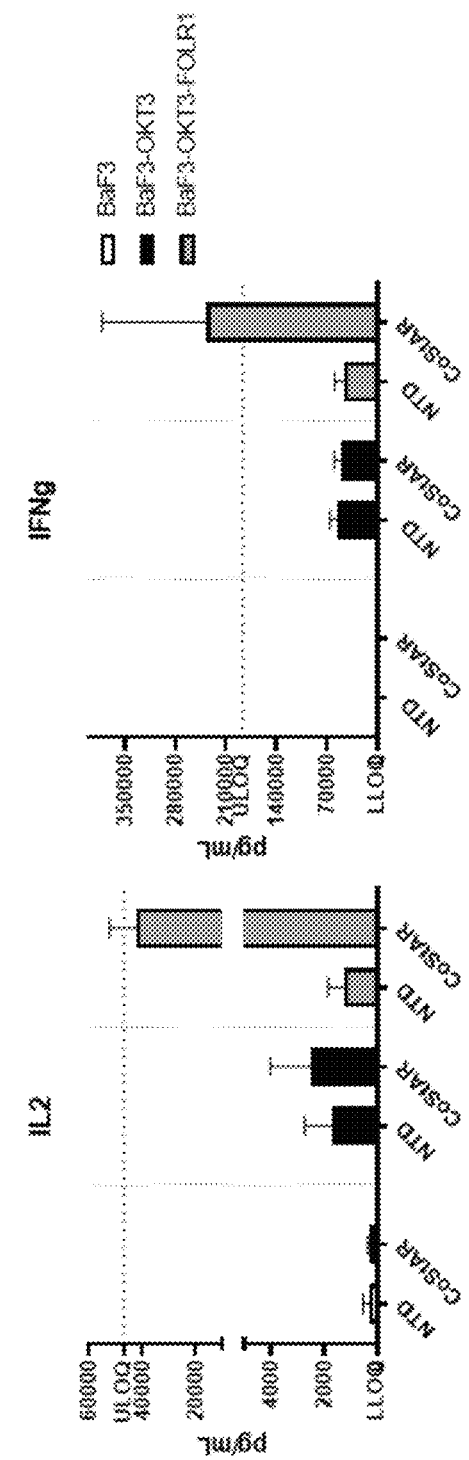
Fig. 34A
Fig. 34B

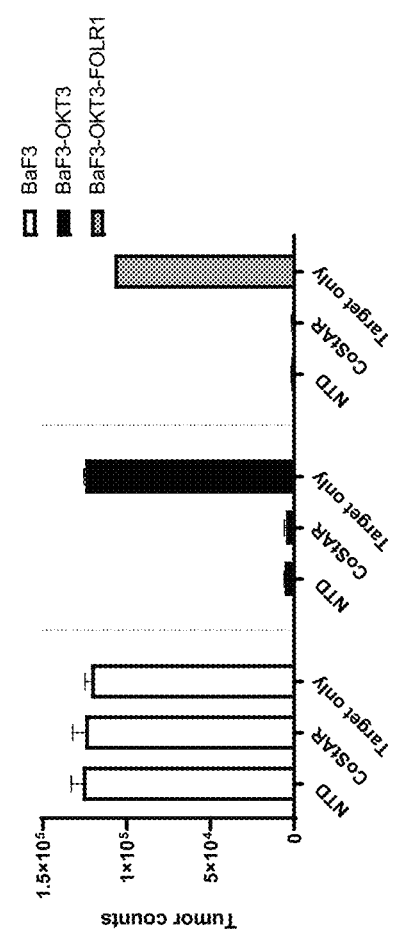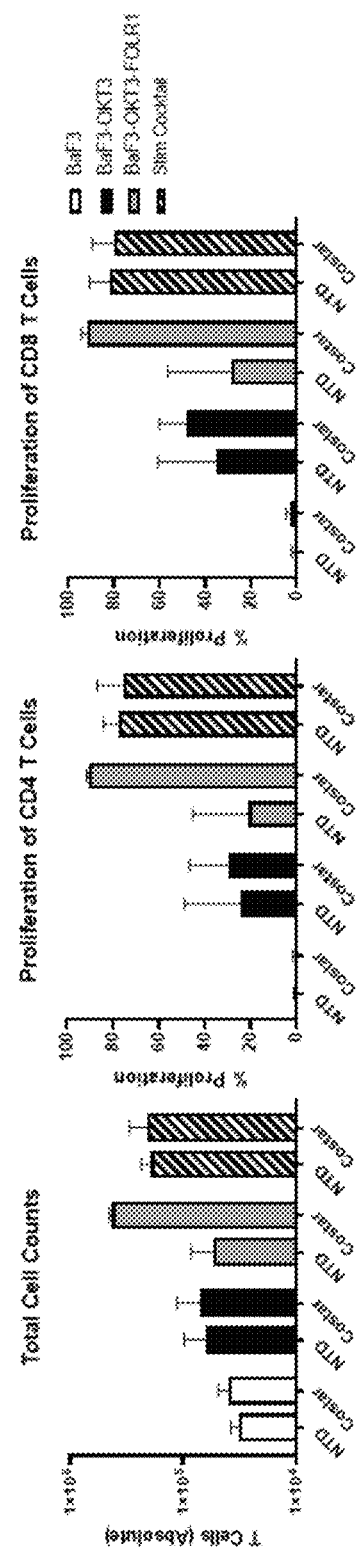
Fig. 34C
Fig. 34D

SEQUENCE LISTING

```
Sequence total quantity: 125
SEQ ID NO: 1            moltype = AA  length = 25
FEATURE                 Location/Qualifiers
REGION                  1..25
                        note = Synthetic peptide
source                  1..25
                        mol_type = protein
                        organism = synthetic construct
SEQUENCE: 1
MGVLLTQRTL LSLVLALLFP SMASM                                          25

SEQ ID NO: 2            moltype = AA  length = 23
FEATURE                 Location/Qualifiers
```

```
REGION                      1..23
                            note = Synthetic peptide
source                      1..23
                            mol_type = protein
                            organism = synthetic construct
SEQUENCE: 2
MQIPQAPWPV VWAVLQLGWR PGW                                             23

SEQ ID NO: 3                moltype = AA   length = 21
FEATURE                     Location/Qualifiers
REGION                      1..21
                            note = Synthetic peptide
source                      1..21
                            mol_type = protein
                            organism = synthetic construct
SEQUENCE: 3
MRWCLLLIWA QGLRQAPLAS G                                               21

SEQ ID NO: 4                moltype = AA   length = 244
FEATURE                     Location/Qualifiers
REGION                      1..244
                            note = Synthetic peptide
source                      1..244
                            mol_type = protein
                            organism = synthetic construct
SEQUENCE: 4
QVQLQQSGAE LVKPGASVKI SCKASGYSFT GYFMNWVKQS HGKSLEWIGR IHPYDGDTFY     60
NQNFKDKATL TVDKSSNTAH MELLSLTSED FAVYYCTRYD GSRAMDYWGQ GTTVTVSSGG    120
GGSGGGGSGG GGSDIELTQS PASLAVSLGQ RAIISCKASQ SVSFAGTSLM HWYHQKPGQQ    180
PKLLIYRASN LEAGVPTRFS GSGSKTDFTL NIHPVEEEDA ATYYCQQSRE YPYTFGGGTK    240
LEIK                                                                244

SEQ ID NO: 5                moltype = AA   length = 242
FEATURE                     Location/Qualifiers
REGION                      1..242
                            note = Synthetic peptide
source                      1..242
                            mol_type = protein
                            organism = synthetic construct
SEQUENCE: 5
QVQLQQSGAE LVRSGTSVKL SCTASGFNIK DSYMHWLRQG PEQGLEWIGW IDPENGDTEY     60
APKFQGKATF TTDTSSNTAY LQLSSLTSED TAVYYCNEGT PTGPYYFDYW GQGTTVTVSS    120
GGGGSGGGGS GGGGSENVLT QSPAIMSASP GEKVTITCSA SSSVSYMHWF QQKPGTSPKL    180
WIYSTSNLAS GVPARFSGSG SGTSYSLTIS RMEAEDAATY YCQQRSSYPL TFGAGTKLEL    240
KR                                                                  242

SEQ ID NO: 6                moltype = AA   length = 136
FEATURE                     Location/Qualifiers
REGION                      1..136
                            note = Synthetic peptide
source                      1..136
                            mol_type = protein
                            organism = synthetic construct
SEQUENCE: 6
RPGWFLDSPD RPWNPPTFSP ALLVVTEGDN ATFTCSFSNT SESFVLNWYR MSPSNQTDKL     60
AAFPEDRSQP GQDCRFRVTQ LPNGRDFHMS VVRARRNDSG TYLCGAISLA PKAQIKESLR    120
AELRVTERRA EVPTAH                                                   136

SEQ ID NO: 7                moltype = AA   length = 120
FEATURE                     Location/Qualifiers
REGION                      1..120
                            note = Synthetic peptide
source                      1..120
                            mol_type = protein
                            organism = synthetic construct
SEQUENCE: 7
MMTGTIETTG NISAEKGGSI ILQCHLSSTT AQVTQVNWEQ QDQLLAICNA DLGWHISPSF     60
KDRVAPGPGL GLTLQSLTVN DTGEYFCIYH TYPDGTYTGR IFLEVLESSV AEHGARFQIP    120

SEQ ID NO: 8                moltype = AA   length = 9
FEATURE                     Location/Qualifiers
REGION                      1..9
                            note = Synthetic peptide
source                      1..9
                            mol_type = protein
                            organism = synthetic construct
SEQUENCE: 8
AAAGSGGSG                                                              9
```

```
SEQ ID NO: 9              moltype = AA   length = 136
FEATURE                   Location/Qualifiers
REGION                    1..136
                          note = Synthetic peptide
source                    1..136
                          mol_type = protein
                          organism = synthetic construct
SEQUENCE: 9
RPGWFLDSPD RPWNPPTFSP ALLVVTEGDN ATFTCSFSNT SESFVLNWYR MSPSNQTDKL   60
AAFPEDRSQP GQDCRFRVTQ LPNGRDFHMS VVRARRNDSG TYLCGAISLA PKAQIKESLR  120
AELRVTERRA EVPTAH                                                  136

SEQ ID NO: 10             moltype = AA   length = 120
FEATURE                   Location/Qualifiers
REGION                    1..120
                          note = Synthetic peptide
source                    1..120
                          mol_type = protein
                          organism = synthetic construct
SEQUENCE: 10
MMTGTIETTG NISAEKGGSI ILQCHLSSTT AQVTQVNWEQ QDQLLAICNA DLGWHISPSF   60
KDRVAPGPGL GLTLQSLTVN DTGEYFCIYH TYPDGTYTGR IFLEVLESSV AEHGARFQIP  120

SEQ ID NO: 11             moltype = AA   length = 159
FEATURE                   Location/Qualifiers
REGION                    1..159
                          note = Synthetic peptide
source                    1..159
                          mol_type = protein
                          organism = synthetic construct
SEQUENCE: 11
ILVKQSPMLV AYDNAVNLSC KYSYNLFSRE FRASLHKGLD SAVEVCVVYG NYSQQLQVYS   60
KTGFNCDGKL GNESVTFYLQ NLYVNQTDIY FCKIEVMYPP PYLDNEKSNG TIIHVKGKHL  120
CPSPLFPGPS KPFWVLVVVG GVLACYSLLV TVAFIIFWV                         159

SEQ ID NO: 12             moltype = AA   length = 83
FEATURE                   Location/Qualifiers
REGION                    1..83
                          note = Syntheti peptide
source                    1..83
                          mol_type = protein
                          organism = synthetic construct
SEQUENCE: 12
FVPVFLPAKP TTTPAPRPPT PAPTIASQPL SLRPEACRPA AGGAVHTRGL DFACDIYIWA   60
PLAGTCGVLL LSLVITLYCN HRN                                           83

SEQ ID NO: 13             moltype = AA   length = 257
FEATURE                   Location/Qualifiers
REGION                    1..257
                          note = Synthetic peptide
source                    1..257
                          mol_type = protein
                          organism = synthetic construct
SEQUENCE: 13
ESKYGPPCPS CPAPEFLGGP SVFLFPPKPK DTLMISRTPE VTCVVVDVSQ EDPEVQFNWY   60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKM FWVLVVVGGV  240
LACYSLLVTV AFIIFWV                                                 257

SEQ ID NO: 14             moltype = AA   length = 39
FEATURE                   Location/Qualifiers
REGION                    1..39
                          note = Syntheti peptide
source                    1..39
                          mol_type = protein
                          organism = synthetic construct
SEQUENCE: 14
CPSPLFPGPS KPFWVLVVVG GVLACYSLLV TVAFIIFWV                          39

SEQ ID NO: 15             moltype = AA   length = 27
FEATURE                   Location/Qualifiers
REGION                    1..27
                          note = Synthetic peptide
source                    1..27
                          mol_type = protein
                          organism = synthetic construct
SEQUENCE: 15
FWVLVVVGGV LACYSLLVTV AFIIFWV                                       27
```

```
SEQ ID NO: 16            moltype = AA   length = 41
FEATURE                  Location/Qualifiers
REGION                   1..41
                         note = Synthetic peptide
source                   1..41
                         mol_type = protein
                         organism = synthetic construct
SEQUENCE: 16
RSKRSRLLHS DYMNMTPRRP GPTRKHYQPY APPRDFAAYR S                         41

SEQ ID NO: 17            moltype = AA   length = 46
FEATURE                  Location/Qualifiers
REGION                   1..46
                         note = Synthetic peptide
source                   1..46
                         mol_type = protein
                         organism = synthetic construct
SEQUENCE: 17
RFSVVKRGRK KLLYIFKQPF MRPVQTTQEE DGCSCRFPEE EEGGCE                    46

SEQ ID NO: 18            moltype = AA   length = 37
FEATURE                  Location/Qualifiers
REGION                   1..37
                         note = Synthetic peptide
source                   1..37
                         mol_type = protein
                         organism = synthetic construct
SEQUENCE: 18
RRDQRLPPDA HKPPGGGSFR TPIQEEQADA HSTLAKI                              37

SEQ ID NO: 19            moltype = AA   length = 116
FEATURE                  Location/Qualifiers
REGION                   1..116
                         note = Synthetic peptide
source                   1..116
                         mol_type = protein
                         organism = synthetic construct
SEQUENCE: 19
KRKKQRSRRN DEELETRAHR VATEERGRKP HQIPASTPQN PATSQHPPPP PGHRSQAPSH     60
RPPPPGHRVQ HQPQKRPPAP SGTQVHQQKG PPLPRPRVQP KPPHGAAENS LSPSSN        116

SEQ ID NO: 20            moltype = AA   length = 58
FEATURE                  Location/Qualifiers
REGION                   1..58
                         note = Synthetic peptide
source                   1..58
                         mol_type = protein
                         organism = synthetic construct
SEQUENCE: 20
QLGLHIWQLR SQCMWPRETQ LLLEVPPSTE DARSCQFPEE ERGERSAEEK GRLGDLWV       58

SEQ ID NO: 21            moltype = AA   length = 47
FEATURE                  Location/Qualifiers
REGION                   1..47
                         note = Synthetic peptide
source                   1..47
                         mol_type = protein
                         organism = synthetic construct
SEQUENCE: 21
KLLMIIHDRR EFAKFEKEKM NAKWDTGENP IYKSAVTTVV NPKYEGK                   47

SEQ ID NO: 22            moltype = AA   length = 75
FEATURE                  Location/Qualifiers
REGION                   1..75
                         note = Synthetic peptide
source                   1..75
                         mol_type = protein
                         organism = synthetic construct
SEQUENCE: 22
RRRGKTNHYQ TTVEKKSLTI YAQVQKPGPL QKKLDSFPAQ DPCTTIYVAA TEPVPESVQE     60
TNSITVYASV TLPES                                                     75

SEQ ID NO: 23            moltype = AA   length = 62
FEATURE                  Location/Qualifiers
REGION                   1..62
                         note = Synthetic peptide
```

```
                        source          1..62
                                        mol_type = protein
                                        organism = synthetic construct
SEQUENCE: 23
KKVAKKPTNK APHPKQEPQE INFPDDLPGS NTAAPVQETL HGCQPVTQED GKESRISVQE    60
RQ                                                                  62

SEQ ID NO: 24           moltype = AA  length = 124
FEATURE                 Location/Qualifiers
REGION                  1..124
                                        note = Synthetic peptide
source                  1..124
                                        mol_type = protein
                                        organism = synthetic construct
SEQUENCE: 24
KKVAKKPTNK APHPKQEPQE INFPDDLPGS NTAAPVQETL HGCQPVTQED GKESRISVQE    60
RQKKVAKKPT NKAPHPKQEP QEINFPDDLP GSNTAAPVQE TLHGCQPVTQ EDGKESRISV   120
QERQ                                                               124

SEQ ID NO: 25           moltype = AA  length = 62
FEATURE                 Location/Qualifiers
REGION                  1..62
                                        note = Synthetic peptide
source                  1..62
                                        mol_type = protein
                                        organism = synthetic construct
SEQUENCE: 25
KKVAKKPTNK AAHPKQEPQE INFPDDLPGS NTAAPVQETL HGCQPVTQED GKESRISVQE    60
RQ                                                                  62

SEQ ID NO: 26           moltype = AA  length = 8
FEATURE                 Location/Qualifiers
REGION                  1..8
                                        note = Synthetic peptide
source                  1..8
                                        mol_type = protein
                                        organism = synthetic construct
SEQUENCE: 26
KPTNKAPH                                                             8

SEQ ID NO: 27           moltype = AA  length = 4
FEATURE                 Location/Qualifiers
REGION                  1..4
                                        note = Synthetic peptide
source                  1..4
                                        mol_type = protein
                                        organism = synthetic construct
SEQUENCE: 27
PKQE                                                                 4

SEQ ID NO: 28           moltype = AA  length = 4
FEATURE                 Location/Qualifiers
REGION                  1..4
                                        note = Synthetic peptide
source                  1..4
                                        mol_type = protein
                                        organism = synthetic construct
SEQUENCE: 28
PVQE                                                                 4

SEQ ID NO: 29           moltype = AA  length = 4
FEATURE                 Location/Qualifiers
REGION                  1..4
                                        note = Synthetic peptide
source                  1..4
                                        mol_type = protein
                                        organism = synthetic construct
SEQUENCE: 29
SVQE                                                                 4

SEQ ID NO: 30           moltype = AA  length = 9
FEATURE                 Location/Qualifiers
REGION                  1..9
                                        note = Synthetic peptide
source                  1..9
                                        mol_type = protein
                                        organism = synthetic construct
SEQUENCE: 30
QEPQEINFP                                                            9
```

```
SEQ ID NO: 31            moltype = AA  length = 7
FEATURE                  Location/Qualifiers
REGION                   1..7
                         note = Synthetic peptide
source                   1..7
                         mol_type = protein
                         organism = synthetic construct
SEQUENCE: 31
KKPTNKA                                                                    7

SEQ ID NO: 32            moltype = AA  length = 7
FEATURE                  Location/Qualifiers
REGION                   1..7
                         note = Synthetid peptide
source                   1..7
                         mol_type = protein
                         organism = synthetic construct
SEQUENCE: 32
SRISVQE                                                                    7

SEQ ID NO: 33            moltype = AA  length = 538
FEATURE                  Location/Qualifiers
REGION                   1..538
                         note = Synthetic peptide
source                   1..538
                         mol_type = protein
                         organism = synthetic construct
SEQUENCE: 33
MGVLLTQRTL LSLVLALLFP SMASMQVQLQ QSGAELVRSG TSVKLSCTAS GFNIKDSYMH    60
WLRQGPEQGL EWIGWIDPEN GDTEYAPKFQ GKATFTTDTS SNTAYLQLSS LTSEDTAVYY   120
CNEGTPTGPY YFDYWGQGTT VTVSSGGGGS GGGGSGGGGS ENVLTQSPAI MSASPGEKVT   180
ITCSASSSVS YMHWFQQKPG TSPKLWIYST SNLASGVPAR FSGSGSGTSY SLTISRMEAE   240
DAATYYCQQR SSYPLTFGAG TKLELKRAAA GSGGGSILVK QSPMLVAYDN AVNLSCKYSY   300
NLFSREFRAS LHKGLDSAVE VCVVYGNYSQ QLQVYSKTGF NCDGKLGNES VTFYLQNLYV   360
NQTDIYFCKI EVMYPPPYLD NEKSNGTIIH VKGKHLCPSP LFPGPSKPFW VLVVVGGVLA   420
CYSLLVTVAF IIFWVRSKRS RLLHSDYMNM TPRRPGPTRK HYQPYAPPRD FAAYRSKKVA   480
KKPTNKAPHP KQEPQEINFP DDLPGSNTAA PVQETLHGCQ PVTQEDGKES RISVQERQ     538

SEQ ID NO: 34            moltype = AA  length = 497
FEATURE                  Location/Qualifiers
REGION                   1..497
                         note = Synthetic peptide
source                   1..497
                         mol_type = protein
                         organism = synthetic construct
SEQUENCE: 34
MGVLLTQRTL LSLVLALLFP SMASMQVQLQ QSGAELVRSG TSVKLSCTAS GFNIKDSYMH    60
WLRQGPEQGL EWIGWIDPEN GDTEYAPKFQ GKATFTTDTS SNTAYLQLSS LTSEDTAVYY   120
CNEGTPTGPY YFDYWGQGTT VTVSSGGGGS GGGGSGGGGS ENVLTQSPAI MSASPGEKVT   180
ITCSASSSVS YMHWFQQKPG TSPKLWIYST SNLASGVPAR FSGSGSGTSY SLTISRMEAE   240
DAATYYCQQR SSYPLTFGAG TKLELKRAAA GSGGGSILVK QSPMLVAYDN AVNLSCKYSY   300
NLFSREFRAS LHKGLDSAVE VCVVYGNYSQ QLQVYSKTGF NCDGKLGNES VTFYLQNLYV   360
NQTDIYFCKI EVMYPPPYLD NEKSNGTIIH VKGKHLCPSP LFPGPSKPFW VLVVVGGVLA   420
CYSLLVTVAF IIFWVKKVAK KPTNKAPHPK QEPQEINFPD DLPGSNTAAP VQETLHGCQP   480
VTQEDGKESR ISVQERQ                                                 497

SEQ ID NO: 35            moltype = AA  length = 543
FEATURE                  Location/Qualifiers
REGION                   1..543
                         note = Synthetic peptide
source                   1..543
                         mol_type = protein
                         organism = synthetic construct
SEQUENCE: 35
MGVLLTQRTL LSLVLALLFP SMASMQVQLQ QSGAELVRSG TSVKLSCTAS GFNIKDSYMH    60
WLRQGPEQGL EWIGWIDPEN GDTEYAPKFQ GKATFTTDTS SNTAYLQLSS LTSEDTAVYY   120
CNEGTPTGPY YFDYWGQGTT VTVSSGGGGS GGGGSGGGGS ENVLTQSPAI MSASPGEKVT   180
ITCSASSSVS YMHWFQQKPG TSPKLWIYST SNLASGVPAR FSGSGSGTSY SLTISRMEAE   240
DAATYYCQQR SSYPLTFGAG TKLELKRAAA GSGGGSILVK QSPMLVAYDN AVNLSCKYSY   300
NLFSREFRAS LHKGLDSAVE VCVVYGNYSQ QLQVYSKTGF NCDGKLGNES VTFYLQNLYV   360
NQTDIYFCKI EVMYPPPYLD NEKSNGTIIH VKGKHLCPSP LFPGPSKPFW VLVVVGGVLA   420
CYSLLVTVAF IIFWVRFSVV KRGRKKLLYI FKQPFMRPVQ TTQEEDGCSC RFPEEEEGGC   480
EKKVAKKPTN KAPHPKQEPQ EINFPDDLPG SNTAAPVQET LHGCQPVTQE DGKESRISVQ   540
ERQ                                                                 543
```

```
SEQ ID NO: 36            moltype = AA   length = 534
FEATURE                  Location/Qualifiers
REGION                   1..534
                         note = Synthetic peptide
source                   1..534
                         mol_type = protein
                         organism = synthetic construct
SEQUENCE: 36
MGVLLTQRTL LSLVLALLFP SMASMQVQLQ QSGAELVRSG TSVKLSCTAS GFNIKDSYMH    60
WLRQGPEQGL EWIGWIDPEN GDTEYAPKFQ GKATFTTDTS SNTAYLQLSS LTSEDTAVYY   120
CNEGTPTGPY YFDYWGQGTT VTVSSGGGGS GGGGSGGGGS ENVLTQSPAI MSASPGEKVT   180
ITCSASSSVS YMHWFQQKPG TSPKLWIYST SNLASGVPAR FSGSGSGTSY SLTISRMEAE   240
DAATYYCQQR SSYPLTFGAG TKLELKRAAA GSGGSGILVK QSPMLVAYDN AVNLSCKYSY   300
NLFSREFRAS LHKGLDSAVE VCVVYGNYSQ QLQVYSKTGF NCDGKLGNES VTFYLQNLYV   360
NQTDIYFCKI EVMYPPPYLD NEKSNGTIIH VKGKHLCPSP LFPGPSKPFW VLVVVGGVLA   420
CYSLLVTVAF IIFWVRRDQR LPPDAHKPPG GGSFRTPIQE EQADAHSTLA KIKKVAKKPT   480
NKAPHPKQEP QEINFPDDLP GSNTAAPVQE TLHGCQPVTQ EDGKESRISV QERQ         534

SEQ ID NO: 37            moltype = AA   length = 613
FEATURE                  Location/Qualifiers
REGION                   1..613
                         note = Synthetic peptide
source                   1..613
                         mol_type = protein
                         organism = synthetic construct
SEQUENCE: 37
MGVLLTQRTL LSLVLALLFP SMASMQVQLQ QSGAELVRSG TSVKLSCTAS GFNIKDSYMH    60
WLRQGPEQGL EWIGWIDPEN GDTEYAPKFQ GKATFTTDTS SNTAYLQLSS LTSEDTAVYY   120
CNEGTPTGPY YFDYWGQGTT VTVSSGGGGS GGGGSGGGGS ENVLTQSPAI MSASPGEKVT   180
ITCSASSSVS YMHWFQQKPG TSPKLWIYST SNLASGVPAR FSGSGSGTSY SLTISRMEAE   240
DAATYYCQQR SSYPLTFGAG TKLELKRAAA GSGGSGILVK QSPMLVAYDN AVNLSCKYSY   300
NLFSREFRAS LHKGLDSAVE VCVVYGNYSQ QLQVYSKTGF NCDGKLGNES VTFYLQNLYV   360
NQTDIYFCKI EVMYPPPYLD NEKSNGTIIH VKGKHLCPSP LFPGPSKPFW VLVVVGGVLA   420
CYSLLVTVAF IIFWVRKKQ RSRRNDEELE TRAHRVATEE RGRKPHQIPA STPQNPATSQ   480
HPPPPPGHRS QAPSHRPPPP GHRVQHQPQK RPPAPSGTQV HQQKGPPLPR PRVQPKPPHG   540
AAENSLSPSS NKKVAKKPTN KAPHPKQEPQ EINFPDDLPG SNTAAPVQET LHGCQPVTQE   600
DGKESRISVQ ERQ                                                     613

SEQ ID NO: 38            moltype = AA   length = 555
FEATURE                  Location/Qualifiers
REGION                   1..555
                         note = Synthetic peptide
source                   1..555
                         mol_type = protein
                         organism = synthetic construct
SEQUENCE: 38
MGVLLTQRTL LSLVLALLFP SMASMQVQLQ QSGAELVRSG TSVKLSCTAS GFNIKDSYMH    60
WLRQGPEQGL EWIGWIDPEN GDTEYAPKFQ GKATFTTDTS SNTAYLQLSS LTSEDTAVYY   120
CNEGTPTGPY YFDYWGQGTT VTVSSGGGGS GGGGSGGGGS ENVLTQSPAI MSASPGEKVT   180
ITCSASSSVS YMHWFQQKPG TSPKLWIYST SNLASGVPAR FSGSGSGTSY SLTISRMEAE   240
DAATYYCQQR SSYPLTFGAG TKLELKRAAA GSGGSGILVK QSPMLVAYDN AVNLSCKYSY   300
NLFSREFRAS LHKGLDSAVE VCVVYGNYSQ QLQVYSKTGF NCDGKLGNES VTFYLQNLYV   360
NQTDIYFCKI EVMYPPPYLD NEKSNGTIIH VKGKHLCPSP LFPGPSKPFW VLVVVGGVLA   420
CYSLLVTVAF IIFWVQLGLH IWQLRSQCMW PRETQLLLEV PPSTEDARSC QFPEEERGER   480
SAEEKGRLGD LWVKKVAKKP TNKAPHPKQE PQEINFPDDL PGSNTAAPVQ ETLHGCQPVT   540
QEDGKESRIS VQERQ                                                   555

SEQ ID NO: 39            moltype = AA   length = 544
FEATURE                  Location/Qualifiers
REGION                   1..544
                         note = Synthetic peptide
source                   1..544
                         mol_type = protein
                         organism = synthetic construct
SEQUENCE: 39
MGVLLTQRTL LSLVLALLFP SMASMQVQLQ QSGAELVRSG TSVKLSCTAS GFNIKDSYMH    60
WLRQGPEQGL EWIGWIDPEN GDTEYAPKFQ GKATFTTDTS SNTAYLQLSS LTSEDTAVYY   120
CNEGTPTGPY YFDYWGQGTT VTVSSGGGGS GGGGSGGGGS ENVLTQSPAI MSASPGEKVT   180
ITCSASSSVS YMHWFQQKPG TSPKLWIYST SNLASGVPAR FSGSGSGTSY SLTISRMEAE   240
DAATYYCQQR SSYPLTFGAG TKLELKRAAA GSGGSGILVK QSPMLVAYDN AVNLSCKYSY   300
NLFSREFRAS LHKGLDSAVE VCVVYGNYSQ QLQVYSKTGF NCDGKLGNES VTFYLQNLYV   360
NQTDIYFCKI EVMYPPPYLD NEKSNGTIIH VKGKHLCPSP LFPGPSKPFW VLVVVGGVLA   420
CYSLLVTVAF IIFWVKLLMI IHDRREFAKF EKEKMNAKWD TGENPIYKSA VTTVVNPKYE   480
GKKKVAKKPT NKAPHPKQEP QEINFPDDLP GSNTAAPVQE TLHGCQPVTQ EDGKESRISV   540
QERQ                                                               544

SEQ ID NO: 40            moltype = AA   length = 572
FEATURE                  Location/Qualifiers
```

```
REGION                  1..572
                        note = Synthetic peptide
source                  1..572
                        mol_type = protein
                        organism = synthetic construct
SEQUENCE: 40
MGVLLTQRTL LSLVLALLFP SMASMQVQLQ QSGAELVRSG TSVKLSCTAS GFNIKDSYMH    60
WLRQGPEQGL EWIGWIDPEN GDTEYAPKFQ GKATFTTDTS SNTAYLQLSS LTSEDTAVYY   120
CNEGTPTGPY YFDYWGQGTT VTVSSGGGGS GGGGSGGGGS ENVLTQSPAI MSASPGEKVT   180
ITCSASSSVS YMHWFQQKPG TSPKLWIYST SNLASGVPAR FSGSGSGTSY SLTISRMEAE   240
DAATYYCQQR SSYPLTFGAG TKLELKRAAA GSGGGSGILVK QSPMLVAYDN AVNLSCKYSY   300
NLFSREFRAS LHKGLDSAVE VCVVYGNYSQ QLQVYSKTGF NCDGKLGNES VTFYLQNLYV   360
NQTDIYFCKI EVMYPPPYLD NEKSNGTIIH VKGKHLCPSP LFPGPSKPFW VLVVVGGVLA   420
CYSLLVTVAF IIFWVRRRGK TNHYQTTVEK KSLTIYAQVQ KPGPLQKKLD SFPAQDPCTT   480
IYVAATEPVP ESVQETNSIT VYASVTLPES KKVAKKPTNK APHPKQEPQE INFPDDLPGS   540
NTAAPVQETL HGCQPVTQED GKESRISVQE RQ                                 572

SEQ ID NO: 41           moltype = AA   length = 462
FEATURE                 Location/Qualifiers
REGION                  1..462
                        note = Synthetic peptide
source                  1..462
                        mol_type = protein
                        organism = synthetic construct
SEQUENCE: 41
MGVLLTQRTL LSLVLALLFP SMASMQVQLQ QSGAELVRSG TSVKLSCTAS GFNIKDSYMH    60
WLRQGPEQGL EWIGWIDPEN GDTEYAPKFQ GKATFTTDTS SNTAYLQLSS LTSEDTAVYY   120
CNEGTPTGPY YFDYWGQGTT VTVSSGGGGS GGGGSGGGGS ENVLTQSPAI MSASPGEKVT   180
ITCSASSSVS YMHWFQQKPG TSPKLWIYST SNLASGVPAR FSGSGSGTSY SLTISRMEAE   240
DAATYYCQQR SSYPLTFGAG TKLELKRAAA GSGGGSFVPV FLPAKPTTTP APRPPTPAPT   300
IASQPLSLRP EACRPAAGGA VHTRGLDFAC DIYIWAPLAG TCGVLLLSLV ITLYCNHRNR   360
SKRSRLLHSD YMNMTPRRPG PTRKHYQPYA PPRDFAAYRS KKVAKKPTNK APHPKQEPQE   420
INFPDDLPGS NTAAPVQETL HGCQPVTQED GKESRISVQE RQ                      462

SEQ ID NO: 42           moltype = AA   length = 421
FEATURE                 Location/Qualifiers
REGION                  1..421
                        note = Synthetic peptide
source                  1..421
                        mol_type = protein
                        organism = synthetic construct
SEQUENCE: 42
MGVLLTQRTL LSLVLALLFP SMASMQVQLQ QSGAELVRSG TSVKLSCTAS GFNIKDSYMH    60
WLRQGPEQGL EWIGWIDPEN GDTEYAPKFQ GKATFTTDTS SNTAYLQLSS LTSEDTAVYY   120
CNEGTPTGPY YFDYWGQGTT VTVSSGGGGS GGGGSGGGGS ENVLTQSPAI MSASPGEKVT   180
ITCSASSSVS YMHWFQQKPG TSPKLWIYST SNLASGVPAR FSGSGSGTSY SLTISRMEAE   240
DAATYYCQQR SSYPLTFGAG TKLELKRAAA GSGGGSFVPV FLPAKPTTTP APRPPTPAPT   300
IASQPLSLRP EACRPAAGGA VHTRGLDFAC DIYIWAPLAG TCGVLLLSLV ITLYCNHRNK   360
KVAKKPTNKA PHPKQEPQEI NFPDDLPGSN TAAPVQETLH GCQPVTQEDG KESRISVQER   420
Q                                                                   421

SEQ ID NO: 43           moltype = AA   length = 467
FEATURE                 Location/Qualifiers
REGION                  1..467
                        note = Synthetic peptide
source                  1..467
                        mol_type = protein
                        organism = synthetic construct
SEQUENCE: 43
MGVLLTQRTL LSLVLALLFP SMASMQVQLQ QSGAELVRSG TSVKLSCTAS GFNIKDSYMH    60
WLRQGPEQGL EWIGWIDPEN GDTEYAPKFQ GKATFTTDTS SNTAYLQLSS LTSEDTAVYY   120
CNEGTPTGPY YFDYWGQGTT VTVSSGGGGS GGGGSGGGGS ENVLTQSPAI MSASPGEKVT   180
ITCSASSSVS YMHWFQQKPG TSPKLWIYST SNLASGVPAR FSGSGSGTSY SLTISRMEAE   240
DAATYYCQQR SSYPLTFGAG TKLELKRAAA GSGGGSFVPV FLPAKPTTTP APRPPTPAPT   300
IASQPLSLRP EACRPAAGGA VHTRGLDFAC DIYIWAPLAG TCGVLLLSLV ITLYCNHRNR   360
FSVVKRGRKK LLYIFKQPFM RPVQTTQEED GCSCRFPEEE EGGCEKKVAK PTNKAPHPK   420
QEPQEINFPD DLPGSNTAAP VQETLHGCQP VTQEDGKESR ISVQERQ                 467

SEQ ID NO: 44           moltype = AA   length = 457
FEATURE                 Location/Qualifiers
REGION                  1..457
                        note = Synthetic peptide
source                  1..457
                        mol_type = protein
                        organism = synthetic construct
SEQUENCE: 44
MGVLLTQRTL LSLVLALLFP SMASMQVQLQ QSGAELVRSG TSVKLSCTAS GFNIKDSYMH    60
WLRQGPEQGL EWIGWIDPEN GDTEYAPKFQ GKATFTTDTS SNTAYLQLSS LTSEDTAVYY   120
CNEGTPTGPY YFDYWGQGTT VTVSSGGGGS GGGGSGGGGS ENVLTQSPAI MSASPGEKVT   180
```

```
ITCSASSSVS YMHWFQQKPG TSPKLWIYST SNLASGVPAR FSGSGSGTSY SLTISRMEAE  240
DAATYYCQQR SSYPLTFGAG TKLELKRAAA GSGGSGFVPV FLPAKPTTTP APRPPTPAPT  300
IASQPLSLRP EACRPAAGGA VHTRGLDFAC DIYIWAPLAG TCGVLLLSLV ITLYCNHRNR  360
RDQRLPPDAH KPPGGGSFRT PIQEEQADAH STLAKIKKVA KKPTNKAPHP KQEPQEINFP  420
DDLPGSNTAA PVQETLHGCQ PVTQEDGKSR ISVQERQ                          457

SEQ ID NO: 45           moltype = AA  length = 537
FEATURE                 Location/Qualifiers
REGION                  1..537
                        note = Synthetic peptide
source                  1..537
                        mol_type = protein
                        organism = synthetic construct
SEQUENCE: 45
MGVLLTQRTL LSLVLALLFP SMASMQVQLQ QSGAELVRSG TSVKLSCTAS GFNIKDSYMH   60
WLRQGPEQGL EWIGWIDPEN GDTEYAPKFQ GKATFTTDTS SNTAYLQLSS LTSEDTAVYY  120
CNEGTPTGPY YFDYWGQGTT VTVSSGGGGS GGGGSGGGGS ENVLTQSPAI MSASPGEKVT  180
ITCSASSSVS YMHWFQQKPG TSPKLWIYST SNLASGVPAR FSGSGSGTSY SLTISRMEAE  240
DAATYYCQQR SSYPLTFGAG TKLELKRAAA GSGGSGFVPV FLPAKPTTTP APRPPTPAPT  300
IASQPLSLRP EACRPAAGGA VHTRGLDFAC DIYIWAPLAG TCGVLLLSLV ITLYCNHRNK  360
RKKQRSRRND EELETRAHRV ATEERGRKPH QIPASTPQNP ATSQHPPPPP GHRSQAPSHR  420
PPPPGHRVQH QPQKRPPAPS GTQVHQQKGP PLPRPRVQPK PPHGAAENSL SPSSNKKVAK  480
KPTNKAPHPK QEPQEINFPD DLPGSNTAAP VQETLHGCQP VTQEDGKESR ISVQERQ     537

SEQ ID NO: 46           moltype = AA  length = 479
FEATURE                 Location/Qualifiers
REGION                  1..479
                        note = Synthetic peptide
source                  1..479
                        mol_type = protein
                        organism = synthetic construct
SEQUENCE: 46
MGVLLTQRTL LSLVLALLFP SMASMQVQLQ QSGAELVRSG TSVKLSCTAS GFNIKDSYMH   60
WLRQGPEQGL EWIGWIDPEN GDTEYAPKFQ GKATFTTDTS SNTAYLQLSS LTSEDTAVYY  120
CNEGTPTGPY YFDYWGQGTT VTVSSGGGGS GGGGSGGGGS ENVLTQSPAI MSASPGEKVT  180
ITCSASSSVS YMHWFQQKPG TSPKLWIYST SNLASGVPAR FSGSGSGTSY SLTISRMEAE  240
DAATYYCQQR SSYPLTFGAG TKLELKRAAA GSGGSGFVPV FLPAKPTTTP APRPPTPAPT  300
IASQPLSLRP EACRPAAGGA VHTRGLDFAC DIYIWAPLAG TCGVLLLSLV ITLYCNHRNQ  360
LGLHIWQLRS QCMWPRETQL LLEVPPSTED ARSCQFPEEE RGERSAEEKG RLGDLWVKKV  420
AKKPTNKAPH PKQEPQEINF PDDLPGSNTA APVQETLHGC QPVTQEDGKE SRISVQERQ   479

SEQ ID NO: 47           moltype = AA  length = 468
FEATURE                 Location/Qualifiers
REGION                  1..468
                        note = Synthetic peptide
source                  1..468
                        mol_type = protein
                        organism = synthetic construct
SEQUENCE: 47
MGVLLTQRTL LSLVLALLFP SMASMQVQLQ QSGAELVRSG TSVKLSCTAS GFNIKDSYMH   60
WLRQGPEQGL EWIGWIDPEN GDTEYAPKFQ GKATFTTDTS SNTAYLQLSS LTSEDTAVYY  120
CNEGTPTGPY YFDYWGQGTT VTVSSGGGGS GGGGSGGGGS ENVLTQSPAI MSASPGEKVT  180
ITCSASSSVS YMHWFQQKPG TSPKLWIYST SNLASGVPAR FSGSGSGTSY SLTISRMEAE  240
DAATYYCQQR SSYPLTFGAG TKLELKRAAA GSGGSGFVPV FLPAKPTTTP APRPPTPAPT  300
IASQPLSLRP EACRPAAGGA VHTRGLDFAC DIYIWAPLAG TCGVLLLSLV ITLYCNHRNK  360
LLMIIHDRRE FAKFEKEKMN AKWDTGENPI YKSAVTTVVN PKYEGKKKVA KKPTNKAPHP  420
KQEPQEINFP DDLPGSNTAA PVQETLHGCQ PVTQEDGKES RISVQERQ               468

SEQ ID NO: 48           moltype = AA  length = 496
FEATURE                 Location/Qualifiers
REGION                  1..496
                        note = Synthetic peptide
source                  1..496
                        mol_type = protein
                        organism = synthetic construct
SEQUENCE: 48
MGVLLTQRTL LSLVLALLFP SMASMQVQLQ QSGAELVRSG TSVKLSCTAS GFNIKDSYMH   60
WLRQGPEQGL EWIGWIDPEN GDTEYAPKFQ GKATFTTDTS SNTAYLQLSS LTSEDTAVYY  120
CNEGTPTGPY YFDYWGQGTT VTVSSGGGGS GGGGSGGGGS ENVLTQSPAI MSASPGEKVT  180
ITCSASSSVS YMHWFQQKPG TSPKLWIYST SNLASGVPAR FSGSGSGTSY SLTISRMEAE  240
DAATYYCQQR SSYPLTFGAG TKLELKRAAA GSGGSGFVPV FLPAKPTTTP APRPPTPAPT  300
IASQPLSLRP EACRPAAGGA VHTRGLDFAC DIYIWAPLAG TCGVLLLSLV ITLYCNHRNR  360
RRGKTNHYQT TVEKKSLTIY AQVQKPGPLQ KKLDSFPAQD PCTTIYVAAT EPVPESVQET  420
NSITVYASVT LPESKKVAKK PTNKAPHPKQ EPQEINFPDD LPGSNTAAPV QETLHGCQPV  480
TQEDGKESRI SVQERQ                                                 496
```

```
SEQ ID NO: 49             moltype = AA   length = 636
FEATURE                   Location/Qualifiers
REGION                    1..636
                          note = Synthetic peptide
source                    1..636
                          mol_type = protein
                          organism = synthetic construct
SEQUENCE: 49
MGVLLTQRTL LSLVLALLFP SMASMQVQLQ QSGAELVRSG TSVKLSCTAS GFNIKDSYMH   60
WLRQGPEQGL EWIGWIDPEN GDTEYAPKFQ GKATFTTDTS SNTAYLQLSS LTSEDTAVYY  120
CNEGTPTGPY YFDYWGQGTT VTVSSGGGGS GGGGSGGGGS ENVLTQSPAI MSASPGEKVT  180
ITCSASSSVS YMHWFQQKPG TSPKLWIYST SNLASGVPAR FSGSGSGTSY SLTISRMEAE  240
DAATYYCQQR SSYPLTFGAG TKLELKRAAA GSGGSGESKY GPPCPSCPAP EFLGGPSVFL  300
FPPKPKDTLM ISRTPEVTCV VVDVSQEDPE VQFNWYVDGV EVHNAKTKPR EEQFNSTYRV  360
VSVLTVLHQD WLNGKEYKCK VSNKGLPSSI EKTISKAKGQ PREPQVYTLP PSQEEMTKNQ  420
VSLTCLVKGF YPSDIAVEWE SNGQPENNYK TTPPVLDSDG SFFLYSRLTV DKSRWQEGNV  480
FSCSVMHEAL HNHYTQKSLS LSLGKMFWVL VVVGGVLACY SLLVTVAFII FWVRSKRSRL  540
LHSDYMNMTP RRPGPTRKHY QPYAPPRDFA AYRSKKVAKK PTNKAPHPKQ EPQEINFPDD  600
LPGSNTAAPV QETLHGCQPV TQEDGKESRI SVQERQ                           636

SEQ ID NO: 50             moltype = AA   length = 595
FEATURE                   Location/Qualifiers
REGION                    1..595
                          note = Synthetic peptide
source                    1..595
                          mol_type = protein
                          organism = synthetic construct
SEQUENCE: 50
MGVLLTQRTL LSLVLALLFP SMASMQVQLQ QSGAELVRSG TSVKLSCTAS GFNIKDSYMH   60
WLRQGPEQGL EWIGWIDPEN GDTEYAPKFQ GKATFTTDTS SNTAYLQLSS LTSEDTAVYY  120
CNEGTPTGPY YFDYWGQGTT VTVSSGGGGS GGGGSGGGGS ENVLTQSPAI MSASPGEKVT  180
ITCSASSSVS YMHWFQQKPG TSPKLWIYST SNLASGVPAR FSGSGSGTSY SLTISRMEAE  240
DAATYYCQQR SSYPLTFGAG TKLELKRAAA GSGGSGESKY GPPCPSCPAP EFLGGPSVFL  300
FPPKPKDTLM ISRTPEVTCV VVDVSQEDPE VQFNWYVDGV EVHNAKTKPR EEQFNSTYRV  360
VSVLTVLHQD WLNGKEYKCK VSNKGLPSSI EKTISKAKGQ PREPQVYTLP PSQEEMTKNQ  420
VSLTCLVKGF YPSDIAVEWE SNGQPENNYK TTPPVLDSDG SFFLYSRLTV DKSRWQEGNV  480
FSCSVMHEAL HNHYTQKSLS LSLGKMFWVL VVVGGVLACY SLLVTVAFII FWVKKVAKKP  540
TNKAPHPKQE PQEINFPDDL PGSNTAAPVQ ETLHGCQPVT QEDGKESRIS VQERQ       595

SEQ ID NO: 51             moltype = AA   length = 595
FEATURE                   Location/Qualifiers
REGION                    1..595
                          note = Synthetic peptide
source                    1..595
                          mol_type = protein
                          organism = synthetic construct
SEQUENCE: 51
MGVLLTQRTL LSLVLALLFP SMASMQVQLQ QSGAELVRSG TSVKLSCTAS GFNIKDSYMH   60
WLRQGPEQGL EWIGWIDPEN GDTEYAPKFQ GKATFTTDTS SNTAYLQLSS LTSEDTAVYY  120
CNEGTPTGPY YFDYWGQGTT VTVSSGGGGS GGGGSGGGGS ENVLTQSPAI MSASPGEKVT  180
ITCSASSSVS YMHWFQQKPG TSPKLWIYST SNLASGVPAR FSGSGSGTSY SLTISRMEAE  240
DAATYYCQQR SSYPLTFGAG TKLELKRAAA GSGGSGESKY GPPCPSCPAP EFLGGPSVFL  300
FPPKPKDTLM ISRTPEVTCV VVDVSQEDPE VQFNWYVDGV EVHNAKTKPR EEQFNSTYRV  360
VSVLTVLHQD WLNGKEYKCK VSNKGLPSSI EKTISKAKGQ PREPQVYTLP PSQEEMTKNQ  420
VSLTCLVKGF YPSDIAVEWE SNGQPENNYK TTPPVLDSDG SFFLYSRLTV DKSRWQEGNV  480
FSCSVMHEAL HNHYTQKSLS LSLGKMFWVL VVVGGVLACY SLLVTVAFII FWVKKVAKKP  540
TNKAPHPKQE PQEINFPDDL PGSNTAAPVQ ETLHGCQPVT QEDGKESRIS VQERQ       595

SEQ ID NO: 52             moltype = AA   length = 632
FEATURE                   Location/Qualifiers
REGION                    1..632
                          note = Synthetic peptide
source                    1..632
                          mol_type = protein
                          organism = synthetic construct
SEQUENCE: 52
MGVLLTQRTL LSLVLALLFP SMASMQVQLQ QSGAELVRSG TSVKLSCTAS GFNIKDSYMH   60
WLRQGPEQGL EWIGWIDPEN GDTEYAPKFQ GKATFTTDTS SNTAYLQLSS LTSEDTAVYY  120
CNEGTPTGPY YFDYWGQGTT VTVSSGGGGS GGGGSGGGGS ENVLTQSPAI MSASPGEKVT  180
ITCSASSSVS YMHWFQQKPG TSPKLWIYST SNLASGVPAR FSGSGSGTSY SLTISRMEAE  240
DAATYYCQQR SSYPLTFGAG TKLELKRAAA GSGGSGESKY GPPCPSCPAP EFLGGPSVFL  300
FPPKPKDTLM ISRTPEVTCV VVDVSQEDPE VQFNWYVDGV EVHNAKTKPR EEQFNSTYRV  360
VSVLTVLHQD WLNGKEYKCK VSNKGLPSSI EKTISKAKGQ PREPQVYTLP PSQEEMTKNQ  420
VSLTCLVKGF YPSDIAVEWE SNGQPENNYK TTPPVLDSDG SFFLYSRLTV DKSRWQEGNV  480
FSCSVMHEAL HNHYTQKSLS LSLGKMFWVL VVVGGVLACY SLLVTVAFII FWVRRDQRLP  540
PDAHKPPGGG SFRTPIQEEQ ADAHSTLAKI KKVAKKPTNK APHPKQEPQE INFPDDLPGS  600
NTAAPVQETL HGCQPVTQED GKESRISVQE RQ                               632
```

```
SEQ ID NO: 53            moltype = AA   length = 711
FEATURE                  Location/Qualifiers
REGION                   1..711
                         note = Synthetic peptide
source                   1..711
                         mol_type = protein
                         organism = synthetic construct
SEQUENCE: 53
MGVLLTQRTL LSLVLALLFP SMASMQVQLQ QSGAELVRSG TSVKLSCTAS GFNIKDSYMH    60
WLRQGPEQGL EWIGWIDPEN GDTEYAPKFQ GKATFTTDTS SNTAYLQLSS LTSEDTAVYY   120
CNEGTPTGPY YFDYWGQGTT VTVSSGGGGS GGGGSGGGGS ENVLTQSPAI MSASPGEKVT   180
ITCSASSSVS YMHWFQQKPG TSPKLWIYST SNLASGVPAR FSGSGSGTSY SLTISRMEAE   240
DAATYYCQQR SSYPLTFGAG TKLELKRAAA GSGGSGESKY GPPCPSCPAP EFLGGPSVFL   300
FPPKPKDTLM ISRTPEVTCV VVDVSQEDPE VQFNWYVDGV EVHNAKTKPR EEQFNSTYRV   360
VSVLTVLHQD WLNGKEYKCK VSNKGLPSSI EKTISKAKGQ PREPQVYTLP PSQEEMTKNQ   420
VSLTCLVKGF YPSDIAVEWE SNGQPENNYK TTPPVLDSDG SFFLYSRLTV DKSRWQEGNV   480
FSCSVMHEAL HNHYTQKSLS LSLGKMFWVL VVVGGVLACY SLLVTVAFII FWVKRKKQRS   540
RRNDEELETR AHRVATEERG RKPHQIPAST PQNPATSQHP PPPPGHRSQA PSHRPPPPGH   600
RVQHQPQKRP PAPSGTQVHQ QKGPPLPRPR VQPKPPHGAA ENSLSPSSNK KVAKKPTNKA   660
PHPKQEPQEI NFPDDLPGSN TAAPVQETLH GCQPVTQEDG KESRISVQER Q           711

SEQ ID NO: 54            moltype = AA   length = 653
FEATURE                  Location/Qualifiers
REGION                   1..653
                         note = Synthetic peptide
source                   1..653
                         mol_type = protein
                         organism = synthetic construct
SEQUENCE: 54
MGVLLTQRTL LSLVLALLFP SMASMQVQLQ QSGAELVRSG TSVKLSCTAS GFNIKDSYMH    60
WLRQGPEQGL EWIGWIDPEN GDTEYAPKFQ GKATFTTDTS SNTAYLQLSS LTSEDTAVYY   120
CNEGTPTGPY YFDYWGQGTT VTVSSGGGGS GGGGSGGGGS ENVLTQSPAI MSASPGEKVT   180
ITCSASSSVS YMHWFQQKPG TSPKLWIYST SNLASGVPAR FSGSGSGTSY SLTISRMEAE   240
DAATYYCQQR SSYPLTFGAG TKLELKRAAA GSGGSGESKY GPPCPSCPAP EFLGGPSVFL   300
FPPKPKDTLM ISRTPEVTCV VVDVSQEDPE VQFNWYVDGV EVHNAKTKPR EEQFNSTYRV   360
VSVLTVLHQD WLNGKEYKCK VSNKGLPSSI EKTISKAKGQ PREPQVYTLP PSQEEMTKNQ   420
VSLTCLVKGF YPSDIAVEWE SNGQPENNYK TTPPVLDSDG SFFLYSRLTV DKSRWQEGNV   480
FSCSVMHEAL HNHYTQKSLS LSLGKMFWVL VVVGGVLACY SLLVTVAFII FWVQLGLHIW   540
QLRSQCMWPR ETQLLLEVPP STEDARSCQF PEEEERGERSA EEKGRLGDLW VKKVAKKPTN   600
KAPHPKQEPQ EINFPDDLPG SNTAAPVQET LHGCQPVTQE DGKESRISVQ ERQ          653

SEQ ID NO: 55            moltype = AA   length = 642
FEATURE                  Location/Qualifiers
REGION                   1..642
                         note = Synthetic peptide
source                   1..642
                         mol_type = protein
                         organism = synthetic construct
SEQUENCE: 55
MGVLLTQRTL LSLVLALLFP SMASMQVQLQ QSGAELVRSG TSVKLSCTAS GFNIKDSYMH    60
WLRQGPEQGL EWIGWIDPEN GDTEYAPKFQ GKATFTTDTS SNTAYLQLSS LTSEDTAVYY   120
CNEGTPTGPY YFDYWGQGTT VTVSSGGGGS GGGGSGGGGS ENVLTQSPAI MSASPGEKVT   180
ITCSASSSVS YMHWFQQKPG TSPKLWIYST SNLASGVPAR FSGSGSGTSY SLTISRMEAE   240
DAATYYCQQR SSYPLTFGAG TKLELKRAAA GSGGSGESKY GPPCPSCPAP EFLGGPSVFL   300
FPPKPKDTLM ISRTPEVTCV VVDVSQEDPE VQFNWYVDGV EVHNAKTKPR EEQFNSTYRV   360
VSVLTVLHQD WLNGKEYKCK VSNKGLPSSI EKTISKAKGQ PREPQVYTLP PSQEEMTKNQ   420
VSLTCLVKGF YPSDIAVEWE SNGQPENNYK TTPPVLDSDG SFFLYSRLTV DKSRWQEGNV   480
FSCSVMHEAL HNHYTQKSLS LSLGKMFWVL VVVGGVLACY SLLVTVAFII FWVKLLMIIH   540
DRREFAKFEK EKMNAKWDTG ENPIYKSAVT TVVNPKYEGK KVAKKPTNK APHPKQEPQE    600
INFPDDLPGS NTAAPVQETL HGCQPVTQED GKESRISVQE RQ                     642

SEQ ID NO: 56            moltype = AA   length = 670
FEATURE                  Location/Qualifiers
REGION                   1..670
                         note = Synthetic peptide
source                   1..670
                         mol_type = protein
                         organism = synthetic construct
SEQUENCE: 56
MGVLLTQRTL LSLVLALLFP SMASMQVQLQ QSGAELVRSG TSVKLSCTAS GFNIKDSYMH    60
WLRQGPEQGL EWIGWIDPEN GDTEYAPKFQ GKATFTTDTS SNTAYLQLSS LTSEDTAVYY   120
CNEGTPTGPY YFDYWGQGTT VTVSSGGGGS GGGGSGGGGS ENVLTQSPAI MSASPGEKVT   180
ITCSASSSVS YMHWFQQKPG TSPKLWIYST SNLASGVPAR FSGSGSGTSY SLTISRMEAE   240
DAATYYCQQR SSYPLTFGAG TKLELKRAAA GSGGSGESKY GPPCPSCPAP EFLGGPSVFL   300
FPPKPKDTLM ISRTPEVTCV VVDVSQEDPE VQFNWYVDGV EVHNAKTKPR EEQFNSTYRV   360
VSVLTVLHQD WLNGKEYKCK VSNKGLPSSI EKTISKAKGQ PREPQVYTLP PSQEEMTKNQ   420
VSLTCLVKGF YPSDIAVEWE SNGQPENNYK TTPPVLDSDG SFFLYSRLTV DKSRWQEGNV   480
FSCSVMHEAL HNHYTQKSLS LSLGKMFWVL VVVGGVLACY SLLVTVAFII FWVRRRGKTN   540
HYQTTVEKKS LTIYAQVQKP GPLQKKLDSF PAQDPCTTIY VAATEPVPES VQETNSITVY   600
```

```
ASVTLPESKK VAKKPTNKAP HPKQEPQEIN FPDDLPGSNT AAPVQETLHG CQPVTQEDGK   660
ESRISVQERQ                                                         670

SEQ ID NO: 57           moltype = AA   length = 658
FEATURE                 Location/Qualifiers
REGION                  1..658
                        note = Synthetic peptide
source                  1..658
                        mol_type = protein
                        organism = synthetic construct
SEQUENCE: 57
MGVLLTQRTL LSLVLALLFP SMASMQVQLQ QSGAELVRSG TSVKLSCTAS GFNIKDSYMH   60
WLRQGPEQGL EWIGWIDPEN GDTEYAPKFQ GKATFTTDTS SNTAYLQLSS LTSEDTAVYY   120
CNEGTPTGPY YFDYWGQGTT VTVSSGGGGS GGGGSGGGGS ENVLTQSPAI MSASPGEKVT   180
ITCSASSSVS YMHWFQQKPG TSPKLWIYST SNLASGVPAR FSGSGSGTSY SLTISRMEAE   240
DAATYYCQQR SSYPLTFGAG TKLELKRAAA GSGGGSESKY GPPCPSCPAP EFLGGPSVFL   300
FPPKPKDTLM ISRTPEVTCV VVDVSQEDPE VQFNWYVDGV EVHNAKTKPR EEQFNSTYRV   360
VSVLTVLHQD WLNGKEYKCK VSNKGLPSSI EKTISKAKGQ PREPQVYTLP PSQEEMTKNQ   420
VSLTCLVKGF YPSDIAVEWE SNGQPENNYK TTPPVLDSDG SFFLYSRLTV DKSRWQEGNV   480
FSCSVMHEAL HNHYTQKSLS LSLGKMFWVL VVVGGVLACY SLLVTVAFII FWVAKKPTNK   540
APHPKQEPQE INFPDDLPGS NTAAPVQETL HGCQPVTQED GKESRISVQE RQKKVAKKPT   600
NKAPHPKQEP QEINFPDDLP GSNTAAPVQE TLHGCQPVTQ EDGKESRISV QERQKKVA    658

SEQ ID NO: 58           moltype = AA   length = 595
FEATURE                 Location/Qualifiers
REGION                  1..595
                        note = Synthetic peptide
source                  1..595
                        mol_type = protein
                        organism = synthetic construct
SEQUENCE: 58
MGVLLTQRTL LSLVLALLFP SMASMQVQLQ QSGAELVRSG TSVKLSCTAS GFNIKDSYMH   60
WLRQGPEQGL EWIGWIDPEN GDTEYAPKFQ GKATFTTDTS SNTAYLQLSS LTSEDTAVYY   120
CNEGTPTGPY YFDYWGQGTT VTVSSGGGGS GGGGSGGGGS ENVLTQSPAI MSASPGEKVT   180
ITCSASSSVS YMHWFQQKPG TSPKLWIYST SNLASGVPAR FSGSGSGTSY SLTISRMEAE   240
DAATYYCQQR SSYPLTFGAG TKLELKRAAA GSGGGSESKY GPPCPSCPAP EFLGGPSVFL   300
FPPKPKDTLM ISRTPEVTCV VVDVSQEDPE VQFNWYVDGV EVHNAKTKPR EEQFNSTYRV   360
VSVLTVLHQD WLNGKEYKCK VSNKGLPSSI EKTISKAKGQ PREPQVYTLP PSQEEMTKNQ   420
VSLTCLVKGF YPSDIAVEWE SNGQPENNYK TTPPVLDSDG SFFLYSRLTV DKSRWQEGNV   480
FSCSVMHEAL HNHYTQKSLS LSLGKMFWVL VVVGGVLACY SLLVTVAFII FWVKKVAKKP   540
TNKAAHPKQE PQEINFPDDL PGSNTAAPVQ ETLHGCQPVT QEDGKESRIS VQERQ       595

SEQ ID NO: 59           moltype = AA   length = 554
FEATURE                 Location/Qualifiers
REGION                  1..554
                        note = Synthetic peptide
source                  1..554
                        mol_type = protein
                        organism = synthetic construct
SEQUENCE: 59
MGVLLTQRTL LSLVLALLFP SMASMQVQLQ QSGAELVRSG TSVKLSCTAS GFNIKDSYMH   60
WLRQGPEQGL EWIGWIDPEN GDTEYAPKFQ GKATFTTDTS SNTAYLQLSS LTSEDTAVYY   120
CNEGTPTGPY YFDYWGQGTT VTVSSGGGGS GGGGSGGGGS ENVLTQSPAI MSASPGEKVT   180
ITCSASSSVS YMHWFQQKPG TSPKLWIYST SNLASGVPAR FSGSGSGTSY SLTISRMEAE   240
DAATYYCQQR SSYPLTFGAG TKLELKRAAA GSGGGSRPGW FLDSPDRPWN PPTFSPALLV   300
VTEGDNATFT CSFSNTSESF VLNWYRMSPS NQTDKLAAFP EDRSQPGQDC RFRVTQLPNG   360
RDFHMSVVRA RRNDSGTYLC GAISLAPKAQ IKESLRAELR VTERRAEVPT AHCPSPLFPG   420
PSKPFWVLVV VGGVLACYSL LVTVAFIIFW VRSKRSLLH SDYMNMTPRR PGPTRKHYQP   480
YAPPRDFAAY RSKKVAKKPT NKAPHPKQEP QEINFPDDLP GSNTAAPVQE TLHGCQPVTQ   540
EDGKESRISV QERQ                                                    554

SEQ ID NO: 60           moltype = AA   length = 513
FEATURE                 Location/Qualifiers
REGION                  1..513
                        note = Synthetic peptide
source                  1..513
                        mol_type = protein
                        organism = synthetic construct
SEQUENCE: 60
MGVLLTQRTL LSLVLALLFP SMASMQVQLQ QSGAELVRSG TSVKLSCTAS GFNIKDSYMH   60
WLRQGPEQGL EWIGWIDPEN GDTEYAPKFQ GKATFTTDTS SNTAYLQLSS LTSEDTAVYY   120
CNEGTPTGPY YFDYWGQGTT VTVSSGGGGS GGGGSGGGGS ENVLTQSPAI MSASPGEKVT   180
ITCSASSSVS YMHWFQQKPG TSPKLWIYST SNLASGVPAR FSGSGSGTSY SLTISRMEAE   240
DAATYYCQQR SSYPLTFGAG TKLELKRAAA GSGGGSRPGW FLDSPDRPWN PPTFSPALLV   300
VTEGDNATFT CSFSNTSESF VLNWYRMSPS NQTDKLAAFP EDRSQPGQDC RFRVTQLPNG   360
RDFHMSVVRA RRNDSGTYLC GAISLAPKAQ IKESLRAELR VTERRAEVPT AHCPSPLFPG   420
PSKPFWVLVV VGGVLACYSL LVTVAFIIFW VKKVAKKPTN KAHPKQEPQ EINFPDDLPG   480
SNTAAPVQET LHGCQPVTQE DGKESRISVQ ERQ                                513
```

```
SEQ ID NO: 61              moltype = AA   length = 526
FEATURE                    Location/Qualifiers
REGION                     1..526
                           note = Synthetic peptide
source                     1..526
                           mol_type = protein
                           organism = synthetic construct
SEQUENCE: 61
MGVLLTQRTL LSLVLALLFP SMASMQVQLQ QSGAELVRSG TSVKLSCTAS GFNIKDSYMH   60
WLRQGPEQGL EWIGWIDPEN GDTEYAPKFQ GKATFTTDTS SNTAYLQLSS LTSEDTAVYY  120
CNEGTPTGPY YFDYWGQGTT VTVSSGGGGS GGGGSGGGGS ENVLTQSPAI MSASPGEKVT  180
ITCSASSSVS YMHWFQQKPG TSPKLWIYST SNLASGVPAR FSGSGSGTSY SLTISRMEAE  240
DAATYYCQQR SSYPLTFGAG TKLELKRAAA GSGGSGMMTG TIETTGNISA EKGGSIILQC  300
HLSSTTAQVT QVNWEQQDQL LAICNADLGW HISPSFKDRV APGPGLGLTL QSLTVNDTGE  360
YFCIYHTYPD GTYTGRIFLE VLESSVAEHG ARFQIPFWVL VVVGGVLACY SLLVTVAFII  420
FWVRSKRSRL LHSDYMNMTP RRPGPTRKHY QPYAPPRDFA AYRSKKVAKK PTNKAPHPKQ  480
EPQEINFPDD LPGSNTAAPV QETLHGCQPV TQEDGKESRI SVQERQ              526

SEQ ID NO: 62              moltype = AA   length = 485
FEATURE                    Location/Qualifiers
REGION                     1..485
                           note = Synthetic peptide
source                     1..485
                           mol_type = protein
                           organism = synthetic construct
SEQUENCE: 62
MGVLLTQRTL LSLVLALLFP SMASMQVQLQ QSGAELVRSG TSVKLSCTAS GFNIKDSYMH   60
WLRQGPEQGL EWIGWIDPEN GDTEYAPKFQ GKATFTTDTS SNTAYLQLSS LTSEDTAVYY  120
CNEGTPTGPY YFDYWGQGTT VTVSSGGGGS GGGGSGGGGS ENVLTQSPAI MSASPGEKVT  180
ITCSASSSVS YMHWFQQKPG TSPKLWIYST SNLASGVPAR FSGSGSGTSY SLTISRMEAE  240
DAATYYCQQR SSYPLTFGAG TKLELKRAAA GSGGSGMMTG TIETTGNISA EKGGSIILQC  300
HLSSTTAQVT QVNWEQQDQL LAICNADLGW HISPSFKDRV APGPGLGLTL QSLTVNDTGE  360
YFCIYHTYPD GTYTGRIFLE VLESSVAEHG ARFQIPFWVL VVVGGVLACY SLLVTVAFII  420
FWVKKVAKKP TNKAPHPKQE PQEINFPDDL PGSNTAAPVQ ETLHGCQPVT QEDGKESRIS  480
VQERQ                                                            485

SEQ ID NO: 63              moltype = AA   length = 540
FEATURE                    Location/Qualifiers
REGION                     1..540
                           note = Synthetic peptide
source                     1..540
                           mol_type = protein
                           organism = synthetic construct
SEQUENCE: 63
MGVLLTQRTL LSLVLALLFP SMASMQVQLQ QSGAELVKPG ASVKISCKAS GYSFTGYFMN   60
WVKQSHGKSL EWIGRIHPYD GDTFYNQNFK DKATLTVDKS SNTAHMELLS LTSEDFAVYY  120
CTRYDGSRAM DYWGQGTTVT VSSGGGGSGG GGSGGGGSDI ELTQSPASLA VSLGQRAIIS  180
CKASQSVSFA GTSLMHWYHQ KPGQQPKLLI YRASNLEAGV PTRFSGSGSK TDFTLNIHPV  240
EEEDAATYYC QQSREYPYTF GGGTKLEIKA AAGSGGSGIL VKQSPMLVAY DNAVNLSCKY  300
SYNLFSREFR ASLHKGLDSA VEVCVVYGNY SQQLQVYSKT GFNCDGKLGN ESVTFYLQNL  360
YVNQTDIYFC KIEVMYPPPY LDNEKSNGTI IHVKGKHLCP SPLFPGPSKP FWVLVVVGGV  420
LACYSLLVTV AFIIFWVRSK RSRLLHSDYM NMTPRRPGPT RKHYQPYAPP RDFAAYRSKK  480
VAKKPTNKAP HPKQEPQEIN FPDDLPGSNT AAPVQETLHG CQPVTQEDGK ESRISVQERQ  540

SEQ ID NO: 64              moltype = AA   length = 499
FEATURE                    Location/Qualifiers
REGION                     1..499
                           note = Synthetic peptide
source                     1..499
                           mol_type = protein
                           organism = synthetic construct
SEQUENCE: 64
MGVLLTQRTL LSLVLALLFP SMASMQVQLQ QSGAELVKPG ASVKISCKAS GYSFTGYFMN   60
WVKQSHGKSL EWIGRIHPYD GDTFYNQNFK DKATLTVDKS SNTAHMELLS LTSEDFAVYY  120
CTRYDGSRAM DYWGQGTTVT VSSGGGGSGG GGSGGGGSDI ELTQSPASLA VSLGQRAIIS  180
CKASQSVSFA GTSLMHWYHQ KPGQQPKLLI YRASNLEAGV PTRFSGSGSK TDFTLNIHPV  240
EEEDAATYYC QQSREYPYTF GGGTKLEIKA AAGSGGSGIL VKQSPMLVAY DNAVNLSCKY  300
SYNLFSREFR ASLHKGLDSA VEVCVVYGNY SQQLQVYSKT GFNCDGKLGN ESVTFYLQNL  360
YVNQTDIYFC KIEVMYPPPY LDNEKSNGTI IHVKGKHLCP SPLFPGPSKP FWVLVVVGGV  420
LACYSLLVTV AFIIFWVKKV AKKPTNKAPH PKQEPQEINF PDDLPGSNTA APVQETLHGC  480
QPVTQEDGKE SRISVQERQ                                             499

SEQ ID NO: 65              moltype = AA   length = 545
FEATURE                    Location/Qualifiers
REGION                     1..545
                           note = Synthetic peptide
source                     1..545
                           mol_type = protein
                           organism = synthetic construct
```

```
SEQUENCE: 65
MGVLLTQRTL LSLVLALLFP SMASMQVQLQ QSGAELVKPG ASVKISCKAS GYSFTGYFMN    60
WVKQSHGKSL EWIGRIHPYD GDTFYNQNFK DKATLTVDKS SNTAHMELLS LTSEDFAVYY   120
CTRYDGSRAM DYWGQGTTVT VSSGGGGSGG GGSGGGGSDI ELTQSPASLA VSLGQRAIIS   180
CKASQSVSFA GTSLMHWYHQ KPGQQPKLLI YRASNLEAGV PTRFSGSGSK TDFTLNIHPV   240
EEEDAATYYC QQSREYPYTF GGGTKLEIKA AAGSGGSGIL VKQSPMLVAY DNAVNLSCKY   300
SYNLFSREFR ASLHKGLDSA VEVCVVYGNY SQQLQVYSKT GFNCDGKLGN ESVTFYLQNL   360
YVNQTDIYFC KIEVMYPPPY LDNEKSNGTI IHVKGKHLCP SPLFPGPSKP FWVLVVVGGV   420
LACYSLLVTV AFIIFWVRFS VVKRGRKKLL YIFKQPFMRP VQTTQEEDGC SCRFPEEEEG   480
GCEKKVAKKP TNKAPHPKQE PQEINFPDDL PGSNTAAPVQ ETLHGCQPVT QEDGKESRIS   540
VQERQ                                                              545

SEQ ID NO: 66           moltype = AA  length = 536
FEATURE                 Location/Qualifiers
REGION                  1..536
                        note = Synthetic peptide
source                  1..536
                        mol_type = protein
                        organism = synthetic construct
SEQUENCE: 66
MGVLLTQRTL LSLVLALLFP SMASMQVQLQ QSGAELVKPG ASVKISCKAS GYSFTGYFMN    60
WVKQSHGKSL EWIGRIHPYD GDTFYNQNFK DKATLTVDKS SNTAHMELLS LTSEDFAVYY   120
CTRYDGSRAM DYWGQGTTVT VSSGGGGSGG GGSGGGGSDI ELTQSPASLA VSLGQRAIIS   180
CKASQSVSFA GTSLMHWYHQ KPGQQPKLLI YRASNLEAGV PTRFSGSGSK TDFTLNIHPV   240
EEEDAATYYC QQSREYPYTF GGGTKLEIKA AAGSGGSGIL VKQSPMLVAY DNAVNLSCKY   300
SYNLFSREFR ASLHKGLDSA VEVCVVYGNY SQQLQVYSKT GFNCDGKLGN ESVTFYLQNL   360
YVNQTDIYFC KIEVMYPPPY LDNEKSNGTI IHVKGKHLCP SPLFPGPSKP FWVLVVVGGV   420
LACYSLLVTV AFIIFWVRRD QRLPPDAHKP PGGGSFRTPI QEEQADAHST LAKIKKVAKK   480
PTNKAPHPKQ EPQEINFPDD LPGSNTAAPV QETLHGCQPV TQEDGKESRI SVQERQ       536

SEQ ID NO: 67           moltype = AA  length = 615
FEATURE                 Location/Qualifiers
REGION                  1..615
                        note = Synthetic peptide
source                  1..615
                        mol_type = protein
                        organism = synthetic construct
SEQUENCE: 67
MGVLLTQRTL LSLVLALLFP SMASMQVQLQ QSGAELVKPG ASVKISCKAS GYSFTGYFMN    60
WVKQSHGKSL EWIGRIHPYD GDTFYNQNFK DKATLTVDKS SNTAHMELLS LTSEDFAVYY   120
CTRYDGSRAM DYWGQGTTVT VSSGGGGSGG GGSGGGGSDI ELTQSPASLA VSLGQRAIIS   180
CKASQSVSFA GTSLMHWYHQ KPGQQPKLLI YRASNLEAGV PTRFSGSGSK TDFTLNIHPV   240
EEEDAATYYC QQSREYPYTF GGGTKLEIKA AAGSGGSGIL VKQSPMLVAY DNAVNLSCKY   300
SYNLFSREFR ASLHKGLDSA VEVCVVYGNY SQQLQVYSKT GFNCDGKLGN ESVTFYLQNL   360
YVNQTDIYFC KIEVMYPPPY LDNEKSNGTI IHVKGKHLCP SPLFPGPSKP FWVLVVVGGV   420
LACYSLLVTV AFIIFWVRKR KQRSRRNDEE LETRAHRVAT EERGRKPHQI PASTPQNPAT   480
SQHPPPPPGH RSQAPSHRPP PPGHRVQHQP QKRPPAPSGT QVHQQKGPPL PRPRVQPKPP   540
HGAAENSLSP SSNKKVAKKP TNKAPHPKQE PQEINFPDDL PGSNTAAPVQ ETLHGCQPVT   600
QEDGKESRIS VQERQ                                                   615

SEQ ID NO: 68           moltype = AA  length = 557
FEATURE                 Location/Qualifiers
REGION                  1..557
                        note = Synthetic peptide
source                  1..557
                        mol_type = protein
                        organism = synthetic construct
SEQUENCE: 68
MGVLLTQRTL LSLVLALLFP SMASMQVQLQ QSGAELVKPG ASVKISCKAS GYSFTGYFMN    60
WVKQSHGKSL EWIGRIHPYD GDTFYNQNFK DKATLTVDKS SNTAHMELLS LTSEDFAVYY   120
CTRYDGSRAM DYWGQGTTVT VSSGGGGSGG GGSGGGGSDI ELTQSPASLA VSLGQRAIIS   180
CKASQSVSFA GTSLMHWYHQ KPGQQPKLLI YRASNLEAGV PTRFSGSGSK TDFTLNIHPV   240
EEEDAATYYC QQSREYPYTF GGGTKLEIKA AAGSGGSGIL VKQSPMLVAY DNAVNLSCKY   300
SYNLFSREFR ASLHKGLDSA VEVCVVYGNY SQQLQVYSKT GFNCDGKLGN ESVTFYLQNL   360
YVNQTDIYFC KIEVMYPPPY LDNEKSNGTI IHVKGKHLCP SPLFPGPSKP FWVLVVVGGV   420
LACYSLLVTV AFIIFWVQLG LHIWQLRSQC MWPRETQLLL EVPPSTEDAR SCQFPEEERG   480
ERSAEEKGRL GDLWVKKVAK KPTNKAPHPK QEPQEINFPD DLPGSNTAAP VQETLHGCQP   540
VTQEDGKESR ISVQERQ                                                 557

SEQ ID NO: 69           moltype = AA  length = 546
FEATURE                 Location/Qualifiers
REGION                  1..546
                        note = Synthetic peptide
source                  1..546
                        mol_type = protein
                        organism = synthetic construct
SEQUENCE: 69
MGVLLTQRTL LSLVLALLFP SMASMQVQLQ QSGAELVKPG ASVKISCKAS GYSFTGYFMN    60
WVKQSHGKSL EWIGRIHPYD GDTFYNQNFK DKATLTVDKS SNTAHMELLS LTSEDFAVYY   120
```

```
CTRYDGSRAM DYWGQGTTVT VSSGGGGSGG GGSGGGGSDI ELTQSPASLA VSLGQRAIIS    180
CKASQSVSFA GTSLMHWYHQ KPGQQPKLLI YRASNLEAGV PTRFSGSGSK TDFTLNIHPV    240
EEEDAATYYC QQSREYPYTF GGGTKLEIKA AAGSGGSGIL VKQSPMLVAY DNAVNLSCKY    300
SYNLFSREFR ASLHKGLDSA VEVCVVYGNY SQQLQVYSKT GFNCDGKLGN ESVTFYLQNL    360
YVNQTDIYFC KIEVMYPPPY LDNEKSNGTI IHVGKHLCP SPLFPGPSKP FWVLVVVGGV    420
LACYSLLVTV AFIIFWVKLL MIIHDRREFA KFEKEKMNAK WDTGENPIYK SAVTTVVNPK    480
YEGKKKVAKK PTNKAPHPKQ EPQEINFPDD LPGSNTAAPV QETLHGCQPV TQEDGKESRI    540
SVQERQ                                                              546

SEQ ID NO: 70          moltype = AA   length = 574
FEATURE                Location/Qualifiers
REGION                 1..574
                       note = Synthetic peptide
source                 1..574
                       mol_type = protein
                       organism = synthetic construct
SEQUENCE: 70
MGVLLTQRTL LSLVLALLFP SMASMQVQLQ QSGAELVKPG ASVKISCKAS GYSFTGYFMN    60
WVKQSHGKSL EWIGRIHPYD GDTFYNQNFK DKATLTVDKS SNTAHMELLS LTSEDFAVYY    120
CTRYDGSRAM DYWGQGTTVT VSSGGGGSGG GGSGGGGSDI ELTQSPASLA VSLGQRAIIS    180
CKASQSVSFA GTSLMHWYHQ KPGQQPKLLI YRASNLEAGV PTRFSGSGSK TDFTLNIHPV    240
EEEDAATYYC QQSREYPYTF GGGTKLEIKA AAGSGGSGIL VKQSPMLVAY DNAVNLSCKY    300
SYNLFSREFR ASLHKGLDSA VEVCVVYGNY SQQLQVYSKT GFNCDGKLGN ESVTFYLQNL    360
YVNQTDIYFC KIEVMYPPPY LDNEKSNGTI IHVGKHLCP SPLFPGPSKP FWVLVVVGGV    420
LACYSLLVTV AFIIFWVRRR GKTNHYQTTV EKKSLTIYAQ VQKPGPLQKK LDSFPAQDPC    480
TTIYVAATEP VPESVQETNS ITVYASVTLP ESKKVAKKPT NKAPHPKQEP QEINFPDDLP    540
GSNTAAPVQE TLHGCQPVTQ EDGKESRISV QERQ                               574

SEQ ID NO: 71          moltype = AA   length = 464
FEATURE                Location/Qualifiers
REGION                 1..464
                       note = Synthetic peptide
source                 1..464
                       mol_type = protein
                       organism = synthetic construct
SEQUENCE: 71
MGVLLTQRTL LSLVLALLFP SMASMQVQLQ QSGAELVKPG ASVKISCKAS GYSFTGYFMN    60
WVKQSHGKSL EWIGRIHPYD GDTFYNQNFK DKATLTVDKS SNTAHMELLS LTSEDFAVYY    120
CTRYDGSRAM DYWGQGTTVT VSSGGGGSGG GGSGGGGSDI ELTQSPASLA VSLGQRAIIS    180
CKASQSVSFA GTSLMHWYHQ KPGQQPKLLI YRASNLEAGV PTRFSGSGSK TDFTLNIHPV    240
EEEDAATYYC QQSREYPYTF GGGTKLEIKA AAGSGGSGFV PVFLPAKPTT TPAPRPPTPA    300
PTIASQPLSL RPEACRPAAG GAVHTRGLDF ACDIYIWAPL AGTCGVLLLS LVITLYCNHR    360
NRSKRSRLLH SDYMNMTPRR PGPTRKHYQP YAPPRDFAAY RSKKVAKKPT NKAPHPKQEP    420
QEINFPDDLP GSNTAAPVQE TLHGCQPVTQ EDGKESRISV QERQ                    464

SEQ ID NO: 72          moltype = AA   length = 423
FEATURE                Location/Qualifiers
REGION                 1..423
                       note = Synthetic peptide
source                 1..423
                       mol_type = protein
                       organism = synthetic construct
SEQUENCE: 72
MGVLLTQRTL LSLVLALLFP SMASMQVQLQ QSGAELVKPG ASVKISCKAS GYSFTGYFMN    60
WVKQSHGKSL EWIGRIHPYD GDTFYNQNFK DKATLTVDKS SNTAHMELLS LTSEDFAVYY    120
CTRYDGSRAM DYWGQGTTVT VSSGGGGSGG GGSGGGGSDI ELTQSPASLA VSLGQRAIIS    180
CKASQSVSFA GTSLMHWYHQ KPGQQPKLLI YRASNLEAGV PTRFSGSGSK TDFTLNIHPV    240
EEEDAATYYC QQSREYPYTF GGGTKLEIKA AAGSGGSGFV PVFLPAKPTT TPAPRPPTPA    300
PTIASQPLSL RPEACRPAAG GAVHTRGLDF ACDIYIWAPL AGTCGVLLLS LVITLYCNHR    360
NKKVAKKPTN KAPHPKQEPQ EINFPDDLPG SNTAAPVQET LHGCQPVTQE DGKESRISVQ    420
ERQ                                                                 423

SEQ ID NO: 73          moltype = AA   length = 469
FEATURE                Location/Qualifiers
REGION                 1..469
                       note = Synthetic peptide
source                 1..469
                       mol_type = protein
                       organism = synthetic construct
SEQUENCE: 73
MGVLLTQRTL LSLVLALLFP SMASMQVQLQ QSGAELVKPG ASVKISCKAS GYSFTGYFMN    60
WVKQSHGKSL EWIGRIHPYD GDTFYNQNFK DKATLTVDKS SNTAHMELLS LTSEDFAVYY    120
CTRYDGSRAM DYWGQGTTVT VSSGGGGSGG GGSGGGGSDI ELTQSPASLA VSLGQRAIIS    180
CKASQSVSFA GTSLMHWYHQ KPGQQPKLLI YRASNLEAGV PTRFSGSGSK TDFTLNIHPV    240
EEEDAATYYC QQSREYPYTF GGGTKLEIKA AAGSGGSGFV PVFLPAKPTT TPAPRPPTPA    300
PTIASQPLSL RPEACRPAAG GAVHTRGLDF ACDIYIWAPL AGTCGVLLLS LVITLYCNHR    360
NRFSVVKRGR KKLLYIFKQP FMRPVQTTQE EDGCSCRFPE EEEGGCEKKV AKKPTNKAPH    420
PKQEPQEINF PDDLPGSNTA APVQETLHGC QPVTQEDGKE SRISVQERQ                469
```

```
SEQ ID NO: 74            moltype = AA   length = 460
FEATURE                  Location/Qualifiers
REGION                   1..460
                         note = Synthetic peptide
source                   1..460
                         mol_type = protein
                         organism = synthetic construct
SEQUENCE: 74
MGVLLTQRTL LSLVLALLFP SMASMQVQLQ QSGAELVKPG ASVKISCKAS GYSFTGYFMN   60
WVKQSHGKSL EWIGRIHPYD GDTFYNQNFK DKATLTVDKS SNTAHMELLS LTSEDFAVYY  120
CTRYDGSRAM DYWGQGTTVT VSSGGGGSGG GGSGGGGSDI ELTQSPASLA VSLGQRAIIS  180
CKASQSVSFA GTSLMHWYHQ KPGQQPKLLI YRASNLEAGV PTRFSGSGSK TDFTLNIHPV  240
EEEDAATYYC QQSREYPYTF GGGTKLEIKA AAGSGGSGFV PVFLPAKPTT TPAPRPPTPA  300
PTIASQPLSL RPEACRPAAG GAVHTRGLDF ACDIYIWAPL AGTCGVLLLS LVITLYCNHR  360
NRRDQRLPPD AHKPPGGGSF RTPIQEEQAD AHSTLAKIKK VAKKPTNKAP HPKQEPQEIN  420
FPDDLPGSNT AAPVQETLHG CQPVTQEDGK ESRISVQERQ                       460

SEQ ID NO: 75            moltype = AA   length = 539
FEATURE                  Location/Qualifiers
REGION                   1..539
                         note = Synthetic peptide
source                   1..539
                         mol_type = protein
                         organism = synthetic construct
SEQUENCE: 75
MGVLLTQRTL LSLVLALLFP SMASMQVQLQ QSGAELVKPG ASVKISCKAS GYSFTGYFMN   60
WVKQSHGKSL EWIGRIHPYD GDTFYNQNFK DKATLTVDKS SNTAHMELLS LTSEDFAVYY  120
CTRYDGSRAM DYWGQGTTVT VSSGGGGSGG GGSGGGGSDI ELTQSPASLA VSLGQRAIIS  180
CKASQSVSFA GTSLMHWYHQ KPGQQPKLLI YRASNLEAGV PTRFSGSGSK TDFTLNIHPV  240
EEEDAATYYC QQSREYPYTF GGGTKLEIKA AAGSGGSGFV PVFLPAKPTT TPAPRPPTPA  300
PTIASQPLSL RPEACRPAAG GAVHTRGLDF ACDIYIWAPL AGTCGVLLLS LVITLYCNHR  360
NKRKKQRSRR NDEELETRAH RVATEERGRK PHQIPASTPQ NPATSQHPPP PGHRSQAPS   420
HRPPPPGHRV QHQPQKRPPA PSGTQVHQQK GPPLPRPRVQ PKPPHGAAEN SLSPSSNKKV  480
AKKPTNKAPH PKQEPQEINF PDDLPGSNTA APVQETLHGC QPVTQEDGKE SRISVQERQ   539

SEQ ID NO: 76            moltype = AA   length = 481
FEATURE                  Location/Qualifiers
REGION                   1..481
                         note = Synthetic peptide
source                   1..481
                         mol_type = protein
                         organism = synthetic construct
SEQUENCE: 76
MGVLLTQRTL LSLVLALLFP SMASMQVQLQ QSGAELVKPG ASVKISCKAS GYSFTGYFMN   60
WVKQSHGKSL EWIGRIHPYD GDTFYNQNFK DKATLTVDKS SNTAHMELLS LTSEDFAVYY  120
CTRYDGSRAM DYWGQGTTVT VSSGGGGSGG GGSGGGGSDI ELTQSPASLA VSLGQRAIIS  180
CKASQSVSFA GTSLMHWYHQ KPGQQPKLLI YRASNLEAGV PTRFSGSGSK TDFTLNIHPV  240
EEEDAATYYC QQSREYPYTF GGGTKLEIKA AAGSGGSGFV PVFLPAKPTT TPAPRPPTPA  300
PTIASQPLSL RPEACRPAAG GAVHTRGLDF ACDIYIWAPL AGTCGVLLLS LVITLYCNHR  360
NQLGLHIWQL RSQCMWPRET QLLLEVPPST EDARSCQFPE EERGERSAEE KGRLGDLWVK  420
KVAKKPTNKA PHPKQEPQEI NFPDDLPGSN TAAPVQETLH GCQPVTQEDG KESRISVQER  480
Q                                                                 481

SEQ ID NO: 77            moltype = AA   length = 470
FEATURE                  Location/Qualifiers
REGION                   1..470
                         note = Synthetic peptide
source                   1..470
                         mol_type = protein
                         organism = synthetic construct
SEQUENCE: 77
MGVLLTQRTL LSLVLALLFP SMASMQVQLQ QSGAELVKPG ASVKISCKAS GYSFTGYFMN   60
WVKQSHGKSL EWIGRIHPYD GDTFYNQNFK DKATLTVDKS SNTAHMELLS LTSEDFAVYY  120
CTRYDGSRAM DYWGQGTTVT VSSGGGGSGG GGSGGGGSDI ELTQSPASLA VSLGQRAIIS  180
CKASQSVSFA GTSLMHWYHQ KPGQQPKLLI YRASNLEAGV PTRFSGSGSK TDFTLNIHPV  240
EEEDAATYYC QQSREYPYTF GGGTKLEIKA AAGSGGSGFV PVFLPAKPTT TPAPRPPTPA  300
PTIASQPLSL RPEACRPAAG GAVHTRGLDF ACDIYIWAPL AGTCGVLLLS LVITLYCNHR  360
NKLLMIIHDR REFAKFEKEK MNAKWDTGEN PIYKSAVTTV VNPKYEGKKK VAKKPTNKAP  420
HPKQEPQEIN FPDDLPGSNT AAPVQETLHG CQPVTQEDGK ESRISVQERQ             470

SEQ ID NO: 78            moltype = AA   length = 498
FEATURE                  Location/Qualifiers
REGION                   1..498
                         note = Synthetic peptide
source                   1..498
                         mol_type = protein
                         organism = synthetic construct
```

```
SEQUENCE: 78
MGVLLTQRTL LSLVLALLFP SMASMQVQLQ QSGAELVKPG ASVKISCKAS GYSFTGYFMN    60
WVKQSHGKSL EWIGRIHPYD GDTFYNQNFK DKATLTVDKS SNTAHMELLS LTSEDFAVYY   120
CTRYDGSRAM DYWGQGTTVT VSSGGGGSGG GGSGGGGSDI ELTQSPASLA VSLGQRAIIS   180
CKASQSVSFA GTSLMHWYHQ KPGQQPKLLI YRASNLEAGV PTRFSGSGSK TDFTLNIHPV   240
EEEDAATYYC QQSREYPYTF GGGTKLEIKA AAGSGGSGFV PVFLPAKPTT TPAPRPPTPA   300
PTIASQPLSL RPEACRPAAG GAVHTRGLDF ACDIYIWAPL AGTCGVLLLS LVITLYCNHR   360
NRRRGKTNHY QTTVEKKSLT IYAQVQKPGP LQKKLDSFPA QDPCTTIYVA ATEPVPESVQ   420
ETNSITVYAS VTLPESKKVA KKPTNKAPHP KQEPQEINFP DDLPGSNTAA PVQETLHGCQ   480
PVTQEDGKES RISVQERQ                                                 498

SEQ ID NO: 79          moltype = AA  length = 638
FEATURE                Location/Qualifiers
REGION                 1..638
                       note = Synthetic peptide
source                 1..638
                       mol_type = protein
                       organism = synthetic construct
SEQUENCE: 79
MGVLLTQRTL LSLVLALLFP SMASMQVQLQ QSGAELVKPG ASVKISCKAS GYSFTGYFMN    60
WVKQSHGKSL EWIGRIHPYD GDTFYNQNFK DKATLTVDKS SNTAHMELLS LTSEDFAVYY   120
CTRYDGSRAM DYWGQGTTVT VSSGGGGSGG GGSGGGGSDI ELTQSPASLA VSLGQRAIIS   180
CKASQSVSFA GTSLMHWYHQ KPGQQPKLLI YRASNLEAGV PTRFSGSGSK TDFTLNIHPV   240
EEEDAATYYC QQSREYPYTF GGGTKLEIKA AAGSGGSGES KYGPPCPSCP APEFLGGPSV   300
FLFPPKPKDT LMISRTPEVT CVVVDVSQED PEVQFNWYVD GVEVHNAKTK PREEQFNSTY   360
RVVSVLTVLH QDWLNGKEYK CKVSNKGLPS SIEKTISKAK GQPREPQVYT LPPSQEEMTK   420
NQVSLTCLVK GFYPSDIAVE WESNGQPENN YKTTPPVLDS DGSFFLYSRL TVDKSRWQEG   480
NVFSCSVMHE ALHNHYTQKS LSLSLGKMFW VLVVVGGVLA CYSLLVTVAF IIFWVRSKRS   540
RLLHSDYMNM TPRRPGPTRK HYQPYAPPRD FAAYRSKKVA KKPTNKAPHP KQEPQEINFP   600
DDLPGSNTAA PVQETLHGCQ PVTQEDGKES RISVQERQ                           638

SEQ ID NO: 80          moltype = AA  length = 597
FEATURE                Location/Qualifiers
REGION                 1..597
                       note = Synthetic peptide
source                 1..597
                       mol_type = protein
                       organism = synthetic construct
SEQUENCE: 80
MGVLLTQRTL LSLVLALLFP SMASMQVQLQ QSGAELVKPG ASVKISCKAS GYSFTGYFMN    60
WVKQSHGKSL EWIGRIHPYD GDTFYNQNFK DKATLTVDKS SNTAHMELLS LTSEDFAVYY   120
CTRYDGSRAM DYWGQGTTVT VSSGGGGSGG GGSGGGGSDI ELTQSPASLA VSLGQRAIIS   180
CKASQSVSFA GTSLMHWYHQ KPGQQPKLLI YRASNLEAGV PTRFSGSGSK TDFTLNIHPV   240
EEEDAATYYC QQSREYPYTF GGGTKLEIKA AAGSGGSGES KYGPPCPSCP APEFLGGPSV   300
FLFPPKPKDT LMISRTPEVT CVVVDVSQED PEVQFNWYVD GVEVHNAKTK PREEQFNSTY   360
RVVSVLTVLH QDWLNGKEYK CKVSNKGLPS SIEKTISKAK GQPREPQVYT LPPSQEEMTK   420
NQVSLTCLVK GFYPSDIAVE WESNGQPENN YKTTPPVLDS DGSFFLYSRL TVDKSRWQEG   480
NVFSCSVMHE ALHNHYTQKS LSLSLGKMFW VLVVVGGVLA CYSLLVTVAF IIFWVKKVAK   540
KPTNKAPHPK QEPQEINFPD DLPGSNTAAP VQETLHGCQP VTQEDGKESR ISVQERQ     597

SEQ ID NO: 81          moltype = AA  length = 643
FEATURE                Location/Qualifiers
REGION                 1..643
                       note = Synthetic peptide
source                 1..643
                       mol_type = protein
                       organism = synthetic construct
SEQUENCE: 81
MGVLLTQRTL LSLVLALLFP SMASMQVQLQ QSGAELVKPG ASVKISCKAS GYSFTGYFMN    60
WVKQSHGKSL EWIGRIHPYD GDTFYNQNFK DKATLTVDKS SNTAHMELLS LTSEDFAVYY   120
CTRYDGSRAM DYWGQGTTVT VSSGGGGSGG GGSGGGGSDI ELTQSPASLA VSLGQRAIIS   180
CKASQSVSFA GTSLMHWYHQ KPGQQPKLLI YRASNLEAGV PTRFSGSGSK TDFTLNIHPV   240
EEEDAATYYC QQSREYPYTF GGGTKLEIKA AAGSGGSGES KYGPPCPSCP APEFLGGPSV   300
FLFPPKPKDT LMISRTPEVT CVVVDVSQED PEVQFNWYVD GVEVHNAKTK PREEQFNSTY   360
RVVSVLTVLH QDWLNGKEYK CKVSNKGLPS SIEKTISKAK GQPREPQVYT LPPSQEEMTK   420
NQVSLTCLVK GFYPSDIAVE WESNGQPENN YKTTPPVLDS DGSFFLYSRL TVDKSRWQEG   480
NVFSCSVMHE ALHNHYTQKS LSLSLGKMFW VLVVVGGVLA CYSLLVTVAF IIFWVRFSVV   540
KRGRKKLLYI FKQPFMRPVQ TTQEEDGCSC RFPEEEEGGC EKKVAKKPTN KAPHPKQEPQ   600
EINFPDDLPG SNTAAPVQET LHGCQPVTQE DGKESRISVQ ERQ                     643

SEQ ID NO: 82          moltype = AA  length = 634
FEATURE                Location/Qualifiers
REGION                 1..634
                       note = Synthetic peptide
source                 1..634
                       mol_type = protein
                       organism = synthetic construct
```

```
SEQUENCE: 82
MGVLLTQRTL LSLVLALLFP SMASMQVQLQ QSGAELVKPG ASVKISCKAS GYSFTGYFMN    60
WVKQSHGKSL EWIGRIHPYD GDTFYNQNFK DKATLTVDKS SNTAHMELLS LTSEDFAVYY   120
CTRYDGSRAM DYWGQGTTVT VSSGGGGSGG GGSGGGGSDI ELTQSPASLA VSLGQRAIIS   180
CKASQSVSFA GTSLMHWYHQ KPGQQPKLLI YRASNLEAGV PTRFSGSGSK TDFTLNIHPV   240
EEEDAATYYC QQSREYPYTF GGGTKLEIKA AAGSGGSGES KYGPPCPSCP APEFLGGPSV   300
FLFPPKPKDT LMISRTPEVT CVVVDVSQED PEVQFNWYVD GVEVHNAKTK PREEQFNSTY   360
RVVSVLTVLH QDWLNGKEYK CKVSNKGLPS SIEKTISKAK GQPREPQVYT LPPSQEEMTK   420
NQVSLTCLVK GFYPSDIAVE WESNGQPENN YKTTPPVLDS DGSFFLYSRL TVDKSRWQEG   480
NVFSCSVMHE ALHNHYTQKS LSLSLGKMFW VLVVVGGVLA CYSLLVTVAF IIFWVRRDQR   540
LPPDAHKPPG GGSFRTPIQE EQADAHSTLA KIKKVAKKPT NKAPHPKQEP QEINFPDDLP   600
GSNTAAPVQE TLHGCQPVTQ EDGKESRISV QERQ                              634

SEQ ID NO: 83           moltype = AA   length = 713
FEATURE                 Location/Qualifiers
REGION                  1..713
                        note = Synthetic peptide
source                  1..713
                        mol_type = protein
                        organism = synthetic construct
SEQUENCE: 83
MGVLLTQRTL LSLVLALLFP SMASMQVQLQ QSGAELVKPG ASVKISCKAS GYSFTGYFMN    60
WVKQSHGKSL EWIGRIHPYD GDTFYNQNFK DKATLTVDKS SNTAHMELLS LTSEDFAVYY   120
CTRYDGSRAM DYWGQGTTVT VSSGGGGSGG GGSGGGGSDI ELTQSPASLA VSLGQRAIIS   180
CKASQSVSFA GTSLMHWYHQ KPGQQPKLLI YRASNLEAGV PTRFSGSGSK TDFTLNIHPV   240
EEEDAATYYC QQSREYPYTF GGGTKLEIKA AAGSGGSGES KYGPPCPSCP APEFLGGPSV   300
FLFPPKPKDT LMISRTPEVT CVVVDVSQED PEVQFNWYVD GVEVHNAKTK PREEQFNSTY   360
RVVSVLTVLH QDWLNGKEYK CKVSNKGLPS SIEKTISKAK GQPREPQVYT LPPSQEEMTK   420
NQVSLTCLVK GFYPSDIAVE WESNGQPENN YKTTPPVLDS DGSFFLYSRL TVDKSRWQEG   480
NVFSCSVMHE ALHNHYTQKS LSLSLGKMFW VLVVVGGVLA CYSLLVTVAF IIFWVKRKKQ   540
RSRRNDEELE TRAHRVATEE RGRKPHQIPA STPQNPATSQ HPPPPPGHRS QAPSHRPPPP   600
GHRVQHQPQK RPPAPSGTQV HQQKGPPLPR PRVQPKPPHG AAENSLSPSS NKKVAKKPTN   660
KAPHPKQEPQ EINFPDDLPG SNTAAPVQET LHGCQPVTQE DGKESRISVQ ERQ          713

SEQ ID NO: 84           moltype = AA   length = 655
FEATURE                 Location/Qualifiers
REGION                  1..655
                        note = Synthetic peptide
source                  1..655
                        mol_type = protein
                        organism = synthetic construct
SEQUENCE: 84
MGVLLTQRTL LSLVLALLFP SMASMQVQLQ QSGAELVKPG ASVKISCKAS GYSFTGYFMN    60
WVKQSHGKSL EWIGRIHPYD GDTFYNQNFK DKATLTVDKS SNTAHMELLS LTSEDFAVYY   120
CTRYDGSRAM DYWGQGTTVT VSSGGGGSGG GGSGGGGSDI ELTQSPASLA VSLGQRAIIS   180
CKASQSVSFA GTSLMHWYHQ KPGQQPKLLI YRASNLEAGV PTRFSGSGSK TDFTLNIHPV   240
EEEDAATYYC QQSREYPYTF GGGTKLEIKA AAGSGGSGES KYGPPCPSCP APEFLGGPSV   300
FLFPPKPKDT LMISRTPEVT CVVVDVSQED PEVQFNWYVD GVEVHNAKTK PREEQFNSTY   360
RVVSVLTVLH QDWLNGKEYK CKVSNKGLPS SIEKTISKAK GQPREPQVYT LPPSQEEMTK   420
NQVSLTCLVK GFYPSDIAVE WESNGQPENN YKTTPPVLDS DGSFFLYSRL TVDKSRWQEG   480
NVFSCSVMHE ALHNHYTQKS LSLSLGKMFW VLVVVGGVLA CYSLLVTVAF IIFWVQLGLH   540
IWQLRSQCMW PRETQLLLEV PPSTEDARSC QFPEEERGER SAEEKGRLGD LWVKKVAKKP   600
TNKAPHPKQE PQEINFPDDL PGSNTAAPVQ ETLHGCQPVT QEDGKESRIS VQERQ        655

SEQ ID NO: 85           moltype = AA   length = 644
FEATURE                 Location/Qualifiers
REGION                  1..644
                        note = Synthetic peptide
source                  1..644
                        mol_type = protein
                        organism = synthetic construct
SEQUENCE: 85
MGVLLTQRTL LSLVLALLFP SMASMQVQLQ QSGAELVKPG ASVKISCKAS GYSFTGYFMN    60
WVKQSHGKSL EWIGRIHPYD GDTFYNQNFK DKATLTVDKS SNTAHMELLS LTSEDFAVYY   120
CTRYDGSRAM DYWGQGTTVT VSSGGGGSGG GGSGGGGSDI ELTQSPASLA VSLGQRAIIS   180
CKASQSVSFA GTSLMHWYHQ KPGQQPKLLI YRASNLEAGV PTRFSGSGSK TDFTLNIHPV   240
EEEDAATYYC QQSREYPYTF GGGTKLEIKA AAGSGGSGES KYGPPCPSCP APEFLGGPSV   300
FLFPPKPKDT LMISRTPEVT CVVVDVSQED PEVQFNWYVD GVEVHNAKTK PREEQFNSTY   360
RVVSVLTVLH QDWLNGKEYK CKVSNKGLPS SIEKTISKAK GQPREPQVYT LPPSQEEMTK   420
NQVSLTCLVK GFYPSDIAVE WESNGQPENN YKTTPPVLDS DGSFFLYSRL TVDKSRWQEG   480
NVFSCSVMHE ALHNHYTQKS LSLSLGKMFW VLVVVGGVLA CYSLLVTVAF IIFWVKLLMI   540
IHDRREFAKF EKEKMNAKWD TGENPIYKSA VTTVVNPKYE GKKKVAKKPT NKAPHPKQEP   600
QEINFPDDLP GSNTAAPVQE TLHGCQPVTQ EDGKESRISV QERQ                   644

SEQ ID NO: 86           moltype = AA   length = 672
FEATURE                 Location/Qualifiers
REGION                  1..672
                        note = Synthetic peptide
```

```
source                  1..672
                        mol_type = protein
                        organism = synthetic construct
SEQUENCE: 86
MGVLLTQRTL LSLVLALLFP SMASMQVQLQ QSGAELVKPG ASVKISCKAS GYSFTGYFMN     60
WVKQSHGKSL EWIGRIHPYD GDTFYNQNFK DKATLTVDKS SNTAHMELLS LTSEDFAVYY    120
CTRYDGSRAM DYWGQGTTVT VSSGGGGSGG GGSGGGGSDI ELTQSPASLA VSLGQRAIIS    180
CKASQSVSFA GTSLMHWYHQ KPGQQPKLLI YRASNLEAGV PTRFSGSGSK TDFTLNIHPV    240
EEEDAATYYC QQSREYPYTF GGGTKLEIKA AAGSGGSGES KYGPPCPSCP APEFLGGPSV    300
FLFPPKPKDT LMISRTPEVT CVVVDVSQED PEVQFNWYVD GVEVHNAKTK PREEQFNSTY    360
RVVSVLTVLH QDWLNGKEYK CKVSNKGLPS SIEKTISKAK GQPREPQVYT LPPSQEEMTK    420
NQVSLTCLVK GFYPSDIAVE WESNGQPENN YKTTPPVLDS DGSFFLYSRL TVDKSRWQEG    480
NVFSCSVMHE ALHNHYTQKS LSLSLGKMFW VLVVVGGVLA CYSLLVTVAF IIFWVRRRGK    540
TNHYQTTVEK KSLTIYAQVQ KPGPLQKKLD SFPAQDPCTT IYVAATEPVP ESVQETNSIT    600
VYASVTLPES KKVAKKPTNK APHPKQEPQE INFPDDLPGS NTAAPVQETL HGCQPVTQED    660
GKESRISVQE RQ                                                        672

SEQ ID NO: 87           moltype = AA  length = 660
FEATURE                 Location/Qualifiers
REGION                  1..660
                        note = Synthetic peptide
source                  1..660
                        mol_type = protein
                        organism = synthetic construct
SEQUENCE: 87
MGVLLTQRTL LSLVLALLFP SMASMQVQLQ QSGAELVKPG ASVKISCKAS GYSFTGYFMN     60
WVKQSHGKSL EWIGRIHPYD GDTFYNQNFK DKATLTVDKS SNTAHMELLS LTSEDFAVYY    120
CTRYDGSRAM DYWGQGTTVT VSSGGGGSGG GGSGGGGSDI ELTQSPASLA VSLGQRAIIS    180
CKASQSVSFA GTSLMHWYHQ KPGQQPKLLI YRASNLEAGV PTRFSGSGSK TDFTLNIHPV    240
EEEDAATYYC QQSREYPYTF GGGTKLEIKA AAGSGGSGES KYGPPCPSCP APEFLGGPSV    300
FLFPPKPKDT LMISRTPEVT CVVVDVSQED PEVQFNWYVD GVEVHNAKTK PREEQFNSTY    360
RVVSVLTVLH QDWLNGKEYK CKVSNKGLPS SIEKTISKAK GQPREPQVYT LPPSQEEMTK    420
NQVSLTCLVK GFYPSDIAVE WESNGQPENN YKTTPPVLDS DGSFFLYSRL TVDKSRWQEG    480
NVFSCSVMHE ALHNHYTQKS LSLSLGKMFW VLVVVGGVLA CYSLLVTVAF IIFWVAKKPT    540
NKAPHPKQEP QEINFPDDLP GSNTAAPVQE TLHGCQPVTQ EDGKESRISV QERQKKVAKK    600
PTNKAPHPKQ EPQEINFPDD LPGSNTAAPV QETLHGCQPV TQEDGKESRI SVQERQKKVA    660

SEQ ID NO: 88           moltype = AA  length = 597
FEATURE                 Location/Qualifiers
REGION                  1..597
                        note = Synthetic peptide
source                  1..597
                        mol_type = protein
                        organism = synthetic construct
SEQUENCE: 88
MGVLLTQRTL LSLVLALLFP SMASMQVQLQ QSGAELVKPG ASVKISCKAS GYSFTGYFMN     60
WVKQSHGKSL EWIGRIHPYD GDTFYNQNFK DKATLTVDKS SNTAHMELLS LTSEDFAVYY    120
CTRYDGSRAM DYWGQGTTVT VSSGGGGSGG GGSGGGGSDI ELTQSPASLA VSLGQRAIIS    180
CKASQSVSFA GTSLMHWYHQ KPGQQPKLLI YRASNLEAGV PTRFSGSGSK TDFTLNIHPV    240
EEEDAATYYC QQSREYPYTF GGGTKLEIKA AAGSGGSGES KYGPPCPSCP APEFLGGPSV    300
FLFPPKPKDT LMISRTPEVT CVVVDVSQED PEVQFNWYVD GVEVHNAKTK PREEQFNSTY    360
RVVSVLTVLH QDWLNGKEYK CKVSNKGLPS SIEKTISKAK GQPREPQVYT LPPSQEEMTK    420
NQVSLTCLVK GFYPSDIAVE WESNGQPENN YKTTPPVLDS DGSFFLYSRL TVDKSRWQEG    480
NVFSCSVMHE ALHNHYTQKS LSLSLGKMFW VLVVVGGVLA CYSLLVTVAF IIFWVKKVAK    540
KPTNKAAHPK QEPQEINFPD DLPGSNTAAP VQETLHGCQP VTQEDGKESR ISVQERQ      597

SEQ ID NO: 89           moltype = AA  length = 297
FEATURE                 Location/Qualifiers
REGION                  1..297
                        note = Synthetic peptide
source                  1..297
                        mol_type = protein
                        organism = synthetic construct
SEQUENCE: 89
MQIPQAPWPV VWAVLQLGWR PGWFLDSPDR PWNPPTFSPA LLVVTEGDNA TFTCSFSNTS     60
ESFVLNWYRM SPSNQTDKLA AFPEDRSQPG QDCRFRVTQL PNGRDFHMSV VRARRNDSGT    120
YLCGAISLAP KAQIKESLRA ELRVTERRAE VPTAHCPSPL FPGPSKPFWV LVVVGGVLAC    180
YSLLVTVAFI IFWVRSKRSR LLHSDYMNMT PRRPGPTRKH YQPYAPPRDF AAYRSKKVAK    240
KPTNKAPHPK QEPQEINFPD DLPGSNTAAP VQETLHGCQP VTQEDGKESR ISVQERQ      297

SEQ ID NO: 90           moltype = AA  length = 256
FEATURE                 Location/Qualifiers
REGION                  1..256
                        note = Synthetic peptide
source                  1..256
                        mol_type = protein
                        organism = synthetic construct
```

```
SEQUENCE: 90
MQIPQAPWPV VWAVLQLGWR PGWFLDSPDR PWNPPTFSPA LLVVTEGDNA TFTCSFSNTS    60
ESFVLNWYRM SPSNQTDKLA AFPEDRSQPG QDCRFRVTQL PNGRDFHMSV VRARRNDSGT   120
YLCGAISLAP KAQIKESLRA ELRVTERRAE VPTAHCPSPL FPGPSKPFWV LVVVGGVLAC   180
YSLLVTVAFI IFWVKKVAKK PTNKAPHPKQ EPQEINFPDD LPGSNTAAPV QETLHGCQPV   240
TQEDGKESRI SVQERQ                                                   256

SEQ ID NO: 91             moltype = AA  length = 271
FEATURE                   Location/Qualifiers
REGION                    1..271
                          note = Synthetic peptide
source                    1..271
                          mol_type = protein
                          organism = synthetic construct
SEQUENCE: 91
MRWCLLLIWA QGLRQAPLAS GMMTGTIETT GNISAEKGGS IILQCHLSST TAQVTQVNWE    60
QQDQLLAICN ADLGWHISPS FKDRVAPGPG LGLTLQSLTV NDTGEYFCIY HTYPDGTYTG   120
RIFLEVLESS VAEHGARFQI PFWVLVVVGG VLACYSLLVT VAFIIFWVRS KRSRLLHSDY   180
MNMTPRRPGP TRKHYQPYAP PRDFAAYRSK KVAKKPTNKA PHPKQEPQEI NFPDDLPGSN   240
TAAPVQETLH GCQPVTQEDG KESRISVQER Q                                  271

SEQ ID NO: 92             moltype = AA  length = 230
FEATURE                   Location/Qualifiers
REGION                    1..230
                          note = Synthetic peptide
source                    1..230
                          mol_type = protein
                          organism = synthetic construct
SEQUENCE: 92
MRWCLLLIWA QGLRQAPLAS GMMTGTIETT GNISAEKGGS IILQCHLSST TAQVTQVNWE    60
QQDQLLAICN ADLGWHISPS FKDRVAPGPG LGLTLQSLTV NDTGEYFCIY HTYPDGTYTG   120
RIFLEVLESS VAEHGARFQI PFWVLVVVGG VLACYSLLVT VAFIIFWVKK VAKKPTNKAP   180
HPKQEPQEIN FPDDLPGSNT AAPVQETLHG CQPVTQEDGK ESRISVQERQ              230

SEQ ID NO: 93             moltype = AA  length = 556
FEATURE                   Location/Qualifiers
REGION                    1..556
                          note = Synthetic peptide
source                    1..556
                          mol_type = protein
                          organism = synthetic construct
SEQUENCE: 93
MGVLLTQRTL LSLVLALLFP SMASMQVQLQ QSGAELVKPG ASVKISCKAS GYSFTGYFMN    60
WVKQSHGKSL EWIGRIHPYD GDTFYNQNFK DKATLTVDKS SNTAHMELLS LTSEDFAVYY   120
CTRYDGSRAM DYWGQGTTVT VSSGGGGSGG GGSGGGGSDI ELTQSPASLA VSLGQRAIIS   180
CKASQSVSFA GTSLMHWYHQ KPGQQPKLLI YRASNLEAGV PTRFSGSGSK TDFTLNIHPV   240
EEEDAATYYC QQSREYPYTF GGGTKLEIKA AAGSGGSGRP GWFLDSPDRP WNPPTFSPAL   300
LVVTEGDNAT FTCSFSNTSE SFVLNWYRMS PSNQTDKLAA FPEDRSQPGQ DCRFRVTQLP   360
NGRDFHMSVV RARRNDSGTY LCGAISLAPK AQIKESLRAE LRVTERRAEV PTAHCPSPLF   420
PGPSKPFWVL VVVGGVLACY SLLVTVAFII FWVRSKRSRL LHSDYMNMTP RRPGPTRKHY   480
QPYAPPRDFA AYRSKKVAKK PTNKAPHPKQ EPQEINFPDD LPGSNTAAPV QETLHGCQPV   540
TQEDGKESRI SVQERQ                                                   556

SEQ ID NO: 94             moltype = AA  length = 515
FEATURE                   Location/Qualifiers
REGION                    1..515
                          note = Synthetic peptide
source                    1..515
                          mol_type = protein
                          organism = synthetic construct
SEQUENCE: 94
MGVLLTQRTL LSLVLALLFP SMASMQVQLQ QSGAELVKPG ASVKISCKAS GYSFTGYFMN    60
WVKQSHGKSL EWIGRIHPYD GDTFYNQNFK DKATLTVDKS SNTAHMELLS LTSEDFAVYY   120
CTRYDGSRAM DYWGQGTTVT VSSGGGGSGG GGSGGGGSDI ELTQSPASLA VSLGQRAIIS   180
CKASQSVSFA GTSLMHWYHQ KPGQQPKLLI YRASNLEAGV PTRFSGSGSK TDFTLNIHPV   240
EEEDAATYYC QQSREYPYTF GGGTKLEIKA AAGSGGSGRP GWFLDSPDRP WNPPTFSPAL   300
LVVTEGDNAT FTCSFSNTSE SFVLNWYRMS PSNQTDKLAA FPEDRSQPGQ DCRFRVTQLP   360
NGRDFHMSVV RARRNDSGTY LCGAISLAPK AQIKESLRAE LRVTERRAEV PTAHCPSPLF   420
PGPSKPFWVL VVVGGVLACY SLLVTVAFII FWVKKVAKKP TNKAPHPKQE PQEINFPDDL   480
PGSNTAAPVQ ETLHGCQPVT QEDGKESRIS VQERQ                              515

SEQ ID NO: 95             moltype = AA  length = 528
FEATURE                   Location/Qualifiers
REGION                    1..528
                          note = Synthetic peptide
source                    1..528
                          mol_type = protein
                          organism = synthetic construct
```

```
SEQUENCE: 95
MGVLLTQRTL LSLVLALLFP SMASMQVQLQ QSGAELVKPG ASVKISCKAS GYSFTGYFMN   60
WVKQSHGKSL EWIGRIHPYD GDTFYNQNFK DKATLTVDKS SNTAHMELLS LTSEDFAVYY  120
CTRYDGSRAM DYWGQGTTVT VSSGGGGSGG GGSGGGGSDI ELTQSPASLA VSLGQRAIIS  180
CKASQSVSFA GTSLMHWYHQ KPGQQPKLLI YRASNLEAGV PTRFSGSGSK TDFTLNIHPV  240
EEEDAATYYC QQSREYPYTF GGGTKLEIKA AAGSGGSGMM TGTIETTGNI SAEKGGSIIL  300
QCHLSSTTAQ VTQVNWEQQD QLLAICNADL GWHISPSFKD RVAPGPGLGL TLQSLTVNDT  360
GEYFCIYHTY PDGTYTGRIF LEVLESSVAE HGARFQIPFW VLVVVGGVLA CYSLLVTVAF  420
IIFWVRSKRS RLLHSDYMNM TPRRPGPTRK HYQPYAPPRD FAAYRSKKVA KKPTNKAPHP  480
KQEPQEINFP DDLPGSNTAA PVQETLHGCQ PVTQEDGKES RISVQERQ              528

SEQ ID NO: 96           moltype = AA  length = 487
FEATURE                 Location/Qualifiers
REGION                  1..487
                        note = Synthetic peptide
source                  1..487
                        mol_type = protein
                        organism = synthetic construct
SEQUENCE: 96
MGVLLTQRTL LSLVLALLFP SMASMQVQLQ QSGAELVKPG ASVKISCKAS GYSFTGYFMN   60
WVKQSHGKSL EWIGRIHPYD GDTFYNQNFK DKATLTVDKS SNTAHMELLS LTSEDFAVYY  120
CTRYDGSRAM DYWGQGTTVT VSSGGGGSGG GGSGGGGSDI ELTQSPASLA VSLGQRAIIS  180
CKASQSVSFA GTSLMHWYHQ KPGQQPKLLI YRASNLEAGV PTRFSGSGSK TDFTLNIHPV  240
EEEDAATYYC QQSREYPYTF GGGTKLEIKA AAGSGGSGMM TGTIETTGNI SAEKGGSIIL  300
QCHLSSTTAQ VTQVNWEQQD QLLAICNADL GWHISPSFKD RVAPGPGLGL TLQSLTVNDT  360
GEYFCIYHTY PDGTYTGRIF LEVLESSVAE HGARFQIPFW VLVVVGGVLA CYSLLVTVAF  420
IIFWVKKVAK KPTNKAPHPK QEPQEINFPD DLPGSNTAAP VQETLHGCQP VTQEDGKESR  480
ISVQERQ                                                            487

SEQ ID NO: 97           moltype = AA  length = 15
FEATURE                 Location/Qualifiers
REGION                  1..15
                        note = Synthetic peptide
source                  1..15
                        mol_type = protein
                        organism = synthetic construct
SEQUENCE: 97
GGGGSGGGGS GGGGS                                                    15

SEQ ID NO: 98           moltype = AA  length = 165
FEATURE                 Location/Qualifiers
REGION                  1..165
                        note = Synthetic peptide
source                  1..165
                        mol_type = protein
                        organism = synthetic construct
SEQUENCE: 98
NKILVKQSPM LVAYDNAVNL SCKYSYNLFS REFRASLHKG LDSAVEVCVV YGNYSQQLQV   60
YSKTGFNCDG KLGNESVTFY LQNLYVNQTD IYFCKIEVMY PPPYLDNEKS NGTIIHVKGK  120
HLCPSPLFPG PSKPFWVLVV VGGVLACYSL LVTVAFIIFW VRSKR                 165

SEQ ID NO: 99           moltype = AA  length = 248
FEATURE                 Location/Qualifiers
REGION                  1..248
                        note = Synthetic peptide
source                  1..248
                        mol_type = protein
                        organism = synthetic construct
SEQUENCE: 99
NKILVKQSPM LVAYDNAVNL SCKYSYNLFS REFRASLHKG LDSAVEVCVV YGNYSQQLQV   60
YSKTGFNCDG KLGNESVTFY LQNLYVNQTD IYFCKIEVMY PPPYLDNEKS NGTIIHVKGK  120
HLCPSPLFPG PSKPFWVLVV VGGVLACYSL LVTVAFIIFW VRSKRSRLLH SDYMNMTPRR  180
PGPTRKHYQP YAPPRDFAAY RSRFSVVKRG RKKLLYIFKQ PFMRPVQTTQ EEDGCSCRFP  240
EEEEGGCE                                                           248

SEQ ID NO: 100          moltype = AA  length = 239
FEATURE                 Location/Qualifiers
REGION                  1..239
                        note = Synthetic peptide
source                  1..239
                        mol_type = protein
                        organism = synthetic construct
SEQUENCE: 100
NKILVKQSPM LVAYDNAVNL SCKYSYNLFS REFRASLHKG LDSAVEVCVV YGNYSQQLQV   60
YSKTGFNCDG KLGNESVTFY LQNLYVNQTD IYFCKIEVMY PPPYLDNEKS NGTIIHVKGK  120
HLCPSPLFPG PSKPFWVLVV VGGVLACYSL LVTVAFIIFW VRSKRSRLLH SDYMNMTPRR  180
PGPTRKHYQP YAPPRDFAAY RSRRDQRLPP DAHKPPGGGS FRTPIQEEQA DAHSTLAKI  239

SEQ ID NO: 101          moltype = AA  length = 318
```

```
FEATURE                 Location/Qualifiers
REGION                  1..318
                        note = Synthetic peptide
source                  1..318
                        mol_type = protein
                        organism = synthetic construct
SEQUENCE: 101
NKILVKQSPM LVAYDNAVNL SCKYSYNLFS REFRASLHKG LDSAVEVCVV YGNYSQQLQV      60
YSKTGFNCDG KLGNESVTFY LQNLYVNQTD IYFCKIEVMY PPPYLDNEKS NGTIIHVKGK     120
HLCPSPLFPG PSKPFWVLVV VGGVLACYSL LVTVAFIIFW VRSKRSRLLH SDYMNMTPRR     180
PGPTRKHYQP YAPPRDFAAY RSKRKKQRSR RNDEELETRA HRVATEERGR KPHQIPASTP     240
QNPATSQHPP PPPGHRSQAP SHRPPPPGHR VQHQPQKRPP APSGTQVHQQ KGPPLPRPRV     300
QPKPPHGAAE NSLSPSSN                                                  318

SEQ ID NO: 102          moltype = AA  length = 249
FEATURE                 Location/Qualifiers
REGION                  1..249
                        note = Synthetic peptide
source                  1..249
                        mol_type = protein
                        organism = synthetic construct
SEQUENCE: 102
NKILVKQSPM LVAYDNAVNL SCKYSYNLFS REFRASLHKG LDSAVEVCVV YGNYSQQLQV      60
YSKTGFNCDG KLGNESVTFY LQNLYVNQTD IYFCKIEVMY PPPYLDNEKS NGTIIHVKGK     120
HLCPSPLFPG PSKPFWVLVV VGGVLACYSL LVTVAFIIFW VRSKRSRLLH SDYMNMTPRR     180
PGPTRKHYQP YAPPRDFAAY RSKLLMIIHD RREFAKFEKE KMNAKWDTGE NPIYKSAVTT     240
VVNPKYEGK                                                            249

SEQ ID NO: 103          moltype = AA  length = 260
FEATURE                 Location/Qualifiers
REGION                  1..260
                        note = Synthetic peptide
source                  1..260
                        mol_type = protein
                        organism = synthetic construct
SEQUENCE: 103
NKILVKQSPM LVAYDNAVNL SCKYSYNLFS REFRASLHKG LDSAVEVCVV YGNYSQQLQV      60
YSKTGFNCDG KLGNESVTFY LQNLYVNQTD IYFCKIEVMY PPPYLDNEKS NGTIIHVKGK     120
HLCPSPLFPG PSKPFWVLVV VGGVLACYSL LVTVAFIIFW VRSKRSRLLH SDYMNMTPRR     180
PGPTRKHYQP YAPPRDFAAY RSQLGLHIWQ LRSQCMWPRE TQLLLEVPPS TEDARSCQFP     240
EEERGERSAE EKGRLGDLWV                                                260

SEQ ID NO: 104          moltype = AA  length = 288
FEATURE                 Location/Qualifiers
REGION                  1..288
                        note = Synthetic peptide
source                  1..288
                        mol_type = protein
                        organism = synthetic construct
SEQUENCE: 104
NKILVKQSPM LVAYDNAVNL SCKYSYNLFS REFRASLHKG LDSAVEVCVV YGNYSQQLQV      60
YSKTGFNCDG KLGNESVTFY LQNLYVNQTD IYFCKIEVMY PPPYLDNEKS NGTIIHVKGK     120
HLCPSPLFPG PSKPFWVLVV VGGVLACYSL LVTVAFIIFW VRSKRSRLLH SDYMNMTPRR     180
PGPTRKHYQP YAPPRDFAAY RSERTMPRIP TLKNLEDLVT EYHGNFSAWS GVSKGLAESL     240
QPDYSERLCL VSEIPPKGGA LGEGPGASPC NQHSPYWAPP CYTLKPET                 288

SEQ ID NO: 105          moltype = AA  length = 264
FEATURE                 Location/Qualifiers
REGION                  1..264
                        note = Synthetic peptide
source                  1..264
                        mol_type = protein
                        organism = synthetic construct
SEQUENCE: 105
NKILVKQSPM LVAYDNAVNL SCKYSYNLFS REFRASLHKG LDSAVEVCVV YGNYSQQLQV      60
YSKTGFNCDG KLGNESVTFY LQNLYVNQTD IYFCKIEVMY PPPYLDNEKS NGTIIHVKGK     120
HLCPSPLFPG PSKPFWVLVV VGGVLACYSL LVTVAFIIFW VRSKRSRLLH SDYMNMTPRR     180
PGPTRKHYQP YAPPRDFAAY RSKKVAKKPT NKAPHPKQEP QEINFPDDLP GSNTAAPVQE     240
TLHGCQPVTQ EDGKESRISV QERQ                                           264

SEQ ID NO: 106          moltype = AA  length = 277
FEATURE                 Location/Qualifiers
REGION                  1..277
                        note = Synthetic peptide
source                  1..277
                        mol_type = protein
                        organism = synthetic construct
```

```
SEQUENCE: 106
NKILVKQSPM LVAYDNAVNL SCKYSYNLFS REFRASLHKG LDSAVEVCVV YGNYSQQLQV    60
YSKTGFNCDG KLGNESVTFY LQNLYVNQTD IYFCKIEVMY PPPYLDNEKS NGTIIHVKGK   120
HLCPSPLFPG PSKPFWVLVV VGGVLACYSL LVTVAFIIFW VRSKRSRLLH SDYMNMTPRR   180
PGPTRKHYQP YAPPRDFAAY RSRRRGKTNH YQTTVEKKSL TIYAQVQKPG PLQKKLDSFP   240
AQDPCTTIYV AATEPVPESV QETNSITVYA SVTLPES                            277

SEQ ID NO: 107           moltype = AA  length = 380
FEATURE                  Location/Qualifiers
REGION                   1..380
                         note = Synthetic peptide
source                   1..380
                         mol_type = protein
                         organism = synthetic construct
SEQUENCE: 107
NKILVKQSPM LVAYDNAVNL SCKYSYNLFS REFRASLHKG LDSAVEVCVV YGNYSQQLQV    60
YSKTGFNCDG KLGNESVTFY LQNLYVNQTD IYFCKIEVMY PPPYLDNEKS NGTIIHVKGK   120
HLCPSPLFPG PSKPFWVLVV VGGVLACYSL LVTVAFIIFW VRSKRSRLLH SDYMNMTPRR   180
PGPTRKHYQP YAPPRDFAAY RSKRKKQRSR RNDEELETRA HRVATEERGR KPHQIPASTP   240
QNPATSQHPP PPPGHRSQAP SHRPPPPGHR VQHQPQKRPP APSGTQVHQQ KGPPLPRPRV   300
QPKPPHGAAE NSLSPSSNKK VAKKPTNKAP HPKQEPQEIN FPDDLPGSNT AAPVQETLHG   360
CQPVTQEDGK ESRISVQERQ                                               380

SEQ ID NO: 108           moltype = AA  length = 98
FEATURE                  Location/Qualifiers
REGION                   1..98
                         note = Synthetic peptide
source                   1..98
                         mol_type = protein
                         organism = synthetic construct
SEQUENCE: 108
NKILVKQSPM LVAYDNAVNL SCKYSYNLFS REFRASLHKG LDSAVEVCVV YGNYSQQLQV    60
YSKTGFNCDG KLGNESVTFY LQNLYVNQTD IYFCKIEV                            98

SEQ ID NO: 109           moltype = AA  length = 295
FEATURE                  Location/Qualifiers
REGION                   1..295
                         note = Synthetic peptide
source                   1..295
                         mol_type = protein
                         organism = synthetic construct
SEQUENCE: 109
MQIPQAPWPV VWAVLQLGWR PGWFLDSPDR PWNPPTFSPA LLVVTEGDNA TFTCSFSNTS    60
ESFVLNWYRM SPSNQTDKLA AFPEDRSQPG QDCRFRVTQL PNGRDFHMSV VRARRNDSGT   120
YLCGAISLAP KAQIKESLRA ELRVTERRAE VPTAHPSPSP RPAGQFWVLV VVGGVLACYS   180
LLVTVAFIIF WVRSKRSRLL HSDYMNMTPR RPGPTRKHYQ PYAPPRDFAA YRSKKVAKKP   240
TNKAPHPKQE PQEINFPDDL PGSNTAAPVQ ETLHGCQPVT QEDGKESRIS VQERQ        295

SEQ ID NO: 110           moltype = AA  length = 538
FEATURE                  Location/Qualifiers
REGION                   1..538
                         note = Synthetic peptide
source                   1..538
                         mol_type = protein
                         organism = synthetic construct
SEQUENCE: 110
MGVLLTQRTL LSLVLALLFP SMASMQVQLQ QSGAELVRSG TSVKLSCTAS GFNIKDSYMH    60
WLRQGPEQGL EWIGWIDPEN GDTEYAPKFQ GKATFTTDTS SNTAYLQLSS LTSEDTAVYY   120
CNEGTPTGPY YFDYWGQGTT VTVSSGGGGS GGGGSGGGGS ENVLTQSPAI MSASPGEKVT   180
ITCSASSSVS YMHWFQQKPG TSPKLWIYST SNLASGVPAR FSGSGSGTSY SLTISRMEAE   240
DAATYYCQQR SSYPLTFGAG TKLELKRAAA GSGGGSGILV KQSPMLVAYD NAVNLSCKYS   300
YNLFSREFRAS LHKGLDSAVE VCVVYGNYSQ QLQVYSKTGF NCDGKLGNES VTFYLQNLYV  360
NQTDIYFCKI EVMYPPPYLD NEKSNGTIIH VKGKHLCPSP LFPGPSKPFW VLVVVGGVLA   420
CYSLLVTVAF IIFWVRSKRS RLLHSDYMNM TPRRPGPTRK HYQPYAPPRD FAAYRSKKVA   480
KKPTNKAPHP KQEPQEINFP DDLPGSNTAA PVQETLHGCQ PVTQEDGKES RIAVQARQ     538

SEQ ID NO: 111           moltype = AA  length = 538
FEATURE                  Location/Qualifiers
REGION                   1..538
                         note = Synthetic peptide
source                   1..538
                         mol_type = protein
                         organism = synthetic construct
SEQUENCE: 111
MGVLLTQRTL LSLVLALLFP SMASMQVQLQ QSGAELVRSG TSVKLSCTAS GFNIKDSYMH    60
WLRQGPEQGL EWIGWIDPEN GDTEYAPKFQ GKATFTTDTS SNTAYLQLSS LTSEDTAVYY   120
CNEGTPTGPY YFDYWGQGTT VTVSSGGGGS GGGGSGGGGS ENVLTQSPAI MSASPGEKVT   180
ITCSASSSVS YMHWFQQKPG TSPKLWIYST SNLASGVPAR FSGSGSGTSY SLTISRMEAE   240
DAATYYCQQR SSYPLTFGAG TKLELKRAAA GSGGGSGILV KQSPMLVAYD NAVNLSCKYS   300
```

```
NLFSREFRAS LHKGLDSAVE VCVVYGNYSQ QLQVYSKTGF NCDGKLGNES VTFYLQNLYV    360
NQTDIYFCKI EVMYPPPYLD NEKSNGTIIH VKGKHLCPSP LFPGPSKPFW VLVVVGGVLA    420
CYSLLVTVAF IIFWVRSKRS RLLHSDYMNM TPRRPGPTRK HYQPYAPPRD FAAYRSKKVA    480
KKPTNKAHPP KQEPQEINFP DDLPGSNTAA PVQETLHGCQ PVTQEDGKES RIAVQARQ      538

SEQ ID NO: 112            moltype = AA   length = 538
FEATURE                   Location/Qualifiers
REGION                    1..538
                          note = Synthetic peptide
source                    1..538
                          mol_type = protein
                          organism = synthetic construct
SEQUENCE: 112
MGVLLTQRTL LSLVLALLFP SMASMQVQLQ QSGAELVRSG TSVKLSCTAS GFNIKDSYMH     60
WLRQGPEQGL EWIGWIDPEN GDTEYAPKFQ GKATFTTDTS SNTAYLQLSS LTSEDTAVYY    120
CNEGTPTGPY YFDYWGQGTT VTVSSGGGGS GGGGSGGGGS ENVLTQSPAI MSASPGEKVT    180
ITCSASSSVS YMHWFQQKPG TSPKLWIYST SNLASGVPAR FSGSGSGTSY SLTISRMEAE    240
DAATYYCQQR SSYPLTFGAG TKLELKRAAA GSGGSGILVK QSPMLVAYDN AVNLSCKYSY    300
NLFSREFRAS LHKGLDSAVE VCVVYGNYSQ QLQVYSKTGF NCDGKLGNES VTFYLQNLYV    360
NQTDIYFCKI EVMYPPPYLD NEKSNGTIIH VKGKHLCPSP LFPGPSKPFW VLVVVGGVLA    420
CYSLLVTVAF IIFWVRSKRS RLLHSDYMNM TPRRPGPTRK HYQPYAPPRD FAAYRSKKVA    480
KKPTNKAHPP KQEAQAINFP DDLPGSNTAA PVQETLHGCQ PVTQEDGKES RISVQERQ      538

SEQ ID NO: 113            moltype = AA   length = 538
FEATURE                   Location/Qualifiers
REGION                    1..538
                          note = Synthetic peptide
source                    1..538
                          mol_type = protein
                          organism = synthetic construct
SEQUENCE: 113
MGVLLTQRTL LSLVLALLFP SMASMQVQLQ QSGAELVRSG TSVKLSCTAS GFNIKDSYMH     60
WLRQGPEQGL EWIGWIDPEN GDTEYAPKFQ GKATFTTDTS SNTAYLQLSS LTSEDTAVYY    120
CNEGTPTGPY YFDYWGQGTT VTVSSGGGGS GGGGSGGGGS ENVLTQSPAI MSASPGEKVT    180
ITCSASSSVS YMHWFQQKPG TSPKLWIYST SNLASGVPAR FSGSGSGTSY SLTISRMEAE    240
DAATYYCQQR SSYPLTFGAG TKLELKRAAA GSGGSGILVK QSPMLVAYDN AVNLSCKYSY    300
NLFSREFRAS LHKGLDSAVE VCVVYGNYSQ QLQVYSKTGF NCDGKLGNES VTFYLQNLYV    360
NQTDIYFCKI EVMYPPPYLD NEKSNGTIIH VKGKHLCPSP LFPGPSKPFW VLVVVGGVLA    420
CYSLLVTVAF IIFWVRSKRS RLLHSDYMNM TPRRPGPTRK HYQPYAPPRD FAAYRSKKVA    480
KKPTNKAAHP KQEPQEINFP DDLPGSNTAA PVQETLHGCQ PVTQEDGKES RISVQERQ      538

SEQ ID NO: 114            moltype = AA   length = 62
FEATURE                   Location/Qualifiers
REGION                    1..62
                          note = Synthetic peptide
source                    1..62
                          mol_type = protein
                          organism = synthetic construct
SEQUENCE: 114
KKVAKKPTNK APHPKQEPQE INFPDDLPGS NTAAPVQETL HGCQPVTAED GKESRISVQE     60
RQ                                                                   62

SEQ ID NO: 115            moltype = AA   length = 600
FEATURE                   Location/Qualifiers
REGION                    1..600
                          note = Synthetic peptide
source                    1..600
                          mol_type = protein
                          organism = synthetic construct
SEQUENCE: 115
MGVLLTQRTL LSLVLALLFP SMASMQVQLQ QSGAELVRSG TSVKLSCTAS GFNIKDSYMH     60
WLRQGPEQGL EWIGWIDPEN GDTEYAPKFQ GKATFTTDTS SNTAYLQLSS LTSEDTAVYY    120
CNEGTPTGPY YFDYWGQGTT VTVSSGGGGS GGGGSGGGGS ENVLTQSPAI MSASPGEKVT    180
ITCSASSSVS YMHWFQQKPG TSPKLWIYST SNLASGVPAR FSGSGSGTSY SLTISRMEAE    240
DAATYYCQQR SSYPLTFGAG TKLELKRAAA GSGGSGILVK QSPMLVAYDN AVNLSCKYSY    300
NLFSREFRAS LHKGLDSAVE VCVVYGNYSQ QLQVYSKTGF NCDGKLGNES VTFYLQNLYV    360
NQTDIYFCKI EVMYPPPYLD NEKSNGTIIH VKGKHLCPSP LFPGPSKPFW VLVVVGGVLA    420
CYSLLVTVAF IIFWVRSKRS RLLHSDYMNM TPRRPGPTRK HYQPYAPPRD FAAYRSKKVA    480
KKPTNKAHPP KQEPQEINFP DDLPGSNTAA PVQETLHGCQ PVTAEDGKES RISVQERQKK    540
VAKKPTNKAP HPKQEPQEIN FPDDLPGSNT AAPVQETLHG CQPVTAEDGK ESRISVQERQ    600

SEQ ID NO: 116            moltype = AA   length = 538
FEATURE                   Location/Qualifiers
REGION                    1..538
                          note = Synthetic peptide
source                    1..538
                          mol_type = protein
                          organism = synthetic construct
```

```
SEQUENCE: 116
MGVLLTQRTL LSLVLALLFP SMASMQVQLQ QSGAELVRSG TSVKLSCTAS GFNIKDSYMH   60
WLRQGPEQGL EWIGWIDPEN GDTEYAPKFQ GKATFTTDTS SNTAYLQLSS LTSEDTAVYY  120
CNEGTPTGPY YFDYWGQGTT VTVSSGGGGS GGGGSGGGGS ENVLTQSPAI MSASPGEKVT  180
ITCSASSSVS YMHWFQQKPG TSPKLWIYST SNLASGVPAR FSGSGSGTSY SLTISRMEAE  240
DAATYYCQQR SSYPLTFGAG TKLELKRAAA GSGGGSILVK QSPMLVAYDN AVNLSCKYSY  300
NLFSREFRAS LHKGLDSAVE VCVVYGNYSQ QLQVYSKTGF NCDGKLGNES VTFYLQNLYV  360
NQTDIYFCKI EVMYPPPYLD NEKSNGTIIH VKGKHLCPSP LFPGPSKPFW VLVVGGVLA   420
CYSLLVTVAF IIFWVRSKRS RLLHSDYMNM TPRRPGPTRK HYQAYAAPRD FAAYRSKKVA  480
KKPTNKAPHP KQEPQEINFP DDLPGSNTAA PVQETLHGCQ PVTQEDGKES RISVQERQ    538

SEQ ID NO: 117           moltype = AA   length = 538
FEATURE                  Location/Qualifiers
REGION                   1..538
                         note = Synthetic peptide
source                   1..538
                         mol_type = protein
                         organism = synthetic construct
SEQUENCE: 117
MGVLLTQRTL LSLVLALLFP SMASMQVQLQ QSGAELVRSG TSVKLSCTAS GFNIKDSYMH   60
WLRQGPEQGL EWIGWIDPEN GDTEYAPKFQ GKATFTTDTS SNTAYLQLSS LTSEDTAVYY  120
CNEGTPTGPY YFDYWGQGTT VTVSSGGGGS GGGGSGGGGS ENVLTQSPAI MSASPGEKVT  180
ITCSASSSVS YMHWFQQKPG TSPKLWIYST SNLASGVPAR FSGSGSGTSY SLTISRMEAE  240
DAATYYCQQR SSYPLTFGAG TKLELKRAAA GSGGGSILVK QSPMLVAYDN AVNLSCKYSY  300
NLFSREFRAS LHKGLDSAVE VCVVYGNYSQ QLQVYSKTGF NCDGKLGNES VTFYLQNLYV  360
NQTDIYFCKI EVMYPPPYLD NEKSNGTIIH VKGKHLCPSP LFPGPSKPFW VLVVGGVLA   420
CYSLLVTVAF IIFWVRSKRS RLLHSDFMNM TPRRPGPTRK HYQPYAPPRD FAAYRSKKVA  480
KKPTNKAPHP KQEPQEINFP DDLPGSNTAA PVQETLHGCQ PVTQEDGKES RISVQERQ    538

SEQ ID NO: 118           moltype = AA   length = 8
FEATURE                  Location/Qualifiers
REGION                   1..8
                         note = Synthetic peptide
source                   1..8
                         mol_type = protein
                         organism = synthetic construct
SEQUENCE: 118
PTNKAPHP                                                             8

SEQ ID NO: 119           moltype = AA   length = 7
FEATURE                  Location/Qualifiers
REGION                   1..7
                         note = Synthetic peptide
source                   1..7
                         mol_type = protein
                         organism = synthetic construct
SEQUENCE: 119
PTNKAPH                                                              7

SEQ ID NO: 120           moltype = AA   length = 5
FEATURE                  Location/Qualifiers
REGION                   1..5
                         note = Synthetic peptide
source                   1..5
                         mol_type = protein
                         organism = synthetic construct
SEQUENCE: 120
PKQET                                                                5

SEQ ID NO: 121           moltype = AA   length = 5
FEATURE                  Location/Qualifiers
REGION                   1..5
                         note = Synthetic peptide
source                   1..5
                         mol_type = protein
                         organism = synthetic construct
SEQUENCE: 121
PVQET                                                                5

SEQ ID NO: 122           moltype = AA   length = 5
FEATURE                  Location/Qualifiers
REGION                   1..5
                         note = Synthetic peptide
source                   1..5
                         mol_type = protein
                         organism = synthetic construct
SEQUENCE: 122
SVQET                                                                5
```

```
SEQ ID NO: 123          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 123
QEPQEINFP                                                                9

SEQ ID NO: 124          moltype = AA  length = 8
FEATURE                 Location/Qualifiers
source                  1..8
                        mol_type = protein
                        organism = synthetic construct
SEQUENCE: 124
DYKDDDDK                                                                 8

SEQ ID NO: 125          moltype = AA  length = 15
FEATURE                 Location/Qualifiers
source                  1..15
                        mol_type = protein
                        organism = synthetic construct
SEQUENCE: 125
GGGGSGGGGS GGGGS                                                        15
```

RECEPTORS PROVIDING TARGETED COSTIMULATION FOR ADOPTIVE CELL THERAPY

RELATED APPLICATIONS AND INCORPORATION BY REFERENCE

This application is a continuation of U.S. patent application Ser. No. 17/843,480, filed Jun. 17, 2022, which is a continuation of P.C.T. Patent Application Serial No. PCT/US2021/042075, filed Jul. 16, 2021, which claims priority to U.S. Provisional patent application Ser. No. 63/053,494, filed Jul. 17, 2020 the contents of which are incorporated herein by reference in their entireties.

Reference is made to GB patent application Serial No. 1900858.0, filed 22 Jan. 2019, U.S. patent application Ser. No. 62/951,770, filed 20 Dec. 2019, International application PCT/GB2020/050120, filed 20 Jan. 2020, U.S. Patent Application Ser. No. 63/053,494, filed Jul. 17, 2020, U.S. Provisional Application No. 63/222,913, filed Jul. 16, 2021, and to International application PCT/US2021/042075, filed Jul. 16, 2021.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

REFERENCE TO SEQUENCE LISTING

The present application is being filed along with a Sequence Listing in electronic format. The Sequence Listing is provided as a file entitled INSTB005C2.xml created on Apr. 26, 2023, which is 198,544 bytes in size. The information in the electronic format of the Sequence Listing is incorporated herein by reference in its entirety.

FIELD OF THE INVENTION

The present invention relates to a chimeric costimulatory antigen receptor (CoStAR) useful in adoptive cell therapy (ACT), and cells comprising the CoStAR. The CoStAR can act as a modulator of cellular activity enhancing responses to defined antigens. The present invention also provides CoStAR proteins, nucleic acids encoding the CoStAR and therapeutic uses thereof.

BACKGROUND OF THE INVENTION

Adoptive cell therapy (ACT) using autologous T-cells to mediate cancer regression has shown much promise in early clinical trials. Several general approaches have been taken such as the use of naturally occurring tumor reactive or tumor infiltrating lymphocytes (TILs) expanded ex vivo. Additionally, T-cells may be genetically modified to retarget them towards defined tumor antigens. This can be done via the gene transfer of peptide (p)-major histocompatibility complex (MHC) specific T-cell Receptors (TCRs) or synthetic fusions between tumor specific single chain antibody fragment (scFv) and T-cell signaling domains (e.g. CD3ζ), the latter being termed chimeric antigen receptors (CARs).

TIL and TCR transfer has proven particularly good when targeting melanoma (Rosenberg et al. 2011; Morgan 2006), whereas CAR therapy has shown much promise in the treatment of certain B-cell malignancies (Grupp et al. 2013).

Costimulatory signals are useful to achieve robust CAR T cell expansion, function, persistence and antitumor activity. The success of CAR therapy in leukemia has been partly attributed to the incorporation of costimulatory domains (e.g. CD28 or CD137) into the CAR construct, signals from which synergize with the signal provided by CD3ζ to enhance anti-tumor activity. The basis of this observation relates to the classical signal 1/signal 2 paradigm of T-cell activation. Here signal 1, provided by the TCR complex, synergizes with signal 2 provided by costimulatory receptors such as CD28, CD137 or CD134 to permit the cells to undergo clonal expansion, IL-2 production and long term survival without the activation induced cell death (AICD) associated with signal 1 alone. Furthermore the involvement of signal 2 enhances the signal generated through signal 1 allowing the cells to respond better to low avidity interactions such as those encountered during anti-tumor responses.

Targeted costimulation will have beneficial effects for non-CAR-based T-cell therapies. For example, incorporating costimulatory domains into a chimeric TCR has been shown to enhance responses of T-cells towards pMHC (Govers 2014). While tumor infiltrating lymphocytes (TILs) utilize their endogenous TCRs to mediate tumor recognition, it has not been possible to engineer the endogenous TCR. Thus TIL are subject to substantial limitations as tumor cells express very few costimulatory ligands. The ability to induce targeted costimulation of TIL, or indeed any other adoptive T-cell therapy product, would be beneficial.

Citation or identification of any document in this application is not an admission that such document is available as prior art to the present invention.

SUMMARY OF THE INVENTION

The invention provides novel chimeric costimulatory antigen receptors (CoStARs) and cells comprising or expressing the CoStARs which are beneficial for CAR and non-CAR based T-cell therapies alike. The present invention uses cells that express a novel chimeric costimulatory receptor to provides a costimulatory signal to T-cells upon engagement with a defined disease-associated, for example tumor-associated, antigen.

There have been several reports in which split signal 1 and signal 2 have been used to drive antigen specific responses in engineered T-cells (Alvarez-Vallina & Hawkins 1996). However, none have utilized the full length CD28 molecule. There are specific advantages to using full length receptors, such as CD28 as opposed to truncated forms. A full length receptors may be capable of dimerization, enabling the receptor to function in its native form, indeed chimeric antigen receptors fail to function optimally when expressed as a monomer (Bridgeman et al. 2010).

In an embodiment, a CoStAR of the invention induces signal 2 upon engagement with a defined antigen such as a disease associated or tumor associated antigen. A full length CD28 molecule contains motifs critical to its native function in binding members of the B7 family of receptors; although this is potentially dangerous from the perspective of CARs carrying CD28 and CD3ζ receptors in tandem, wherein ligation of CAR by B7 could trigger T-cell activation, there are beneficial qualities for receptors harboring signal 2 receptors alone. In an aspect, the invention provides a targeted chimeric costimulatory receptor (CoStAR) which comprises an extracellular antigen binding domain operatively linked to a transmembrane domain, a first signaling domain, and a CD40 signaling domain or a signaling fragment thereof. The inventors have discovered that costimulatory receptors comprising a CD40 signaling domain display novel and improved activity profiles.

In certain embodiments of the invention, the CD40 signaling domain comprises SEQ ID NO:23, SEQ ID NO:24, or SEQ ID NO:25. In certain embodiments, the CD40 signaling fragment comprises, consists, or consists essentially of an SH3 motif (KPTNKAPH (SEQ ID NO:26), PTNKAPHP (SEQ ID NO:118) or PTNKAPH(SEQ ID NO:119), TRAF2 motif (PKQE (SEQ ID NO:27), PKQET (SEQ ID NO:120), PVQE (SEQ ID NO:28), PVQET (SEQ ID NO:121), SVQE (SEQ ID NO:29), SVQET (SEQ ID NO:122)), TRAF6 motif (QEPQEINFP (SEQ ID NO:30) or QEPQEINFP (SEQ ID NO:123)), PKA motif (KKPTNKA (SEQ ID NO:31), SRISVQE (SEQ ID NO:32), or a combination thereof, or is a full length CD40 intracellular domain. In certain embodiments, one or more of the SH3, TRAF2, TRAF6, or PKA motifs of the CD40 signaling domain is mutated. In certain embodiments, one or more of the SH3, TRAF2, TRAF6, or PKA motifs of the CD40 signaling domain is present in multiple copies.

In certain embodiments, the first signaling domain of the CoStAR comprises a signaling domain or signaling fragment of a receptor, such as, for example a tumor necrosis factor receptor superfamily (TNFRSF) receptor, including but not limited to CD2, CD9, CD26, CD27, CD28, CD29, CD38, CD40, CD43, CD46, CD49d, CD55, CD73, CD81, CD82, CD99, CD100, CD134 (OX40), CD137 (41BB), CD150 (SLAM), CD270 (HVEM), CD278 (ICOS), CD357 (GITR), or EphB6. In certain embodiments, the CoStAR comprises CD2, CD9, CD26, CD27, CD28, CD29, CD38, CD40, CD43, CD46, CD49d, CD55, CD73, CD81, CD82, CD99, CD100, CD134 (OX40), CD137 (41BB), CD150 (SLAM), CD270 (HVEM), CD278 (ICOS), CD357 (GITR), or EphB6. In embodiments, wherein the first signaling domain comprises a CD40 signaling domain thus the CoStAR comprises elements of two CD40 signaling domains.

In certain embodiments, the CoStAR comprises a second signaling domain or signaling fragment of a receptor, such as, for example a tumor necrosis factor receptor superfamily (TNFRSF) receptor, including but not limited to CD2, CD9, CD26, CD27, CD28, CD29, CD38, CD40, CD43, CD46, CD49d, CD55, CD73, CD81, CD82, CD99, CD100, CD134 (OX40), CD137 (41BB), CD150 (SLAM), CD270 (HVEM), CD278 (ICOS), CD357 (GITR), or EphB6. The first signaling domain or signaling fragment, the CD40 signaling domain or signaling fragment, and the second signaling domain or signaling fragment can be in any order. Exemplary embodiments include, without limitation, CoStAR which comprise CD28, CD137, and CD40 signaling domains, CD28, CD134, and CD40 signaling domains, CD28, CD2, and CD40 signaling domains, CD28, GITR, and CD40 signaling domains, CD28, CD29, and CD40 signaling domains, or CD28, CD150, and CD40 signaling domains.

In certain embodiments a CoStAR of the invention is engineered not to provide signal 1. Accordingly, in certain embodiments, a CoStAR of the invention does not comprise a signal 1 signaling domain. In certain embodiments, a CoStAR of the invention does not comprise a CD3ζ signaling domain.

In certain embodiments, a CoStAR of the invention is engineered to provide signal 2 in a cell that is capable of providing signal 1 upon antigen binding (e.g., a T cell receptor provides signal 1 upon antigen engagement). In certain embodiments, a CoStAR of the invention is engineered to provide signal 2 in a cell in response to antigen-specific binding by the CoStAR when the antigen is on the surface of a target cell. In certain embodiments, a CoStAR of the invention is engineered not to provide signal 2 in a cell in response to antigen-specific binding by the CoStAR when the antigen is soluble and not attached to the surface of a target cell.

In certain embodiments, the extracellular binding domain of a CoStAR of the invention is operatively linked to the transmembrane domain by a linker and/or a spacer. In certain embodiments, the linker comprises from about 5 to about 20 amino acids. In certain embodiments, the linker comprises AAAGSGGSG (SEQ ID NO:8).

In certain embodiments, a CoStAR of the invention comprises a spacer which operatively links the extracellular binding domain to the transmembrane domain and comprises from about 10 to about 250 amino acids. In certain embodiments, the spacer comprises an extracellular sequence of CD8 or CD28 or a fragment thereof. In certain embodiments, the CoStAR comprises a second extracellular binding domain. In certain embodiments, the second binding domain comprises an extracellular ligand binding domain from CD8 or CD28. In certain embodiments, the spacer comprises one or more immunoglobulin domains or an immunoglobulin constant region. In certain embodiments, the spacer comprises one or more immunoglobulin domains or an immunoglobulin constant region of SEQ ID NO:13.

In certain embodiments the transmembrane domain of a CoStAR of the invention comprises a transmembrane domain of a TNFRSF protein. In certain embodiments, a transmembrane domain of a CoStAR of the invention comprises a transmembrane domain of CD28 or CD8. In certain embodiments, a transmembrane domain of a CoStAR of the invention comprises a transmembrane sequence of SEQ ID NO:11 or SEQ ID NO:12.

The CoStARs of the invention are useful to stimulate immune an immune response against a selected target. In certain embodiments, a CoStAR of the invention comprises an extracellular binding domain that binds to a tumor associated antigen. In certain embodiments, a CoStAR of the invention comprises an extracellular binding domain that binds to a tumor microenvironment associated antigen. In certain embodiments, the CoStAR comprises two or more extracellular binding domains. In certain embodiments, the extracellular binding domain binds to CD70, CD146, FOLR1, carcinoembryonic antigen (CEA), 5T4, melanotransferrin (CD228), Her2, EGFR, GPC3, melanoma-associated chondroitin sulphate proteoglycan (MCSP/CSPG4), CD71, EPCAM, SM5-1, folate receptor or CA125, PDL-1, CD155 PD-1, mesothelin, or a tumor specific peptide (p)-major histocompatability (MHC) complex, or a tumor specific pMHC complex antigen specific single chain T-cell receptor (scTCR), or transferrin, or an antibody or antigen binding protein.

In certain embodiments wherein the binding domain binds to PDL1, the CoStAR comprises SEQ ID NO:6. In certain embodiments wherein the extracellular binding domain binds to CEA, the CoStAR comprises SEQ ID NO:5. In certain embodiments wherein the extracellular binding domain binds to FOLR1, the CoStAR comprises SEQ ID NO:4. In certain embodiments wherein the binding domain binds to CD155, CD112 or CD113, the CoStAR comprises SEQ ID NO:7.

According to the invention, an extracellular binding domain can comprise, without limit, an scFv, a peptide, an antigen binding portion of an antibody, an antibody heavy-chain, a ligand of a target receptor or a ligand binding portion of a receptor.

In certain embodiments, a CoStAR of the invention comprises a CD3ζ signaling domain, for example located at the C-terminus.

In certain embodiments, a CoStAR of the invention comprises an N-terminal signal peptide.

In an aspect of the invention, there is provided a nucleic acid which encodes a CoStAR of the invention. The nucleic acid may be optimized, for example be codon optimized for expression in a host cell. In a non-limiting embodiment, the nucleic acid is codon optimized for expression in a human cell.

In an aspect of the invention, there is provided vector which encodes and is capable of expressing a CoStAR of the invention.

In an aspect of the invention, there is provided a cell which expresses a CoStAR of the invention. In certain embodiments, the cell expresses a CoStAR that binds to FOLR1. In other embodiments, the cell expresses a CoStAR that binds to CA125.

In an aspect, the invention provides a cell which expresses a CoStAR that is specific for FOLR1 wherein the cell is activated when the CoStAR reacts with or binds to FOLR1 on the surface of a target cell but not when the CoStAR binds to or reacts with soluble FOLR1. In an embodiment, the cell is a T cell or a TIL that expresses a T cell receptor or other receptor specific for a tumor associated antigen expressed by the target cell.

In other embodiments, the cell expresses a CoStAR specific for PDL1. In other embodiments, the cell expresses a CoStAR specific for CEA. In certain embodiments, the cell expresses two or more CoStARs of the invention. In a particular embodiment, the cell expresses a CoStAR that binds to FOLR1 and a CoStAR that binds to CA125, such as but not limited to anti-FOLR1.CD28.CD40 and anti-CA125.41BB.CD40. In a particular embodiment, the cell expresses a CoStAR which binds to FOLR1 and a CoStAR which binds to PDL1, such as but not limited to anti-FOLR1.CD28.CD40 and PD1.CD28.CD40.

In certain embodiments, a cell engineered to express a CoStAR of the invention comprises an alpha-beta T cell, gamma-delta T cell, T regulatory cell, TIL, NKT cell or NK cell. In certain embodiments, a cell engineered to express a CoStAR of the invention coexpresses a chimeric antigen receptor (CAR) or a T cell receptor (TCR).

In an aspect, the invention provides a method of making the cell which expresses a CoStAR which comprises transducing or transfecting a cell with a vector which encodes and is capable of expressing a CoStAR of the invention.

The invention provides a method for preparing a population of cells that express a CoStAR of the invention by transducing or transfecting cells, detecting expression of the CoStAR and enriching, expanding, and/or selecting cells that express the CoStAR.

In an aspect, the invention provides a method of treating a disease in a subject by administering a population of cells which express a CoStAR of the invention.

In an aspect, the invention provides a method of preparing TIL comprising disaggregating a resected tumor to obtain a refined resected tumor product, performing a first expansion by culturing the refined resected tumor product in a cell culture medium comprising IL-2 to produce a first population of TILs, performing a second expansion by culturing the first population of TILs with additional IL-2, OKT-3, and antigen presenting cells (APCs), to produce a second population of TILs; and harvesting and/or cryopreserving the second population of TILs, wherein the method comprises transfecting or transducing the TILs to express a CoStAR of the invention. In an embodiment, the tumor comprises an ovarian tumor. In an embodiment, the tumor comprises a renal tumor. In an embodiment, the tumor comprises a lung tumor.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U. S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIGS. 2A-2G—Genomic organisation of potential CoStAR configurations—The CoStAR consists of an antigen binding domain, an optional spacer domain and a costimulatory domain as shown in figure and described in claims. The CoStAR may be expressed as shown; alone from a promoter with the CoStAR consisting of a single (FIG. 2A) or fusion (FIG. 2B) costimulatory receptor; (FIG. 2C) may be expressed with an epitope tag (e.g. His tag, DYKDDDDK (SEQ ID NO: 124) etc.) at the N or C-terminus to enable direct staining of the CoStAR; (FIG. 2D) along with a marker gene separated using a 2A cleavage sequence or internal ribosomal entry site (IRES); (FIG. 2E) along with a marker gene which is expressed from a second promoter; (FIG. 2F) along with a protein of interest such as a chimeric antigen receptor or T-cell receptor separated using a 2A cleavage sequence or internal ribosomal entry site (IRES); (FIG. 2G) along with a protein of interest such as a chimeric antigen receptor or T-cell receptor which is expressed from a second promoter. It would be clear to an individual with sufficient knowledge that the CoStAR and marker gene/chimeric antigen receptor/T-cell receptor/other protein of interest could be expressed in either orientation or 3' (3-prime) or 5' (5-prime) to one another.

FIGS. 3A-3E—Functional activity of CoStAR in T-cells in response to LS174T and LoVo tumor presented antigen. Normal donor T-cell populations from donor 1 (FIGS. 3A & 3D), donor 2 (FIG. 3B) and donor 3 (FIGS. 3C & 3E) were lentivirally engineered to express a CoStAR which targets carcinoembryonic antigen and magnetically sorted to enrich for the transgene using CD34 magnetic selection. T-cells were mixed with wild-type un-engineered CEA+ tumor cells (Non-activating tumor) or CEA+ tumor cells engineered to express a cell surface anchored anti-CD3 single chain antibody fragment (Activating tumor) at the indicated effector to target ratios and IL-2 measured in the supernatant by ELISA. Data obtained using LS174T cells (A, B & C) and LoVo (D & E).

(FIG. 12A) In the absence of stimulation by tumor and IL-2 cells declined in number as would be expected. (FIG. 12B) In the absence of stimulation but presence of IL-2 there was a more apparent survival of the cells, but no specific growth. (FIG. 12C) In the presence of tumor, but absence of IL-2 mock cells did not show specific survival. MFE23.CD28 CoStAR mediated an apparent doubling in expansion over the first four days followed by decline. MFE23.CD28.CD40 mediated a greater expansion up to day 7 followed by a steady decline. (FIG. 12D) Under the same conditions but in the presence of IL-2 both mock and MFE23.CD28 transduced cells demonstrated a 20-fold expansion over 18 days, whereas MFE23.CD28.CD40 cells expanded by over 60-fold. Thus CD28.CD40 based receptors demonstrate superior expansion and survival under conditions of stimulation both in the presence and absence of exogenous IL-2.

FIGS. 13A-13M depict cytokine production by mock, MFE23.CD28 or MFE23.CD28.CD40 engineered T-cells. Bead array analysis was performed on supernatants obtained from T-cell/tumor cocultures. Engineered T-cells were incubated at a 1:1 effector:target ratio with LoVo-OKT3 cells for 24 hours and supernatant collected. Conditioned supernatant was also collected from an equal number of T-cells alone, or LoVo-OKT3 cells alone. Cytokine production was analysed using a Legendplex™ Human TH1/TH2 cytokine panel (Biolegend). (FIG. 13A) IL-2; (FIG. 13B) IFN-γ; (FIG. 13C) TNFα; (FIG. 13D) IL-4; (FIG. 13E) IL-5; (FIG. 13F) IL-13; (FIG. 13G) IL-17A; (FIG. 13H) IL-17F; (FIG. 13I) IL-22; (FIG. 13J) IL-6; (FIG. 13K) IL-10; (FIG. 13L) IL-9; (FIG. 13M) IL-21. Cytokines were either very low or undetectable in media from T-cells or tumor alone. When cocultured with tumor, cytokine production was enhanced. MFE23.CD28 enhanced production of IL-2, IL-5, IL-17A/17F, IL-10, IL-9 and IL-21 compared to mock. MFE23.CD28.CD40 also enhanced production of TNFα, IL-13 and IL-22. MFE23.CD28.CD40 and further enhanced the production of a number of cytokines greater than that provided by MFE23.CD28 (IL-2, IL-9 and IL-17F), as well as reducing the production of some cytokines below the levels seen with MFE23.CD28 (IL-5 and IL-10). Together this data demonstrates that addition of CD40 to CD28-based costimulatory receptors enhances and/or modulates their specific activity with respect to cytokine production.

FIGS. 14A-14M depict an analysis of chemokines using a Legendplex™ Human Pro inflammatory chemokine panel. (FIG. 14A) IL-8 (CXCL8); (FIG. 14B) IP-10 (CSCL10); (FIG. 14C) Eotaxin (CCL11); (FIG. 14D) TARC (CCL17); (FIG. 14E) MCP-1 (CCL2); (FIG. 14F) RANTES (CCL5); (FIG. 14G) MIP-1α (CCL3) (FIG. 14H) MIG (CXCL9) (FIG. 14I) ENA-78 (CXCL5) (FIG. 14J) MIP-3α (CCL20) (FIG. 14K) GROα (CXCL1) (FIG. 14L) I-TAC (CXCL11) (FIG. 14M) MEP-1β (CCL4). Chemokines were either very low or undetectable in media from T-cells alone. When cocultured with tumor, chemokine production was enhanced. MFE23.CD28 enhanced production of CXCL5, CXCL10, CXCL11, CCL17 and CCL20 compared to mock. MFE23.CD28.CD40 also enhanced production of CCL2, CXCL1 and CXCL9. MFE23.CD28.CD40 further enhanced the production of a number of cytokines greater than that provided by MFE23.CD28 (CXCL1, CXCL9, CXCL10, CXCL11, CCL17, CCL2, CXCL9, CCL5 and CCL20), as well as reducing the production of some cytokines below the levels seen with MFE23.CD28 (CCL4). Together this data demonstrates that addition of CD40 to CD28-based costimulatory receptors enhances and/or modulates their specific activity with respect to chemokine production.

FIGS. 17A-17C depict enhancement of effector functions. A FolR targeting CoStAR enhanced CD137 expression from ~20% to ~50% (FIG. 17A), TNFα production from 10% to 15% (FIG. 17B) and IL-2 production from 2% to 5%. (FIG. 17C) in response to FolR+ tumor digest.

FIGS. 21A-21C depict increased amount of IL-2 in PD-1 fusion CD40 CoStAR compared to mock transduced T cells. Donor cells activated with Dynabeads and transduced with CTP188, CTP189, CTP194 (FIG. 21A) or mock-transduced were enriched for CD34 (transduction marker) expression (FIG. 21B), expanded following the rapid expansion protocol (REP) and frozen for subsequent experiments. After thaw, cells were rested for 3-4 days in complete RPMI supplemented with IL-2. The viability and absolute count were assessed after overnight IL-2 starvation using DRAQ-7 (1:200) by flow cytometry (Novocyte) and data were analysed using the NovoExpress 1.5.0 software. Transduced T cells were cocultured in absence of IL-2 with LoVo (CCL-229™ from ATCC) or LoVo.OKT3.GFP tumor cells at 8:1 effector to target ratio. After 24 hours, supernatants were collected and frozen. LoVo and LoVo.OKT3.GFP naturally express CEA and PD-L1 on their surface, conferring signal 2 through the CoStAR alone (LoVo) or associated with signal 1 (LoVo.OKT3.GFP) to the transduced T cells. Cocultures were performed in triplicates and corresponding negative (T cells alone, tumor cells alone) and positive (PMA+ionomycin) controls were included in the experiment. After thaw, secreted IL-2 and IFN-γ were detected by ELISA and the absorbance was measured using the FLUOstar Omega microplate reader and subsequently analysed with the Omega MARS 3.42 R5 software. Each dot represents the mean of triplicates for one donor. Note that negative controls (T cells alone, tumor cells alone) were all below the detection range (#) (FIG. 21C).

(FIG. 24A) Healthy donor T cells were activated with Dynabeads and transduced with CTP190, CTP191, CTP192, CTP193, CTP194 or mock transduced. The correlation between the expression of CD34 marker gene and MFE23 scFv on the surface of transduced T cells from one subject (lower left panel), was assessed 8 days following transduction by flow cytometry. Cells were then enriched for CD34 marker expression, expanded following the rapid expansion protocol (REP) and frozen for subsequent experiments. After thaw, cells were rested for 3-4 days in complete RPMI supplemented with IL-2 and their transduction rate was determined looking at the CD34 marker gene expression (lower right panel). (FIG. 24B) The viability and absolute count were assessed after overnight IL-2 starvation using DRAQ-7 (1:200) by flow cytometry (Novocyte) and data were analysed using the NovoExpress 1.5.0 software. Transduced T cells were cocultured in absence of IL-2 with LoVo (CCL-229™ from ATCC) or LoVo.OKT3.GFP tumor cells at 8:1 effector to target ratio. After 24 hours, supernatants were collected and frozen. LoVo and LoVo.OKT3.GFP naturally express CEA and PD-L1 on their surface, conferring signal 2 through the CoStAR alone (LoVo) or associated with signal 1 (LoVo.OKT3.GFP) to the transduced T cells. Cocultures were performed in triplicates and corresponding negative (T cells alone, tumor cells alone) and positive (PMA+ionomycin) controls were included in the experiment. After thaw, secreted IL-2 and IFN-γ were detected by ELISA and the absorbance was measured using the FLUOstar Omega microplate reader and subsequently analysed with the Omega MARS 3.42 R5 software. Each dot represents the mean of triplicates for one donor. Note that negative controls (T cells alone, tumor cells alone) were all below the detection range (#)(FIG. 24B).

(FIG. 27A) Cells of three donors were activated with Dynabeads and transduced with CTP194, CTP195, CTP196, CTP197, CTP198, CTP199, CTP200 or mock transduced. Cells were enriched for CD34 marker expression, expanded following the rapid expansion protocol (REP) and frozen for subsequent experiments. After thaw, cells were rested for 3-4 days in complete RPMI supplemented with IL-2 and their transduction rate was determined looking at the CD34 marker gene expression (A, lower panel). (FIG. 27B) The viability and absolute count were assessed after overnight IL-2 starvation using DRAQ-7 (1:200) by flow cytometry (Novocyte) and data were analysed using the NovoExpress 1.5.0 software. Transduced T cells were cocultured in absence of IL-2 with LoVo (CCL-229™ from ATCC) or LoVo.OKT3.GFP tumor cells at 8:1 effector to target ratio. After 24 hours, supernatants were collected and frozen. LoVo and LoVo.OKT3.GFP naturally express CEA and PD-L1 on their surface, conferring signal 2 through the CoStAR alone (LoVo) or associated with signal 1 (LoVo.OKT3.GFP) to the transduced T cells. Cocultures were performed in triplicates and corresponding negative (T cells alone, tumor cells alone) and positive (PMA+ ionomycin) controls were included in the experiment. After thaw, secreted IL-2 and IFN-γ were detected by ELISA and the absorbance was measured using the FLUOstar Omega microplate reader and subsequently analysed with the Omega MARS 3.42 R5 software. Each dot represents the mean of triplicates for one donor. Note that negative controls (T cells alone, tumor cells alone) were all below the detection range (#).

(lower panels) T cells were assessed by flow cytometry and shown as mean+/−SD of n≤3 donors.

Figure 30A:
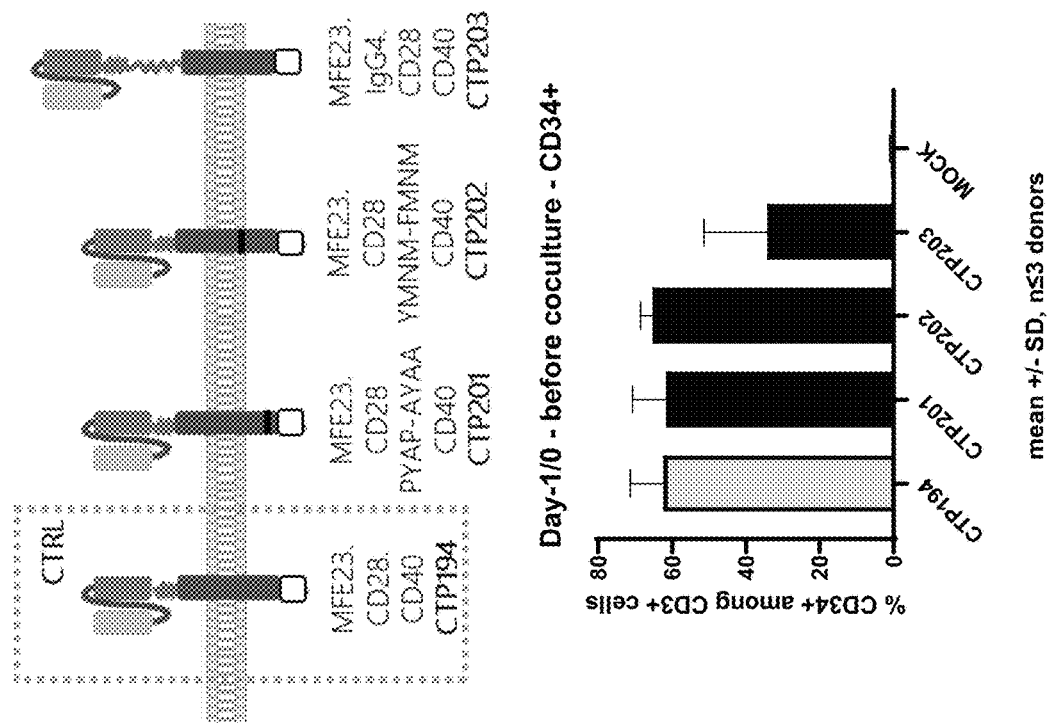
Figure 30B:
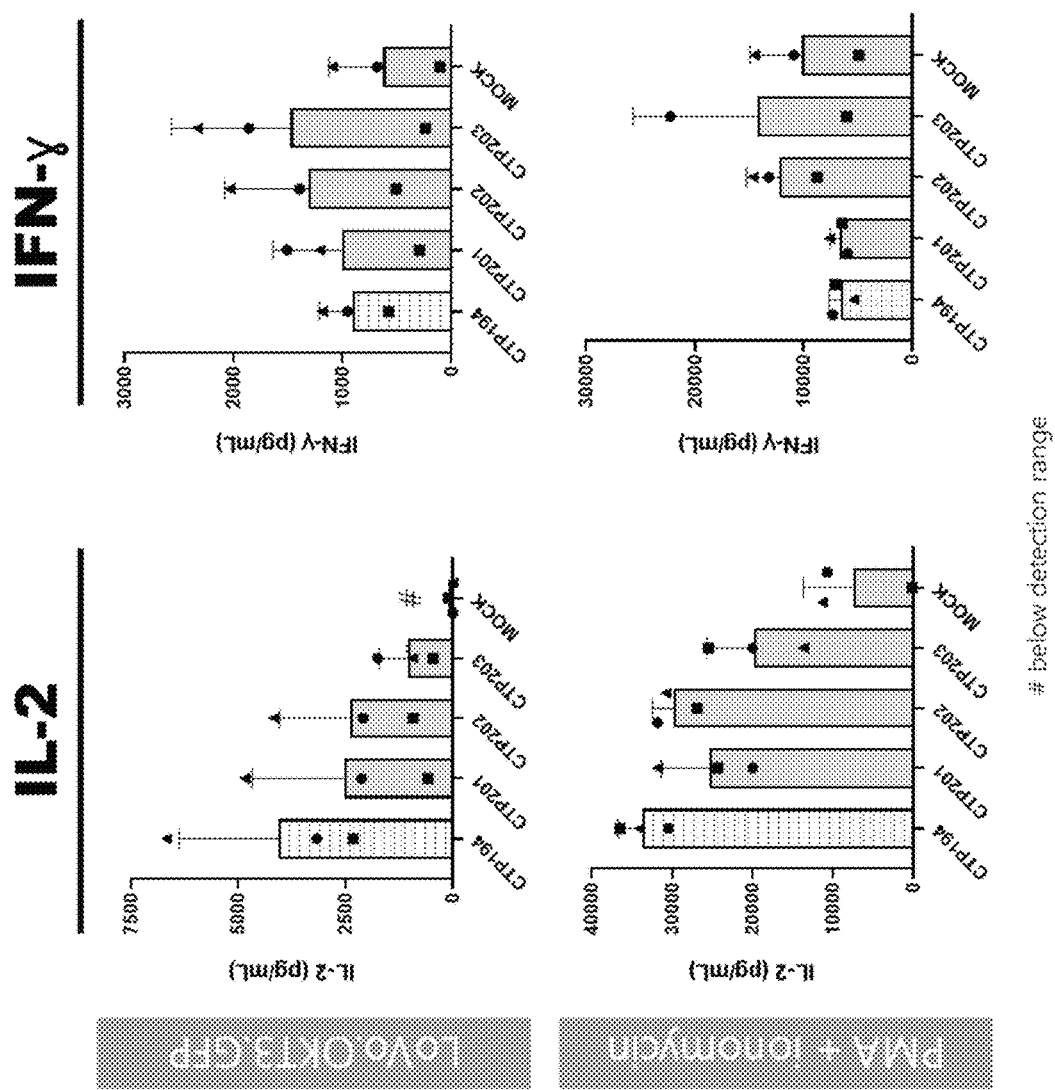

FIGS. 30A-30B depict CD28 mutants and IgG4 CD40 CoStAR transduced T cells secreting higher amount of IL-2 and IFN-γ following activation compared to mock transduced T cells. (FIG. 30A) Cells of three donors were activated with Dynabeads and transduced with CTP194, CTP201, CTP202, CTP203 or mock transduced. Cells were enriched for CD34 marker expression, expanded following the rapid expansion protocol (REP) and frozen for subsequent experiments. After thaw, cells were rested for 3-4 days in complete RPMI supplemented with IL-2 and their transduction rate was determined looking at the CD34 marker gene expression (A, lower panel). (FIG. 30B) The viability and absolute count were assessed after overnight IL-2 starvation using DRAQ-7 (1:200) by flow cytometry (Novocyte) and data were analysed using the NovoExpress 1.5.0 software. Transduced T cells were cocultured in absence of IL-2 with LoVo (CCL-229™ from ATCC) or LoVo.OKT3.GFP tumor cells at 8:1 effector to target ratio. After 24 hours, supernatants were collected and frozen. LoVo and LoVo.OKT3.GFP naturally express CEA and PD-L1 on their surface, conferring signal 2 through the CoStAR alone (LoVo) or associated with signal 1 (LoVo.OKT3.GFP) to the transduced T cells. Cocultures were performed in triplicates and corresponding negative (T cells alone, tumor cells alone) and positive (PMA+ionomycin) controls were included in the experiment. After thaw, secreted IL-2 and IFN-γ were detected by ELISA and the absorbance was measured using the FLUOstar Omega microplate reader and subsequently analysed with the Omega MARS 3.42 R5 software. Each dot represents the mean of triplicates for one donor. Note that negative controls (T cells alone, tumor cells alone) were all below the detection range (#).

Figure 31:
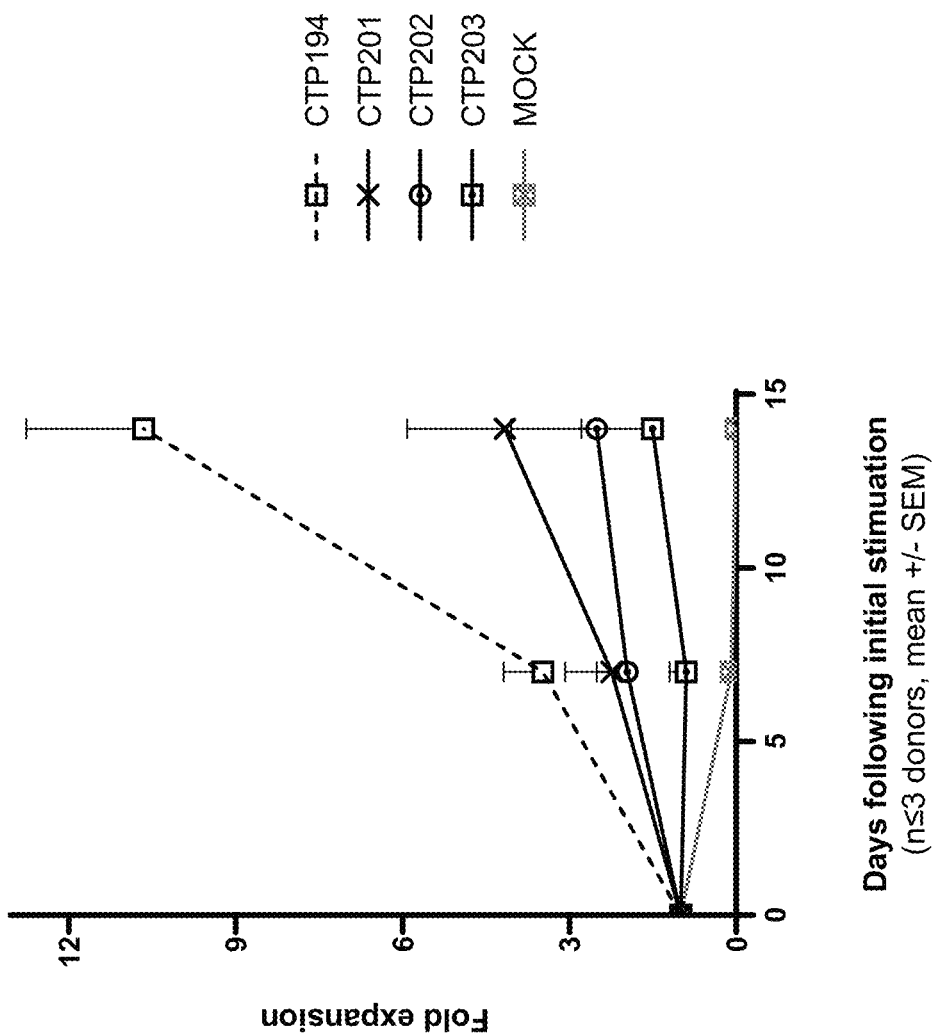

FIG. 31 depicts the critical role of CD28 PYAP and YMNM motifs in the long term survival and proliferation of CD40 CoStAR transduced T cells when cocultured with LoVo.OKT3. Cells of three donors were activated with Dynabeads and transduced with CTP194, CTP201, CTP202, CTP203 or mock transduced. Cells were enriched for CD34 marker expression, expanded following the rapid expansion protocol (REP) and frozen for subsequent experiments. After thaw, cells were rested for 3-4 days in complete RPMI supplemented with IL-2. The viability and absolute count were assessed after overnight IL-2 starvation using DRAQ-7 (1:200) by flow cytometry (Novocyte) and data were analysed using the NovoExpress 1.5.0 software. Transduced T cells were cocultured in absence of IL-2 for 6-8 days with LoVo.OKT3.GFP tumor cells at 8:1 effector to target ratio, changing half of the culture medium every 3-4 days. LoVo.OKT3.GFP naturally expresses CEA and PD-L1 on their surface, conferring both signal 2 and signal 1 (OKT3) to the transduced T cells. After 6-8 days, the viability and absolute count were assessed, and live T cells were rechallenged for an additional week with fresh LoVo.OKT3.GFP tumor cells as described above. At the end of the long-term coculture, the viability and absolute count were measured, and the fold expansion was calculated. Data shown as mean+/−SEM of n≤3 donors analysed in triplicates.

Figure 32B:
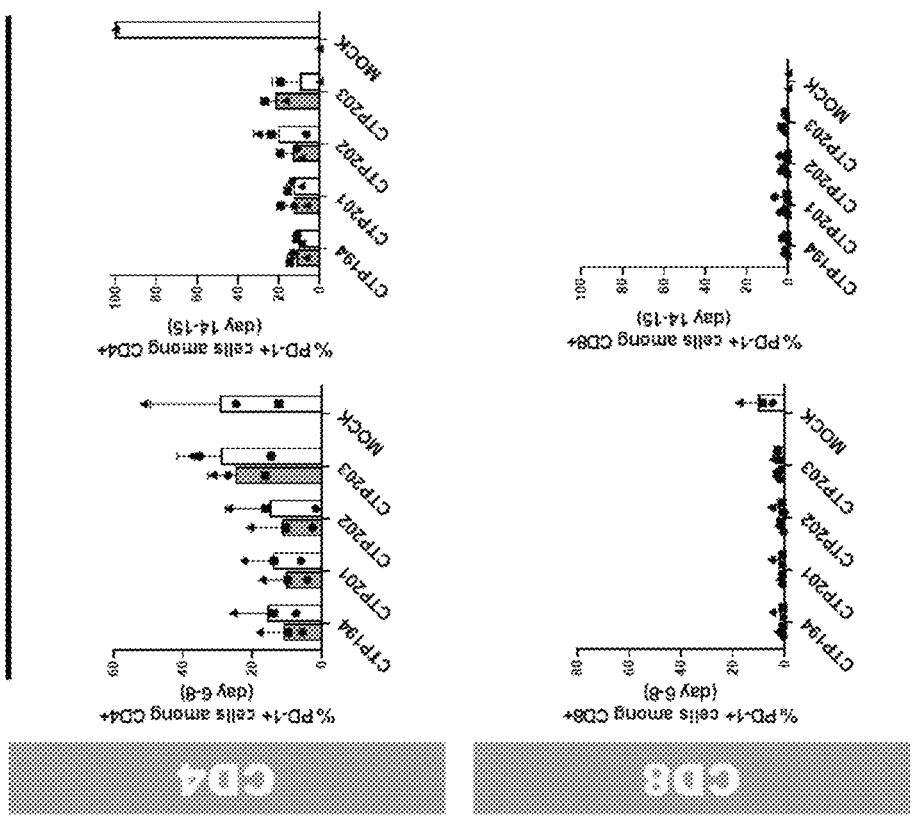
Figure 32A:
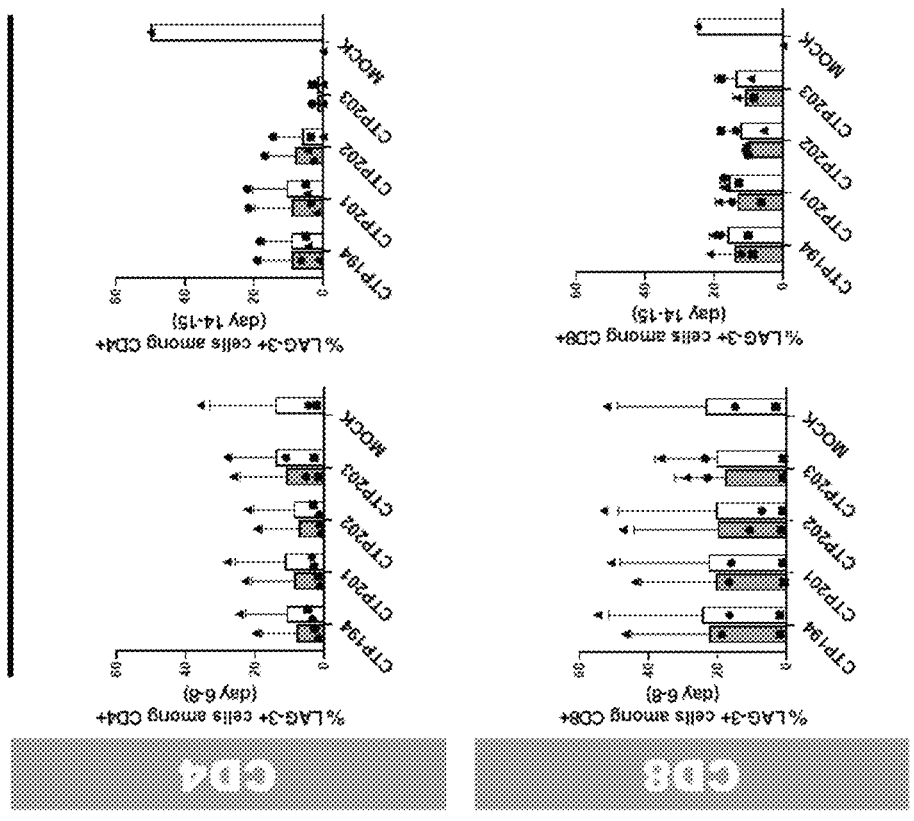
Figure 32C:
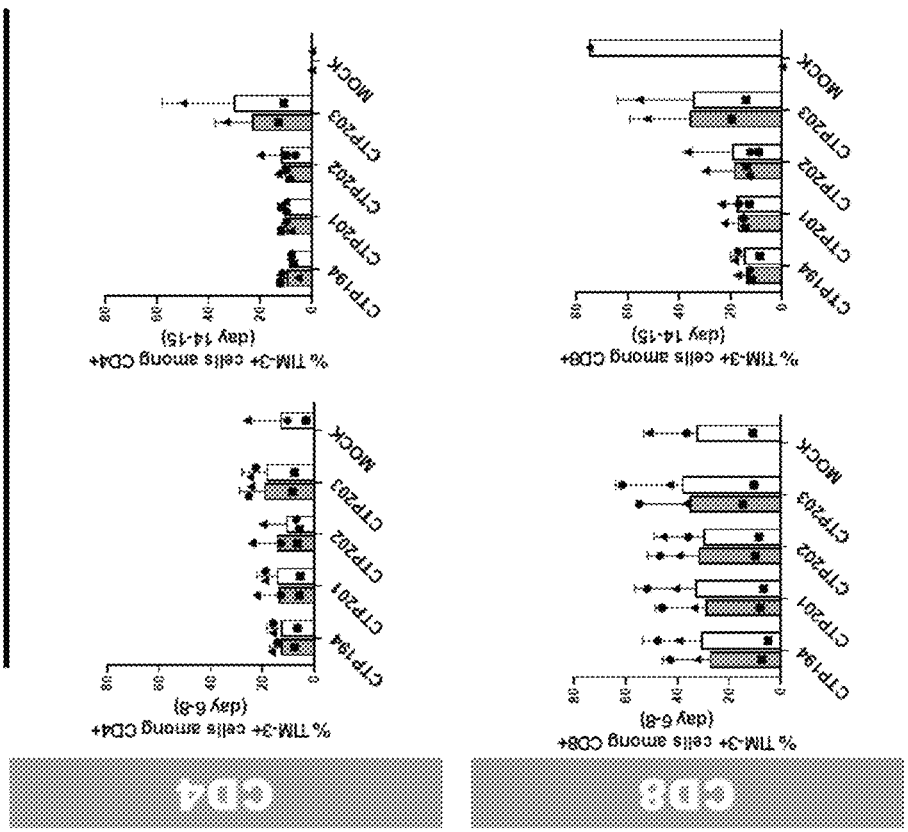

FIGS. 32A-32C depict exhaustion profiles of transduced T cells with CD28 mutant CD40 CoStAR constructs after tumor challenge. Cells of three donors were activated with Dynabeads and transduced (spinoculation, MOI 5) with CTP194, CTP201, CTP202, CTP203 or mock transduced. Cells were enriched for CD34 marker expression, expanded following the rapid expansion protocol (REP) and frozen for subsequent experiments. After thaw, cells were rested for 3-4 days in complete RPMI supplemented with IL-2. The viability and absolute count were assessed after overnight IL-2 starvation using DRAQ-7 (1:200) by flow cytometry (Novocyte) and data were analysed using the NovoExpress 1.5.0 software. Transduced T cells were cocultured in absence of IL-2 for 6-8 days with LoVo.OKT3.GFP tumor cells at 8:1 effector to target ratio, changing half of the culture medium every 3-4 days. LoVo.OKT3.GFP naturally expresses CEA and PD-L1 on their surface, conferring both signal 2 and signal 1 (OKT3) to the transduced T cells. After 6-8 days, the viability and the absolute count were assessed, and live T cells were rechallenged for an additional week with fresh LoVo.OKT3.GFP tumor cells as described above. Exhaustion profiles (LAG-3 (FIG. 32A), PD-1 (FIG. 32B), TIM-3 (FIG. 32C)) of transduced (CD34+ (grey)) or non-transduced (CD34− (white)) CD4 (upper panels) and CD8 (lower panels) T cells were assessed by flow cytometry and shown as mean+/−SD of n≤3 donors.

Figure 33:
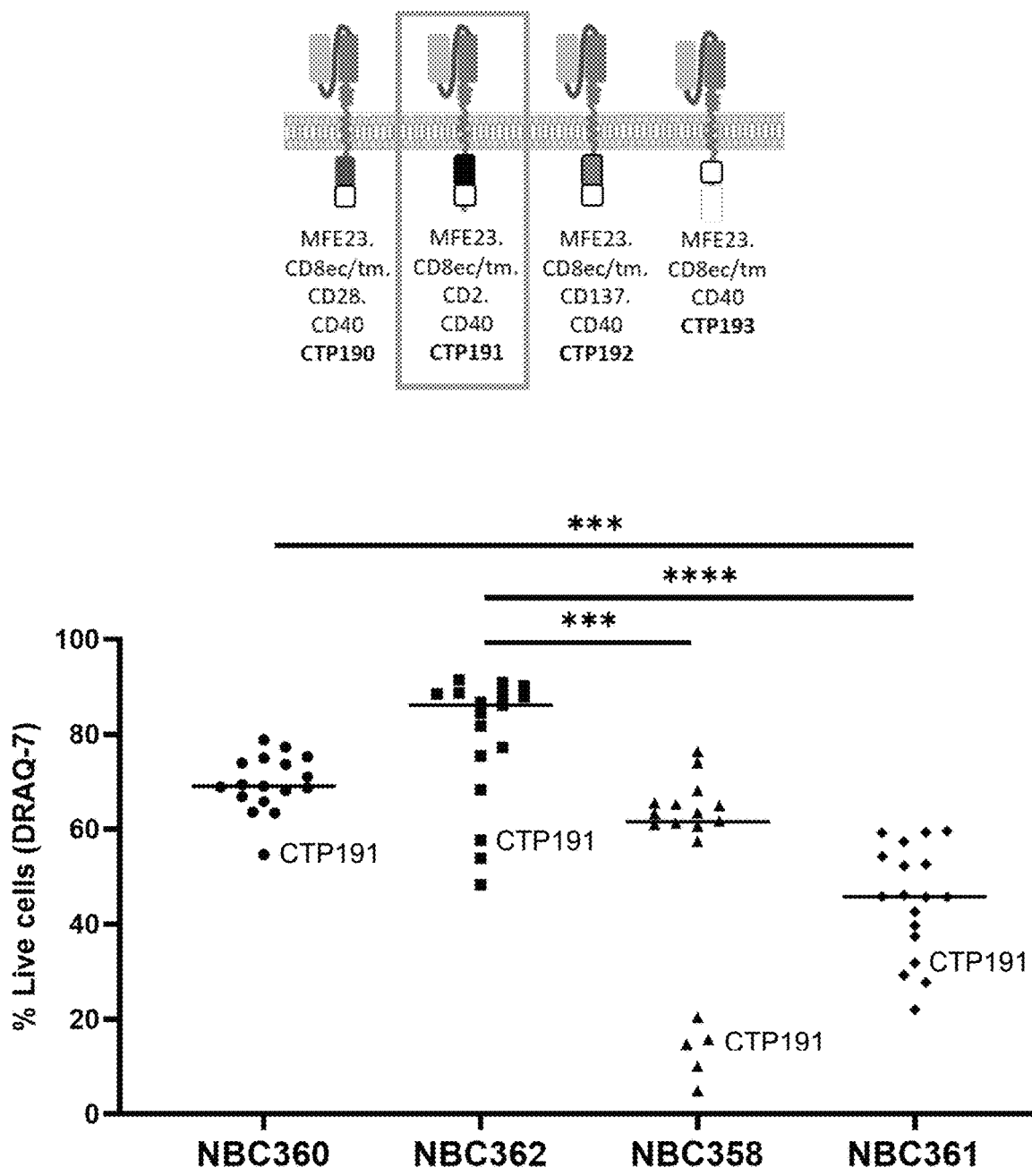

FIG. 33 depicts generation of transduced T cells from four healthy donors following CD34 enrichment and expansion. T cells of 4 healthy donors (NBC360, NBC362, NBC358, NBC361) were activated with Dynabeads and transduced with CTP188, CTP189, CTP190, CTP191, CTP192, CTP193, CTP194, CTP195, CTP196, CTP197, CTP198, CTP199, CTP200, CTP201, CTP202, CTP203, CTP204 or mock transduced. Cells were then magnetically enriched for their CD34 expression and expanded following the rapid expansion protocol (REP). Viability of each sample 10-11 days after REP was assessed by flow cytometry (Novocyte). Data were analysed with NovoExpress 1.5.0 software. Each dot within the same donor represents a different construct.

FIGS. 34A-34D depict expression of activation markers and cytokine production of non-transduced (NTD) or anti-FOLR1 CoStAR modified T cells (CoStAR) from 3 healthy donors co-cultured overnight with Ba/F3 targets. Expression of activation markers 4-1BB and CD69 (FIG. 34A) and production of IL-2 and IFNγ (FIG. 34B) was determined. CoStAR engagement enhances cytokine secretion. (FIG. 34C) Non-transduced and CoStAR cytotoxicity is comparable. Tumor counts of Ba/F3 targets were assessed by flow cytometry after overnight coculture with non-transduced (NTD) and CoStAR T cells. (FIG. 34D) CoStAR engagement enhances both CD4 and CD8 T cell proliferation. NTD and CoStAR T cell counts as well as proliferation were assessed by flow cytometry after overnight or 5-day coculture with Ba/F3 targets.

FIGS. 35A-35D depicts expression of activation markers of anti-FOLR1 CoStAR modified T cells (CoStAR) from 3 healthy donors preincubated with soluble folate receptor (sFOLR1) followed by co-culture overnight with Ba/F3 targets. X-axis shows sFOLR1 as ng/mL. In each group, bars 1-4 are non-transduced, bars 5-8 are CoStAR transduced. Soluble FOLR1 does not impact upregulation of activation markers on CoStAR T cells. Expression of activation markers 4-1BB (FIG. 35A) and CD69 (FIG. 35B) was determined. (FIG. 35C) sFOLR1 does not impact cytoxicity of CoStAR T cells. Tumor counts of Ba/F3 targets were assessed by flow cytometry after overnight coculture with non-transduced (NTD) or CoStAR transduced T cells preincubated with increasing concentrations of sFOLR. (FIG. 35D) sFOLR1 does not impact cytokine secretion. IL-2 production is shown in anti-FOLR1 CoStAR modified T cells preincubated with soluble folate receptor (sFOLR) followed by co-culture overnight with Ba/F3 targets.

FIGS. 36A-36D depict FOLR1 CoStAR requires signal 1 to function. (FIGS. 36A and 36B) Expression of activation markers (FIG. 36A) and cytokine production (FIG. 36B) respectively, from non-transduced (NTD) and anti-FOLR1 CoStAR modified T cells (CoStAR) from 3 healthy donors co-cultured overnight with Ba/F3 targets. (FIG. 36A) There is minimal upregulation of activation markers with signal 2 only. (FIG. 36B) No cytokine secretion was observed with signal 2 only. (FIG. 36C) Tumor counts of Ba/F3 targets assessed by flow cytometry after overnight coculture with NTD and CoStAR T cells. No cytoxicity was observed with signal 2 only. (FIG. 36D) NTD and CoStAR T cell counts were assessed by flow cytometry after overnight or 5-day coculture with Ba/F3 targets. Proliferation was not observed with signal 2 only.

Figure 37A:
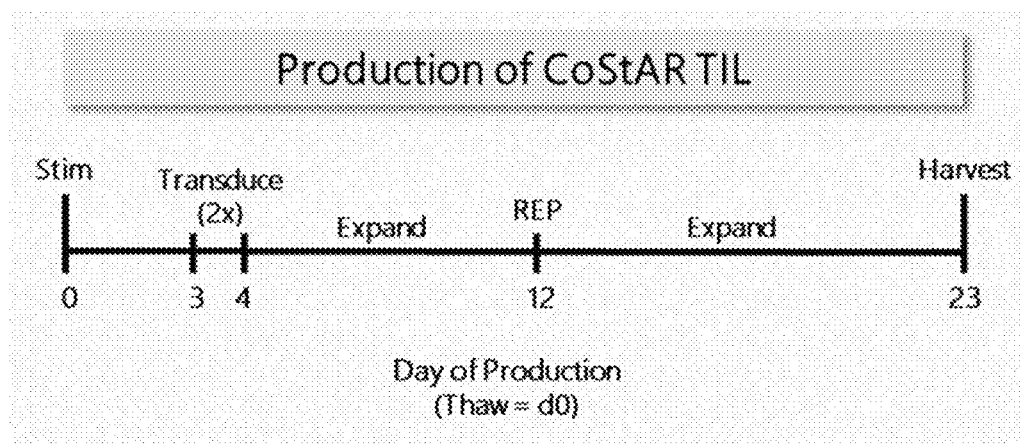
Figure 37B:
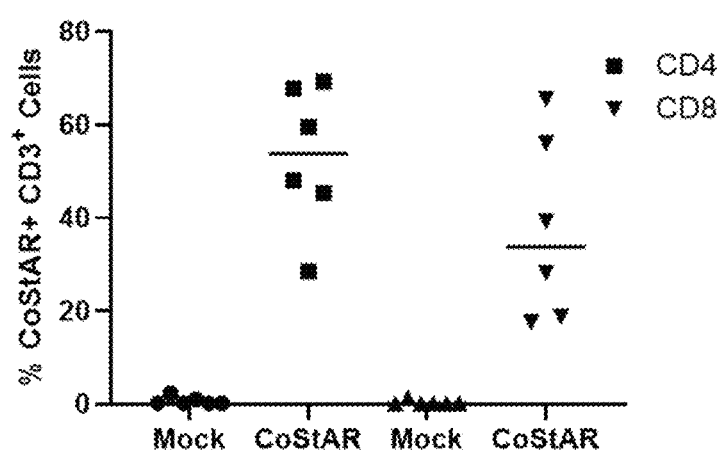
Figure 37C:
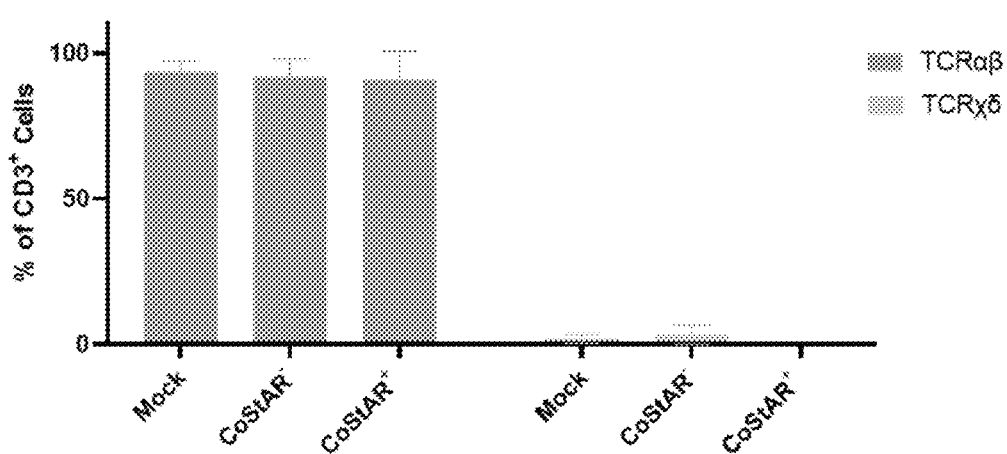

FIGS. 37A-37C depict TIL function with CoStAR in ovarian cancer. (FIG. 37A) TIL from 6 ovarian tumors were liberated by digestion and cultured in 3000U IL-2. Transduction with a $3^{rd}$ generation lentiviral vector encoding a CoStAR molecule with and scFv targeting human FOLR1, linker, full length CD28 fused to truncated CD40 cytoplasmic domain was carried out at an MOI of 5, both 48 h and 72 h after tumor digestion. Rapid expansion protocol was carried out on days 12-23. (FIG. 37B) Flow cytometric analysis was used to determine the frequency of CD4 and CD8 T-cells expressing the CoStAR molecule using an anti-idiotype antibody for surface detection. (FIG. 37C) Flow cytometric analysis was used to determine the frequency of cells expressing TCRαβ and TCRγδ by flow cytometric surface staining. Mock—untransduced cells. CoStAR$^{-/+}$: cells negative or positive for CoStAR molecule in the treated cell population as determined by flow cytometry gating.

Figure 38A:
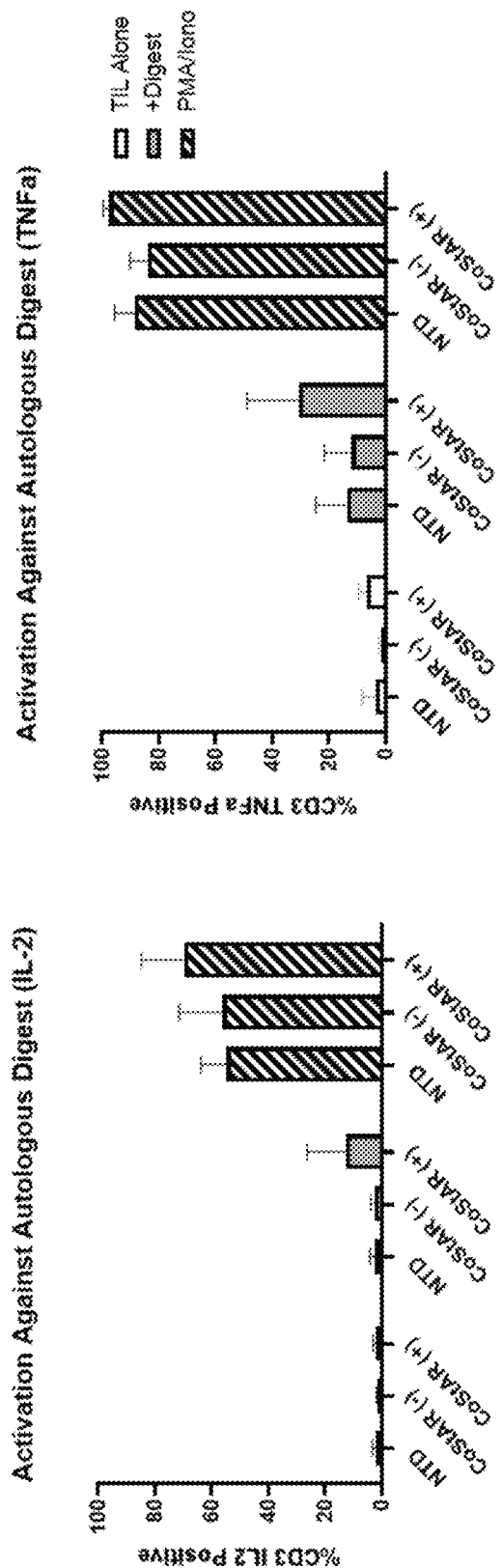
Figure 38B:
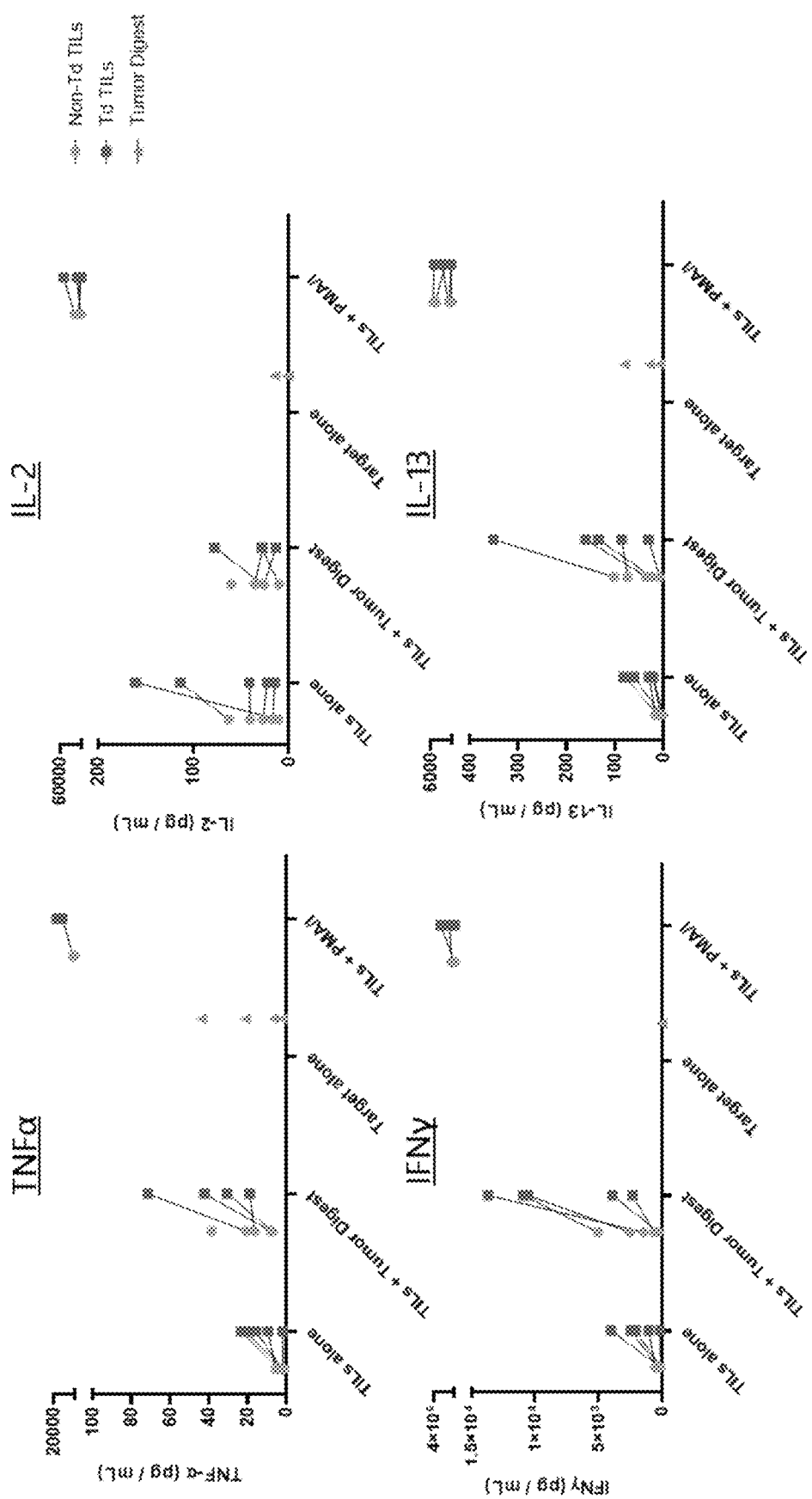

FIGS. 38A-38B depict TIL function with CoStAR in ovarian cancer. (FIG. 38A) CoStAR modified TIL from 5 ovarian tumors were co-cultured with autologous digest overnight in the presence of brefeldin A. The frequency of cells expressing IL-2 or TNFα was assessed the following day by flow cytometry. The frequency of TIL reacting to autologous digest is enhanced by the CoStAR molecule. NTD: untransduced cells. CoStAR$^{-/+}$: cells negative or positive for CoStAR molecule in the treated cell population as determined by flow cytometry gating. (FIG. 38B) CoStAR modified TIL from 5 ovarian tumors were co-cultured with autologous digest and supernatant assessed for cytokine release. CoStAR modified cells had increased effector functions as demonstrated by increased IFNγ, TNFα and IL-13 release. Maximal levels of these molecules was similar in response to stimulation with PMA (Phorbol 12-myristate 13-acetate) and ionomycin.

Figure 39A:
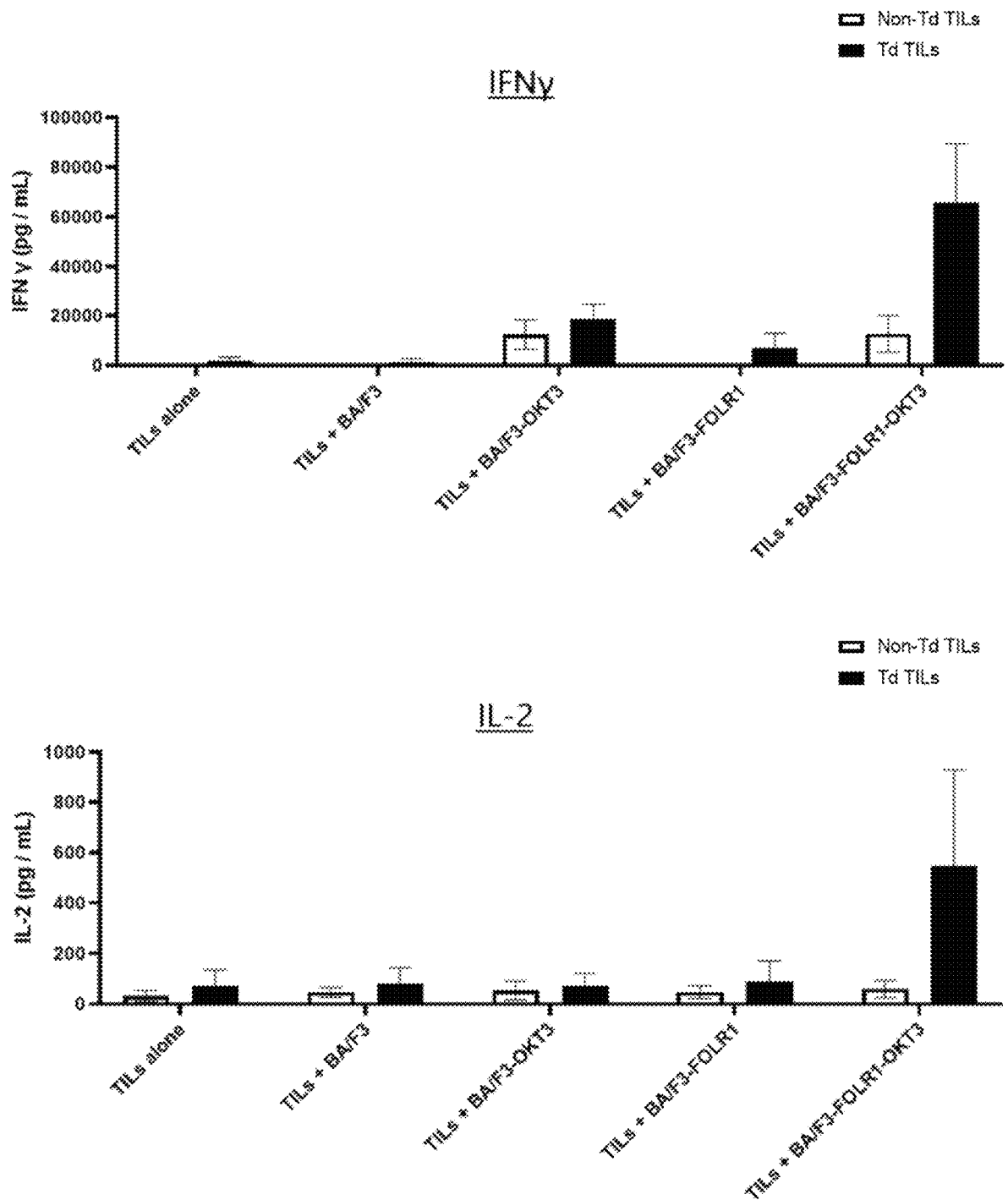
Figure 39B:
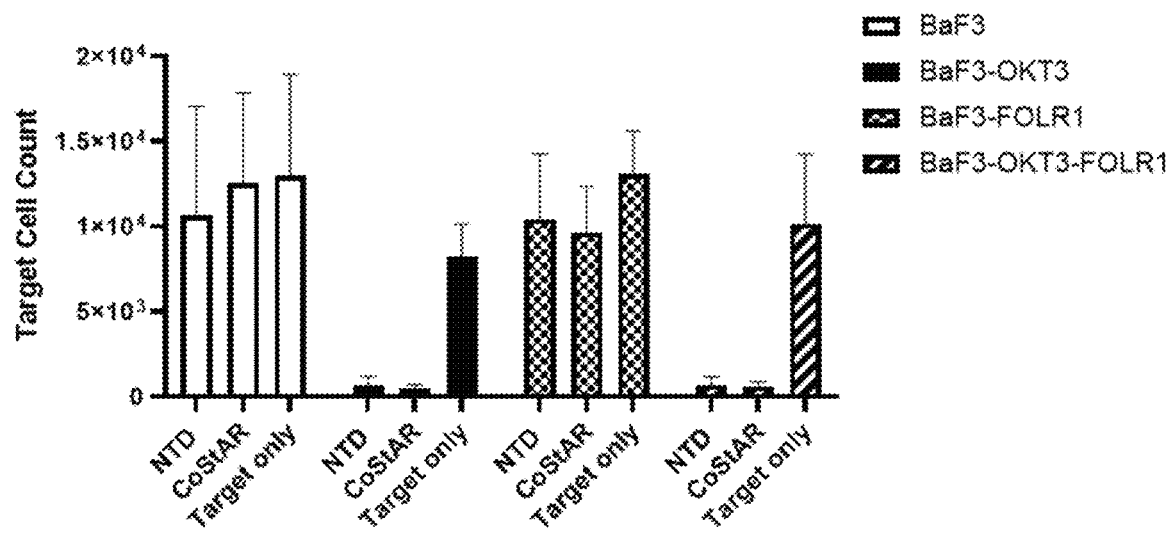
Figure 39C:
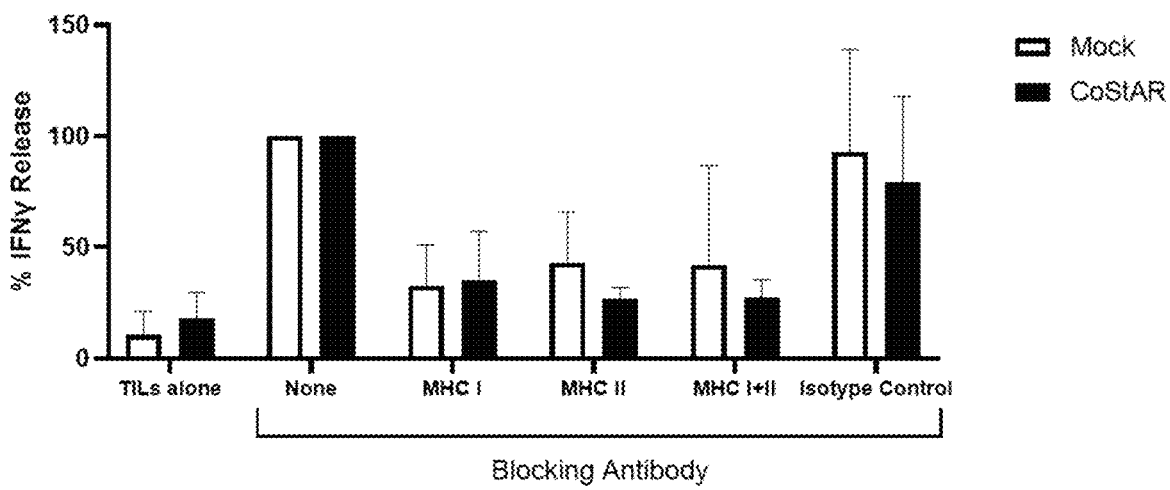

FIGS. 39A-39C depict CoStAR TIL retain robust effector functions and retain a requirement for signal 1 and 2. (FIG. 39A) CoStAR modified TIL from 5 ovarian tumors were co-cultured with BA/F3 cells or BA/F3 cells engineered to express OKT3, FOLR1 or both. Cytokine secretion of non-modified and CoStAR modified TIL was equivalent when co-cultured with non-modified BA/F3 or BA/F3 expressing OKT3 alone or FOLR1 alone. CoStAR modified TIL secreted increased levels of cytokines when co-cultured with BA/F3 modified to express both FOLR1 and OKT3. (FIG. 39B) CoStAR modified TIL from 5 ovarian tumors were co-cultured with BA/F3 cells or BA/F3 cells engineered to express OKT3, FOLR1 or both. Cytotoxicity towards BA/F3 target cells was assessed via cell counts, determined by flow cytometric analysis of mouse CD45. Non-modified and CoStAR modified cells kill cells expressing OKT3 equivalently. CoStAR modified TILs do not kill BA/F3 cells expressing FOLR1 alone. (FIG. 39C) Mock or CoStAR modified TIL from 3 ovarian cancer patients were co-cultured with autologous tumor in the presence of no blocking, MHCI, MHC II or MHC I+MHC II blocking or antibodies or isotype control. Supernatant was assessed for the level of IFNγ release. Normalized to levels of release without antibody, IFNγ levels are similarly reduced mock and CoStAR modified TIL relative to no antibody or isotype control conditions, showing that activity is led by endogenous TCR-MHC peptide interactions.

DETAILED DESCRIPTION OF THE INVENTION

The inventors have discovered that costimulatory receptors comprising a CD40 signaling domain display novel and improved activity profiles. The activity profiles can be modulated by selecting an intracellular domain of a receptor protein for joining to the CD40 signaling domain and/or by selecting elements of the CD40 signaling domains to join to the intracellular domain of a receptor protein. Provided herein are recombinant costimulatory antigen receptors (CoStARs) comprising: (i) a disease- or tumor-associated antigen binding domain, (ii) a first intracellular segment comprising an intracellular signaling domain of a receptor protein, and (iii) a second intracellular signaling domain of a CD40 receptor protein or signal transducing fragment thereof. Optionally, the CoStAR comprises an extracellular segment of a stimulatory receptor protein. In certain embodiments, the extracellular segment of the stimulatory receptor protein is capable of binding ligand. In certain embodiments, the extracellular segment of a stimulatory receptor protein is truncated and does not bind ligand. In certain embodiments the extracellular segment of the stimulatory receptor protein operates as an adjustable length spacer allowing the disease- or tumor-associated antigen binding domain to be located away from the surface of the cell in which it is expressed for example to form a more optimal immune synapse. In certain embodiments, the extracellular segment of a stimulatory receptor protein and the first intracellular segment comprise segments of the same receptor protein. In certain embodiments, the extracellular segment and the first intracellular segment comprise segments of different receptor proteins. The CoStARs comprise an intervening transmembrane domain between the disease or tumor antigen binding domain and the first intracellular domain. When an extracellular segment of a stimulatory receptor protein is present, the transmembrane domain is intervening between the extracellular segment and the first intracellular signaling domain.

As used herein, "full length protein" or "full length receptor" refers to a receptor protein, such as, for example, a CD28 receptor protein. The term "full length" encompasses receptor proteins lacking up to about 5 or up to 10 amino acids, for example 1, 2, 3, 4, 5, 6, 7, 8, 9, or 10 amino acids, at the N-terminal of the mature receptor protein once its signal peptide has been cleaved. For instance, while a specific cleavage site of a receptors N-terminal signal peptide may be defined, variability in exact point of cleavage has been observed. The term "full length" does not imply presence or absence of amino acids of the receptors N-terminal signal peptide. In one embodiment, the term "full length" (e.g. a full length CD28 or a full length CD40 intracellular domain, according to certain aspects of the invention) encompasses mature receptor proteins (e.g. CD28 according to certain aspects of the invention) lacking the N terminal signal peptide lacking up to about 5, for example 1, 2, 3, 4, 5, or up to 10 amino acids at the N-terminal of the mature receptor protein once its signal peptide has been cleaved. As mentioned above, a "full length" CD28 receptor or other receptor or tumor antigen binding domain according to the various aspects of the invention does not include the signal peptide and may lack up to about 5, for example 1, 2, 3, 4, 5, or up to 10 amino acids at the N-terminal of the mature receptor protein (e.g. N terminal residues N, K, I, L and/or V). This is shown in the exemplary fusions, e.g. SEQ ID Nos. 4-12 (note that these may lack up to about 5, for example 1, 2, 3, 4, 5, or up to 10 amino acids at the N-terminal of the mature receptor protein as shown in the boxed region).

CoStARs have modular form and can be constructed to comprise extracellular, transmembrane and intracellular domains obtained from a one or more proteins, along with the scFv obtained from an antibody that binds to a disease-associated antigen, for example, a tumor associated antigen.

According to the invention, in one embodiment, a CoStAR comprises a disease-associated, for example a tumor-associated, antigen receptor, such as but not limited to a tumor-associated antigen specific scFv, and a primary costimulatory receptor protein that is capable of binding to its cognate ligand and providing an intracellular signal. In certain embodiments, the primary costimulatory receptor can be less than a full length protein but is sufficient to bind cognate ligand and transduce a signal. In certain embodiments, the primary costimulatory receptor domain is full length, such as but not limited to, full length CD28. Thus, both the antigen specific binding domain and the ligand specific receptor are capable of binding cognate antigen and ligand respectively. The amino acid sequences provided herein provide embodiments of several CoStAR constructs. These include CoStARs constructs that comprise an antigen binding domain, an optional spacer, an optional costimulatory receptor protein comprising an extracellular ligand binding segment or fragment thereof and intracellular CD40 signaling domain. In another embodiment, a CoStAR comprises an antigen binding domain, an optional spacer, an extracellular ligand-binding portion of a costimulatory receptor protein, a transmembrane domain, and an intracellular signaling domain of a selected costimulatory receptor protein and intracellular CD40 signaling domain. In certain embodiments, the extracellular ligand-binding portion comprises a CD28 truncation, for example, a C-terminal CD28 truncation after amino acids IEV, and is followed by an intracellular signaling domain. In certain embodiments, the intracellular signaling domain is from CD40. The transmembrane domain separating the extracellular ligand-binding and intracellular signaling domains can be from, with limitation, CD28, CD40. In further embodiments, CoStARs can comprise additional costimulatory domains, for example a third, intracellular costimulatory signaling domain and in this respect may be similar to certain chimeric antigen receptors (CARs), which have been classified into first (CD3ζ only), second (one costimulatory domain+CD30ζ), or third generation (more than one costimulatory domain+ CD30ζ.

Costimulatory receptor proteins useful in CoStARs of the invention include, without limitation, CD2, CD9, CD26, CD27, CD28, CD29, CD38, CD40, CD43, CD46, CD49d, CD55, CD73, CD81, CD82, CD99, CD100, CD134 (OX40), CD137 (41BB), CD150 (SLAM), CD270 (HVEM), CD278 (ICOS), CD357 (GITR), or EphB6, which in their natural form comprise extracellular ligand binding domains and intracellular signal transducing domains. For example, CD2 is characterized as a cell adhesion molecule found on the surface of T cells and is capable of initiating intracellular signals necessary for T cell activation. CD27 is characterized as a type II transmembrane glycoprotein belonging to the TNFR superfamily (TNFRSF) whose expression on B cells is induced by antigen-receptor activation in B cells. CD28 is one of the proteins on T cells and is the receptor for CD80 (B7.1) and CD86 (B7.2) ligands on antigen-presenting cells. CD137 (4-1BB) ligand is found on most leukocytes and on some non-immune cells. OX40 ligand is expressed on many antigen-presenting cells such as DC2s (dendritic cells), macrophages, and B lymphocytes. In one embodiment, the costimulatory receptor protein is full length CD28 as defined herein.

CD40 is a member of the tumor necrosis factor receptor (TNFR) superfamily and several isoforms are generated by alternative splicing. Its ligand, CD154 (also called CD40L) is a protein that is primarily expressed on activated T cells. For reference, the human CD40 isoform 1 protein sequence is set forth in GenBank accession No. NP_001241.1, including signal peptide (amino acids 1-20), transmembrane domain (amino acids 194-215), and cytoplasmic domain (amino acids 216-277)(SEQ ID NO:22). CD40 receptor signaling involves adaptor proteins including but not limited to TNF receptor-associated factors (TRAF), and the CD40 cytoplasmic domain comprises signaling components, including amino acid sequences fitting an SH3 motif (KPTNKAPH or PTNKAPHP or PTNKAPH), TRAF2 motif (PKQE, PKQET, PVQE, PVQET, SVQE, SVQET), TRAF6 motif (QEPQEINF or QEPQEINFP) and PKA motif (KKPTNKA, SRISVQE). The invention further includes engineered signaling domains, such as engineered CD40 signaling domains, comprising TRAF-binding amino acid sequences. Engineered signaling domains that bind to TRAF1, TRAF2, TRAF3, and TRAF5 may comprise the major consensus sequence (P/S/A/T)X(Q/E)E or minor consensus sequence PXQXXD and can be identified in or obtained from, without limitation, TNFR family members such as CD30, Ox40, 4-1BB, and the EBV oncoprotein LMP1. (See, e.g., Ye, H et al., *The Structural Basis for the Recognition of Diverse Receptor Sequences by TRAF2.* Molecular Cell, 1999; 4(3):321-30. doi: 10.1016/S1097-2765(00)80334-2; Park H H, *Structure of TRAF Family: Current Understanding of Receptor Recognition.* Front. Immunol. 2018; 9:1999. doi: 10.3389/fimmu.2018.01999; Chung, J. Y. et al., *All TRAFs are not created equal: common and distinct molecular mechanisms of TRAF-mediated signal transduction.* Journal of Cell Science 2002; 115:679-688).

Examples disclosed herein demonstrate operation of CD40 as a costimulatory signaling domain in a CoStAR and further that cytokine and chemokine expression profiles are altered by signaling domain selection. In certain embodiments, the costimulatory CD40 signaling domain of a CoStAR promotes pro-inflammatory cytokines (e.g., IL-2, TNFα). In certain embodiments, the costimulatory CD40 signaling domain of a CoStAR reduces immunosuppressive cytokines (e.g., IL-5, IL-10). Costimulatory activity of a CD40 signaling domain or fragment can be observed in combination with a first receptor signaling domain such as but not limited to CD2, CD9, CD26, CD27, CD28, CD29, CD38, CD40, CD43, CD46, CD49d, CD55, CD73, CD81, CD82, CD99, CD100, CD134 (OX40), CD137 (41BB), CD150 (SLAM), CD270 (HVEM), CD278 (ICOS), CD357 (GITR), or EphB6, as compared to activity of the first receptor signaling domain without the CD40 signaling domain or fragment. In this regard, the CD40 signaling domains of the invention, including signaling fragments comprising particular factor binding sites or wherein particular factor binding sites are mutated, in combination with a costimulatory first signaling domain, are capable of promoting or suppressing relative expression of particular cytokines and/or chemokines as compared to the first signaling domain alone. activity of a costimulatory signaling domain. (See, e.g., Ahonen, C L et al., *The CD40-TRAF6 axis controls affinity maturation and the generation of long-lived plasma cells.* Nat Immunol. 2002; 3: 451-456; Mackey M F et al., *Distinct contributions of different CD40 TRAF binding sites to CD154-induced dendritic cell maturation and IL-12 secretion.* Eur J Immunol. 2003; 33: 779-789; Mukundan L et al., *TNF receptor-associated factor 6 is an essential mediator of CD40-activated proinflammatory pathways in monocytes and macrophages.* J Immunol. 2005; 174: 1081-1090.

In certain embodiments, a CoStAR of the invention comprises substantially all of a CD40 costimulatory domain. In certain embodiments, a CoStAR of the invention comprises two or more CD40 costimulatory domains. In certain embodiments, a CoStAR of the invention comprises a CD40 costimulatory domain signaling component or motif, including but not limited to an SH3 motif (KPTNKAPH), TRAF2 motif (PKQE, PVQE, SVQE), TRAF3 motif, TRAF6 motif (QEPQEINFP) or PKA motif (KKPTNKA, SRISVQE) as well as two or more, or three or more, or four or more such components of motifs, which can be in multiple copies and arranged in any order. In certain embodiments, a CoStAR of the invention comprises a CD40 costimulatory domain and a CD40 costimulatory domain signaling component or motif. In certain embodiments, the SH3 motif, TRAF2 motif, and TRAF6 motif are sufficient to modulate pro-inflammatory and/or immunosuppressive cytokines. In certain embodiments, adding tandem copies of those motifs and/or mutating certain motifs amplifies these effects.

In certain embodiments, selection of one or more costimulatory domain signaling component or motif is guided by the cell in which the CoStAR is to be expressed and/or a desired costimulatory activity more closely identified with a signaling component or motif, or avoidance of a costimulatory activity more closely identified with a signaling component or motif.

In certain embodiments, a CoStAR signaling domain comprises, in addition to a CD40 costimulatory domain or signaling component or motif thereof, or two or more such domains or components or motifs or combinations thereof, an additional full length costimulatory domain or signaling component thereof from, without limitation, CD2, CD9, CD26, CD27, CD28, CD29, CD38, CD40, CD43, CD46, CD49d, CD55, CD73, CD81, CD82, CD99, CD100, CD134 (OX40), CD137 (41BB), CD150 (SLAM), CD270 (HVEM), CD278 (ICOS), CD357 (GITR), or EphB6, For reference, the human CD28 protein sequence is set forth in GenBank accession No. NP_006130.1, including signal peptide (amino acids 1-18), extracellular domain (amino acids 19-152), transmembrane domain (amino acids 153-179) and cytoplasmic domain (amino acids 180-200). The extracellular domain includes an immunoglobulin type domain (amino acids 21-136) which contains amino acids with compose the antigen binding site and amino acids that form the homodimer interface. The extracellular domain includes several asparagine residues which may be glycosylated, and the intracellular domain comprises serine and tyrosine residues, which may be phosphorylated.

For reference, the human CD8 alpha chain protein sequence is set forth by GenBank accession No. NP_001139345.1, including signal peptide (amino acids 1-21), extracellular domain (amino acids 22-182), transmembrane domain (amino acids 183-203), and cytoplasmic domain (amino acids 204-235). The extracellular domain includes an immunoglobulin type domain (amino acids 28-128) which contains amino acids with compose the antigen binding site and amino acids that form the homodimer interface. The extracellular domain includes several asparagine residues which may be glycosylated, and the intracellular domain comprises serine and tyrosine residues, which may be phosphorylated.

For reference, the human IgG4 constant region sequence is set forth in UniProtKB/Swiss-Prot: accession No. P01861.1, including CH1 (amino acids 1-98), hinge (amino acids 99-110), CH2 (amino acids 111-220), CH3 (amino acids 221-327). The CH2 region includes asparagine at amino acid 177, which is the glycosylated and associated with Fc receptor and antibody-dependent cell-mediated cytotoxicity (ADCC).

For reference, the protein sequence of human CD137 (4-1BB), another TNFR superfamily member, is set forth by GenBank accession No. NP_001552.2, including signal peptide (amino acids 1-23), extracellular domain (amino acids 24-186), transmembrane domain (amino acids 187-213), and cytoplasmic domain (amino acids 214-255). Binding of CD137L ligand trimers expressed on antigen presenting cells to CD137 leads to receptor trimerization and activation of signaling cascades involved in T cell reactivity and survival (Li et al., *Limited Cross-Linking of 4-1BB by 4-1BB Ligand and the Agonist Monoclonal Antibody Utomilumab.* Cell Reports 2018; 25:909-920). Coimmunoprecipitation of CD137 with the signaling adaptors TRAF-2 and TRAF-1 and the structural basis for the interactions has been reported (Ye, H et al., Molecular Cell, 1999; 4(3):321-30).

For reference, the human CD134 (OX40) protein sequence is set forth by GenBank accession No. NP_003318.1, including signal peptide (amino acids 1-28), extracellular domain (amino acids 29-214), transmembrane domain (amino acids 215-235), and cytoplasmic domain (amino acids 236-277). This receptor has been shown to activate NF-kappaB through its interaction with adaptor proteins TRAF2 and TRAF5 and studies suggest that this receptor promotes expression of apoptosis inhibitors BCL2 and BCL21L1/BCL2-XL.

The human T-cell surface antigen CD2 has at least two isoforms. For reference, the human CD2 isoform1 protein sequence is set forth by NP_001315538.1, including signal peptide (amino acids 1-24), extracellular domain (amino acids 25-235), transmembrane domain (amino acids 236-261), and cytoplasmic domain (amino acids 262-377). The human CD2 isoform2 protein sequence is set forth by NP_001758.2

For reference, the human CD357 (GITR) isoform-1 protein sequence is set forth by GenBank accession No. NP_004186.1, including signal peptide (amino acids 1-25), extracellular domain (amino acids 26-162), transmembrane domain (amino acids 163-183), and cytoplasmic domain (amino acids 184-241).

For reference, the human CD29 (beta1 integrin) protein sequence is set forth by GenBank accession No. NP_596867, including signal peptide (amino acids 1-20), extracellular domain (amino acids 21-728), transmembrane domain (amino acids 729-751), and cytoplasmic domain (amino acids 752-798).

The human CD150 (SLAM) protein sequence has at several isoforms. In addition to the transmembrane form of CD150 (mCD150), cells of hematopoietic lineage express mRNA encoding the secreted form of CD150 (sCD150), which lacks the entire transmembrane region of 30 amino acids. For reference, human SLAM isoform b is set forth by GenBank accession No. NP_003028.1, including signal peptide (amino acids 1-20), extracellular domain (amino acids 21-237), transmembrane domain (amino acids 238-258), and cytoplasmic domain (amino acids 259-335). Human SLAM isoform a is set forth by GenBank accession No. NP_001317683.1.

In embodiments of the invention, a CoStAR may be expressed alone under the control of a promoter in a therapeutic population of cells that have therapeutic activity, for example, Tumor Infiltrating Lymphocytes (TILs). Alternatively, the CoStAR may be expressed along with a therapeutic transgene such as a chimeric antigen receptor (CAR) and/or T-cell Receptor (TCR), for example as described in SEQ ID NOS:67-79 (note that may lack up to about 5, for example 1, 2, 3, 4, 5, or up to 10 amino acids at the N-terminal of the mature receptor protein). Thus, in one aspect, the invention also relates to CoStAR constructs having a sequence as shown in any of SEQ ID NOS:67-79, including one of these sequences which lacks up to about 5, for example 1, 2, 3, 4, 5, or up to 10 amino acids at the N-terminal of the mature receptor protein). Suitable TCRs and CARs are well known in the literature, for example HLA-A*02-NYESO-1 specific TCRs (Rapoport et al. Nat Med 2015) or anti-CD19scFv.CD3ζ fusion CARs (Kochenderfer et al. J Clin Oncol 2015) which have been successfully used to treat Myeloma or B-cell malignancies respectively. The CoStARs described herein may be expressed with any known CAR or TCR thus providing the cell with a regulatable growth switch to allow cell expansion in-vitro or in-vivo, and a conventional activation mechanism in the form of the TCR or CAR for anti-cancer activity. Thus the invention provides a cell for use in adoptive cell therapy comprising a CoStAR as described herein and a TCR and/or CAR that specifically binds to a tumor associated antigen. An exemplary CoStAR comprising CD28 includes an extracellular antigen binding domain and an extracellular, transmembrane and intracellular signaling domain.

The term "antigen binding domain" as used herein refers to an antibody fragment including, but not limited to, a diabody, a Fab, a Fab', a F(ab')2, an Fv fragment, a disulfide stabilized Fv fragment (dsFv), a (dsFv)2, a bispecific dsFv (dsFv-dsFv'), a disulfide stabilized diabody (ds diabody), a single-chain antibody molecule (scFv), an scFv dimer (bivalent diabody), a multispecific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen binding domain is capable of binding to the same antigen to which the parent antibody or a parent antibody fragment (e.g., a parent scFv) binds. In some embodiments, an antigen-binding fragment may comprise one or more complementarity determining regions (CDRs) from a particular human antibody grafted to frameworks (FRs) from one or more different human antibodies.

The antigen binding domain can be made specific for any disease-associated antigen, including but not limited to tumor-associated antigens (TAAs) and infectious disease-associated antigens. In certain embodiments, the ligand binding domain is bispecific. Antigens have been identified in most of the human cancers, including Burkitt lymphoma, neuroblastoma, melanoma, osteosarcoma, renal cell carcinoma, breast cancer, prostate cancer, lung carcinoma, and colon cancer. TAA's include, without limitation, CD19, CD20, CD22, CD24, CD33, CD38, CD123, CD228, CD138, BCMA, GPC3, CEA, folate receptor (FRα), mesothelin, CD276, gp100, 5T4, GD2, EGFR, MUC-1, PSMA, EpCAM, MCSP, SM5-1, MICA, MICB, ULBP and HER-2. TAAs further include neoantigens, peptide/MHC complexes, and HSP/peptide complexes.

In certain embodiments, the antigen binding domain comprises a T-cell receptor or binding fragment thereof that binds to a defined tumor specific peptide-MHC complex. The term "T cell receptor," or "TCR," refers to a heterodimeric receptor composed of αβ or γδ chains that pair on the surface of a T cell. Each α, β, γ, and δ chain is composed of two Ig– like domains: a variable domain (V) that confers antigen recognition through the complementarity determining regions (CDR), followed by a constant domain (C) that is anchored to cell membrane by a connecting peptide and a transmembrane (TM) region. The TM region associates with the invariant subunits of the CD3ζ signaling apparatus. Each of the V domains has three CDRs. These CDRs interact with a complex between an antigenic peptide bound to a protein encoded by the major histocompatibility complex (pMHC) (Davis and Bjorkman (1988) Nature, 334, 395-402; Davis et al. (1998) Annu Rev Immunol, 16, 523-544; Murphy (2012), xix, 868 p.).

In certain embodiments, the antigen binding domain comprises a natural ligand of a tumor expressed protein or tumor-binding fragment thereof. A non-limiting example is PD1 which binds to PDL1. Another example is the transferrin receptor 1 (TfR1), also known as CD71, a homodimeric protein that is a key regulator of cellular iron homeostasis and proliferation. Although TfR1 is expressed at a low level in a broad variety of cells, it is expressed at higher levels in rapidly proliferating cells, including malignant cells in which overexpression has been associated with poor prognosis. In an embodiment of the invention, the antigen binding domain comprises transferrin or a transferrin receptor-binding fragment thereof.

In certain embodiments, the antigen binding domain is specific to a defined tumor associated antigen, such as but not limited to FRα, CEA, 5T4, CA125, SM5-1 or CD71. In certain embodiments, the tumor associated antigen can be a tumor-specific peptide-MHC complex. In certain such embodiments, the peptide is a neoantigen. In other embodiments, the tumor associated antigen it a peptide-heat shock protein complex.

In various embodiments, the invention provides a CoStAR which comprises
 i. an scFv that binds to carcinoembryonic antigen (CEA), a spacer and transmembrane sequence of CD28, a CD28 signaling domain, and a CD40 signaling domain.
 ii. an scFv that binds to CEA, a spacer and transmembrane sequence of CD28, and a CD40 signaling domain.
 iii. an scFv that binds to CEA, a spacer and transmembrane sequence of CD28, a CD137 signaling domain, and a CD40 signaling domain.
 iv. an scFv that binds to CEA, a spacer and transmembrane sequence of CD28, a CD134 signaling domain, and a CD40 signaling domain.
 v. an scFv that binds to CEA, a spacer and transmembrane sequence of CD28, a CD2 signaling domain, and a CD40 signaling domain.
 vi. an scFv that binds to CEA, a spacer and transmembrane sequence of CD28, a GITR signaling domain, and a CD40 signaling domain.
 vii. an scFv that binds to CEA, a spacer and transmembrane sequence of CD28, a CD29 signaling domain, and a CD40 signaling domain.
 viii. an scFv that binds to CEA, a spacer and transmembrane sequence of CD28, a CD150 signaling domain, and a CD40 signaling domain.

ix. an scFv that binds to CEA, a spacer and transmembrane sequence of CD8, a CD28 signaling domain, and a CD40 signaling domain.
x. an scFv that binds to CEA, a spacer and transmembrane sequence of CD8, and a CD40 signaling domain.
xi. an scFv that binds to CEA, a spacer and transmembrane sequence of CD8, a CD137 signaling domain, and a CD40 signaling domain.
xii. an scFv that binds to CEA, a spacer and transmembrane sequence of CD8, a CD134 signaling domain, and a CD40 signaling domain.
xiii. an scFv that binds to CEA, a spacer and transmembrane sequence of CD8, a CD2 signaling domain, and a CD40 signaling domain.
xiv. an scFv that binds to CEA, a spacer and transmembrane sequence of CD8, a GITR signaling domain, and a CD40 signaling domain.
xv. an scFv that binds to CEA, a spacer and transmembrane sequence of CD8, a CD29 signaling domain, and a CD40 signaling domain.
xvi. an scFv that binds to CEA, a spacer and transmembrane sequence of CD8, a CD150 signaling domain, and a CD40 signaling domain.
xvii. an scFv that binds to CEA, a spacer comprising an IgG4 constant region and CD28 transmembrane sequence, a CD28 signaling domain, and a CD40 signaling domain.
xviii. an scFv that binds to CEA, a spacer comprising an IgG4 constant region and CD28 transmembrane sequence, and a CD40 signaling domain.
xix. an scFv that binds to CEA, a spacer comprising an IgG4 constant region and CD28 transmembrane sequence, a CD137 signaling domain, and a CD40 signaling domain.
xx. an scFv that binds to CEA, a spacer comprising an IgG4 constant region and CD28 transmembrane sequence, a CD134 signaling domain, and a CD40 signaling domain.
xxi. an scFv that binds to CEA, a spacer comprising an IgG4 constant region and CD28 transmembrane sequence, a CD2 signaling domain, and a CD40 signaling domain.
xxii. an scFv that binds to CEA, a spacer comprising an IgG4 constant region and CD28 transmembrane sequence, a GITR signaling domain, and a CD40 signaling domain.
xxiii. an scFv that binds to CEA, a spacer comprising an IgG4 constant region and CD28 transmembrane sequence, a CD29 signaling domain, and a CD40 signaling domain.
xxiv. an scFv that binds to CEA, a spacer comprising an IgG4 constant region and CD28 transmembrane sequence, a CD150 signaling domain, and a CD40 signaling domain.
xxv. an scFv that binds to CEA, a spacer comprising an IgG4 constant region and CD28 transmembrane sequence, a first CD40 signaling domain and a second CD40 signaling domain
xxvi. an scFv that binds to CEA, a spacer comprising an IgG4 constant region and CD28 transmembrane sequence, a first CD40 signaling domain and a second mutated CD40 signaling domain
xxvii. a binding domain that binds to PDL1, a short spacer and transmembrane sequence of CD28, a CD28 signaling domain, and a CD40 signaling domain.
xxviii. a binding domain that binds to PDL1, a short spacer and transmembrane sequence of CD28, and a CD40 signaling domain.
xxix. an binding domain that binds to CD155, CD112, or CD113, a CD28 transmembrane domain, a CD28 signaling domain, and a CD40 signaling domain.
xxx. a binding domain that binds to CD155, CD112, or CD113, a CD28 transmembrane domain, and a CD40 signaling domain.
xxxi. an scFv that binds to CEA, a binding domain that binds to PDL1, a short spacer and transmembrane sequence of CD28, a CD28 signaling domain, and a CD40 signaling domain.
xxxii. an scFv that binds to CEA, a binding domain that binds to PDL1, a short spacer and transmembrane sequence of CD28, and a CD40 signaling domain.
xxxiii. an scFv that binds to CEA, a binding domain that binds to CD155, CD112, or CD113, a short spacer and transmembrane sequence of CD28, a CD28 signaling domain, and a CD40 signaling domain.
xxxiv. an scFv that binds to CEA, a binding domain that binds to CD155, CD112, or CD113, a short spacer and transmembrane sequence of CD28, and a CD40 signaling domain.

In various embodiments, the invention provides a CoStAR which comprises the spacer, transmembrane, and signaling domain structure of any one of i-xxxiv and binds to FOLR1.

In various embodiments, the invention provides a CoStAR which comprises
i. an scFv that binds to FOLR1, a spacer and transmembrane sequence of CD28, a CD28 signaling domain, and a CD40 signaling domain.
ii. an scFv that binds to FOLR1, a spacer and transmembrane sequence of CD28, and a CD40 signaling domain.
iii. an scFv that binds to FOLR1, a spacer and transmembrane sequence of CD28, a CD137 signaling domain, and a CD40 signaling domain.
iv. an scFv that binds to FOLR1, a spacer and transmembrane sequence of CD28, a CD134 signaling domain, and a CD40 signaling domain.
v. an scFv that binds to FOLR1, a spacer and transmembrane sequence of CD28, a CD2 signaling domain, and a CD40 signaling domain.
vi. an scFv that binds to FOLR1, a spacer and transmembrane sequence of CD28, a GITR signaling domain, and a CD40 signaling domain.
vii. an scFv that binds to FOLR1, a spacer and transmembrane sequence of CD28, a CD29 signaling domain, and a CD40 signaling domain.
viii. an scFv that binds to FOLR1, a spacer and transmembrane sequence of CD28, a CD150 signaling domain, and a CD40 signaling domain.
ix. an scFv that binds to FOLR1, a spacer and transmembrane sequence of CD8, a CD28 signaling domain, and a CD40 signaling domain.
x. an scFv that binds to FOLR1, a spacer and transmembrane sequence of CD8, and a CD40 signaling domain.
xi. an scFv that binds to FOLR1, a spacer and transmembrane sequence of CD8, a CD137 signaling domain, and a CD40 signaling domain.
xii. an scFv that binds to FOLR1, a spacer and transmembrane sequence of CD8, a CD134 signaling domain, and a CD40 signaling domain.

xiii. an scFv that binds to FOLR1, a spacer and transmembrane sequence of CD8, a CD2 signaling domain, and a CD40 signaling domain.
xiv. an scFv that binds to FOLR1, a spacer and transmembrane sequence of CD8, a GITR signaling domain, and a CD40 signaling domain.
xv. an scFv that binds to FOLR1, a spacer and transmembrane sequence of CD8, a CD29 signaling domain, and a CD40 signaling domain.
xvi. an scFv that binds to FOLR1, a spacer and transmembrane sequence of CD8, a CD150 signaling domain, and a CD40 signaling domain.
xvii. an scFv that binds to FOLR1, a spacer comprising an IgG4 constant region and CD28 transmembrane sequence, a CD28 signaling domain, and a CD40 signaling domain.
xviii. an scFv that binds to FOLR1, a spacer comprising an IgG4 constant region and CD28 transmembrane sequence, and a CD40 signaling domain.
xix. an scFv that binds to FOLR1, a spacer comprising an IgG4 constant region and CD28 transmembrane sequence, a CD137 signaling domain, and a CD40 signaling domain.
xx. an scFv that binds to FOLR1, a spacer comprising an IgG4 constant region and CD28 transmembrane sequence, a CD134 signaling domain, and a CD40 signaling domain.
xxi. an scFv that binds to FOLR1, a spacer comprising an IgG4 constant region and CD28 transmembrane sequence, a CD2 signaling domain, and a CD40 signaling domain.
xxii. an scFv that binds to FOLR1, a spacer comprising an IgG4 constant region and CD28 transmembrane sequence, a GITR signaling domain, and a CD40 signaling domain.
xxiii. an scFv that binds to FOLR1, a spacer comprising an IgG4 constant region and CD28 transmembrane sequence, a CD29 signaling domain, and a CD40 signaling domain.
xxiv. an scFv that binds to FOLR1, a spacer comprising an IgG4 constant region and CD28 transmembrane sequence, a CD150 signaling domain, and a CD40 signaling domain.
xxv. an scFv that binds to FOLR1, a spacer comprising an IgG4 constant region and CD28 transmembrane sequence, a first CD40 signaling domain and a second CD40 signaling domain
xxvi. an scFv that binds to FOLR1, a spacer comprising an IgG4 constant region and CD28 transmembrane sequence, a first CD40 signaling domain and a second mutated CD40 signaling domain As use herein, the term "specifically binds" or "is specific for" refers to measurable and reproducible interactions, such as binding between a target and an antibody or antibody moiety that is determinative of the presence of the target in the presence of a heterogeneous population of molecules, including biological molecules. For example, an antibody moiety that specifically binds to a target (which can be an epitope) is an antibody moiety that binds the target with greater affinity, avidity, more readily, and/or with greater duration than its bindings to other targets. In some embodiments, an antibody moiety that specifically binds to an antigen reacts with one or more antigenic determinants of the antigen (for example a cell surface antigen or a peptide/MHC protein complex) with a binding affinity that is at least about 10 times its binding affinity for other targets.

Spacer

A CoStAR of the invention optionally comprises a spacer region between the antigen binding domain and the costimulatory receptor. As used herein, the term "spacer" refers to the extracellular structural region of a CoStAR that separates the antigen binding domain from the external ligand binding domain of the costimulatory protein. The spacer provides flexibility to access the targeted antigen and receptor ligand. In certain embodiments long spacers are employed, for example to target membrane-proximal epitopes or glycosylated antigens (see Guest R. D. et al. The role of extracellular spacer regions in the optimal design of chimeric immune receptors: evaluation of four different scFvs and antigens. J. Immunother. 2005; 28:203-211; Wilkie S. et al., Retargeting of human T cells to tumor-associated MUC1: the evolution of a chimeric antigen receptor. J. Immunol. 2008; 180:4901-4909). In other embodiments, CoStARs bear short spacers, for example to target membrane distal epitopes (see Hudecek M. et al., Receptor affinity and extracellular domain modifications affect tumor recognition by ROR1-specific chimeric antigen receptor T cells. Clin. Cancer Res. 2013; 19:3153-3164; Hudecek M. et al., The nonsignalling extracellular spacer domain of chimeric antigen receptors is decisive for in vivo antitumor activity. Cancer Immunol. Res. 2015; 3:125-135). In certain embodiments, the spacer comprises all or part of or is derived from an IgG hinge, including but not limited to IgG1, IgG2, or IgG4. By "derived from an Ig hinge" is meant a spacer comprising insertions, deletions, or mutations in an IgG hinge. In certain embodiments, a spacer can comprise all or part of one or more antibody constant domains, such as but not limited to CH2 and/or CH3 domains. In certain embodiments, in a spacer comprising all or part of a CH2 domain, the CH2 domain is modified so as not to bind to an Fc receptor. For example, Fc receptor binding in myeloid cells has been found to impair CAR T cell functionality. In certain embodiments, the spacer comprises all or part of an Ig-like hinge from CD28, CD8, or other protein comprising a hinge region. In certain embodiments of the invention that comprise a spacer, the spacer is from 1 and 50 amino acids in length.

In an non-limiting embodiment, the spacer comprises essentially all of an extracellular domain, for example a CD28 extracellular domain (i.e. from about amino acid 19, 20, 21, or 22 to about amino acid 152) or an extracellular domain of another protein, including but not limited to another TNFR superfamily member. In an embodiment, the spacer comprises a portion of an extracellular domain, for example a portion of a CD28 extracellular domain, and may lack all or most of the Ig domain. In another embodiment, the spacer includes amino acids of CD28 from about 141 to about 152 but not other portions of the CD28 extracellular domain. In another embodiment, the spacer includes amino acids of CD8 from about 128 to about 182 but not other portions of the CD8 extracellular domain.

Linker

In certain embodiments, the CoStAR extracellular domain comprises a linker. Linkers comprise short runs of amino acids used to connect domains, for example a binding domain with a spacer or transmembrane domain. In order for there to be flexibility to bind ligand, a ligand binding domain will usually be connected to a spacer or a transmembrane domain by flexible linker comprising from about 5 to 25 amino acids, such as, for example, AAAGSGGSG (SEQ ID NO: 8), GGGGSGGGGSGGGGS (SEQ ID NO: 125). In certain embodiments, a CoStAR comprises a binding domain joined directly to a transmembrane domain by a linker, and without a spacer. In certain embodiments, a CoStAR comprises a binding domain joined directly to a transmembrane by a spacer and without a linker, exemplified by SEQ ID NOS: 58 and 59.

Signaling Domain

As discussed above, in certain embodiments, a CoStAR comprises a full length primary costimulatory receptor which can comprise an extracellular ligand binding and intracellular signaling portion of, without limitation, CD2, CD9, CD26, CD27, CD28, CD29, CD38, CD40, CD43, CD46, CD49d, CD55, CD73, CD81, CD82, CD99, CD100, CD134 (OX40), CD137 (41BB), CD150 (SLAM), CD270 (HVEM), CD278 (ICOS), CD357 (GITR), or EphB6. In other embodiments, the costimulatory receptor comprises a chimeric protein, for instance comprising an extracellular ligand binding domain of one of the aforementioned proteins and an intracellular signaling domain of another of the aforementioned proteins. In certain embodiments, the signaling portion of the CoStAR comprises a single signaling domain. In other embodiments, the signaling portion of the CoStAR comprises a second intracellular signaling domain such as but not limited to: CD2, CD27, CD28, CD40, CD134 (OX40), CD137 (4-1BB), CD150 (SLAM). In certain embodiments, the first and second intracellular signaling domains are the same. In other embodiments, the first and second intracellular signaling domains are different. In certain embodiments, the costimulatory receptor is capable of dimerization. Without being bound by theory, it is thought that CoStARs dimerize or associate with other accessory molecules for signal initiation. In certain embodiments, CoStARs dimerize or associate with accessory molecules through transmembrane domain interactions. In certain embodiments, dimerization or association with accessory molecules is assisted by costimulatory receptor interactions in the intracellular portion, and/or the extracellular portion of the costimulatory receptor.

Transmembrane Domain

Although the main function of the transmembrane is to anchor the CoStAR in the T cell membrane, in certain embodiments, the transmembrane domain influences CoStAR function. In certain embodiments, the transmembrane domain is comprised by the full length primary costimulatory receptor domain. In embodiments of the invention wherein the CoStAR construct comprises an extracellular domain of one receptor and an intracellular signaling domain of a second receptor, the transmembrane domain can be that of the extracellular domain or the intracellular domain. In certain embodiments, the transmembrane domain is from CD4, CD8α, CD28, or ICOS. Gueden et al. associated use of the ICOS transmembrane domain with increased CAR T cell persistence and overall anti-tumor efficacy (Guedan S. et al., Enhancing CAR T cell persistence through ICOS and 4-1BB costimulation. JCI Insight. 2018; 3:96976). In an embodiment, the transmembrane domain comprises a hydrophobic α helix that spans the cell membrane.

In an embodiment, the transmembrane domain comprises amino acids of the CD28 transmembrane domain from about amino acid 153 to about amino acid 179. In another embodiment, the transmembrane domain comprises amino acids of the CD8 transmembrane domain from about amino acid 183 to about amino acid 203. In certain embodiments, the CoStARs of the invention may include several amino acids between the transmembrane domain and signaling domain. For example, in one construct described herein the link from a CD8 transmembrane domain to a signaling domain comprises several amino acids of the CD8 cytoplasmic domain (e.g., amino acids 204-210 of CD8).

Variants

In some embodiments, amino acid sequence variants of the antibody moieties or other moieties provided herein are contemplated. For example, it may be desirable to improve the binding affinity and/or other biological properties of the antibody moiety. Amino acid sequence variants of an antibody moiety may be prepared by introducing appropriate modifications into the nucleotide sequence encoding the antibody moiety, or by peptide synthesis. Such modifications include, for example, deletions from, and/or insertions into and/or substitutions of residues within the amino acid sequences of the antibody moiety. Any combination of deletion, insertion, and substitution can be made to arrive at the final construct, provided that the final construct possesses the desired characteristics, e.g., antigen-binding.

In some embodiments, antibody binding domain moieties comprising one or more amino acid substitutions, deletions, or insertions are provided. Sites of interest for mutational changes include the antibody binding domain heavy and light chain variable regions (VRs) and frameworks (FRs). Amino acid substitutions may be introduced into a binding domain of interest and the products screened for a desired activity, e.g., retained/improved antigen binding or decreased immunogenicity. In certain embodiments, amino acid substitutions may be introduced into one or more of the primary co-stimulatory receptor domain (extracellular or intracellular), secondary costimulatory receptor domain, or extracellular co-receptor domain. Accordingly, the invention encompasses CoStAR proteins and component parts particularly disclosed herein as well as variants thereof, i.e. CoStAR proteins and component parts having at least 75%, at least 80%, at least 85%, at least 87%, at least 90%, at least 91%, at least 92%, at least 93%, at least 94%, at least 95%, at least 96%, at least 97%, at least 98%, at least 99% sequence identity to the amino acid sequences particularly disclosed herein. The terms "percent similarity," "percent identity," and "percent homology" when referring to a particular sequence are used as set forth in the University of Wisconsin GCG software program BestFit. Other algorithms may be used, e.g. BLAST, psiBLAST or TBLASTN (which use the method of Altschul et al. (1990) J. Mol. Biol. 215: 405-410), FASTA (which uses the method of Pearson and Lipman (1988) PNAS USA 85: 2444-2448).

Particular amino acid sequence variants may differ from a reference sequence by insertion, addition, substitution or deletion of 1 amino acid, 2, 3, 4, 5-10, 10-20 or 20-30 amino acids. In some embodiments, a variant sequence may comprise the reference sequence with 1, 2, 3, 4, 5, 6, 7, 8, 9, 10 or more residues inserted, deleted or substituted. For example, 5, 10, 15, up to 20, up to 30 or up to 40 residues may be inserted, deleted or substituted.

In some preferred embodiments, a variant may differ from a reference sequence by 1, 2, 3, 4, 5, 6, 7, 8, 9, 10 or more conservative substitutions. Conservative substitutions involve the replacement of an amino acid with a different amino acid having similar properties. For example, an aliphatic residue may be replaced by another aliphatic residue, a non-polar residue may be replaced by another non-polar residue, an acidic residue may be replaced by another acidic residue, a basic residue may be replaced by another basic residue, a polar residue may be replaced by another polar residue or an aromatic residue may be replaced by another aromatic residue. Conservative substitutions may, for example, be between amino acids within the following groups:

Conservative substitutions are shown in the Table below.

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp; Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped into different classes according to common side-chain properties: a. hydrophobic: Norleucine, Met, Ala, Val, Leu, Ile; b. neutral hydrophilic: Cys, Ser, Thr, Asn, Gln; c. acidic: Asp, Glu; d. basic: His, Lys, Arg; e. residues that influence chain orientation: Gly, Pro; aomatic: Trp, Tyr, Phe. Non-conservative substitutions will entail exchanging a member of one of these classes for another class.

Cells

The cells used in the present invention may be any lymphocyte that is useful in adoptive cell therapy, such as a T-cell or a natural killer (NK) cell, an NKT cell, a gamma/delta T-cell or T regulatory cell. The cells may be allogeneic or autologous to the patient.

T cells or T lymphocytes are a type of lymphocyte that have a central role in cell-mediated immunity. They can be distinguished from other lymphocytes, such as B cells and natural killer cells (NK cells), by the presence of a T-cell receptor (TCR) on the cell surface. There are various types of T cell, as summarised below. Cytotoxic T cells (TC cells, or CTLs) destroy virally infected cells and tumor cells, and are also implicated in transplant rejection. CTLs express the CD8 molecule at their surface.

These cells recognize their targets by binding to antigen associated with MHC class I, which is present on the surface of all nucleated cells. Through IL-10, adenosine and other molecules secreted by regulatory T cells, the CD8+ cells can be inactivated to an anergic state, which prevent autoimmune diseases such as experimental autoimmune encephalomyelitis.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells (TCM cells) and two types of effector memory T cells (TEM cells and TEMRA cells). Memory cells may be either CD4+ or CD8+. Memory T cells typically express the cell surface protein CD45RO. Regulatory T cells (Treg cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus.

Two major classes of CD4+ Treg cells have been described—naturally occurring Treg cells and adaptive Treg cells. Naturally occurring Treg cells (also known as CD4$^+$CD25$^+$FoxP3$^+$ Treg cells) arise in the thymus and have been linked to interactions between developing T cells with both myeloid (CD11c$^+$) and plasmacytoid (CD123$^+$) dendritic cells that have been activated with TSLP. Naturally occurring Treg cells can be distinguished from other T cells by the presence of an intracellular molecule called FoxP3. Adaptive Treg cells (also known as Tr1 cells or Th3 cells) may originate during a normal immune response.

Natural Killer Cells (or NK cells) are a type of cytolytic cell which form part of the innate immune system. NK cells provide rapid responses to innate signals from virally infected cells in an MHC independent manner. NK cells (belonging to the group of innate lymphoid cells) are defined as large granular lymphocytes (LGL) and constitute the third kind of cells differentiated from the common lymphoid progenitor generating B and T lymphocytes.

In certain embodiments, therapeutic cells of the invention comprise autologous cells engineered to express a CoStAR. In certain embodiments, therapeutic cells of the invention comprise allogeneic cells engineered to express a CoStAR. Autologous cells expressing CoStARs may be advantageous in avoiding graft-versus-host disease (GVHD) due to TCR-mediated recognition of recipient alloantigens. Also, the immune system of a CoStAR recipient could attack the infused CoStAR cells, causing rejection. In certain embodiments, to prevent GVHD, and to reduce rejection, endogenous TcR is removed from allogeneic CoStAR cells by genome editing.

Nucleic Acids

An aspect of the invention provides a nucleic acid sequence of the invention, encoding any of the CoStARs, polypeptides, or proteins described herein (including functional portions and functional variants thereof). As used herein, the terms "polynucleotide", "nucleotide", and "nucleic acid" are intended to be synonymous with each other. It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed, e.g. codon optimisation. Nucleic acids according to the invention may comprise DNA or RNA. They may be single stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present invention, it is to be understood that the polynucleotides may be modified by any method available in the art. Such modifications may be carried out in order to enhance the in vivo activity or life span of polynucleotides of interest.

The terms "variant", "homologue" or "derivative" in relation to a nucleotide sequence include any substitution of, variation of, modification of, replacement of, deletion of or addition of one (or more) nucleic acid from or to the sequence.

The nucleic acid sequence may encode the protein sequence shown as SEQ ID NO:2 or a variant thereof. The nucleotide sequence may comprise a codon optimised nucleic acid sequence shown engineered for expression in human cells.

The invention also provides a nucleic acid sequence which comprises a nucleic acid sequence encoding a CoStAR and a further nucleic acid sequence encoding a T-cell receptor (TCR) and/or chimeric antigen receptor (CAR).

The nucleic acid sequences may be joined by a sequence allowing co-expression of the two or more nucleic acid sequences. For example, the construct may comprise an internal promoter, an internal ribosome entry sequence (IRES) sequence or a sequence encoding a cleavage site. The cleavage site may be self-cleaving, such that when the polypeptide is produced, it is immediately cleaved into the discrete proteins without the need for any external cleavage activity. Various self-cleaving sites are known, including the Foot- and Mouth disease virus (FMDV) and the 2A self-cleaving peptide. The co-expressing sequence may be an internal ribosome entry sequence (IRES). The co-expressing sequence may be an internal promoter.

Vectors

In an aspect, the present invention provides a vector which comprises a nucleic acid sequence or nucleic acid construct of the invention.

Such a vector may be used to introduce the nucleic acid sequence(s) or nucleic acid construct(s) into a host cell so that it expresses one or more CoStAR(s) according to the first aspect of the invention and, optionally, one or more other proteins of interest (POI), for example a TCR or a CAR. The vector may, for example, be a plasmid or a viral vector, such as a retroviral vector or a lentiviral vector, or a transposon-based vector or synthetic mRNA.

The nucleic acids of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties.

Vectors derived from retroviruses, such as the lentivirus, are suitable tools to achieve long-term gene transfer since they allow long-term, stable integration of a transgene and its propagation in daughter cells. The vector may be capable of transfecting or transducing a lymphocyte including a T cell or an NK cell. The present invention also provides vectors in which a nucleic acid of the present invention is inserted. The expression of natural or synthetic nucleic acids encoding a CoStAR, and optionally a TCR or CAR is typically achieved by operably linking a nucleic acid encoding the CoStAR and TCR/CAR polypeptide or portions thereof to one or more promoters, and incorporating the construct into an expression vector.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, MSCV promoter, MND promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter.

The vectors can be suitable for replication and integration in eukaryotic cells. Typical cloning vectors contain transcription and translation terminators, initiation sequences, and promoters useful for regulation of the expression of the desired nucleic acid sequence. Viral vector technology is well known in the art and is described, for example, in Sambrook et al. (2001, Molecular Cloning: A Laboratory Manual, Cold Spring Harbor Laboratory, New York), and in other virology and molecular biology manuals, see also, WO 01/96584; WO 01/29058; and U.S. Pat. No. 6,326,193). In some embodiments, the constructs expressed are as shown in SEQ ID NOS:32-65 and 67-79. In some embodiments the nucleic acids are multi-cistronic constructs that permit the expression of multiple transgenes (e.g., CoStAR and a TCR and/or CAR etc.) under the control of a single promoter. In some embodiments, the transgenes (e.g., CoStAR and a TCR and/or CAR etc.) are separated by a self-cleaving 2A peptide. Examples of 2A peptides useful in the nucleic acid constructs of the invention include F2A, P2A, T2A and E2A. In other embodiments of the invention, the nucleic acid construct of the invention is a multi-cistronic construct comprising two promoters; one promoter driving the expression of CoStAR and the other promoter driving the expression of the TCR or CAR. In some embodiments, the dual promoter constructs of the invention are uni-directional. In other embodiments, the dual promoter constructs of the invention are bi-directional. In order to assess the expression of the CoStAR polypeptide or portions thereof, the expression vector to be introduced into a cell can also contain either a selectable marker gene or a reporter gene or both to facilitate identification and selection of expressing cells from the population of cells sought to be transfected or transduced through viral vectors.

Sources of Cells

Prior to expansion and genetic modification, a source of cells (e.g., immune effector cells, e.g., T cells or NK cells) is obtained from a subject. The term "subject" is intended to include living organisms in which an immune response can be elicited (e.g., mammals). Examples of subjects include humans, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors.

In one aspect, T cells are isolated from peripheral blood lymphocytes by lysing the red blood cells and depleting the monocytes, for example, by centrifugation through a PERCOLL™ gradient or by counterflow centrifugal elutriation. T cell may be collected at an apheresis center and cell storage facility where T cells can be harvested, maintained, and easily transferred. The T cells can be cryopreserved and stored for later use. An acceptable duration of storage may be determined and validated and can be up to 6 months, up to a year, or longer.

In another aspect, Tumor infiltrating cells (TILs) are isolated and/or expanded from a tumor, for example by a fragmented, dissected, or enzyme digested tumor biopsy or mass. The TILs may be produced in a two-stage process using a tumor biopsy as the starting material: Stage 1 (generally performed over 2-3 hours) initial collection and processing of tumor material using dissection, enzymatic digestion and homogenization to produce a single cell suspension which can be directly cryopreserved to stabilize the starting material for subsequent manufacture and Stage 2 which can occur days or years later. Stage 2 may be performed over 4 weeks, which may be a continuous process starting with thawing of the product of Stage 1 and growth of the TIL out of the tumor starting material (about 2 weeks) followed by a rapid expansion process of the TIL cells (about 2 weeks) to increase the amount of cells and therefore dose. The TILs may be concentrated and washed prior to formulation as a liquid suspension of cells.

The TIL population can be transduced at any point following collection. In certain embodiments, a cryopreserved TIL population is transduced to express a CoStAR following thawing. In certain embodiments, a TIL population is transduced to express a CoStAR during outgrowth or initial expansion from tumor starting material. In certain embodiments, a TIL population is transduced to express a CoStAR during REP, for example but not limited to from about day 8 to about day 10 of REP. An exemplary TIL preparation is described in Applicant's U.S. patent application Ser. No. 62/951,559, filed Dec. 20, 2019.

A specific subpopulation of T cells, such as CD3+, CD28+, CD4+, CD8+, CD45RA+, and CD45RO+T cells, can be further isolated by positive or negative selection techniques. For example, in one aspect, T cells are isolated by incubation with anti-CD3/anti-CD28-conjugated beads, such as DYNABEADS® M-450 CD3/CD28 T, for a time period sufficient for positive selection of the desired T cells. In one aspect, the time period is about 30 minutes. In a further aspect, the time period ranges from 30 minutes to 36 hours or longer and all integer values there between. In a further aspect, the time period is at least 1, 2, 3, 4, 5, or 6 hours. In yet another preferred aspect, the time period is 10 to 24 hours. In one aspect, the incubation time period is 24 hours. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3ζ and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain aspects, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD16, HLA-DR, and CD8. In certain aspects, it may be desirable to enrich for or positively select for regulatory T cells which typically express CD4+, CD25+, CD62Lhi, GITR+, CD137, PD1, TIM3, LAG-3, CD150 and FoxP3+. Alternatively, in certain aspects, T regulatory cells are depleted by anti-CD25 conjugated beads or other similar method of selection.

The methods described herein can include, e.g., selection of a specific subpopulation of immune effector cells, e.g., T cells, that are a T regulatory cell-depleted population, CD25+ depleted cells, using, e.g., a negative selection technique, e.g., described herein. Preferably, the population of T regulatory depleted cells contains less than 30%, 25%, 20%, 15%, 10%, 5%, 4%, 3%, 2%, 1% of CD25+ cells.

A specific subpopulation of CoStAR effector cells that specifically bind to a target antigen can be enriched for by positive selection techniques. For example, in some embodiments, effector cells are enriched for by incubation with target antigen-conjugated beads for a time period sufficient for positive selection of the desired abTCR effector cells. In some embodiments, the time period is about 30 minutes. In some embodiments, the time period ranges from 30 minutes to 36 hours or longer (including all ranges between these values). In some embodiments, the time period is at least one, 2, 3, 4, 5, or 6 hours. In some embodiments, the time period is 10 to 24 hours. In some embodiments, the incubation time period is 24 hours. For isolation of effector cells present at low levels in the heterogeneous cell population, use of longer incubation times, such as 24 hours, can increase cell yield. Longer incubation times may be used to isolate effector cells in any situation where there are few effector cells as compared to other cell types. The skilled artisan would recognize that multiple rounds of selection can also be used in the context of this invention.

T cells for stimulation can also be frozen after a washing step. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

Allogeneic CoStAR

In embodiments described herein, the immune effector cell can be an allogeneic immune effector cell, e.g., T cell or NK cell. For example, the cell can be an allogeneic T cell, e.g., an allogeneic T cell lacking expression of endogenous T cell receptor (TCR) and/or human leukocyte antigen (HLA), e.g., HLA class I and/or HLA class II.

A T cell lacking a functional endogenous TCR can be, e.g., engineered such that it does not express any functional TCR on its surface, engineered such that it does not express one or more subunits that comprise a functional TCR (e.g., engineered such that it does not express (or exhibits reduced expression) of TCR alpha, TCR beta, TCR gamma, TCR delta, TCR epsilon, and/or TCR zeta) or engineered such that it produces very little functional TCR on its surface. Alternatively, the T cell can express a substantially impaired TCR, e.g., by expression of mutated or truncated forms of one or more of the subunits of the TCR. The term "substantially impaired TCR" means that this TCR will not elicit an adverse immune reaction in a host.

A T cell described herein can be, e.g., engineered such that it does not express a functional HLA on its surface. For example, a T cell described herein, can be engineered such that cell surface expression HLA, e.g., HLA class 1 and/or HLA class II, is downregulated. In some aspects, downregulation of HLA may be accomplished by reducing or eliminating expression of beta-2 microglobulin (B2M).

In some embodiments, the T cell can lack a functional TCR and a functional HLA, e.g., HLA class I and/or HLA class II. Modified T cells that lack expression of a functional TCR and/or HLA can be obtained by any suitable means, including a knock out or knock down of one or more subunit of TCR or HLA. For example, the T cell can include a knock down of TCR and/or HLA using siRNA, shRNA, clustered regularly interspaced short palindromic repeats (CRISPR) transcription-activator like effector nuclease (TALEN), or zinc finger endonuclease (ZFN).

In some embodiments, the allogeneic cell can be a cell which does not expresses or expresses at low levels an inhibitory molecule, e.g. a cell engineered by any method described herein. For example, the cell can be a cell that does not express or expresses at low levels an inhibitory molecule, e.g., that can decrease the ability of a CoStAR-expressing cell to mount an immune effector response. Examples of inhibitory molecules include PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MEW class I, MEW class II, Ga19, adenosine, and TGFR beta). Inhibition of an inhibitory molecule, e.g., by inhibition at the DNA, RNA or protein level, can optimize a CAR-expressing cell performance. In embodiments, an inhibitory nucleic acid, e.g., an inhibitory nucleic acid, e.g., a dsRNA, e.g., an siRNA or shRNA, a clustered regularly interspaced short palindromic repeats (CRISPR), a transcription-activator like effector nuclease (TALEN), or a zinc finger endonuclease (ZFN), e.g., as described herein, can be used.

Use of siRNA or shRNA to Inhibit Endogenous TCR or HLA

In some embodiments, TCR expression and/or HLA expression can be inhibited using siRNA or shRNA that targets a nucleic acid encoding a TCR and/or HLA, and/or an inhibitory molecule described herein (e.g., PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, Ga19, adenosine, and TGFR beta), in a T cell.

Expression of siRNA and shRNAs in T cells can be achieved using any conventional expression system, e.g., such as a lentiviral expression system. Exemplary shRNAs that downregulate expression of components of the TCR are described, e.g., in US Publication No. 2012/0321667. Exemplary siRNA and shRNA that downregulate expression of HLA class I and/or HLA class II genes are described, e.g., in U.S. publication No. US 2007/0036773.

CRISPR to Inhibit TCR or HLA

"CRISPR" or "CRISPR to inhibit TCR and/or HLA" as used herein refers to a set of clustered regularly interspaced short palindromic repeats, or a system comprising such a set of repeats. "Cas", as used herein, refers to a CRISPR-associated protein. A "CRISPR/Cas" system refers to a system derived from CRISPR and Cas which can be used to silence or mutate a TCR and/or HLA gene, and/or an inhibitory molecule described herein (e.g., PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GALS, adenosine, and TGFR beta).

Naturally-occurring CRISPR/Cas systems are found in approximately 40% of sequenced eubacteria genomes and 90% of sequenced archaea. Grissa et al. (2007) BMC Bioinformatics 8: 172. This system is a type of prokaryotic immune system that confers resistance to foreign genetic elements such as plasmids and phages and provides a form of acquired immunity. Barrangou et al. (2007) Science 315: 1709-1712; Marragini et al. (2008) Science 322: 1843-1845.

Activation and Expansion of T Cells

T cells may be activated and expanded generally using methods as described, for example, in U.S. Pat. Nos. 6,352, 694; 6,534,055; 6,905,680; 6,692,964; 5,858,358; 6,887, 466; 6,905,681; 7,144,575; 7,067,318; 7,172,869; 7,232, 566; 7,175,843; 5,883,223; 6,905,874; 6,797,514; 6,867, 041; and U.S. Patent Application Publication No. 20060121005.

Generally, the T cells of the invention may be expanded by contact with a surface having attached thereto an agent that stimulates a CD3/TCR complex associated signal and a ligand that stimulates a costimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3ζ antibody and an anti-CD28 antibody can be used. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In some embodiments, expansion can be performed using flasks or containers, or gas-permeable containers known by those of skill in the art and can proceed for 7 days, 8 days, 9 days, 10 days, 11 days, 12 days, 13 days, or 14 days, about 7 days to about 14 days, about 8 days to about 14 days, about 9 days to about 14 days, about 10 days to about 14 days, about 11 days to about 14 days, about 12 days to about 14 days, or about 13 days to about 14 days. In some embodiments, the second TIL expansion can proceed for about 14 days.

In certain embodiments, the expansion can be performed using non-specific T-cell receptor stimulation in the presence of interleukin-2 (IL-2) or interleukin-15 (IL-15). The non-specific T-cell receptor stimulus can include, for example, an anti-CD3 antibody, such as about 30 ng/ml of OKT3, a mouse monoclonal anti-CD3 antibody (commercially available from Ortho-McNeil, Raritan, N.J. or Miltenyi Biotech, Auburn, Calif.) or UHCT-1 (commercially available from BioLegend, San Diego, Calif., USA). CoStAR cells can be expanded in vitro by including one or more antigens, including antigenic portions thereof, such as epitope(s), of a cancer, which can be optionally expressed from a vector, such as a human leukocyte antigen A2 (HLA-A2) binding peptide, e.g., 0.3 .mu.M MART-1:26-35 (27L) or gp100: 209-217 (210M), optionally in the presence of a T-cell growth factor, such as 300 IU/mL IL-2 or IL-15. Other suitable antigens may include, e.g., NY-ESO-1, TRP-1, TRP-2, tyrosinase cancer antigen, MAGE-A3, SSX-2, and VEGFR2, or antigenic portions thereof. CoStAR cells may also be rapidly expanded by restimulation with the same antigen(s) of the cancer pulsed onto HLA-A2-expressing antigen-presenting cells. Alternatively, the CoStAR cells can be further stimulated with, e.g., example, irradiated, autologous lymphocytes or with irradiated HLA-A2+ allogeneic lymphocytes and IL-2. In some embodiments, the stimulation occurs as part of the expansion. In some embodiments, the expansion occurs in the presence of irradiated, autologous lymphocytes or with irradiated HLA-A2+ allogeneic lymphocytes and IL-2.

In certain embodiments, the cell culture medium comprises IL-2. In some embodiments, the cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL, or between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or between 8000 IU/mL of IL-2.

In certain embodiments, the cell culture medium comprises OKT3 antibody. In some embodiments, the cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, about 1 μg/mL or between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, or between 50 ng/mL and 100 ng/mL of OKT3 antibody.

In certain embodiments, a combination of IL-2, IL-7, IL-15, and/or IL-21 are employed as a combination during the expansion. In some embodiments, IL-2, IL-7, IL-15, and/or IL-21 as well as any combinations thereof can be included during the expansion. In some embodiments, a combination of IL-2, IL-15, and IL-21 are employed as a combination during the expansion. In some embodiments, IL-2, IL-15, and IL-21 as well as any combinations thereof can be included.

In certain embodiments, the expansion can be conducted in a supplemented cell culture medium comprising IL-2, OKT-3, and antigen-presenting feeder cells.

In certain embodiments, the expansion culture media comprises about 500 IU/mL of IL-15, about 400 IU/mL of IL-15, about 300 IU/mL of IL-15, about 200 IU/mL of IL-15, about 180 IU/mL of IL-15, about 160 IU/mL of IL-15, about 140 IU/mL of IL-15, about 120 IU/mL of IL-15, or about 100 IU/mL of IL-15, or about 500 IU/mL of IL-15 to about 100 IU/mL of IL-15, or about 400 IU/mL of IL-15 to about 100 IU/mL of IL-15 or about 300 IU/mL of IL-15 to about 100 IU/mL of IL-15 or about 200 IU/mL of IL-15, or about 180 IU/mL of IL-15.

In some embodiments, the expansion culture media comprises about 20 IU/mL of IL-21, about 15 IU/mL of IL-21, about 12 IU/mL of IL-21, about 10 IU/mL of IL-21, about 5 IU/mL of IL-21, about 4 IU/mL of IL-21, about 3 IU/mL of IL-21, about 2 IU/mL of IL-21, about 1 IU/mL of IL-21, or about 0.5 IU/mL of IL-21, or about 20 IU/mL of IL-21 to about 0.5 IU/mL of IL-21, or about 15 IU/mL of IL-21 to about 0.5 IU/mL of IL-21, or about 12 IU/mL of IL-21 to about 0.5 IU/mL of IL-21, or about 10 IU/mL of IL-21 to about 0.5 IU/mL of IL-21, or about 5 IU/mL of IL-21 to about 1 IU/mL of IL-21, or about 2 IU/mL of IL-21. In some embodiments, the cell culture medium comprises about 1 IU/mL of IL-21, or about 0.5 IU/mL of IL-21.

In some embodiments the antigen-presenting feeder cells (APCs) are PBMCs. In an embodiment, the ratio of CoStAR cells to PBMCs and/or antigen-presenting cells in the expansion is about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500, or between 1 to 50 and 1 to 300, or between 1 to 100 and 1 to 200.

In certain aspects, the primary stimulatory signal and the costimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one aspect, the agent providing the costimulatory signal is bound to a cell surface and the agent providing the primary activation signal is in solution or coupled to a surface. In certain aspects, both agents can be in solution. In one aspect, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one aspect, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the costimulatory signal is an anti-CD28 antibody or antigen-binding fragment thereof; and both agents are co-immobilized to the same bead in equivalent molecular amounts. In one aspect, a 1:1 ratio of each antibody bound to the beads for CD4+ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular aspect an increase of from about 1 to about 3 fold is observed as compared to the expansion observed using a ratio of 1:1. In one aspect, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain aspects of the invention, the ratio of anti CD28 antibody to anti CD3 antibody bound to the beads is greater than 2:1. In one particular aspect, a 1:100 CD3:CD28 ratio of antibody bound to beads is used. In one aspect, a 1:75 CD3:CD28 ratio of antibody bound to beads is used. In a further aspect, a 1:50 CD3:CD28 ratio of antibody bound to beads is used. In one aspect, a 1:30 CD3:CD28 ratio of antibody bound to beads is used. In one preferred aspect, a 1:10 CD3:CD28 ratio of antibody bound to beads is used. In one aspect, a 1:3 CD3:CD28 ratio of antibody bound to the beads is used. In yet one aspect, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain aspects the ratio of cells to particles ranges from 1:100 to 100:1 and any integer values in-between and in further aspects the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one aspect, a ratio of particles to cells of 1:1 or less is used. In one particular aspect, a preferred particle: cell ratio is 1:5. In further aspects, the ratio of particles to cells can be varied depending on the day of stimulation. For example, in one aspect, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular aspect, the ratio of particles to cells is 1:1 on the first day of stimulation and adjusted to 1:5 on the third and fifth days of stimulation. In one aspect, particles are added on a daily or every other day basis to a final ratio of 1:1 on the first day, and 1:5 on the third and fifth days of stimulation. In one aspect, the ratio of particles to cells is 2:1 on the first day of stimulation and adjusted to 1:10 on the third and fifth days of stimulation. In one aspect, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type. In one aspect, the most typical ratios for use are in the neighborhood of 1:1, 2:1 and 3:1 on the first day.

In further aspects of the present invention, the cells, such as T cells, are combined with agent-coated beads, the beads and the cells are subsequently separated, and then the cells are cultured. In an alternative aspect, prior to culture, the agent-coated beads and cells are not separated but are cultured together. In a further aspect, the beads and cells are first concentrated by application of a force, such as a magnetic force, resulting in increased ligation of cell surface markers, thereby inducing cell stimulation.

Preparation of CoStAR Cells

Viral- and non-viral-based genetic engineering tools can be used to generate CoStAR cells, including without limitation T cells, NK cells resulting in permanent or transient expression of therapeutic genes. Retrovirus-based gene delivery is a mature, well-characterized technology, which has been used to permanently integrate CARs into the host cell genome (Scholler J., e.g. Decade-long safety and function of retroviral-modified chimeric antigen receptor T cells. Sci. Transl. Med. 2012; 4:132ra53; Rosenberg S. A. et al., Gene transfer into humans—immunotherapy of patients with advanced melanoma, using tumor-infiltrating lymphocytes modified by retroviral gene transduction. N. Engl. J. Med. 1990; 323:570-578)

Non-viral DNA transfection methods can also be used. For example, Singh et al describes use of the Sleeping Beauty (SB) transposon system developed to engineer CAR T cells (Singh H., et al., Redirecting specificity of T-cell populations for CD19 using the Sleeping Beauty system. Cancer Res. 2008; 68:2961-2971) and is being used in clinical trials (see e.g., ClinicalTrials.gov: NCT00968760 and NCT01653717). The same technology is applicable to engineer CoStARs cells.

Multiple SB enzymes have been used to deliver transgenes. Mátés describes a hyperactive transposase (SB100X) with approximately 100-fold enhancement in efficiency when compared to the first-generation transposase. SB100X supported 35-50% stable gene transfer in human CD34(+) cells enriched in hematopoietic stem or progenitor cells. (Mátés L. et al., Molecular evolution of a novel hyperactive Sleeping Beauty transposase enables robust stable gene transfer in vertebrates. Nat. Genet. 2009; 41:753-761) and multiple transgenes can be delivered from multicistronic single plasmids (e.g., Thokala R. et al., Redirecting specificity of T cells using the Sleeping Beauty system to express chimeric antigen receptors by mix-and-matching of VL and VH domains targeting CD123+ tumors. PLoS ONE. 2016; 11:e0159477) or multiple plasmids (e.g., Hurton L. V. et al., Tethered IL-15 augments antitumor activity and promotes a stem-cell memory subset in tumor-specific T cells. Proc. Natl. Acad. Sci. USA. 2016; 113:E7788-E7797). Such systems are used with CoStARs of the invention.

Morita et al, describes the piggyBac transposon system to integrate larger transgenes (Morita D. et al., Enhanced expression of anti-CD19 chimeric antigen receptor in piggyBac transposon-engineered T cells. Mol. Ther. Methods Clin. Dev. 2017; 8:131-140) Nakazawa et al. describes use of the system to generate EBV-specific cytotoxic T-cells expressing HER2-specific chimeric antigen receptor (Nakazawa Y et al, PiggyBac-mediated cancer immunotherapy using EBV-specific cytotoxic T-cells expressing HER2-specific chimeric antigen receptor. Mol. Ther. 2011; 19:2133-2143). Manuri et al used the system to generate CD-19 specific T cells (Manuri P. V. R. et al., piggyBac transposon/transposase system to generate CD19-specific T cells for the treatment of B-lineage malignancies. Hum. Gene Ther. 2010; 21:427-437).

Transposon technology is easy and economical. One potential drawback is the longer expansion protocols currently employed may result in T cell differentiation, impaired activity and poor persistence of the infused cells. Monjezi et al describe development minicircle vectors that minimize these difficulties through higher efficiency integrations (Monjezi R. et al., Enhanced CAR T-cell engineering using non-viral Sleeping Beauty transposition from minicircle vectors. Leukemia. 2017; 31:186-194). These transposon technologies can be used for CoStARs of the invention.

Pharmaceutical Compositions

The present invention also relates to a pharmaceutical composition containing a vector or a CoStAR expressing cell of the invention together with a pharmaceutically acceptable carrier, diluent or excipient, and optionally one or more further pharmaceutically active polypeptides and/or compounds.

In some embodiments, a pharmaceutical composition is provided comprising a CoStAR described above and a pharmaceutically acceptable carrier. In some embodiments, a pharmaceutical composition is provided comprising a nucleic acid encoding a CoStAR according to any of the embodiments described above and a pharmaceutically acceptable carrier. In some embodiments, a pharmaceutical composition is provided comprising an effector cell expressing a CoStAR described above and a pharmaceutically acceptable carrier. Such a formulation may, for example, be in a form suitable for intravenous infusion.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

An aspect of the invention provides a population of modified T cells expressing a recombinant CoStAR. A suitable population may be produced by a method described above.

The population of modified T cells may be for use as a medicament. For example, a population of modified T cells as described herein may be used in cancer immunotherapy therapy, for example adoptive T cell therapy.

Other aspects of the invention provide the use of a population of modified T cells as described herein for the manufacture of a medicament for the treatment of cancer, a population of modified T cells as described herein for the treatment of cancer, and a method of treatment of cancer may comprise administering a population of modified T cells as described herein to an individual in need thereof.

The population of modified T cells may be autologous i.e. the modified T cells were originally obtained from the same individual to whom they are subsequently administered (i.e. the donor and recipient individual are the same). A suitable population of modified T cells for administration to the individual may be produced by a method comprising providing an initial population of T cells obtained from the individual, modifying the T cells to express a cAMP PDE or fragment thereof and an antigen receptor which binds specifically to cancer cells in the individual, and culturing the modified T cells.

The population of modified T cells may be allogeneic i.e. the modified T cells were originally obtained from a different individual to the individual to whom they are subsequently administered (i.e. the donor and recipient individual are different). The donor and recipient individuals may be HLA matched to avoid GVHD and other undesirable immune effects. A suitable population of modified T cells for administration to a recipient individual may be produced by a method comprising providing an initial population of T cells obtained from a donor individual, modifying the T cells to express a CoStAR which binds specifically to cancer cells in the recipient individual, and culturing the modified T cells.

Following administration of the modified T cells, the recipient individual may exhibit a T cell mediated immune response against cancer cells in the recipient individual. This may have a beneficial effect on the cancer condition in the individual.

Cancer conditions may be characterised by the abnormal proliferation of malignant cancer cells and may include leukaemias, such as AML, CML, ALL and CLL, lymphomas, such as Hodgkin lymphoma, non-Hodgkin lymphoma and multiple myeloma, and solid cancers such as sarcomas, skin cancer, melanoma, bladder cancer, brain cancer, breast cancer, uterus cancer, ovary cancer, prostate cancer, lung cancer, colorectal cancer, cervical cancer, liver cancer, head and neck cancer, oesophageal cancer, pancreas cancer, renal cancer, adrenal cancer, stomach cancer, testicular cancer, cancer of the gall bladder and biliary tracts, thyroid cancer, thymus cancer, cancer of bone, and cerebral cancer, as well as cancer of unknown primary (CUP).

Cancer cells within an individual may be immunologically distinct from normal somatic cells in the individual (i.e. the cancerous tumor may be immunogenic). For example, the cancer cells may be capable of eliciting a systemic immune response in the individual against one or more antigens expressed by the cancer cells. The tumor antigens that elicit the immune response may be specific to cancer cells or may be shared by one or more normal cells in the individual.

An individual suitable for treatment as described above may be a mammal, such as a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orang-utan, gibbon), or a human.

In preferred embodiments, the individual is a human. In other preferred embodiments, non-human mammals, especially mammals that are conventionally used as models for demonstrating therapeutic efficacy in humans (e.g. murine, primate, porcine, canine, or rabbit animals) may be employed.

Method of Treatment

The term "therapeutically effective amount" refers to an amount of a CoStAR or composition comprising a CoStAR as disclosed herein, effective to "treat" a disease or disorder in an individual. In the case of cancer, the therapeutically effective amount of a CoStAR or composition comprising a CoStAR as disclosed herein can reduce the number of cancer cells; reduce the tumor size or weight; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent a CoStAR or composition comprising a CoStAR as disclosed herein can prevent growth and/or kill existing cancer cells, it can be cytostatic and/or cytotoxic. In some embodiments, the therapeutically effective amount is a growth inhibitory amount. In some embodiments, the therapeutically effective amount is an amount that improves progression free survival of a patient. In the case of infectious disease, such as viral infection, the therapeutically effective amount of a CoStAR or composition comprising a CoStAR as disclosed herein can reduce the number of cells infected by the pathogen; reduce the production or release of pathogen-derived antigens; inhibit (i.e., slow to some extent and preferably stop) spread of the pathogen to uninfected cells; and/or relieve to some extent one or more symptoms associated with the infection. In some embodiments, the therapeutically effective amount is an amount that extends the survival of a patient.

Cells, including T and NK cells, expressing CoStARs for use in the methods of the present may either be created ex vivo either from a patient's own peripheral blood (autologous), or in the setting of a haematopoietic stem cell transplant from donor peripheral blood (allogenic), or peripheral blood from an unconnected donor (allogenic). Alternatively, T-cells or NK cells may be derived from ex-vivo differentiation of inducible progenitor cells or embryonic progenitor cells to T-cells or NK cells. In these instances, T-cells expressing a CoStAR and, optionally, a CAR and/or TCR, are generated by introducing DNA or RNA coding for the CoStAR and, optionally, a CAR and/or TCR, by one of many means including transduction with a viral vector, transfection with DNA or RNA.

T or NK cells expressing a CoStAR of the present invention and, optionally, expressing a TCR and/or CAR may be used for the treatment of haematological cancers or solid tumors.

A method for the treatment of disease relates to the therapeutic use of a vector or cell, including a T or NK cell, of the invention. In this respect, the vector, or T or NK cell may be administered to a subject having an existing disease or condition in order to lessen, reduce or improve at least one symptom associated with the disease and/or to slow down, reduce or block the progression of the disease. The method of the invention may cause or promote T-cell mediated killing of cancer cells. The vector, or T or NK cell according to the present invention may be administered to a patient with one or more additional therapeutic agents. The one or more additional therapeutic agents can be co-administered to the patient. By "co-administering" is meant administering one or more additional therapeutic agents and the vector, or T or NK cell of the present invention sufficiently close in time such that the vector, or T or NK cell can enhance the effect of one or more additional therapeutic agents, or vice versa. In this regard, the vectors or cells can be administered first and the one or more additional therapeutic agents can be administered second, or vice versa. Alternatively, the vectors or cells and the one or more additional therapeutic agents can be administered simultaneously. One co-administered therapeutic agent that may be useful is IL-2, as this is currently used in existing cell therapies to boost the activity of administered cells. However, IL-2 treatment is associated with toxicity and tolerability issues.

As mentioned, for administration to a patient, the CoStAR effector cells can be allogeneic or autologous to the patient. In certain embodiments, allogeneic cells are further genetically modified, for example by gene editing, so as to minimize or prevent GVHD and/or a patient's immune response against the CoStAR cells.

The CoStAR effector cells are used to treat cancers and neoplastic diseases associated with a target antigen. Cancers and neoplastic diseases that may be treated using any of the methods described herein include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the CoStAR effector cells of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, plasmacytoma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include adrenocortical carcinoma, cholangiocarcinoma, fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, stomach cancer, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, thyroid cancer (e.g., medullary thyroid carcinoma and papillary thyroid carcinoma), pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer (e.g., cervical carcinoma and pre-invasive cervical dysplasia), colorectal cancer, cancer of the anus, anal canal, or anorectum, vaginal cancer, cancer of the vulva (e.g., squamous cell carcinoma, intraepithelial carcinoma, adenocarcinoma, and fibrosarcoma), penile cancer, oropharyngeal cancer, esophageal cancer, head cancers (e.g., squamous cell carcinoma), neck cancers (e.g., squamous cell carcinoma), testicular cancer (e.g., seminoma, teratoma, embryonal carcinoma, teratocarcinoma, choriocarcinoma, sarcoma, Leydig cell tumor, fibroma, fibroadenoma, adenomatoid tumors, and lipoma), bladder carcinoma, kidney cancer, melanoma, cancer of the uterus (e.g., endometrial carcinoma), urothelial cancers (e.g., squamous cell carcinoma, transitional cell carcinoma, adenocarcinoma, ureter cancer, and urinary bladder cancer), and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

When "an immunologically effective amount," "an anti-tumor effective amount," "a tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, in some instances $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988).

Combination Therapies

A CoStAR-expressing cell described herein may be used in combination with other known agents and therapies. Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

A CoStAR-expressing cell described herein and the at least one additional therapeutic agent can be administered simultaneously, in the same or in separate compositions, or sequentially. For sequential administration, the CAR-expressing cell described herein can be administered first, and the additional agent can be administered second, or the order of administration can be reversed.

The CoStAR therapy and/or other therapeutic agents, procedures or modalities can be administered during periods of active disorder, or during a period of remission or less active disease. The CoStAR therapy can be administered before the other treatment, concurrently with the treatment, post-treatment, or during remission of the disorder.

When administered in combination, the therapy and the additional agent (e.g., second or third agent), or all, can be administered in an amount or dose that is higher, lower or the same than the amount or dosage of each agent used individually, e.g., as a monotherapy. In certain embodiments, the administered amount or dosage of the CoStAR therapy, the additional agent (e.g., second or third agent), or all, is lower (e.g., at least 20%, at least 30%, at least 40%, or at least 50%) than the amount or dosage of each agent used individually, e.g., as a monotherapy. In other embodiments, the amount or dosage of the CoStAR therapy, the additional agent (e.g., second or third agent), or all, that results in a desired effect (e.g., treatment of cancer) is lower (e.g., at least 20%, at least 30%, at least 40%, or at least 50% lower) than the amount or dosage of each agent used individually, e.g., as a monotherapy, required to achieve the same therapeutic effect.

In further aspects, a CoStAR-expressing cell described herein may be used in a treatment regimen in combination with surgery, chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludarabine, cyclosporin, FK506, rapamycin, mycophenolic acid, steroids, FR901228, cytokines, and irradiation, peptide vaccine, such as that described in Izumoto et al. 2008 J Neurosurg 108:963-971.

In certain instances, compounds of the present invention are combined with other therapeutic agents, such as other anti-cancer agents, anti-allergic agents, anti-nausea agents (or anti-emetics), pain relievers, cytoprotective agents, and combinations thereof.

In one embodiment, a CoStAR-expressing cell described herein can be used in combination with a chemotherapeutic agent. Exemplary chemotherapeutic agents include an anthracycline (e.g., doxorubicin (e.g., liposomal doxorubicin)), a vinca alkaloid (e.g., vinblastine, vincristine, vindesine, vinorelbine), an alkylating agent (e.g., cyclophosphamide, decarbazine, melphalan, ifosfamide, temozolomide), an immune cell antibody (e.g., alemtuzamab, gemtuzumab, rituximab, ofatumumab, tositumomab, brentuximab), an antimetabolite (including, e.g., folic acid antagonists, pyrimidine analogs, purine analogs and adenosine deaminase inhibitors (e.g., fludarabine)), an mTOR inhibitor, a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide).

General Chemotherapeutic agents considered for use in combination therapies include busulfan (Myleran®), busulfan injection (Busulfex®), cladribine (Leustatin®), cyclophosphamide (Cytoxan® or Neosar®), cytarabine, cytosine arabinoside (Cytosar-U®), cytarabine liposome injection (DepoCyt®), daunorubicin hydrochloride (Cerubidine®), daunorubicin citrate liposome injection (DaunoXome®), dexamethasone, doxorubicin hydrochloride (Adriamycin®, Rubex®), etoposide (Vepesid®), fludarabine phosphate (Fludara®), hydroxyurea (Hydrea®), Idarubicin (Idamycin®), mitoxantrone (Novantrone®), Gemtuzumab Ozogamicin (Mylotarg®).

In embodiments, general chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Treatments can be evaluated, for example, by tumor regression, tumor weight or size shrinkage, time to progression, duration of survival, progression free survival, overall response rate, duration of response, quality of life, protein expression and/or activity. Approaches to determining efficacy of the therapy can be employed, including for example, measurement of response through radiological imaging.

Sequences

The following sequences include complete CoStARs and CoStAR components and are non-limiting. Components include signal peptides (SP), binding domains (BD), linkers, spacers and transmembrane domains (STM), a CD28 transmembrane fragment without extracellular or intracellular sequences (STM-CD28TM), intracellular signal domains (SD) and CD40 domains and motifs. SEQ ID NOS:33-108 comprise CoStARs with N-terminal signal peptides. Component locations within whole proteins can be confirmed from GenBank and other sources. The constructs and components are illustrative as to precise sizes and extents and components can be from more than one source. Where there is more than one intracellular signaling domain or signaling fragment, the multiple domains can be in any order. It will be understood that whereas certain proteins may comprise N-terminal signal peptides when expressed, those signal peptides are cleaved and may be imprecisely cleaved when the proteins are expressed, and that the resulting proteins from which signal peptides are removed comprise binding domains having variation of up to about five amino acids in the location of the N-terminal amino acid.

TABLE OF SEQUENCES

| ID NO: | Components | Sequence |
|---|---|---|
| 1 | SP-OSM | MGVLLTQRTL LSLVLALLFP SMASM |
| 2 | SP-PD1 | MQIPQAPWPV VWAVLQLGWR PGW |
| 3 | SP-TGIT | MRWCLLLIWA QGLRQAPLAS G |
| 4 | BD1-MOV19 | QVQLQQSGAE LVKPGASVKI SCKASGYSFT GYFMNWVKQS HGKSLEWIGR IHPYDGDTFY NQNFKDKATL TVDKSSNTAH MELLSLTSED FAVYYCTRYD GSRAMDYWGQ GTTVTVSSGG GGSGGGGSGG GGSDIELTQS PASLAVSLGQ RAIISCKASQ SVSFAGTSLM HWYHQKPGQQ PKLLIYRASN LEAGVPTRFS GSGSKTDFTL NIHPVEEEDA ATYYCQQSRE YPYTFGGGTK LEIK |
| 5 | BD1-MFE23 | QVQLQQSGAE LVRSGTSVKL SCTASGFNIK DSYMHWLRQG PEQGLEWIGW IDPENGDTEY APKFQGKATF TTDTSSNTAY LQLSSLTSED TAVYYCNEGT PTGPYYFDYW GQGTTVTVSS GGGGSGGGGS GGGGSENVLT QSPAIMSASP GEKVTITCSA SSSVSYMHWF QQKPGTSPKL WIYSTSNLAS GVPARFSGSG SGTSYSLTIS RMEAEDAATY YCQQRSSYPL TFGAGTKLEL KR |
| 6 | BD1-PD1 | RPGWFLDSPD RPWNPPTFSP ALLVVTEGDN ATFTCSFSNT SESFVLNWYR MSPSNQTDKL AAFPEDRSQP GQDCRFRVTQ LPNGRDFHMS VVRARRNDSG TYLCGAISLA PKAQIKESLR AELRVTERRA EVPTAH |
| 7 | BD1-TIGIT | MMTGTIETTG NISAEKGGSI ILQCHLSSTT AQVTQVNWEQ QDQLLAICNA DLGWHISPSF KDRVAPGPGL GLTLQSLTVN DTGEYFCIYH TYPDGTYTGR IFLEVLESSV AEHGARFQIP |
| 8 | 3xA3xGS | AAAGSGGSG |
| 9 | BD2-PD1 | RPGWFLDSPD RPWNPPTFSP ALLVVTEGDN ATFTCSFSNT SESFVLNWYR MSPSNQTDKL AAFPEDRSQP GQDCRFRVTQ LPNGRDFHMS VVRARRNDSG TYLCGAISLA PKAQIKESLR AELRVTERRA EVPTAH |
| 10 | BD2-TGIT | MMTGTIETTG NISAEKGGSI ILQCHLSSTT AQVTQVNWEQ QDQLLAICNA DLGWHISPSF KDRVAPGPGL GLTLQSLTVN DTGEYFCIYH TYPDGTYTGR IFLEVLESSV AEHGARFQIP |
| 11 | STM-spCD28 | ILVKQSPMLV AYDNAVNLSC KYSYNLFSRE FRASLHKGLD SAVEVCVVYG NYSQQLQVYS KTGFNCDGKL GNESVTFYLQ NLYVNQTDIY FCKIEVMYPP PYLDNEKSNG TIIHVKGKHL CPSPLFPGPS KPFWVLVVVG GVLACYSLLV TVAFIIFWV |
| 12 | STM-spCD8 | FVPVFLPAKP TTTPAPRPPT PAPTIASQPL SLRPEACRPA AGGAVHTRGL DFACDIYIWA PLAGTCGVLL LSLVITLYCN HRN |

TABLE OF SEQUENCES-continued

| ID NO: | Components | Sequence |
|---|---|---|
| 13 | STM-spIG4 | ESKYGPPCPS CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGKM FWVLVVVGGV LACYSLLVTV AFIIFWV |
| 14 | STM-sCD28TM | CPSPLFPGPS KPFWVLVVVG GVLACYSLLV TVAFIIFWV |
| 15 | STM-CD28TM | FWVLVVVGGV LACYSLLVTV AFIIFWV |
| 16 | Sig-CD28 | RSKRSRLLHS DYMNMTPRRP GPTRKHYQPY APPRDFAAYR S |
| 17 | Sig-CD137 | RFSVVKRGRK KLLYIFKQPF MRPVQTTQEE DGCSCRFPEE EEGGCE |
| 18 | Sig-CD134 | RRDQRLPPDA HKPPGGGSFR TPIQEEQADA HSTLAKI |
| 19 | Sig-CD2 | KRKKQRSRRN DEELETRAHR VATEERGRKP HQIPASTPQN PATSQHPPPP PGHRSQAPSH RPPPPGHRVQ HQPQKRPPAP SGTQVHQQKG PPLPRPRVQP KPPHGAAENS LSPSSN |
| 20 | SigGITR | QLGLHIWQLR SQCMWPRETQ LLLEVPPSTE DARSCQFPEE ERGERSAEEK GRLGDLWV |
| 21 | Sig-CD29 | KLLMIIHDRR EFAKFEKEKM NAKWDTGENP IYKSAVTTVV NPKYEGK |
| 22 | Sig-CD150 | RRRGKTNHYQ TTVEKKSLTI YAQVQKPGPL QKKLDSFPAQ DPCTTIYVAA TEPVPESVQE TNSITVYASV TLPES |
| 23 | CD40 | KKVAKKPTNK APHPKQEPQE INFPDDLPGS NTAAPVQETL HGCQPVTQED GKESRISVQE RQ |
| 24 | CD40_tandem | KKVAKKPTNK APHPKQEPQE INFPDDLPGS NTAAPVQETL HGCQPVTQED GKESRISVQE RQKKVAKKPT NKAPHPKQEP QEINFPDDLP GSNTAAPVQE TLHGCQPVTQ EDGKESRISV QERQ |
| 25 | CD40P227A | KKVAKKPTNK AAHPKQEPQE INFPDDLPGS NTAAPVQETL HGCQPVTQED GKESRISVQE RQ |
| 26 | SH3_motif | KPTNKAPH |
| 27 | TRAF2_motif1 | PKQE |
| 28 | TRAF2_motif2 | PVQE |
| 29 | TRAF2_motif3 | SVQE |
| 30 | TRAF6_motif | QEPQEINFP |
| 31 | PKA_motif1 | KKPTNKA |
| 32 | PKA_motif2 | SRISVQE |
| 33 | CTP194 OSM_MFE23_spCD28_ CD28CD40 | MGVLLTQRTL LSLVLALLFP SMASMQVLQ QSGAELVRSG TSVKLSCTAS GFNIKDSYMH WLRQGPEQGL EWIGWIDPEN GDTEYAPKFQ GKATFTTDTS SNTAYLQLSS LTSEDTAVYY CNEGTPTGPY YFDYWGQGTT VTVSSGGGGS GGGGSGGGGS ENVLTQSPAI MSASPGEKVT ITCSASSSVS YMHWFQQKPG TSPKLWIYST SNLASGVPAR FSGSGSGTSY SLTISRMEAE DAATYYCQQR SSYPLTFGAG TKLELKRAAA GSGGSGILVK QSPMLVAYDN AVNLSCKYSY NLFSREFRAS LHKGLDSAVE VCVVYGNYSQ QLQVYSKTGF NCDGKLGNES VTFYLQNLYV NQTDIYFCKI EVMYPPPYLD NEKSNGTIIH VKGKHLCPSP LFPGPSKPFW VLVVVGGVLA CYSLLVTVAF IIFWVRSKRS RLLHSDYMNM TPRRPGPTRK HYQPYAPPRD FAAYRSKKVA KKPTNKAPHP KQEPQEINFP DDLPGSNTAA PVQETLHGCQ PVTQEDGKES RISVQERQ |
| 34 | OSM_MFE23_spCD28_ CD40 | MGVLLTQRTL LSLVLALLFP SMASMQVLQ QSGAELVRSG TSVKLSCTAS GFNIKDSYMH WLRQGPEQGL EWIGWIDPEN GDTEYAPKFQ GKATFTTDTS SNTAYLQLSS LTSEDTAVYY CNEGTPTGPY YFDYWGQGTT VTVSSGGGGS GGGGSGGGGS |

TABLE OF SEQUENCES-continued

| ID NO: Components | Sequence |
|---|---|
| | ENVLTQSPAI MSASPGEKVT ITCSASSSVS YMHWFQQKPG TSPKLWIYST SNLASGVPAR FSGSGSGTSY SLTISRMEAE DAATYYCQQR SSYPLTFGAG TKLELKRAAA GSGGSGILVK QSPMLVAYDN AVNLSCKYSY NLFSREFRAS LHKGLDSAVE VCVVYGNYSQ QLQVYSKTGF NCDGKLGNES VTFYLQNLYV NQTDIYFCKI EVMYPPPYLD NEKSNGTIIH VKGKHLCPSP LFPGPSKPFW VLVVVGGVLA CYSLLVTVAF IIFWVKKVAK KPTNKAPHPK QEPQEINFPD DLPGSNTAAP VQETLHGCQP VTQEDGKESR ISVQERQ |
| 35 OSM_MFE23_spCD28_ CD137_CD40 | MGVLLTQRTL LSLVLALLFP SMASMQVQLQ QSGAELVRSG TSVKLSCTAS GFNIKDSYMH WLRQGPEQGL EWIGWIDPEN GDTEYAPKFQ GKATFTTDTS SNTAYLQLSS LTSEDTAVYY CNEGTPTGPY YFDYWGQGTT VTVSSGGGGS GGGGSGGGGS ENVLTQSPAI MSASPGEKVT ITCSASSSVS YMHWFQQKPG TSPKLWIYST SNLASGVPAR FSGSGSGTSY SLTISRMEAE DAATYYCQQR SSYPLTFGAG TKLELKRAAA GSGGSGILVK QSPMLVAYDN AVNLSCKYSY NLFSREFRAS LHKGLDSAVE VCVVYGNYSQ QLQVYSKTGF NCDGKLGNES VTFYLQNLYV NQTDIYFCKI EVMYPPPYLD NEKSNGTIIH VKGKHLCPSP LFPGPSKPFW VLVVVGGVLA CYSLLVTVAF IIFWVRFSVV KRGRKKLLYI FKQPFMRPVQ TTQEEDGCSC RFPEEEEGGC EKKVAKKPTN KAPHPKQEPQ EINFPDDLPG SNTAAPVQET LHGCQPVTQE DGKESRISVQ ERQ |
| 36 OSM_MFE23_spCD28_ CD134_CD40 | MGVLLTQRTL LSLVLALLFP SMASMQVQLQ QSGAELVRSG TSVKLSCTAS GFNIKDSYMH WLRQGPEQGL EWIGWIDPEN GDTEYAPKFQ GKATFTTDTS SNTAYLQLSS LTSEDTAVYY CNEGTPTGPY YFDYWGQGTT VTVSSGGGGS GGGGSGGGGS ENVLTQSPAI MSASPGEKVT ITCSASSSVS YMHWFQQKPG TSPKLWIYST SNLASGVPAR FSGSGSGTSY SLTISRMEAE DAATYYCQQR SSYPLTFGAG TKLELKRAAA GSGGSGILVK QSPMLVAYDN AVNLSCKYSY NLFSREFRAS LHKGLDSAVE VCVVYGNYSQ QLQVYSKTGF NCDGKLGNES VTFYLQNLYV NQTDIYFCKI EVMYPPPYLD NEKSNGTIIH VKGKHLCPSP LFPGPSKPFW VLVVVGGVLA CYSLLVTVAF IIFWVRRDQR LPPDAHKPPG GGSFRTPIQE EQADAHSTLA KIKKVAKKPT NKAPHPKQEP QEINFPDDLP GSNTAAPVQE TLHGCQPVTQ EDGKESRISV QERQ |
| 37 OSM_MFE23_spCD28_ CD2_CD40 | MGVLLTQRTL LSLVLALLFP SMASMQVQLQ QSGAELVRSG TSVKLSCTAS GFNIKDSYMH WLRQGPEQGL EWIGWIDPEN GDTEYAPKFQ GKATFTTDTS SNTAYLQLSS LTSEDTAVYY CNEGTPTGPY YFDYWGQGTT VTVSSGGGGS GGGGSGGGGS ENVLTQSPAI MSASPGEKVT ITCSASSSVS YMHWFQQKPG TSPKLWIYST SNLASGVPAR FSGSGSGTSY SLTISRMEAE DAATYYCQQR SSYPLTFGAG TKLELKRAAA GSGGSGILVK QSPMLVAYDN AVNLSCKYSY NLFSREFRAS LHKGLDSAVE VCVVYGNYSQ QLQVYSKTGF NCDGKLGNES VTFYLQNLYV NQTDIYFCKI EVMYPPPYLD NEKSNGTIIH VKGKHLCPSP LFPGPSKPFW VLVVVGGVLA CYSLLVTVAF IIFWVKRKKQ RSRRNDEELE TRAHRVATEE RGRKPHQIPA STPQNPATSQ HPPPPPGHRS QAPSHRPPPP GHRVQHQPQK RPPAPSGTQV HQQKGPPLPR PRVQPKPPHG AAENSLSPSS NKKVAKKPTN KAPHPKQEPQ EINFPDDLPG SNTAAPVQET LHGCQPVTQE DGKESRISVQ ERQ |
| 38 OSM_MFE23_spCD28_ GITR_CD40 | MGVLLTQRTL LSLVLALLFP SMASMQVQLQ QSGAELVRSG TSVKLSCTAS GFNIKDSYMH WLRQGPEQGL EWIGWIDPEN GDTEYAPKFQ GKATFTTDTS SNTAYLQLSS LTSEDTAVYY CNEGTPTGPY YFDYWGQGTT VTVSSGGGGS GGGGSGGGGS ENVLTQSPAI MSASPGEKVT ITCSASSSVS YMHWFQQKPG TSPKLWIYST SNLASGVPAR FSGSGSGTSY SLTISRMEAE DAATYYCQQR SSYPLTFGAG TKLELKRAAA GSGGSGILVK QSPMLVAYDN AVNLSCKYSY NLFSREFRAS LHKGLDSAVE VCVVYGNYSQ QLQVYSKTGF NCDGKLGNES VTFYLQNLYV NQTDIYFCKI EVMYPPPYLD NEKSNGTIIH VKGKHLCPSP LFPGPSKPFW VLVVVGGVLA CYSLLVTVAF IIFWVQLGLH IWQLRSQCMW PRETQLLLEV PPSTEDARSC QFPEEERGER SAEEKGRLGD LWVKKVAKKP TNKAPHPKQE PQEINFPDDL PGSNTAAPVQ ETLHGCQPVT QEDGKESRIS VQERQ |
| 39 OSM_MFE23_spCD28_ CD29_CD40 | MGVLLTQRTL LSLVLALLFP SMASMQVQLQ QSGAELVRSG TSVKLSCTAS GFNIKDSYMH WLRQGPEQGL EWIGWIDPEN GDTEYAPKFQ GKATFTTDTS SNTAYLQLSS LTSEDTAVYY CNEGTPTGPY YFDYWGQGTT VTVSSGGGGS GGGGSGGGGS ENVLTQSPAI MSASPGEKVT ITCSASSSVS YMHWFQQKPG |

TABLE OF SEQUENCES-continued

| ID NO: Components | Sequence |
|---|---|
| | TSPKLWIYST SNLASGVPAR FSGSGSGTSY SLTISRMEAE<br>DAATYYCQQR SSYPLTFGAG TKLELKRAAA GSGGSGILVK<br>QSPMLVAYDN AVNLSCKYSY NLFSREFRAS LHKGLDSAVE<br>VCVVYGNYSQ QLQVYSKTGF NCDGKLGNES VTFYLQNLYV<br>NQTDIYFCKI EVMYPPPYLD NEKSNGTIIH VKGKHLCPSP<br>LFPGPSKPFW VLVVGGVLA CYSLLVTVAF IIFWVKLLMI<br>IHDRREFAKF EKEKMNAKWD TGENPIYKSA VTTVVNPKYE<br>GKKKVAKKPT NKAPHPKQEP QEINFPDDLP GSNTAAPVQE<br>TLHGCQPVTQ EDGKESRISV QERQ |
| 40 OSM_MFE23_spCD28_<br>CD150_CD40 | MGVLLTQRTL LSLVLALLFP SMASMQVQLQ QSGAELVRSG<br>TSVKLSCTAS GFNIKDSYMH WLRQGPEQGL EWIGWIDPEN<br>GDTEYAPKFQ GKATFTTDTS SNTAYLQLSS LTSEDTAVYY<br>CNEGTPTGPY YFDYWGQGTT VTVSSGGGGS GGGGSGGGGS<br>ENVLTQSPAI MSASPGEKVT ITCSASSSVS YMHWFQQKPG<br>TSPKLWIYST SNLASGVPAR FSGSGSGTSY SLTISRMEAE<br>DAATYYCQQR SSYPLTFGAG TKLELKRAAA GSGGSGILVK<br>QSPMLVAYDN AVNLSCKYSY NLFSREFRAS LHKGLDSAVE<br>VCVVYGNYSQ QLQVYSKTGF NCDGKLGNES VTFYLQNLYV<br>NQTDIYFCKI EVMYPPPYLD NEKSNGTIIH VKGKHLCPSP<br>LFPGPSKPFW VLVVGGVLA CYSLLVTVAF IIFWVRRRGK<br>TNHYQTTVEK KSLTIYAQVQ KPGPLQKKLD SFPAQDPCTT<br>IYVAATEPVP ESVQETNSIT VYASVTLPES KKVAKKPTNK<br>APHPKQEPQE INFPDDLPGS NTAAPVQETL HGCQPVTQED<br>GKESRISVQE RQ |
| 41 CTP190<br>OSM_MFE23_spCD8_<br>CD28_CD40 | MGVLLTQRTL LSLVLALLFP SMASMQVQLQ QSGAELVRSG<br>TSVKLSCTAS GFNIKDSYMH WLRQGPEQGL EWIGWIDPEN<br>GDTEYAPKFQ GKATFTTDTS SNTAYLQLSS LTSEDTAVYY<br>CNEGTPTGPY YFDYWGQGTT VTVSSGGGGS GGGGSGGGGS<br>ENVLTQSPAI MSASPGEKVT ITCSASSSVS YMHWFQQKPG<br>TSPKLWIYST SNLASGVPAR FSGSGSGTSY SLTISRMEAE<br>DAATYYCQQR SSYPLTFGAG TKLELKRAAA GSGGSGFVPV<br>FLPAKPTTTP APRPPTPAPT IASQPLSLRP EACRPAAGGA<br>VHTRGLDFAC DIYIWAPLAG TCGVLLLSLV ITLYCNHRNR<br>SKRSRLLHSD YMNMTPRRPG PTRKHYQPYA PPRDFAAYRS<br>KKVAKKPTNK APHPKQEPQE INFPDDLPGS NTAAPVQETL<br>HGCQPVTQED GKESRISVQE RQ |
| 42 CTP193<br>OSM_MFE23_spCD8_<br>CD40 | MGVLLTQRTL LSLVLALLFP SMASMQVQLQ QSGAELVRSG<br>TSVKLSCTAS GFNIKDSYMH WLRQGPEQGL EWIGWIDPEN<br>GDTEYAPKFQ GKATFTTDTS SNTAYLQLSS LTSEDTAVYY<br>CNEGTPTGPY YFDYWGQGTT VTVSSGGGGS GGGGSGGGGS<br>ENVLTQSPAI MSASPGEKVT ITCSASSSVS YMHWFQQKPG<br>TSPKLWIYST SNLASGVPAR FSGSGSGTSY SLTISRMEAE<br>DAATYYCQQR SSYPLTFGAG TKLELKRAAA GSGGSGFVPV<br>FLPAKPTTTP APRPPTPAPT IASQPLSLRP EACRPAAGGA<br>VHTRGLDFAC DIYIWAPLAG TCGVLLLSLV ITLYCNHRNK<br>KVAKKPTNKA PHPKQEPQEI NFPDDLPGSN TAAPVQETLH<br>GCQPVTQEDG KESRISVQER Q |
| 43 CTP192<br>OSM_MFE23_spCD8_<br>CD137_CD40 | MGVLLTQRTL LSLVLALLFP SMASMQVQLQ QSGAELVRSG<br>TSVKLSCTAS GFNIKDSYMH WLRQGPEQGL EWIGWIDPEN<br>GDTEYAPKFQ GKATFTTDTS SNTAYLQLSS LTSEDTAVYY<br>CNEGTPTGPY YFDYWGQGTT VTVSSGGGGS GGGGSGGGGS<br>ENVLTQSPAI MSASPGEKVT ITCSASSSVS YMHWFQQKPG<br>TSPKLWIYST SNLASGVPAR FSGSGSGTSY SLTISRMEAE<br>DAATYYCQQR SSYPLTFGAG TKLELKRAAA GSGGSGFVPV<br>FLPAKPTTTP APRPPTPAPT IASQPLSLRP EACRPAAGGA<br>VHTRGLDFAC DIYIWAPLAG TCGVLLLSLV ITLYCNHRNR<br>FSVVKRGRKK LLYIFKQPFM RPVQTTQEED GCSCRFPEEE<br>EGGCEKKVAK KPTNKAPHPK QEPQEINFPD DLPGSNTAAP<br>VQETLHGCQP VTQEDGKESR ISVQERQ |
| 44 OSM_MFE23_spCD8_<br>CD134_CD40 | MGVLLTQRTL LSLVLALLFP SMASMQVQLQ QSGAELVRSG<br>TSVKLSCTAS GFNIKDSYMH WLRQGPEQGL EWIGWIDPEN<br>GDTEYAPKFQ GKATFTTDTS SNTAYLQLSS LTSEDTAVYY<br>CNEGTPTGPY YFDYWGQGTT VTVSSGGGGS GGGGSGGGGS<br>ENVLTQSPAI MSASPGEKVT ITCSASSSVS YMHWFQQKPG<br>TSPKLWIYST SNLASGVPAR FSGSGSGTSY SLTISRMEAE<br>DAATYYCQQR SSYPLTFGAG TKLELKRAAA GSGGSGFVPV<br>FLPAKPTTTP APRPPTPAPT IASQPLSLRP EACRPAAGGA<br>VHTRGLDFAC DIYIWAPLAG TCGVLLLSLV ITLYCNHRNR<br>RDQRLPPDAH KPPGGGSFRT PIQEEQADAH STLAKIKKVA<br>KKPTNKAPHP KQEPQEINFP DDLPGSNTAA PVQETLHGCQ<br>PVTQEDGKSR ISVQERQ |

TABLE OF SEQUENCES-continued

| ID NO: | Components | Sequence |
|---|---|---|
| 45 | CTP191 OSM_MFE23_spCD8_ CD2_CD40 | MGVLLTQRTL LSLVLALLFP SMASMQVQLQ QSGAELVRSG TSVKLSCTAS GFNIKDSYMH WLRQGPEQGL EWIGWIDPEN GDTEYAPKFQ GKATFTTDTS SNTAYLQLSS LTSEDTAVYY CNEGTPTGPY YFDYWGQGTT VTVSSGGGGS GGGGSGGGGS ENVLTQSPAI MSASPGEKVT ITCSASSSVS YMHWFQQKPG TSPKLWIYST SNLASGVPAR FSGSGSGTSY SLTISRMEAE DAATYYCQQR SSYPLTFGAG TKLELKRAAA GSGGSGFVPV FLPAKPTTTP APRPPTPAPT IASQPLSLRP EACRPAAGGA VHTRGLDFAC DIYIWAPLAG TCGVLLLSLV ITLYCNHRNK RKKQRSRRND EELETRAHRV ATEERGRKPH QIPASTPQNP ATSQHPPPPP GHRSQAPSHR PPPPGHRVQH QPQKRPPAPS GTQVHQQKGP PLPRPRVQPK PPHGAAENSL SPSSNKKVAK KPTNKAPHPK QEPQEINFPD DLPGSNTAAP VQETLHGCQP VTQEDGKESR ISVQERQ |
| 46 | OSM_MFE23_spCD8_ GITR_CD40 | MGVLLTQRTL LSLVLALLFP SMASMQVQLQ QSGAELVRSG TSVKLSCTAS GFNIKDSYMH WLRQGPEQGL EWIGWIDPEN GDTEYAPKFQ GKATFTTDTS SNTAYLQLSS LTSEDTAVYY CNEGTPTGPY YFDYWGQGTT VTVSSGGGGS GGGGSGGGGS ENVLTQSPAI MSASPGEKVT ITCSASSSVS YMHWFQQKPG TSPKLWIYST SNLASGVPAR FSGSGSGTSY SLTISRMEAE DAATYYCQQR SSYPLTFGAG TKLELKRAAA GSGGSGFVPV FLPAKPTTTP APRPPTPAPT IASQPLSLRP EACRPAAGGA VHTRGLDFAC DIYIWAPLAG TCGVLLLSLV ITLYCNHRNQ LGLHIWQLRS QCMWPRETQL LLEVPPSTED ARSCQFPEEE RGERSAEEKG RLGDLWVKKV AKKPTNKAPH PKQEPQEINF PDDLPGSNTA APVQETLHGC QPVTQEDGKE SRISVQERQ |
| 47 | OSM_MFE23_spCD8_ CD29_CD40 | MGVLLTQRTL LSLVLALLFP SMASMQVQLQ QSGAELVRSG TSVKLSCTAS GFNIKDSYMH WLRQGPEQGL EWIGWIDPEN GDTEYAPKFQ GKATFTTDTS SNTAYLQLSS LTSEDTAVYY CNEGTPTGPY YFDYWGQGTT VTVSSGGGGS GGGGSGGGGS ENVLTQSPAI MSASPGEKVT ITCSASSSVS YMHWFQQKPG TSPKLWIYST SNLASGVPAR FSGSGSGTSY SLTISRMEAE DAATYYCQQR SSYPLTFGAG TKLELKRAAA GSGGSGFVPV FLPAKPTTTP APRPPTPAPT IASQPLSLRP EACRPAAGGA VHTRGLDFAC DIYIWAPLAG TCGVLLLSLV ITLYCNHRNK LLMIIHDRRE FAKFEKEKMN AKWDTGENPI YKSAVTTVVN PKYEGKKKVA KKPTNKAPHP KQEPQEINFP DDLPGSNTAA PVQETLHGCQ PVTQEDGKES RISVQERQ |
| 48 | OSM_MFE23_spCD8_ CD150_CD40 | MGVLLTQRTL LSLVLALLFP SMASMQVQLQ QSGAELVRSG TSVKLSCTAS GFNIKDSYMH WLRQGPEQGL EWIGWIDPEN GDTEYAPKFQ GKATFTTDTS SNTAYLQLSS LTSEDTAVYY CNEGTPTGPY YFDYWGQGTT VTVSSGGGGS GGGGSGGGGS ENVLTQSPAI MSASPGEKVT ITCSASSSVS YMHWFQQKPG TSPKLWIYST SNLASGVPAR FSGSGSGTSY SLTISRMEAE DAATYYCQQR SSYPLTFGAG TKLELKRAAA GSGGSGFVPV FLPAKPTTTP APRPPTPAPT IASQPLSLRP EACRPAAGGA VHTRGLDFAC DIYIWAPLAG TCGVLLLSLV ITLYCNHRNR RRGKTNHYQT TVEKKSLTIY AQVQKPGPLQ KKLDSFPAQD PCTTIYVAAT EPVPESVQET NSITVYASVT LPESKKVAKK PTNKAPHPKQ EPQEINFPDD LPGSNTAAPV QETLHGCQPV TQEDGKESRI SVQERQ |
| 49 | CTP203 OSM_MFE23_spIG4_ CD28_CD40 | MGVLLTQRTL LSLVLALLFP SMASMQVQLQ QSGAELVRSG TSVKLSCTAS GFNIKDSYMH WLRQGPEQGL EWIGWIDPEN GDTEYAPKFQ GKATFTTDTS SNTAYLQLSS LTSEDTAVYY CNEGTPTGPY YFDYWGQGTT VTVSSGGGGS GGGGSGGGGS ENVLTQSPAI MSASPGEKVT ITCSASSSVS YMHWFQQKPG TSPKLWIYST SNLASGVPAR FSGSGSGTSY SLTISRMEAE DAATYYCQQR SSYPLTFGAG TKLELKRAAA GSGGSESKY GPPCPSCPAP EFLGGPSVFL FPPKPKDTLM ISRTPEVTCV VVDVSQEDPE VQFNWYVDGV EVHNAKTKPR EEQFNSTYRV VSVLTVLHQD WLNGKEYKCK VSNKGLPSSI EKTISKAKGQ PREPQVYTLP PSQEEMTKNQ VSLTCLVKGF YPSDIAVEWE SNGQPENNYK TTPPVLDSDG SFFLYSRLTV DKSRWQEGNV FSCSVMHEAL HNHYTQKSLS LSLGKMFWVL VVVGGVLACY SLLVTVAFII FWVRSKRSRL LHSDYMNMTP RRPGPTRKHY QPYAPPRDFA AYRSKKVAKK PTNKAPHPKQ EPQEINFPDD LPGSNTAAPV QETLHGCQPV TQEDGKESRI SVQERQ |
| 50 | OSM_MFE23_spIG4_ CD40 | MGVLLTQRTL LSLVLALLFP SMASMQVQLQ QSGAELVRSG TSVKLSCTAS GFNIKDSYMH WLRQGPEQGL EWIGWIDPEN GDTEYAPKFQ GKATFTTDTS SNTAYLQLSS LTSEDTAVYY CNEGTPTGPY YFDYWGQGTT VTVSSGGGGS GGGGSGGGGS ENVLTQSPAI MSASPGEKVT ITCSASSSVS YMHWFQQKPG |

TABLE OF SEQUENCES-continued

| ID NO: Components | Sequence |
|---|---|
| | TSPKLWIYST SNLASGVPAR FSGSGSGTSY SLTISRMEAE |
| | DAATYYCQQR SSYPLTFGAG TKLELKRAAA GSGGSGESKY |
| | GPPCPSCPAP EFLGGPSVFL FPPKPKDTLM ISRTPEVTCV |
| | VVDVSQEDPE VQFNWYVDGV EVHNAKTKPR EEQFNSTYRV |
| | VSVLTVLHQD WLNGKEYKCK VSNKGLPSSI EKTISKAKGQ |
| | PREPQVYTLP PSQEEMTKNQ VSLTCLVKGF YPSDIAVEWE |
| | SNGQPENNYK TTPPVLDSDG SFFLYSRLTV DKSRWQEGNV |
| | FSCSVMHEAL HNHYTQKSLS LSLGKMFWVL VVVGGVLACY |
| | SLLVTVAFII FWVKKVAKKP TNKAPHPKQE PQEINFPDDL |
| | PGSNTAAPVQ ETLHGCQPVT QEDGKESRIS VQERQ |
| 51 OSM_MFE23_spIG4_CD137_CD40 | MGVLLTQRTL LSLVLALLFP SMASMQVQLQ QSGAELVRSG |
| | TSVKLSCTAS GFNIKDSYMH WLRQGPEQGL EWIGWIDPEN |
| | GDTEYAPKFQ GKATFTTDTS SNTAYLQLSS LTSEDTAVYY |
| | CNEGTPTGPY YFDYWGQGTT VTVSSGGGGS GGGGSGGGGS |
| | ENVLTQSPAI MSASPGEKVT ITCSASSSVS YMHWFQQKPG |
| | TSPKLWIYST SNLASGVPAR FSGSGSGTSY SLTISRMEAE |
| | DAATYYCQQR SSYPLTFGAG TKLELKRAAA GSGGSGESKY |
| | GPPCPSCPAP EFLGGPSVFL FPPKPKDTLM ISRTPEVTCV |
| | VVDVSQEDPE VQFNWYVDGV EVHNAKTKPR EEQFNSTYRV |
| | VSVLTVLHQD WLNGKEYKCK VSNKGLPSSI EKTISKAKGQ |
| | PREPQVYTLP PSQEEMTKNQ VSLTCLVKGF YPSDIAVEWE |
| | SNGQPENNYK TTPPVLDSDG SFFLYSRLTV DKSRWQEGNV |
| | FSCSVMHEAL HNHYTQKSLS LSLGKMFWVL VVVGGVLACY |
| | SLLVTVAFII FWVKKVAKKP TNKAPHPKQE PQEINFPDDL |
| | PGSNTAAPVQ ETLHGCQPVT QEDGKESRIS VQERQ |
| 52 OSM_MFE23_spIG4_CD134_CD40 | MGVLLTQRTL LSLVLALLFP SMASMQVQLQ QSGAELVRSG |
| | TSVKLSCTAS GFNIKDSYMH WLRQGPEQGL EWIGWIDPEN |
| | GDTEYAPKFQ GKATFTTDTS SNTAYLQLSS LTSEDTAVYY |
| | CNEGTPTGPY YFDYWGQGTT VTVSSGGGGS GGGGSGGGGS |
| | ENVLTQSPAI MSASPGEKVT ITCSASSSVS YMHWFQQKPG |
| | TSPKLWIYST SNLASGVPAR FSGSGSGTSY SLTISRMEAE |
| | DAATYYCQQR SSYPLTFGAG TKLELKRAAA GSGGSGESKY |
| | GPPCPSCPAP EFLGGPSVFL FPPKPKDTLM ISRTPEVTCV |
| | VVDVSQEDPE VQFNWYVDGV EVHNAKTKPR EEQFNSTYRV |
| | VSVLTVLHQD WLNGKEYKCK VSNKGLPSSI EKTISKAKGQ |
| | PREPQVYTLP PSQEEMTKNQ VSLTCLVKGF YPSDIAVEWE |
| | SNGQPENNYK TTPPVLDSDG SFFLYSRLTV DKSRWQEGNV |
| | FSCSVMHEAL HNHYTQKSLS LSLGKMFWVL VVVGGVLACY |
| | SLLVTVAFII FWVRRDQRLP PDAHKPPGGG SFRTPIQEEQ |
| | ADAHSTLAKI KKVAKKPTNK APHPKQEPQE INFPDDLPGS |
| | NTAAPVQETL HGCQPVTQED GKESRISVQE RQ |
| 53 OSM_MFE23_spIG4_CD2_CD40 | MGVLLTQRTL LSLVLALLFP SMASMQVQLQ QSGAELVRSG |
| | TSVKLSCTAS GFNIKDSYMH WLRQGPEQGL EWIGWIDPEN |
| | GDTEYAPKFQ GKATFTTDTS SNTAYLQLSS LTSEDTAVYY |
| | CNEGTPTGPY YFDYWGQGTT VTVSSGGGGS GGGGSGGGGS |
| | ENVLTQSPAI MSASPGEKVT ITCSASSSVS YMHWFQQKPG |
| | TSPKLWIYST SNLASGVPAR FSGSGSGTSY SLTISRMEAE |
| | DAATYYCQQR SSYPLTFGAG TKLELKRAAA GSGGSGESKY |
| | GPPCPSCPAP EFLGGPSVFL FPPKPKDTLM ISRTPEVTCV |
| | VVDVSQEDPE VQFNWYVDGV EVHNAKTKPR EEQFNSTYRV |
| | VSVLTVLHQD WLNGKEYKCK VSNKGLPSSI EKTISKAKGQ |
| | PREPQVYTLP PSQEEMTKNQ VSLTCLVKGF YPSDIAVEWE |
| | SNGQPENNYK TTPPVLDSDG SFFLYSRLTV DKSRWQEGNV |
| | FSCSVMHEAL HNHYTQKSLS LSLGKMFWVL VVVGGVLACY |
| | SLLVTVAFII FWVKRKKQRS RRNDEELETR AHRVATEERG |
| | RKPHQIPAST PQNPATSQHP PPPPGHRSQA PSHRPPPPGH |
| | RVQHQPQKRP PAPSGTQVHQ QKGPPLPRPR VQPKPPHGAA |
| | ENSLSPSSNK KVAKKPTNKA PHPKQEPQEI NFPDDLPGSN |
| | TAAPVQETLH GCQPVTQEDG KESRISVQER Q |
| 54 OSM_MFE23_spIG4_GITR_CD40 | MGVLLTQRTL LSLVLALLFP SMASMQVQLQ QSGAELVRSG |
| | TSVKLSCTAS GFNIKDSYMH WLRQGPEQGL EWIGWIDPEN |
| | GDTEYAPKFQ GKATFTTDTS SNTAYLQLSS LTSEDTAVYY |
| | CNEGTPTGPY YFDYWGQGTT VTVSSGGGGS GGGGSGGGGS |
| | ENVLTQSPAI MSASPGEKVT ITCSASSSVS YMHWFQQKPG |
| | TSPKLWIYST SNLASGVPAR FSGSGSGTSY SLTISRMEAE |
| | DAATYYCQQR SSYPLTFGAG TKLELKRAAA GSGGSGESKY |
| | GPPCPSCPAP EFLGGPSVFL FPPKPKDTLM ISRTPEVTCV |
| | VVDVSQEDPE VQFNWYVDGV EVHNAKTKPR EEQFNSTYRV |
| | VSVLTVLHQD WLNGKEYKCK VSNKGLPSSI EKTISKAKGQ |
| | PREPQVYTLP PSQEEMTKNQ VSLTCLVKGF YPSDIAVEWE |
| | SNGQPENNYK TTPPVLDSDG SFFLYSRLTV DKSRWQEGNV |
| | FSCSVMHEAL HNHYTQKSLS LSLGKMFWVL VVVGGVLACY |
| | SLLVTVAFII FWVQLGLHIW QLRSQCMWPR ETQLLLEVPP |

TABLE OF SEQUENCES-continued

| ID NO: Components | Sequence |
|---|---|
| | STEDARSCQF PEEERGERSA EEKGRLGDLW VKKVAKKPTN KAPHPKQEPQ EINFPDDLPG SNTAAPVQET LHGCQPVTQE DGKESRISVQ ERQ |
| 55 OSM_MFE23_spIG4_CD29_CD40 | MGVLLTQRTL LSLVLALLFP SMASMQVLQ QSGAELVRSG TSVKLSCTAS GFNIKDSYMH WLRQGPEQGL EWIGWIDPEN GDTEYAPKFQ GKATFTTDTS SNTAYLQLSS LTSEDTAVYY CNEGTPTGPY YFDYWGQGTT VTVSSGGGGS GGGGSGGGGS ENVLTQSPAI MSASPGEKVT ITCSASSSVS YMHWFQQKPG TSPKLWIYST SNLASGVPAR FSGSGSGTSY SLTISRMEAE DAATYYCQQR SSYPLTFGAG TKLELKRAAA GSGGSGESKY GPPCPSCPAP EFLGGPSVFL FPPKPKDTLM ISRTPEVTCV VVDVSQEDPE VQFNWYVDGV EVHNAKTKPR EEQFNSTYRV VSVLTVLHQD WLNGKEYKCK VSNKGLPSSI EKTISKAKGQ PREPQVYTLP PSQEEMTKNQ VSLTCLVKGF YPSDIAVEWE SNGQPENNYK TTPPVLDSDG SFFLYSRLTV DKSRWQEGNV FSCSVMHEAL HNHYTQKSLS LSLGKMFWVL VVVGGVLACY SLLVTVAFII FWVKLLMIIH DRREFAKFEK EKMNAKWDTG ENPIYKSAVT TVVNPKYEGK KKVAKKPTNK APHPKQEPQE INFPDDLPGS NTAAPVQETL HGCQPVTQED GKESRISVQE RQ |
| 56 OSM_MFE23_spIG4_CD150_CD40 | MGVLLTQRTL LSLVLALLFP SMASMQVLQ QSGAELVRSG TSVKLSCTAS GFNIKDSYMH WLRQGPEQGL EWIGWIDPEN GDTEYAPKFQ GKATFTTDTS SNTAYLQLSS LTSEDTAVYY CNEGTPTGPY YFDYWGQGTT VTVSSGGGGS GGGGSGGGGS ENVLTQSPAI MSASPGEKVT ITCSASSSVS YMHWFQQKPG TSPKLWIYST SNLASGVPAR FSGSGSGTSY SLTISRMEAE DAATYYCQQR SSYPLTFGAG TKLELKRAAA GSGGSGESKY GPPCPSCPAP EFLGGPSVFL FPPKPKDTLM ISRTPEVTCV VVDVSQEDPE VQFNWYVDGV EVHNAKTKPR EEQFNSTYRV VSVLTVLHQD WLNGKEYKCK VSNKGLPSSI EKTISKAKGQ PREPQVYTLP PSQEEMTKNQ VSLTCLVKGF YPSDIAVEWE SNGQPENNYK TTPPVLDSDG SFFLYSRLTV DKSRWQEGNV FSCSVMHEAL HNHYTQKSLS LSLGKMFWVL VVVGGVLACY SLLVTVAFII FWVRRRGKTN HYQTTVEKKS LTIYAQVQKP GPLQKKLDSF PAQDPCTTIY VAATEPVPES VQETNSITVY ASVTLPESKK VAKKPTNKAP HPKQEPQEIN FPDDLPGSNT AAPVQETLHG CQPVTQEDGK ESRISVQERQ |
| 57 OSM_MFE23_spIG4_CD40_tandem | MGVLLTQRTL LSLVLALLFP SMASMQVLQ QSGAELVRSG TSVKLSCTAS GFNIKDSYMH WLRQGPEQGL EWIGWIDPEN GDTEYAPKFQ GKATFTTDTS SNTAYLQLSS LTSEDTAVYY CNEGTPTGPY YFDYWGQGTT VTVSSGGGGS GGGGSGGGGS ENVLTQSPAI MSASPGEKVT ITCSASSSVS YMHWFQQKPG TSPKLWIYST SNLASGVPAR FSGSGSGTSY SLTISRMEAE DAATYYCQQR SSYPLTFGAG TKLELKRAAA GSGGSGESKY GPPCPSCPAP EFLGGPSVFL FPPKPKDTLM ISRTPEVTCV VVDVSQEDPE VQFNWYVDGV EVHNAKTKPR EEQFNSTYRV VSVLTVLHQD WLNGKEYKCK VSNKGLPSSI EKTISKAKGQ PREPQVYTLP PSQEEMTKNQ VSLTCLVKGF YPSDIAVEWE SNGQPENNYK TTPPVLDSDG SFFLYSRLTV DKSRWQEGNV FSCSVMHEAL HNHYTQKSLS LSLGKMFWVL VVVGGVLACY SLLVTVAFII FWVAKKPTNK APHPKQEPQE INFPDDLPGS NTAAPVQETL HGCQPVTQED GKESRISVQE RQKKVAKKPT NKAPHPKQEP QEINFPDDLP GSNTAAPVQE TLHGCQPVTQ EDGKESRISV QERQKKVA |
| 58 OSM_MFE23_spIG4_CD40_P227A | MGVLLTQRTL LSLVLALLFP SMASMQVLQ QSGAELVRSG TSVKLSCTAS GFNIKDSYMH WLRQGPEQGL EWIGWIDPEN GDTEYAPKFQ GKATFTTDTS SNTAYLQLSS LTSEDTAVYY CNEGTPTGPY YFDYWGQGTT VTVSSGGGGS GGGGSGGGGS ENVLTQSPAI MSASPGEKVT ITCSASSSVS YMHWFQQKPG TSPKLWIYST SNLASGVPAR FSGSGSGTSY SLTISRMEAE DAATYYCQQR SSYPLTFGAG TKLELKRAAA GSGGSGESKY GPPCPSCPAP EFLGGPSVFL FPPKPKDTLM ISRTPEVTCV VVDVSQEDPE VQFNWYVDGV EVHNAKTKPR EEQFNSTYRV VSVLTVLHQD WLNGKEYKCK VSNKGLPSSI EKTISKAKGQ PREPQVYTLP PSQEEMTKNQ VSLTCLVKGF YPSDIAVEWE SNGQPENNYK TTPPVLDSDG SFFLYSRLTV DKSRWQEGNV FSCSVMHEAL HNHYTQKSLS LSLGKMFWVL VVVGGVLACY SLLVTVAFII FWVKKVAKKP TNKAAHPKQE PQEINFPDDL PGSNTAAPVQ ETLHGCQPVT QEDGKESRIS VQERQ |
| 59 CTP204 OSM_MFE23_PD1_sCD28TM_CD28_CD40 | MGVLLTQRTL LSLVLALLFP SMASMQVLQ QSGAELVRSG TSVKLSCTAS GFNIKDSYMH WLRQGPEQGL EWIGWIDPEN GDTEYAPKFQ GKATFTTDTS SNTAYLQLSS LTSEDTAVYY |

TABLE OF SEQUENCES-continued

| ID NO: Components | Sequence |
|---|---|
| | CNEGTPTGPY YFDYWGQGTT VTVSSGGGGS GGGGSGGGGS ENVLTQSPAI MSASPGEKVT ITCSASSSVS YMHWFQQKPG TSPKLWIYST SNLASGVPAR FSGSGSGTSY SLTISRMEAE DAATYYCQQR SSYPLTFGAG TKLELKRAAA GSGGSGRPGW FLDSPDRPWN PPTFSPALLV VTEGDNATFT CSFSNTSESF VLNWYRMSPS NQTDKLAAFP EDRSQPGQDC RFRVTQLPNG RDFHMSVVRA RRNDSGTYLC GAISLAPKAQ IKESLRAELR VTERRAEVPT AHCPSPLFPG PSKPFWVLVV VGGVLACYSL LVTVAFIIFW VRSKRSRLLH SDYMNMTPRR PGPTRKHYQP YAPPRDFAAY RSKKVAKKPT NKAPHPKQEP QEINFPDDLP GSNTAAPVQE TLHGCQPVTQ EDGKESRISV QERQ |
| 60 OSM_MFE23_PD1_ sCD28TM_CD40 | MGVLLTQRTL LSLVLALLFP SMASMQVQLQ QSGAELVRSG TSVKLSCTAS GFNIKDSYMH WLRQGPEQGL EWIGWIDPEN GDTEYAPKFQ GKATFTTDTS SNTAYLQLSS LTSEDTAVYY CNEGTPTGPY YFDYWGQGTT VTVSSGGGGS GGGGSGGGGS ENVLTQSPAI MSASPGEKVT ITCSASSSVS YMHWFQQKPG TSPKLWIYST SNLASGVPAR FSGSGSGTSY SLTISRMEAE DAATYYCQQR SSYPLTFGAG TKLELKRAAA GSGGSGRPGW FLDSPDRPWN PPTFSPALLV VTEGDNATFT CSFSNTSESF VLNWYRMSPS NQTDKLAAFP EDRSQPGQDC RFRVTQLPNG RDFHMSVVRA RRNDSGTYLC GAISLAPKAQ IKESLRAELR VTERRAEVPT AHCPSPLFPG PSKPFWVLVV VGGVLACYSL LVTVAFIIFW VKKVAKKPTN KAPHPKQEPQ EINFPDDLPG SNTAAPVQET LHGCQPVTQE DGKESRISVQ ERQ |
| 61 OSM_MFE23_TIGIT_ sCD28TM_CD28_ CD40 | MGVLLTQRTL LSLVLALLFP SMASMQVQLQ QSGAELVRSG TSVKLSCTAS GFNIKDSYMH WLRQGPEQGL EWIGWIDPEN GDTEYAPKFQ GKATFTTDTS SNTAYLQLSS LTSEDTAVYY CNEGTPTGPY YFDYWGQGTT VTVSSGGGGS GGGGSGGGGS ENVLTQSPAI MSASPGEKVT ITCSASSSVS YMHWFQQKPG TSPKLWIYST SNLASGVPAR FSGSGSGTSY SLTISRMEAE DAATYYCQQR SSYPLTFGAG TKLELKRAAA GSGGSGMMTG TIETTGNISA EKGGSIILQC HLSSTTAQVT QVNWEQQDQL LAICNADLGW HISPSFKDRV APGPGLGLTL QSLTVNDTGE YFCIYHTYPD GTYTGRIFLE VLESSVAEHG ARFQIPFWVL VVVGGVLACY SLLVTVAFII FWVRSKRSRL LHSDYMNMTP RRPGPTRKHY QPYAPPRDFA AYRSKKVAKK PTNKAPHPKQ EPQEINFPDD LPGSNTAAPV QETLHGCQPV TQEDGKESRI SVQERQ |
| 62 OSM_MFE23_TIGIT_ sCD28TM_CD40 | MGVLLTQRTL LSLVLALLFP SMASMQVQLQ QSGAELVRSG TSVKLSCTAS GFNIKDSYMH WLRQGPEQGL EWIGWIDPEN GDTEYAPKFQ GKATFTTDTS SNTAYLQLSS LTSEDTAVYY CNEGTPTGPY YFDYWGQGTT VTVSSGGGGS GGGGSGGGGS ENVLTQSPAI MSASPGEKVT ITCSASSSVS YMHWFQQKPG TSPKLWIYST SNLASGVPAR FSGSGSGTSY SLTISRMEAE DAATYYCQQR SSYPLTFGAG TKLELKRAAA GSGGSGMMTG TIETTGNISA EKGGSIILQC HLSSTTAQVT QVNWEQQDQL LAICNADLGW HISPSFKDRV APGPGLGLTL QSLTVNDTGE YFCIYHTYPD GTYTGRIFLE VLESSVAEHG ARFQIPFWVL VVVGGVLACY SLLVTVAFII FWVKKVAKKP TNKAPHPKQE PQEINFPDDL PGSNTAAPVQ ETLHGCQPVT QEDGKESRIS VQERQ |
| 63 OSM_MOV19_spCD28_ CD28_CD40 | MGVLLTQRTL LSLVLALLFP SMASMQVQLQ QSGAELVKPG ASVKISCKAS GYSFTGYFMN WVKQSHGKSL EWIGRIHPYD GDTFYNQNFK DKATLTVDKS SNTAHMELLS LTSEDFAVYY CTRYDGSRAM DYWGQGTTVT VSSGGGGSGG GGSGGGGSDI ELTQSPASLA VSLGQRAIIS CKASQSVSFA GTSLMHWYHQ KPGQQPKLLI YRASNLEAGV PTRFSGSGSK TDFTLNIHPV EEEDAATYYC QQSREYPYTF GGGTKLEIKA AAGSGGSGIL VKQSPMLVAY DNAVNLSCKY SYNLFSREFR ASLHKGLDSA VEVCVVYGNY SQQLVYSKT GFNCDGKLGN ESVTFYLQNL YVNQTDIYFC KIEVMYPPPY LDNEKSNGTI IHVKGKHLCP SPLFPGPSKP FWVLVVVGGV LACYSLLVTV AFIIFWVRSK RSRLLHSDYM NMTPRRPGPT RKHYQPYAPP RDFAAYRSKK VAKKPTNKAP HPKQEPQEIN FPDDLPGSNT AAPVQETLHG CQPVTQEDGK ESRISVQERQ |
| 64 OSM_MOV19_spCD28_ CD40 | MGVLLTQRTL LSLVLALLFP SMASMQVQLQ QSGAELVKPG ASVKISCKAS GYSFTGYFMN WVKQSHGKSL EWIGRIHPYD GDTFYNQNFK DKATLTVDKS SNTAHMELLS LTSEDFAVYY CTRYDGSRAM DYWGQGTTVT VSSGGGGSGG GGSGGGGSDI ELTQSPASLA VSLGQRAIIS CKASQSVSFA GTSLMHWYHQ KPGQQPKLLI YRASNLEAGV PTRFSGSGSK TDFTLNIHPV EEEDAATYYC QQSREYPYTF GGGTKLEIKA AAGSGGSGIL |

TABLE OF SEQUENCES-continued

| ID NO: | Components | Sequence |
|---|---|---|
| | | VKQSPMLVAY DNAVNLSCKY SYNLFSREFR ASLHKGLDSA VEVCVVYGNY SQQLQVYSKT GFNCDGKLGN ESVTFYLQNL YVNQTDIYFC KIEVMYPPPY LDNEKSNGTI IHVKGKHLCP SPLFPGPSKP FWVLVVVGGV LACYSLLVTV AFIIFWVKKV AKKPTNKAPH PKQEPQEINF PDDLPGSNTA APVQETLHGC QPVTQEDGKE SRISVQERQ |
| 65 | OSM_MOV19_spCD28_ CD137_CD40 | MGVLLTQRTL LSLVLALLFP SMASMQVQLQ QSGAELVKPG ASVKISCKAS GYSFTGYFMN WVKQSHGKSL EWIGRIHPYD GDTFYNQNFK DKATLTVDKS SNTAHMELLS LTSEDFAVYY CTRYDGSRAM DYWGQGTTVT VSSGGGGSGG GGSGGGGSDI ELTQSPASLA VSLGQRAIIS CKASQSVSFA GTSLMHWYHQ KPGQQPKLLI YRASNLEAGV PTRFSGSGSK TDFTLNIHPV EEEDAATYYC QQSREYPYTF GGGTKLEIKA AAGSGGSGIL VKQSPMLVAY DNAVNLSCKY SYNLFSREFR ASLHKGLDSA VEVCVVYGNY SQQLQVYSKT GFNCDGKLGN ESVTFYLQNL YVNQTDIYFC KIEVMYPPPY LDNEKSNGTI IHVKGKHLCP SPLFPGPSKP FWVLVVVGGV LACYSLLVTV AFIIFWVRFS VVKRGRKKLL YIFKQPFMRP VQTTQEEDGC SCRFPEEEEG GCEKKVAKKP TNKAPHPKQE PQEINFPDDL PGSNTAAPVQ ETLHGCPVT QEDGKESRIS VQERQ |
| 66 | OSM_MOV19_spCD28_ CD134_CD40 | MGVLLTQRTL LSLVLALLFP SMASMQVQLQ QSGAELVKPG ASVKISCKAS GYSFTGYFMN WVKQSHGKSL EWIGRIHPYD GDTFYNQNFK DKATLTVDKS SNTAHMELLS LTSEDFAVYY CTRYDGSRAM DYWGQGTTVT VSSGGGGSGG GGSGGGGSDI ELTQSPASLA VSLGQRAIIS CKASQSVSFA GTSLMHWYHQ KPGQQPKLLI YRASNLEAGV PTRFSGSGSK TDFTLNIHPV EEEDAATYYC QQSREYPYTF GGGTKLEIKA AAGSGGSGIL VKQSPMLVAY DNAVNLSCKY SYNLFSREFR ASLHKGLDSA VEVCVVYGNY SQQLQVYSKT GFNCDGKLGN ESVTFYLQNL YVNQTDIYFC KIEVMYPPPY LDNEKSNGTI IHVKGKHLCP SPLFPGPSKP FWVLVVVGGV LACYSLLVTV AFIIFWVRRD QRLPPDAHKP GGGSFRTPI QEEQADAHST LAKIKKVAKK PTNKAPHPKQ EPQEINFPDD LPGSNTAAPV QETLHGCQPV TQEDGKESRI SVQERQ |
| 67 | OSM_MOV19_spCD28_ CD2_CD40 | MGVLLTQRTL LSLVLALLFP SMASMQVQLQ QSGAELVKPG ASVKISCKAS GYSFTGYFMN WVKQSHGKSL EWIGRIHPYD GDTFYNQNFK DKATLTVDKS SNTAHMELLS LTSEDFAVYY CTRYDGSRAM DYWGQGTTVT VSSGGGGSGG GGSGGGGSDI ELTQSPASLA VSLGQRAIIS CKASQSVSFA GTSLMHWYHQ KPGQQPKLLI YRASNLEAGV PTRFSGSGSK TDFTLNIHPV EEEDAATYYC QQSREYPYTF GGGTKLEIKA AAGSGGSGIL VKQSPMLVAY DNAVNLSCKY SYNLFSREFR ASLHKGLDSA VEVCVVYGNY SQQLQVYSKT GFNCDGKLGN ESVTFYLQNL YVNQTDIYFC KIEVMYPPPY LDNEKSNGTI IHVKGKHLCP SPLFPGPSKP FWVLVVVGGV LACYSLLVTV AFIIFWVKRK KQRSRRNDEE LETRAHRVAT EERGRKPHQI PASTPQNPAT SQHPPPPPGH RSQAPSHRPP PPGHRVQHQP QKRPPAPSGT QVHQQKGPPL PRPRVQPKPP HGAAENSLSP SSNKKVAKKP TNKAPHPKQE PQEINFPDDL PGSNTAAPVQ ETLHGCPVT QEDGKESRIS VQERQ |
| 68 | OSM_MOV19_spCD28_ GITR_CD40 | MGVLLTQRTL LSLVLALLFP SMASMQVQLQ QSGAELVKPG ASVKISCKAS GYSFTGYFMN WVKQSHGKSL EWIGRIHPYD GDTFYNQNFK DKATLTVDKS SNTAHMELLS LTSEDFAVYY CTRYDGSRAM DYWGQGTTVT VSSGGGGSGG GGSGGGGSDI ELTQSPASLA VSLGQRAIIS CKASQSVSFA GTSLMHWYHQ KPGQQPKLLI YRASNLEAGV PTRFSGSGSK TDFTLNIHPV EEEDAATYYC QQSREYPYTF GGGTKLEIKA AAGSGGSGIL VKQSPMLVAY DNAVNLSCKY SYNLFSREFR ASLHKGLDSA VEVCVVYGNY SQQLQVYSKT GFNCDGKLGN ESVTFYLQNL YVNQTDIYFC KIEVMYPPPY LDNEKSNGTI IHVKGKHLCP SPLFPGPSKP FWVLVVVGGV LACYSLLVTV AFIIFWVQLG LHIWQLRSQC MWPRETQLLL EVPPSTEDAR SCQFPEEERG ERSAEEKGRL GDLWVKKVAK KPTNKAPHPK QEPQEINFPD DLPGSNTAAP VQETLHGCQP VTQEDGKESR ISVQERQ |
| 69 | OSM_MOV19_spCD28_ CD29_CD40 | MGVLLTQRTL LSLVLALLFP SMASMQVQLQ QSGAELVKPG ASVKISCKAS GYSFTGYFMN WVKQSHGKSL EWIGRIHPYD GDTFYNQNFK DKATLTVDKS SNTAHMELLS LTSEDFAVYY CTRYDGSRAM DYWGQGTTVT VSSGGGGSGG GGSGGGGSDI ELTQSPASLA VSLGQRAIIS CKASQSVSFA GTSLMHWYHQ KPGQQPKLLI YRASNLEAGV PTRFSGSGSK TDFTLNIHPV EEEDAATYYC QQSREYPYTF GGGTKLEIKA AAGSGGSGIL VKQSPMLVAY DNAVNLSCKY SYNLFSREFR ASLHKGLDSA |

TABLE OF SEQUENCES-continued

| ID NO: Components | Sequence |
|---|---|
| | VEVCVVYGNY SQQLQVYSKT GFNCDGKLGN ESVTFYLQNL YVNQTDIYFC KIEVMYPPPY LDNEKSNGTI IHVKGKHLCP SPLFPGPSKP FWVLVVVGGV LACYSLLVTV AFIIFWVKLL MIIHDRREFA KFEKEKMNAK WDTGENPIYK SAVTTVVNPK YEGKKKVAKK PTNKAPHPKQ EPQEINFPDD LPGSNTAAPV QETLHGCQPV TQEDGKESRI SVQERQ |
| 70 OSM_MOV19_spCD28_ CD150_CD40 | MGVLLTQRTL LSLVLALLFP SMASMQVQLQ QSGAELVKPG ASVKISCKAS GYSFTGYFMN WVKQSHGKSL EWIGRIHPYD GDTFYNQNFK DKATLTVDKS SNTAHMELLS LTSEDFAVYY CTRYDGSRAM DYWGQGTTVT VSSGGGGSGG GGSGGGGSDI ELTQSPASLA VSLGQRAIIS CKASQSVSFA GTSLMHWYHQ KPGQQPKLLI YRASNLEAGV PTRFSGSGSK TDFTLNIHPV EEEDAATYYC QQSREYPYTF GGGTKLEIKA AAGSGGSGIL VKQSPMLVAY DNAVNLSCKY SYNLFSREFR ASLHKGLDSA VEVCVVYGNY SQQLQVYSKT GFNCDGKLGN ESVTFYLQNL YVNQTDIYFC KIEVMYPPPY LDNEKSNGTI IHVKGKHLCP SPLFPGPSKP FWVLVVVGGV LACYSLLVTV AFIIFWVRRR GKTNHYQTTV EKKSLTIYAQ VQKPGPLQKK LDSFPAQDPC TTIYVAATEP VPESVQETNS ITVYASVTLP ESKKVAKKPT NKAPHPKQEP QEINFPDDLP GSNTAAPVQE TLHGCQPVTQ EDGKESRISV QERQ |
| 71 OSM_MOV19_spCD8_ CD28_CD40 | MGVLLTQRTL LSLVLALLFP SMASMQVQLQ QSGAELVKPG ASVKISCKAS GYSFTGYFMN WVKQSHGKSL EWIGRIHPYD GDTFYNQNFK DKATLTVDKS SNTAHMELLS LTSEDFAVYY CTRYDGSRAM DYWGQGTTVT VSSGGGGSGG GGSGGGGSDI ELTQSPASLA VSLGQRAIIS CKASQSVSFA GTSLMHWYHQ KPGQQPKLLI YRASNLEAGV PTRFSGSGSK TDFTLNIHPV EEEDAATYYC QQSREYPYTF GGGTKLEIKA AAGSGGSGFV PVFLPAKPTT TPAPRPPTPA PTIASQPLSL RPEACRPAAG GAVHTRGLDF ACDIYIWAPL AGTCGVLLLS LVITLYCNHR NRSKRSRLLH SDYMNMTPRR PGPTRKHYQP YAPPRDFAAY RSKKVAKKPT NKAPHPKQEP QEINFPDDLP GSNTAAPVQE TLHGCQPVTQ EDGKESRISV QERQ |
| 72 OSM_MOV19_spCD8_ CD40 | MGVLLTQRTL LSLVLALLFP SMASMQVQLQ QSGAELVKPG ASVKISCKAS GYSFTGYFMN WVKQSHGKSL EWIGRIHPYD GDTFYNQNFK DKATLTVDKS SNTAHMELLS LTSEDFAVYY CTRYDGSRAM DYWGQGTTVT VSSGGGGSGG GGSGGGGSDI ELTQSPASLA VSLGQRAIIS CKASQSVSFA GTSLMHWYHQ KPGQQPKLLI YRASNLEAGV PTRFSGSGSK TDFTLNIHPV EEEDAATYYC QQSREYPYTF GGGTKLEIKA AAGSGGSGFV PVFLPAKPTT TPAPRPPTPA PTIASQPLSL RPEACRPAAG GAVHTRGLDF ACDIYIWAPL AGTCGVLLLS LVITLYCNHR NKKVAKKPTN KAPHPKQEPQ EINFPDDLPG SNTAAPVQET LHGCQPVTQE DGKESRISVQ ERQ |
| 73 OSM_MOV19_spCD8_ CD137_CD40 | MGVLLTQRTL LSLVLALLFP SMASMQVQLQ QSGAELVKPG ASVKISCKAS GYSFTGYFMN WVKQSHGKSL EWIGRIHPYD GDTFYNQNFK DKATLTVDKS SNTAHMELLS LTSEDFAVYY CTRYDGSRAM DYWGQGTTVT VSSGGGGSGG GGSGGGGSDI ELTQSPASLA VSLGQRAIIS CKASQSVSFA GTSLMHWYHQ KPGQQPKLLI YRASNLEAGV PTRFSGSGSK TDFTLNIHPV EEEDAATYYC QQSREYPYTF GGGTKLEIKA AAGSGGSGFV PVFLPAKPTT TPAPRPPTPA PTIASQPLSL RPEACRPAAG GAVHTRGLDF ACDIYIWAPL AGTCGVLLLS LVITLYCNHR NRFSVVKRGR KKLLYIFKQP FMRPVQTTQE EDGCSCRFPE EEEGGCEKKV AKKPTNKAPH PKQEPQEINF PDDLPGSNTA APVQETLHGC QPVTQEDGKE SRISVQERQ |
| 74 OSM_MOV19_spCD8_ CD134_CD40 | MGVLLTQRTL LSLVLALLFP SMASMQVQLQ QSGAELVKPG ASVKISCKAS GYSFTGYFMN WVKQSHGKSL EWIGRIHPYD GDTFYNQNFK DKATLTVDKS SNTAHMELLS LTSEDFAVYY CTRYDGSRAM DYWGQGTTVT VSSGGGGSGG GGSGGGGSDI ELTQSPASLA VSLGQRAIIS CKASQSVSFA GTSLMHWYHQ KPGQQPKLLI YRASNLEAGV PTRFSGSGSK TDFTLNIHPV EEEDAATYYC QQSREYPYTF GGGTKLEIKA AAGSGGSGFV PVFLPAKPTT TPAPRPPTPA PTIASQPLSL RPEACRPAAG GAVHTRGLDF ACDIYIWAPL AGTCGVLLLS LVITLYCNHR NRRDQRLPPD AHKPPGGGSF RTPIQEEQAD AHSTLAKIKK VAKKPTNKAP HPKQEPQEIN FPDDLPGSNT AAPVQETLHG CQPVTQEDGK SRISVQERQ |
| 75 OSM_MOV19_spCD8_ CD2_CD40 | MGVLLTQRTL LSLVLALLFP SMASMQVQLQ QSGAELVKPG ASVKISCKAS GYSFTGYFMN WVKQSHGKSL EWIGRIHPYD GDTFYNQNFK DKATLTVDKS SNTAHMELLS LTSEDFAVYY |

TABLE OF SEQUENCES-continued

| ID NO: Components | Sequence |
|---|---|
| | CTRYDGSRAM DYWGQGTTVT VSSGGGGSGG GGSGGGGSDI ELTQSPASLA VSLGQRAIIS CKASQSVSFA GTSLMHWYHQ KPGQQPKLLI YRASNLEAGV PTRFSGSGSK TDFTLNIHPV EEEDAATYYC QQSREYPYTF GGGTKLEIKA AAGSGGSGFV PVFLPAKPTT TPAPRPPTPA PTIASQPLSL RPEACRPAAG GAVHTRGLDF ACDIYIWAPL AGTCGVLLLS LVITLYCNHR NKRKKQRSRR NDEELETRAH RVATEERGRK PHQIPASTPQ NPATSQHPPP PPGHRSQAPS HRPPPPGHRV QHQPQKRPPA PSGTQVHQQK GPPLPRPRVQ PKPPHGAAEN SLSPSSNKKV AKKPTNKAPH PKQEPQEINF PDDLPGSNTA APVQETLHGC QPVTQEDGKE SRISVQERQ |
| 76 OSM_MOV19_spCD8_GITR_CD40 | MGVLLTQRTL LSLVLALLFP SMASMQVQLQ QSGAELVKPG ASVKISCKAS GYSFTGYFMN WVKQSHGKSL EWIGRIHPYD GDTFYNQNFK DKATLTVDKS SNTAHMELLS LTSEDFAVYY CTRYDGSRAM DYWGQGTTVT VSSGGGGSGG GGSGGGGSDI ELTQSPASLA VSLGQRAIIS CKASQSVSFA GTSLMHWYHQ KPGQQPKLLI YRASNLEAGV PTRFSGSGSK TDFTLNIHPV EEEDAATYYC QQSREYPYTF GGGTKLEIKA AAGSGGSGFV PVFLPAKPTT TPAPRPPTPA PTIASQPLSL RPEACRPAAG GAVHTRGLDF ACDIYIWAPL AGTCGVLLLS LVITLYCNHR NQLGLHIWQL RSQCMWPRET QLLLEVPPST EDARSCQFPE EERGERSAEE KGRLGDLWVK KVAKKPTNKA PHPKQEPQEI NFPDDLPGSN TAAPVQETLH GCQPVTQEDG KESRISVQER Q |
| 77 OSM_MOV19_spCD8_CD29CD40 | MGVLLTQRTL LSLVLALLFP SMASMQVQLQ QSGAELVKPG ASVKISCKAS GYSFTGYFMN WVKQSHGKSL EWIGRIHPYD GDTFYNQNFK DKATLTVDKS SNTAHMELLS LTSEDFAVYY CTRYDGSRAM DYWGQGTTVT VSSGGGGSGG GGSGGGGSDI ELTQSPASLA VSLGQRAIIS CKASQSVSFA GTSLMHWYHQ KPGQQPKLLI YRASNLEAGV PTRFSGSGSK TDFTLNIHPV EEEDAATYYC QQSREYPYTF GGGTKLEIKA AAGSGGSGFV PVFLPAKPTT TPAPRPPTPA PTIASQPLSL RPEACRPAAG GAVHTRGLDF ACDIYIWAPL AGTCGVLLLS LVITLYCNHR NKLLMIIHDR REFAKFEKEK MNAKWDTGEN PIYKSAVTTV VNPKYEGKKK VAKKPTNKAP HPKQEPQEIN FPDDLPGSNT AAPVQETLHG CQPVTQEDGK ESRISVQERQ |
| 78 OSM_MOV19_spCD8_CD150_CD40 | MGVLLTQRTL LSLVLALLFP SMASMQVQLQ QSGAELVKPG ASVKISCKAS GYSFTGYFMN WVKQSHGKSL EWIGRIHPYD GDTFYNQNFK DKATLTVDKS SNTAHMELLS LTSEDFAVYY CTRYDGSRAM DYWGQGTTVT VSSGGGGSGG GGSGGGGSDI ELTQSPASLA VSLGQRAIIS CKASQSVSFA GTSLMHWYHQ KPGQQPKLLI YRASNLEAGV PTRFSGSGSK TDFTLNIHPV EEEDAATYYC QQSREYPYTF GGGTKLEIKA AAGSGGSGFV PVFLPAKPTT TPAPRPPTPA PTIASQPLSL RPEACRPAAG GAVHTRGLDF ACDIYIWAPL AGTCGVLLLS LVITLYCNHR NRRRGKTNHY QTTVEKKSLT IYAQVQKPGP LQKKLDSFPA QDPCTTIYVA ATEPVPESVQ ETNSITVYAS VTLPESKKVA KKPTNKAHPH KQEPQEINFP DDLPGSNTAA PVQETLHGCQ PVTQEDGKES RISVQERQ |
| 79 OSM_MOV19_spIG4_CD28_CD40 | MGVLLTQRTL LSLVLALLFP SMASMQVQLQ QSGAELVKPG ASVKISCKAS GYSFTGYFMN WVKQSHGKSL EWIGRIHPYD GDTFYNQNFK DKATLTVDKS SNTAHMELLS LTSEDFAVYY CTRYDGSRAM DYWGQGTTVT VSSGGGGSGG GGSGGGGSDI ELTQSPASLA VSLGQRAIIS CKASQSVSFA GTSLMHWYHQ KPGQQPKLLI YRASNLEAGV PTRFSGSGSK TDFTLNIHPV EEEDAATYYC QQSREYPYTF GGGTKLEIKA AAGSGGSGES KYGPPCPSCP APEFLGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVYT LPPSQEEMTK NQVSLTCLVK GFYPSDIAVE WESNGQPENN YKTTPPVLDS DGSFFLYSRL TVDKSRWQEG NVFSCSVMHE ALHNHYTQKS LSLSLGKMFW VLVVVGGVLA CYSLLVTVAF IIFWVRSKRS RLLHSDYMNM TPRRPGPTRK HYQPYAPPRD FAAYRSKKVA KKPTNKAHPH KQEPQEINFP DDLPGSNTAA PVQETLHGCQ PVTQEDGKES RISVQERQ |
| 80 OSM_MOV19_spIG4_CD40 | MGVLLTQRTL LSLVLALLFP SMASMQVQLQ QSGAELVKPG ASVKISCKAS GYSFTGYFMN WVKQSHGKSL EWIGRIHPYD GDTFYNQNFK DKATLTVDKS SNTAHMELLS LTSEDFAVYY CTRYDGSRAM DYWGQGTTVT VSSGGGGSGG GGSGGGGSDI ELTQSPASLA VSLGQRAIIS CKASQSVSFA GTSLMHWYHQ KPGQQPKLLI YRASNLEAGV PTRFSGSGSK TDFTLNIHPV EEEDAATYYC QQSREYPYTF GGGTKLEIKA AAGSGGSGES |

TABLE OF SEQUENCES-continued

| ID NO: Components | Sequence |
|---|---|
| | KYGPPCPSCP APEFLGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVYT LPPSQEEMTK NQVSLTCLVK GFYPSDIAVE WESNGQPENN YKTTPPVLDS DGSFFLYSRL TVDKSRWQEG NVFSCSVMHE ALHNHYTQKS LSLSLGKMFW VLVVVGGVLA CYSLLVTVAF IIFWVKKVAK KPTNKAPHPK QEPQEINFPD DLPGSNTAAP VQETLHGCQP VTQEDGKESR ISVQERQ |
| 81 OSM_MOV19_spIG4_ CD137_CD40 | MGVLLTQRTL LSLVLALLFP SMASMQVQLQ QSGAELVKPG ASVKISCKAS GYSFTGYFMN WVKQSHGKSL EWIGRIHPYD GDTFYNQNFK DKATLTVDKS SNTAHMELLS LTSEDFAVYY CTRYDGSRAM DYWGQGTTVT VSSGGGGSGG GGSGGGGSDI ELTQSPASLA VSLGQRAIIS CKASQSVSFA GTSLMHWYHQ KPGQQPKLLI YRASNLEAGV PTRFSGSGSK TDFTLNIHPV EEEDAATYYC QQSREYPYTF GGGTKLEIKA AAGSGGSGES KYGPPCPSCP APEFLGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVYT LPPSQEEMTK NQVSLTCLVK GFYPSDIAVE WESNGQPENN YKTTPPVLDS DGSFFLYSRL TVDKSRWQEG NVFSCSVMHE ALHNHYTQKS LSLSLGKMFW VLVVVGGVLA CYSLLVTVAF IIFWVKKVAK KPTNKAPHPK QEPQEINFPD DLPGSNTAAP VQETLHGCQP VTQEDGKESR ISVQERQ |
| 82 OSM_MOV19_spIG4_ CD134_CD40 | MGVLLTQRTL LSLVLALLFP SMASMQVQLQ QSGAELVKPG ASVKISCKAS GYSFTGYFMN WVKQSHGKSL EWIGRIHPYD GDTFYNQNFK DKATLTVDKS SNTAHMELLS LTSEDFAVYY CTRYDGSRAM DYWGQGTTVT VSSGGGGSGG GGSGGGGSDI ELTQSPASLA VSLGQRAIIS CKASQSVSFA GTSLMHWYHQ KPGQQPKLLI YRASNLEAGV PTRFSGSGSK TDFTLNIHPV EEEDAATYYC QQSREYPYTF GGGTKLEIKA AAGSGGSGES KYGPPCPSCP APEFLGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVYT LPPSQEEMTK NQVSLTCLVK GFYPSDIAVE WESNGQPENN YKTTPPVLDS DGSFFLYSRL TVDKSRWQEG NVFSCSVMHE ALHNHYTQKS LSLSLGKMFW VLVVVGGVLA CYSLLVTVAF IIFWVRRDQR LPPDAHKPPG GGSFRTPIQE EQADAHSTLA KIKKVAKKPT NKAPHPKQEP QEINFPDDLP GSNTAAPVQE TLHGCQPVTQ EDGKESRISV QERQ |
| 83 OSM_MOV19_spIG4_ CD2_CD40 | MGVLLTQRTL LSLVLALLFP SMASMQVQLQ QSGAELVKPG ASVKISCKAS GYSFTGYFMN WVKQSHGKSL EWIGRIHPYD GDTFYNQNFK DKATLTVDKS SNTAHMELLS LTSEDFAVYY CTRYDGSRAM DYWGQGTTVT VSSGGGGSGG GGSGGGGSDI ELTQSPASLA VSLGQRAIIS CKASQSVSFA GTSLMHWYHQ KPGQQPKLLI YRASNLEAGV PTRFSGSGSK TDFTLNIHPV EEEDAATYYC QQSREYPYTF GGGTKLEIKA AAGSGGSGES KYGPPCPSCP APEFLGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVYT LPPSQEEMTK NQVSLTCLVK GFYPSDIAVE WESNGQPENN YKTTPPVLDS DGSFFLYSRL TVDKSRWQEG NVFSCSVMHE ALHNHYTQKS LSLSLGKMFW VLVVVGGVLA CYSLLVTVAF IIFWVKRKKQ RSRRNDEELE TRAHRVATEE RGRKPHQIPA STPQNPATSQ HPPPPPGHRS QAPSHRPPPP GHRVQHQPQK RPPAPSGTQV HQQKGPPLPR PRVQPKPPHG AAENSLSPSS NKKVAKKPTN KAPHPKQEPQ EINFPDDLPG SNTAAPVQET LHGCQPVTQE DGKESRISVQ ERQ |
| 84 OSM_MOV19_spIG4_ GITR_CD40 | MGVLLTQRTL LSLVLALLFP SMASMQVQLQ QSGAELVKPG ASVKISCKAS GYSFTGYFMN WVKQSHGKSL EWIGRIHPYD GDTFYNQNFK DKATLTVDKS SNTAHMELLS LTSEDFAVYY CTRYDGSRAM DYWGQGTTVT VSSGGGGSGG GGSGGGGSDI ELTQSPASLA VSLGQRAIIS CKASQSVSFA GTSLMHWYHQ KPGQQPKLLI YRASNLEAGV PTRFSGSGSK TDFTLNIHPV EEEDAATYYC QQSREYPYTF GGGTKLEIKA AAGSGGSGES KYGPPCPSCP APEFLGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVYT LPPSQEEMTK NQVSLTCLVK GFYPSDIAVE WESNGQPENN YKTTPPVLDS DGSFFLYSRL TVDKSRWQEG NVFSCSVMHE ALHNHYTQKS LSLSLGKMFW VLVVVGGVLA CYSLLVTVAF IIFWVQLGLH IWQLRSQCMW PRETQLLLEV |

TABLE OF SEQUENCES-continued

| ID NO: Components | Sequence |
|---|---|
| | PPSTEDARSC QFPEEERGER SAEEKGRLGD LWVKKVAKKP TNKAPHPKQE PQEINFPDDL PGSNTAAPVQ ETLHGCQPVT QEDGKESRIS VQERQ |
| 85 OSM_MOV19_spIG4_CD29_CD40 | MGVLLTQRTL LSLVLALLFP SMASMQVQLQ QSGAELVKPG ASVKISCKAS GYSFTGYFMN WVKQSHGKSL EWIGRIHPYD GDTFYNQNFK DKATLTVDKS SNTAHMELLS LTSEDFAVYY CTRYDGSRAM DYWGQGTTVT VSSGGGGSGG GGSGGGGSDI ELTQSPASLA VSLGQRAIIS CKASQSVSFA GTSLMHWYHQ KPGQQPKLLI YRASNLEAGV PTRFSGSGSK TDFTLNIHPV EEEDAATYYC QQSREYPYTF GGGTKLEIKA AAGSGGSGES KYGPPCPSCP APEFLGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVYT LPPSQEEMTK NQVSLTCLVK GFYPSDIAVE WESNGQPENN YKTTPPVLDS DGSFFLYSRL TVDKSRWQEG NVFSCSVMHE ALHNHYTQKS LSLSLGKMFW VLVVVGGVLA CYSLLVTVAF IIFWVKLLMI IHDRREFAKF EKEKMNAKWD TGENPIYKSA VTTVVNPKYE GKKKVAKKPT NKAPHPKQEP QEINFPDDLP GSNTAAPVQE TLHGCQPVTQ EDGKESRISV QERQ |
| 86 OSM_MOV19_spIG4_CD150_CD40 | MGVLLTQRTL LSLVLALLFP SMASMQVQLQ QSGAELVKPG ASVKISCKAS GYSFTGYFMN WVKQSHGKSL EWIGRIHPYD GDTFYNQNFK DKATLTVDKS SNTAHMELLS LTSEDFAVYY CTRYDGSRAM DYWGQGTTVT VSSGGGGSGG GGSGGGGSDI ELTQSPASLA VSLGQRAIIS CKASQSVSFA GTSLMHWYHQ KPGQQPKLLI YRASNLEAGV PTRFSGSGSK TDFTLNIHPV EEEDAATYYC QQSREYPYTF GGGTKLEIKA AAGSGGSGES KYGPPCPSCP APEFLGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVYT LPPSQEEMTK NQVSLTCLVK GFYPSDIAVE WESNGQPENN YKTTPPVLDS DGSFFLYSRL TVDKSRWQEG NVFSCSVMHE ALHNHYTQKS LSLSLGKMFW VLVVVGGVLA CYSLLVTVAF IIFWVRRRGK TNHYQTTVEK KSLTIYAQVQ KPGPLQKKLD SFPAQDPCTT IYVAATEPVP ESVQETNSIT VYASVTLPES KKVAKKPTNK APHPKQEPQE INFPDDLPGS NTAAPVQETL HGCQPVTQED GKESRISVQE RQ |
| 87 OSM_MOV19_spIG4_CD40_tandem | MGVLLTQRTL LSLVLALLFP SMASMQVQLQ QSGAELVKPG ASVKISCKAS GYSFTGYFMN WVKQSHGKSL EWIGRIHPYD GDTFYNQNFK DKATLTVDKS SNTAHMELLS LTSEDFAVYY CTRYDGSRAM DYWGQGTTVT VSSGGGGSGG GGSGGGGSDI ELTQSPASLA VSLGQRAIIS CKASQSVSFA GTSLMHWYHQ KPGQQPKLLI YRASNLEAGV PTRFSGSGSK TDFTLNIHPV EEEDAATYYC QQSREYPYTF GGGTKLEIKA AAGSGGSGES KYGPPCPSCP APEFLGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVYT LPPSQEEMTK NQVSLTCLVK GFYPSDIAVE WESNGQPENN YKTTPPVLDS DGSFFLYSRL TVDKSRWQEG NVFSCSVMHE ALHNHYTQKS LSLSLGKMFW VLVVVGGVLA CYSLLVTVAF IIFWVAKKPT NKAPHPKQEP QEINFPDDLP GSNTAAPVQE TLHGCQPVTQ EDGKESRISV QERQKKVAKK PTNKAPHPKQ EPQEINFPDD LPGSNTAAPV QETLHGCQPV TQEDGKESRI SVQERQKKVA |
| 88 OSM_MOV19_spIG4_CD40_P227A | MGVLLTQRTL LSLVLALLFP SMASMQVQLQ QSGAELVKPG ASVKISCKAS GYSFTGYFMN WVKQSHGKSL EWIGRIHPYD GDTFYNQNFK DKATLTVDKS SNTAHMELLS LTSEDFAVYY CTRYDGSRAM DYWGQGTTVT VSSGGGGSGG GGSGGGGSDI ELTQSPASLA VSLGQRAIIS CKASQSVSFA GTSLMHWYHQ KPGQQPKLLI YRASNLEAGV PTRFSGSGSK TDFTLNIHPV EEEDAATYYC QQSREYPYTF GGGTKLEIKA AAGSGGSGES KYGPPCPSCP APEFLGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVYT LPPSQEEMTK NQVSLTCLVK GFYPSDIAVE WESNGQPENN YKTTPPVLDS DGSFFLYSRL TVDKSRWQEG NVFSCSVMHE ALHNHYTQKS LSLSLGKMFW VLVVVGGVLA CYSLLVTVAF IIFWVKKVAK KPTNKAAHPK QEPQEINFPD DLPGSNTAAP VQETLHGCQP VTQEDGKESR ISVQERQ |
| 89 CTP188 PD1_PD1_sCD28TM_CD28_CD40 | MQIPQAPWPV VWAVLQLGWR PGWFLDSPDR PWNPPTFSPA LLVVTEGDNA TFTCSFSNTS ESFVLNWYRM SPSNQTDKLA AFPEDRSQPG QDCRFRVTQL PNGRDFHMSV VRARRNDSGT |

TABLE OF SEQUENCES-continued

| ID NO: | Components | Sequence |
|---|---|---|
| | (dimeric) | YLCGAISLAP KAQIKESLRA ELRVTERRAE VPTAHCPSPL FPGPSKPFWV LVVVGGVLAC YSLLVTVAFI IFWVRSKRSR LLHSDYMNMT PRRPGPTRKH YQPYAPPRDF AAYRSKKVAK KPTNKAPHPK QEPQEINFPD DLPGSNTAAP VQETLHGCQP VTQEDGKESR ISVQERQ |
| 90 | PD1_PD1_sCD28TM_CD40 | MQIPQAPWPV VWAVLQLGWR PGWFLDSPDR PWNPPTFSPA LLVVTEGDNA TFTCSFSNTS ESFVLNWYRM SPSNQTDKLA AFPEDRSQPG QDCRFRVTQL PNGRDFHMSV VRARRNDSGT YLCGAISLAP KAQIKESLRA ELRVTERRAE VPTAHCPSPL FPGPSKPFWV LVVVGGVLAC YSLLVTVAFI IFWVKKVAKK PTNKAPHPKQ EPQEINFPDD LPGSNTAAPV QETLHGCQPV TQEDGKESRI SVQERQ |
| 91 | TIGIT_TIGIT_CD28TM_CD28_CD40 | MRWCLLLIWA QGLRQAPLAS GMMTGTIETT GNISAEKGGS IILQCHLSST TAQVTQVNWE QQDQLLAICN ADLGWHISPS FKDRVAPGPG LGLTLQSLTV NDTGEYFCIY HTYPDGTYTG RIFLEVLESS VAEHGARFQI PFWVLVVVGG VLACYSLLVT VAFIIFWVRS KRSRLLHSDY MNMTPRRPGP TRKHYQPYAP PRDFAAYRSK KVAKKPTNKA PHPKQEPQEI NFPDDLPGSN TAAPVQETLH GCQPVTQEDG KESRISVQER Q |
| 92 | TIGIT_TIGIT_CD28TM_CD40 | MRWCLLLIWA QGLRQAPLAS GMMTGTIETT GNISAEKGGS IILQCHLSST TAQVTQVNWE QQDQLLAICN ADLGWHISPS FKDRVAPGPG LGLTLQSLTV NDTGEYFCIY HTYPDGTYTG RIFLEVLESS VAEHGARFQI PFWVLVVVGG VLACYSLLVT VAFIIFWVKK VAKKPTNKAP HPKQEPQEIN FPDDLPGSNT AAPVQETLHG CQPVTQEDGK ESRISVQERQ |
| 93 | OSM_MOV19_PD1_sCD28TM_CD28_CD40 | MGVLLTQRTL LSLVLALLFP SMASMQVQLQ QSGAELVKPG ASVKISCKAS GYSFTGYFMN WVKQSHGKSL EWIGRIHPYD GDTFYNQNFK DKATLTVDKS SNTAHMELLS LTSEDFAVYY CTRYDGSRAM DYWGQGTTVT VSSGGGGSGG GGSGGGGSDI ELTQSPASLA VSLGQRAIIS CKASQSVSFA GTSLMHWYHQ KPGQQPKLLI YRASNLEAGV PTRFSGSGSK TDFTLNIHPV EEEDAATYYC QQSREYPYTF GGGTKLEIKA AAGSGGSGRP GWFLDSPDRP WNPPTFSPAL LVVTEGDNAT FTCSFSNTSE SFVLNWYRMS PSNQTDKLAA FPEDRSQPGQ DCRFRVTQLP NGRDFHMSVV RARRNDSGTY LCGAISLAPK AQIKESLRAE LRVTERRAEV PTAHCPSPLF PGPSKPFWVL VVVGGVLACY SLLVTVAFII FWVRSKRSRL LHSDYMNMTP RRPGPTRKHY QPYAPPRDFA AYRSKKVAKK PTNKAPHPKQ EPQEINFPDD LPGSNTAAPV QETLHGCQPV TQEDGKESRI SVQERQ |
| 94 | OSM_MOV19_PD1_sCD28TM_CD40 | MGVLLTQRTL LSLVLALLFP SMASMQVQLQ QSGAELVKPG ASVKISCKAS GYSFTGYFMN WVKQSHGKSL EWIGRIHPYD GDTFYNQNFK DKATLTVDKS SNTAHMELLS LTSEDFAVYY CTRYDGSRAM DYWGQGTTVT VSSGGGGSGG GGSGGGGSDI ELTQSPASLA VSLGQRAIIS CKASQSVSFA GTSLMHWYHQ KPGQQPKLLI YRASNLEAGV PTRFSGSGSK TDFTLNIHPV EEEDAATYYC QQSREYPYTF GGGTKLEIKA AAGSGGSGRP GWFLDSPDRP WNPPTFSPAL LVVTEGDNAT FTCSFSNTSE SFVLNWYRMS PSNQTDKLAA FPEDRSQPGQ DCRFRVTQLP NGRDFHMSVV RARRNDSGTY LCGAISLAPK AQIKESLRAE LRVTERRAEV PTAHCPSPLF PGPSKPFWVL VVVGGVLACY SLLVTVAFII FWVKKVAKKP TNKAPHPKQE PQEINFPDDL PGSNTAAPVQ ETLHGCQPVT QEDGKESRIS VQERQ |
| 95 | OSM_MOV19_TIGIT_sCD28TM_CD28_CD40 | MGVLLTQRTL LSLVLALLFP SMASMQVQLQ QSGAELVKPG ASVKISCKAS GYSFTGYFMN WVKQSHGKSL EWIGRIHPYD GDTFYNQNFK DKATLTVDKS SNTAHMELLS LTSEDFAVYY CTRYDGSRAM DYWGQGTTVT VSSGGGGSGG GGSGGGGSDI ELTQSPASLA VSLGQRAIIS CKASQSVSFA GTSLMHWYHQ KPGQQPKLLI YRASNLEAGV PTRFSGSGSK TDFTLNIHPV EEEDAATYYC QQSREYPYTF GGGTKLEIKA AAGSGGSGMM TGTIETTGNI SAEKGGSIIL QCHLSSTTAQ VTQVNWEQQD QLLAICNADL GWHISPSFKD RVAPGPGLGL TLQSLTVNDT GEYFCIYHTY PDGTYTGRIF LEVLESSVAE HGARFQIPFW VLVVVGGVLA CYSLLVTVAF IIFWVRSKRS RLLHSDYMNM TPRRPGPTRK HYQPYAPPRD FAAYRSKKVA KKPTNKAPHP KQEPQEINFP DDLPGSNTAA PVQETLHGCQ PVTQEDGKES RISVQERQ |
| 96 | OSM_MOV19_TIGIT_sCD28TM_CD40 | MGVLLTQRTL LSLVLALLFP SMASMQVQLQ QSGAELVKPG ASVKISCKAS GYSFTGYFMN WVKQSHGKSL EWIGRIHPYD GDTFYNQNFK DKATLTVDKS SNTAHMELLS LTSEDFAVYY CTRYDGSRAM DYWGQGTTVT VSSGGGGSGG GGSGGGGSDI |

TABLE OF SEQUENCES-continued

| ID NO: Components | Sequence |
|---|---|
| | ELTQSPASLA VSLGQRAIIS CKASQSVSFA GTSLMHWYHQ KPGQQPKLLI YRASNLEAGV PTRFSGSGSK TDFTLNIHPV EEEDAATYYC QQSREYPYTF GGGTKLEIKA AAGSGGSGMM TGTIETTGNI SAEKGGSIIL QCHLSSTTAQ VTQVNWEQQD QLLAICNADL GWHISPSFKD RVAPGPGLGL TLQSLTVNDT GEYFCIYHTY PDGTYTGRIF LEVLESSVAE HGARFQIPFW VLVVVGGVLA CYSLLVTVAF IIFWVKKVAK KPTNKAPHPK QEPQEINFPD DLPGSNTAAP VQETLHGCQP VTQEDGKESR ISVQERQ |
| 97 linker | GGGGSGGGGS GGGGS |
| 98 Truncated Cytoplasmic domain CD28 Variant | NKILVKQSPM LVAYDNAVNL SCKYSYNLFS REFRASLHKG LDSAVEVCVV YGNYSQQLQV YSKTGFNCDG KLGNESVTFY LQNLYVNQTD IYFCKIEVMY PPPYLDNEKS NGTIIHVKGK HLCPSPLFPG PSKPFWVLVV GGVLACYSL LVTVAFIIFW VRSKR |
| 99 CD28.CD137 fusion | NKILVKQSPM LVAYDNAVNL SCKYSYNLFS REFRASLHKG LDSAVEVCVV YGNYSQQLQV YSKTGFNCDG KLGNESVTFY LQNLYVNQTD IYFCKIEVMY PPPYLDNEKS NGTIIHVKGK HLCPSPLFPG PSKPFWVLVV GGVLACYSL LVTVAFIIFW VRSKRSRLLH SDYMNMTPRR PGPTRKHYQP YAPPRDFAAY RSRFSVVKRG RKKLLYIFKQ PFMRPVQTTQ EEDGCSCRFP EEEEGGCE |
| 100 CD28.CD134 fusion | NKILVKQSPM LVAYDNAVNL SCKYSYNLFS REFRASLHKG LDSAVEVCVV YGNYSQQLQV YSKTGFNCDG KLGNESVTFY LQNLYVNQTD IYFCKIEVMY PPPYLDNEKS NGTIIHVKGK HLCPSPLFPG PSKPFWVLVV GGVLACYSL LVTVAFIIFW VRSKRSRLLH SDYMNMTPRR PGPTRKHYQP YAPPRDFAAY RSRRDQRLPP DAHKPPGGGS FRTPIQEEQA DAHSTLAKI |
| 101 CD28.CD2 fusion | NKILVKQSPM LVAYDNAVNL SCKYSYNLFS REFRASLHKG LDSAVEVCVV YGNYSQQLQV YSKTGFNCDG KLGNESVTFY LQNLYVNQTD IYFCKIEVMY PPPYLDNEKS NGTIIHVKGK HLCPSPLFPG PSKPFWVLVV GGVLACYSL LVTVAFIIFW VRSKRSRLLH SDYMNMTPRR PGPTRKHYQP YAPPRDFAAY RSKRKKQRSR RNDEELETRA HRVATEERGR KPHQIPASTP QNPATSQHPP PPPGHRSQAP SHRPPPPGHR VQHQPQKRPP APSGTQVHQQ KGPPLPRPRV QPKPPHGAAE NSLSPSSN |
| 102 CD28.CD29 fusion | NKILVKQSPM LVAYDNAVNL SCKYSYNLFS REFRASLHKG LDSAVEVCVV YGNYSQQLQV YSKTGFNCDG KLGNESVTFY LQNLYVNQTD IYFCKIEVMY PPPYLDNEKS NGTIIHVKGK HLCPSPLFPG PSKPFWVLVV GGVLACYSL LVTVAFIIFW VRSKRSRLLH SDYMNMTPRR PGPTRKHYQP YAPPRDFAAY RSKLLMIIHD RREFAKFEKE KMNAKWDTGE NPIYKSAVTT VVNPKYEGK |
| 103 CD28.GITR fusion | NKILVKQSPM LVAYDNAVNL SCKYSYNLFS REFRASLHKG LDSAVEVCVV YGNYSQQLQV YSKTGFNCDG KLGNESVTFY LQNLYVNQTD IYFCKIEVMY PPPYLDNEKS NGTIIHVKGK HLCPSPLFPG PSKPFWVLVV GGVLACYSL LVTVAFIIFW VRSKRSRLLH SDYMNMTPRR PGPTRKHYQP YAPPRDFAAY RSQLGLHIWQ LRSQCMWPRE TQLLLEVPPS TEDARSCQFP EEERGERSAE EKGRLGDLWV |
| 104 CD28.IL2Rγ fusion | NKILVKQSPM LVAYDNAVNL SCKYSYNLFS REFRASLHKG LDSAVEVCVV YGNYSQQLQV YSKTGFNCDG KLGNESVTFY LQNLYVNQTD IYFCKIEVMY PPPYLDNEKS NGTIIHVKGK HLCPSPLFPG PSKPFWVLVV GGVLACYSL LVTVAFIIFW VRSKRSRLLH SDYMNMTPRR PGPTRKHYQP YAPPRDFAAY RSERTMPRIP TLKNLEDLVT EYHGNFSAWS GVSKGLAESL QPDYSERLCL VSEIPPKGGA LGEGPGASPC NQHSPYWAPP CYTLKPET |
| 105 CD28.CD40 fusion | NKILVKQSPM LVAYDNAVNL SCKYSYNLFS REFRASLHKG LDSAVEVCVV YGNYSQQLQV YSKTGFNCDG KLGNESVTFY LQNLYVNQTD IYFCKIEVMY PPPYLDNEKS NGTIIHVKGK HLCPSPLFPG PSKPFWVLVV GGVLACYSL LVTVAFIIFW VRSKRSRLLH SDYMNMTPRR PGPTRKHYQP YAPPRDFAAY RSKKVAKKPT NKAPHPKQEP QEINFPDDLP GSNTAAPVQE TLHGCQPVTQ EDGKESRISV QERQ |
| 106 CD28.CD150 fusion | NKILVKQSPM LVAYDNAVNL SCKYSYNLFS REFRASLHKG LDSAVEVCVV YGNYSQQLQV YSKTGFNCDG KLGNESVTFY |

TABLE OF SEQUENCES-continued

| ID NO: | Components | Sequence |
|---|---|---|
| | | LQNLYVNQTD IYFCKIEVMY PPPYLDNEKS NGTIIHVKGK HLCPSPLFPG PSKPFWVLVV VGGVLACYSL LVTVAFIIFW VRSKRSRLLH SDYMNMTPRR PGPTRKHYQP YAPPRDFAAY RSRRRGKTNH YQTTVEKKSL TIYAQVQKPG PLQKKLDSFP AQDPCTTIYV AATEPVPESV QETNSITVYA SVTLPES |
| 107 | CD28.CD2.CD40 fusion | NKILVKQSPM LVAYDNAVNL SCKYSYNLFS REFRASLHKG LDSAVEVCVV YGNYSQQLQV YSKTGFNCDG KLGNESVTFY LQNLYVNQTD IYFCKIEVMY PPPYLDNEKS NGTIIHVKGK HLCPSPLFPG PSKPFWVLVV VGGVLACYSL LVTVAFIIFW VRSKRSRLLH SDYMNMTPRR PGPTRKHYQP YAPPRDFAAY RSKRKKQRSR RNDEELETRA HRVATEERGR KPHQIPASTP QNPATSQHPP PPPGHRSQAP SHRPPPPGHR VQHQPQKRPP APSGTQVHQQ KGPPLPRPRV QPKPPHGAAE NSLSPSSNKK VAKKPTNKAP HPKQEPQEIN FPDDLPGSNT AAPVQETLHG CQPVTQEDGK ESRISVQERQ |
| 108 | CD28(IEV) Variant | IEVMYPPPYL DNEKSNGTII HVKGKHLCPS PLFPGPSKPF WVLVVVGGVL ACYSLLVTVA FIIFWVRSKR SRLLHSDYMN MTPRRPGPTR KHYQPYAPPR DFAAYRS |
| 109 | CTP189 PD1_PD1_sCD28TM_ CD28_CD40 (monomeric) | MQIPQAPWPV VWAVLQLGWR PGWFLDSPDR PWNPPTFSPA LLVVTEGDNA TFTCSFSNTS ESFVLNWYRM SPSNQTDKLA AFPEDRSQPG QDCRFRVTQL PNGRDFHMSV VRARRNDSGT YLCGAISLAP KAQIKESLRA ELRVTERRAE VPTAHSPSPS RPAGQFWVLV VVGGVLACYS LLVTVAFIIF WVRSKRSRLL HSDYMNMTPR RPGPTRKHYQ PYAPPRDFAA YRSKKVAKKP TNKAPHPKQE PQEINFPDDL PGSNTAAPVQ ETLHGCQPVT QEDGKESRIS VQERQ |
| 110 | CTP195 OSM_MFE23_spCD28_ CD28_CD40 (SVQE-AVQA) | MGVLLTQRTL LSLVLALLFP SMASMQVQLQ QSGAELVRSG TSVKLSCTAS GFNIKDSYMH WLRQGPEQGL EWIGWIDPEN GDTEYAPKFQ GKATFTTDTS SNTAYLQLSS LTSEDTAVYY CNEGTPTGPY YFDYWGQGTT VTVSSGGGGS GGGGSGGGGS ENVLTQSPAI MSASPGEKVT ITCSASSSVS YMHWFQQKPG TSPKLWIYST SNLASGVPAR FSGSGSGTSY SLTISRMEAE DAATYYCQQR SSYPLTFGAG TKLELKRAAA GSGGSGILVK QSPMLVAYDN AVNLSCKYSY NLFSREFRAS LHKGLDSAVE VCVVYGNYSQ QLQVYSKTGF NCDGKLGNES VTFYLQNLYV NQTDIYFCKI EVMYPPPYLD NEKSNGTIIH VKGKHLCPSP LFPGPSKPFW VLVVGGVLA CYSLLVTVAF IIFWVRSKRS RLLHSDYMNM TPRRPGPTRK HYQPYAPPRD FAAYRSKKVA KKPTNKAPHP KQEPQEINFP DDLPGSNTAA PVQETLHGCQ PVTQEDGKES RIAVQARQ |
| 111 | CTP196 OSM_MFE23_spCD28_ CD28_CD40 (PVQET-AVAEA) | MGVLLTQRTL LSLVLALLFP SMASMQVQLQ QSGAELVRSG TSVKLSCTAS GFNIKDSYMH WLRQGPEQGL EWIGWIDPEN GDTEYAPKFQ GKATFTTDTS SNTAYLQLSS LTSEDTAVYY CNEGTPTGPY YFDYWGQGTT VTVSSGGGGS GGGGSGGGGS ENVLTQSPAI MSASPGEKVT ITCSASSSVS YMHWFQQKPG TSPKLWIYST SNLASGVPAR FSGSGSGTSY SLTISRMEAE DAATYYCQQR SSYPLTFGAG TKLELKRAAA GSGGSGILVK QSPMLVAYDN AVNLSCKYSY NLFSREFRAS LHKGLDSAVE VCVVYGNYSQ QLQVYSKTGF NCDGKLGNES VTFYLQNLYV NQTDIYFCKI EVMYPPPYLD NEKSNGTIIH VKGKHLCPSP LFPGPSKPFW VLVVGGVLA CYSLLVTVAF IIFWVRSKRS RLLHSDYMNM TPRRPGPTRK HYQPYAPPRD FAAYRSKKVA KKPTNKAPHP KQEPQEINFP DDLPGSNTAA AVAEALHGCQ PVTQEDGKES RISVQERQ |
| 112 | CTP197 OSM_MFE23_spCD28_ CD28_CD40 (PQEINF-AQAINF) | MGVLLTQRTL LSLVLALLFP SMASMQVQLQ QSGAELVRSG TSVKLSCTAS GFNIKDSYMH WLRQGPEQGL EWIGWIDPEN GDTEYAPKFQ GKATFTTDTS SNTAYLQLSS LTSEDTAVYY CNEGTPTGPY YFDYWGQGTT VTVSSGGGGS GGGGSGGGGS ENVLTQSPAI MSASPGEKVT ITCSASSSVS YMHWFQQKPG TSPKLWIYST SNLASGVPAR FSGSGSGTSY SLTISRMEAE DAATYYCQQR SSYPLTFGAG TKLELKRAAA GSGGSGILVK QSPMLVAYDN AVNLSCKYSY NLFSREFRAS LHKGLDSAVE VCVVYGNYSQ QLQVYSKTGF NCDGKLGNES VTFYLQNLYV NQTDIYFCKI EVMYPPPYLD NEKSNGTIIH VKGKHLCPSP LFPGPSKPFW VLVVGGVLA CYSLLVTVAF IIFWVRSKRS RLLHSDYMNM TPRRPGPTRK HYQPYAPPRD FAAYRSKKVA KKPTNKAPHP KQEAQAINFP DDLPGSNTAA PVQETLHGCQ PVTQEDGKES RISVQERQ |
| 113 | CTP198 OSM_MFE23_spCD28_ | MGVLLTQRTL LSLVLALLFP SMASMQVQLQ QSGAELVRSG TSVKLSCTAS GFNIKDSYMH WLRQGPEQGL EWIGWIDPEN |

TABLE OF SEQUENCES-continued

| ID NO: Components | Sequence |
|---|---|
| CD28_CD40 (P227A) | GDTEYAPKFQ GKATFTTDTS SNTAYLQLSS LTSEDTAVYY CNEGTPTGPY YFDYWGQGTT VTVSSGGGGS GGGGSGGGGS ENVLTQSPAI MSASPGEKVT ITCSASSSVS YMHWFQQKPG TSPKLWIYST SNLASGVPAR FSGSGSGTSY SLTISRMEAE DAATYYCQQR SSYPLTFGAG TKLELKRAAA GSGGSGILVK QSPMLVAYDN AVNLSCKYSY NLFSREFRAS LHKGLDSAVE VCVVYGNYSQ QLQVYSKTGF NCDGKLGNES VTFYLQNLYV NQTDIYFCKI EVMYPPPYLD NEKSNGTIIH VKGKHLCPSP LFPGPSKPFW VLVVVGGVLA CYSLLVTVAF IIFWVRSKRS RLLHSDYMNM TPRRPGPTRK HYQPYAPPRD FAAYRSKKVA KKPTNKAAHP KQEPQEINFP DDLPGSNTAA PVQETLHGCQ PVTQEDGKES RISVQERQ |
| 114 CTP199 OSM_MFE23_spCD28_ CD28_CD40 (Q263A) | KKVAKKPTNK APHPKQEPQE INFPDDLPGS NTAAPVQETL HGCQPVTAED GKESRISVQE RQ |
| 115 CTP200 OSM_MFE23_spCD28_ CD28_CD40_CD40_ CD40 | MGVLLTQRTL LSLVLALLFP SMASMQVQLQ QSGAELVRSG TSVKLSCTAS GFNIKDSYMH WLRQGPEQGL EWIGWIDPEN GDTEYAPKFQ GKATFTTDTS SNTAYLQLSS LTSEDTAVYY CNEGTPTGPY YFDYWGQGTT VTVSSGGGGS GGGGSGGGGS ENVLTQSPAI MSASPGEKVT ITCSASSSVS YMHWFQQKPG TSPKLWIYST SNLASGVPAR FSGSGSGTSY SLTISRMEAE DAATYYCQQR SSYPLTFGAG TKLELKRAAA GSGGSGILVK QSPMLVAYDN AVNLSCKYSY NLFSREFRAS LHKGLDSAVE VCVVYGNYSQ QLQVYSKTGF NCDGKLGNES VTFYLQNLYV NQTDIYFCKI EVMYPPPYLD NEKSNGTIIH VKGKHLCPSP LFPGPSKPFW VLVVVGGVLA CYSLLVTVAF IIFWVRSKRS RLLHSDYMNM TPRRPGPTRK HYQPYAPPRD FAAYRSKKVA KKPTNKAHP KQEPQEINFP DDLPGSNTAA PVQETLHGCQ PVTAEDGKES RISVQERQKK VAKKPTNKAP HPKQEPQEIN FPDDLPGSNT AAPVQETLHG CQPVTAEDGK ESRISVQERQ |
| 116 CTP201 OSM_MFE23_spCD28_ CD28 (PYAPP-AYAA)_CD40 | MGVLLTQRTL LSLVLALLFP SMASMQVQLQ QSGAELVRSG TSVKLSCTAS GFNIKDSYMH WLRQGPEQGL EWIGWIDPEN GDTEYAPKFQ GKATFTTDTS SNTAYLQLSS LTSEDTAVYY CNEGTPTGPY YFDYWGQGTT VTVSSGGGGS GGGGSGGGGS ENVLTQSPAI MSASPGEKVT ITCSASSSVS YMHWFQQKPG TSPKLWIYST SNLASGVPAR FSGSGSGTSY SLTISRMEAE DAATYYCQQR SSYPLTFGAG TKLELKRAAA GSGGSGILVK QSPMLVAYDN AVNLSCKYSY NLFSREFRAS LHKGLDSAVE VCVVYGNYSQ QLQVYSKTGF NCDGKLGNES VTFYLQNLYV NQTDIYFCKI EVMYPPPYLD NEKSNGTIIH VKGKHLCPSP LFPGPSKPFW VLVVVGGVLA CYSLLVTVAF IIFWVRSKRS RLLHSDYMNM TPRRPGPTRK HYQAYAAPRD FAAYRSKKVA KKPTNKAHP KQEPQEINFP DDLPGSNTAA PVQETLHGCQ PVTQEDGKES RISVQERQ |
| 117 CTP202 OSM_MFE23_spCD28_ CD28 (YMNM-FMNM)_CD40 | MGVLLTQRTL LSLVLALLFP SMASMQVQLQ QSGAELVRSG TSVKLSCTAS GFNIKDSYMH WLRQGPEQGL EWIGWIDPEN GDTEYAPKFQ GKATFTTDTS SNTAYLQLSS LTSEDTAVYY CNEGTPTGPY YFDYWGQGTT VTVSSGGGGS GGGGSGGGGS ENVLTQSPAI MSASPGEKVT ITCSASSSVS YMHWFQQKPG TSPKLWIYST SNLASGVPAR FSGSGSGTSY SLTISRMEAE DAATYYCQQR SSYPLTFGAG TKLELKRAAA GSGGSGILVK QSPMLVAYDN AVNLSCKYSY NLFSREFRAS LHKGLDSAVE VCVVYGNYSQ QLQVYSKTGF NCDGKLGNES VTFYLQNLYV NQTDIYFCKI EVMYPPPYLD NEKSNGTIIH VKGKHLCPSP LFPGPSKPFW VLVVVGGVLA CYSLLVTVAF IIFWVRSKRS RLLHSDFMNM TPRRPGPTRK HYQPYAPPRD FAAYRSKKVA KKPTNKAHP KQEPQEINFP DDLPGSNTAA PVQETLHGCQ PVTQEDGKES RISVQERQ |
| 118 SH3 motif2 | PTNKAPHP |
| 119 SH3 motif | PTNKAPH |
| 120 TRAF2_motif4 | PKQET |
| 121 TRAF2_motif5 | PVQET |
| 122 TRAF2_motif6 | SVQET |
| 123 TRAF6-Motif2 | QEPQEINFP |

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1—Production of T-Cells Expressing CoStAR

Materials and Methods

Construct design—The MFE23 CoStAR consists of an MFE23 derived single chain antibody fragment nucleotide sequence with an oncostatin M1 leader sequence fused to the entire human CD28 nucleic acid sequence. The CoStAR nucleotide sequence was codon optimised and gene synthesised by Genewiz Inc. The constructs were cloned into pSF.Lenti (Oxford Genetics) via an XbaI and NheI site.

Lentiviral Production—Lentiviral production was performed using a three-plasmid packaging system (Cell Biolabs, San Diego, USA) by mixing 10 µg of each plasmid, plus 10 µg of the pSF.Lenti lentiviral plasmid containing the transgene, together in serum free RPMI containing 50 mM $CaCl_2$. The mixture was added dropwise to a 50% confluent monolayer of 293T cells in 75 $cm^2$ flasks. The viral supernatants were collected at 48 and 72 h post transfection, pooled and concentrated using LentiPac lentiviral supernatant concentration (GeneCopoeia, Rockville, Maryland, USA) solution according to the manufacturer's instructions. Lentiviral supernatants were concentrated 10-fold and used to directly infect primary human T-cells in the presence of 4 µg/ml polybrene (Sigma-Aldrich, Dorset, UK). Peripheral blood mononuclear cells were isolated from normal healthy donors before activation for 24 hours with T-cell activation and expansion beads (Invitrogen) according to the manufacturer's instructions before addition of lentiviral supernatants.

Cell transduction was assessed 96 hours post infection using CEA.hFc protein and anti-hFc-PE secondary, plus anti-CD34-APC or by anti-CD34-PE antibodies alone. Cells were then expanded further using ×10 donor mismatched irradiated PBMC feeders at a 1:20-1:200 ratio in RPMI+ 10% FCS with the addition of 1 µg/ml PHA and 200 IU/ml IL-2. After 14 days the cells were stained as previous and stored ready for assay.

Functionality assays were performed by mixing CoStAR positive or negative cells with wild-type or OKT3 engineered CEA-Positive LoVo or LS174T cells. Briefly, T-cells were mixed with LoVo cells at varying ratios in 96-well plates and IFNγ or IL-2 measured by ELISA. The remaining cells were incubated with 1:10 dilution of WST-1 reagent (Sigma, UK) for 30 min before absorbance reading at 450 nm. % Cytotoxicity was determined using the following equation =100−((Experimental reading−T-cells alone)/(tumor alone))×100.

Proliferation assays were performed by first loading T-cells with 10 µM eFluor450 proliferation dye (eBioscience, UK) for 10 min at 37° C. at a concentration of $1 \times 10^7$ cells/ml before incubating the cells in 5 volumes of cold T-cell media for 5 min on ice. Cells were then washed excessively to remove unbound dye and added to cocultures containing tumor cells. Cells were removed at 2, 6 and 10 days, 1:200 dilution of DRAQ7 added and the cells analysed using a MACSQuant cytometer and MACSQuantify software.

Cell counts for proliferation assays were performed by taking cells from the wells and staining with anti-CD2 PerCP eFluor710 antibody (eBioscience, UK) for 20 min in the dark, followed by DRAQ7 staining and counts made using a MACSQuant analyser.

Results

Primary human T-cells were isolated from Buffy coats obtained from commercial suppliers (Lonza or NHSBT). T-cells were isolated by Ficoll-mediated isolation and T-cell negative isolation kits (StemCell Technologies). The isolated T-cells were activated with human T-cell activation and expansion beads (Invitrogen, UK). Cells were incubated with concentrated lentiviral particles and expanded over a number of days. The lentivirus contained the DNA sequence of the MFE.CoStAR.2A.tCD34 construct (MFE23.scFv fused to full length human CD28 co-expressed with truncated human CD34 via a 2A cleavage sequence). Successfully transduced cells were further expanded using irradiated feeders as outlined in materials and methods. Donor 1 transduction was measured at 22.69% (17.15 CD34+/CoStAR+ plus 5.53% CD34−/CoStAR+), donor 2 was measured at 20.73%, and donor 3 at 13.34%. Cells were enriched for CoStAR expression using anti-CD34 antibodies to obtain T-cell populations greater than 90% CoStAR positive.

To generate a physiologically relevant in vitro model to test the impact of CoStAR on T-cell activity, the non-transduced and transduced cells were tested against the CEA+ tumor cell lines LoVo and LS174T. To enable activation of the T-cells in response to the unmatched tumor lines we engineered the tumor cells to express an anti-CD3 single chain antibody fragment anchored to the cell membrane by way of a synthetic transmembrane domain and split from the GFP marker gene using an IRES element to visualise transduced cells using flow cytometry.

Single cell clones of LoVo and LS174T were generated from bulk transfectants. Non-transduced and CoStAR transduced T-cells were mixed at varying effector:target ratios with wild-type non-transduced or OKT3-engineered LS174T or LoVo cells. After 24 hours coculture media was taken for IL-2 ELISA measurement. Activation dependent IL-2 secretion was observed from both CoStAR+ and CoStAR− T-cell populations from three donors in response to OKT3 engineered LS174T cells with only background IL-2 secretion seen from transduced and non-transduced T-cells in response to un-engineered tumor cells (FIGS. 3A-3C). CoStAR enhanced IL-2 secretion towards OKT3 engineered tumor cells was found in all three donors tested. The effect was most evident at E:T ratios of 8:1 and 16:1 and at higher E:T ratios IL-2 secretion was too low to measure accurately. At lower effector to target ratios it appeared that IL-2 secretion was saturating from non-transduced cells. These observations were repeated in LoVo cells with two of the three donors tested against LS174T with similar results (FIGS. 3D & E).

Figure 1:
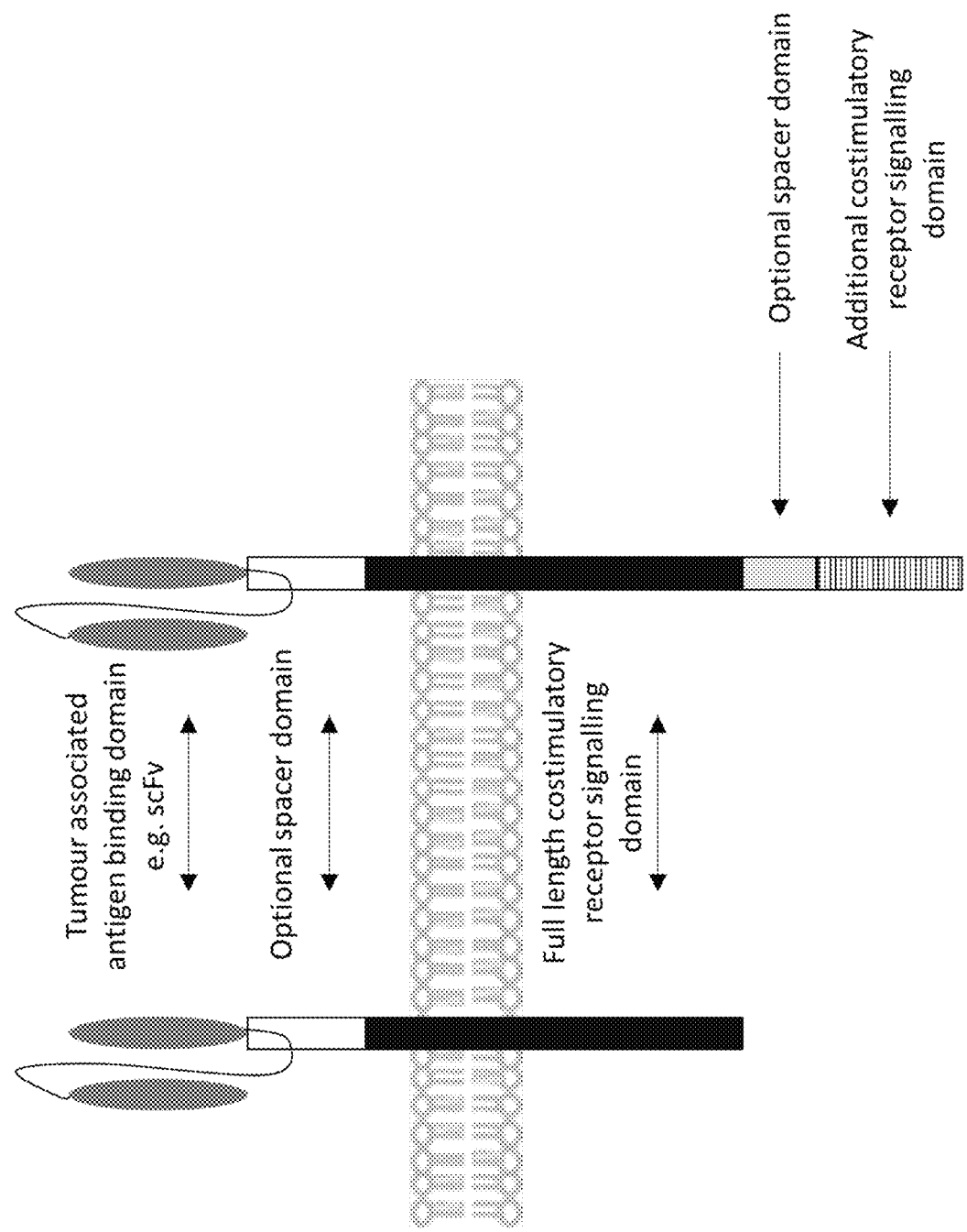
FIG. 1—Structural organisation of single costimulatory and fusion costimulatory domain receptors. A schematic representation of CoStAR receptors set out in the claims is shown. First a CoStAR based on a single costimulatory receptor, and secondly a fusion CoStAR consisting of a full length costimulatory receptor signalling domain fused to a second costimulatory domain.
Figure 4A:
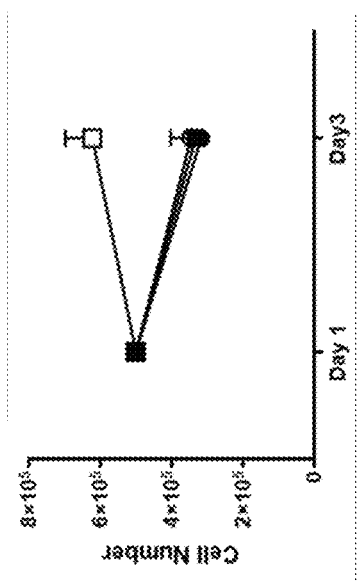
FIGS. 4A-4D—Effect of CoStAR on T-cell proliferation. $5 \times 10^5$ transduced and non transduced T-cells were mixed with $6.25 \times 10^3$ wild-type LoVo or LoVo-OKT3 cells in the presence (FIG. 4A) or absence (FIG. 4B) of IL-2 and cell counts made after three days. In another assay under the same cell ratios T-cells from two donors (FIGS. 4C and 4D) were loaded with proliferation dye and the number of proliferation cycles the cells had gone through determined by dye dilution after six days using flow cytometry.
Figure 4B:
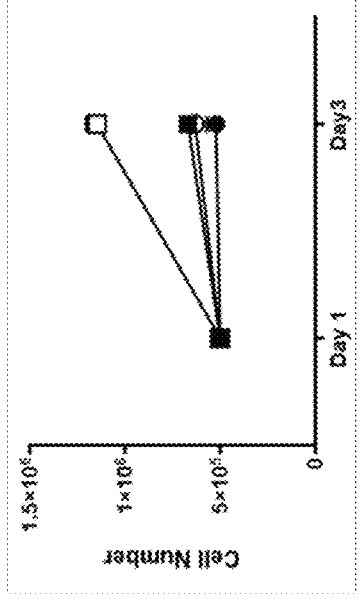

To determine the impact of CoStAR on T-cell expansion, transduced or non-transduced T-cells were mixed with wild-type or OKT3-GFP engineered LoVo cells the number of total cells after 3 days was counted. CoStAR enhanced survival and/or proliferation of engineered T-cells in response to LoVo-OKT3 but not wild-type LoVo cells in the presence of IL-2 (FIG. 4A) and absence of IL-2 (FIG. 4B).

Figure 4C:
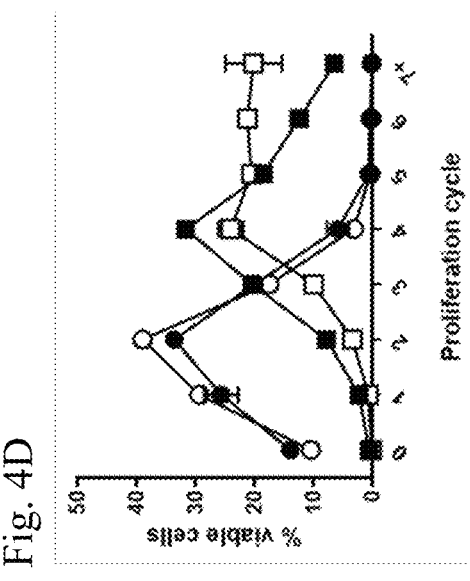
Figure 4D:
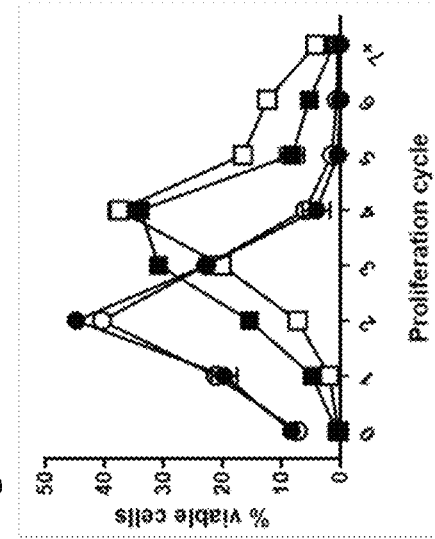

To further investigate this phenomenon, cell proliferation analysis was performed in T-cells from two donors using proliferation dye to count the number of cell cycles each population went through over 6 days (FIGS. 4C & D). A larger proportion of CoStAR engineered cells went through 5, 6 or 7 proliferation cycles over 6 days compared to non-engineered cells in response to LoVo-OKT3, whereas CoStAR transduced and non-transduced cells went through an average of approximately 2 cycles over the same duration in response to wild-type LoVo.

Figure 5:
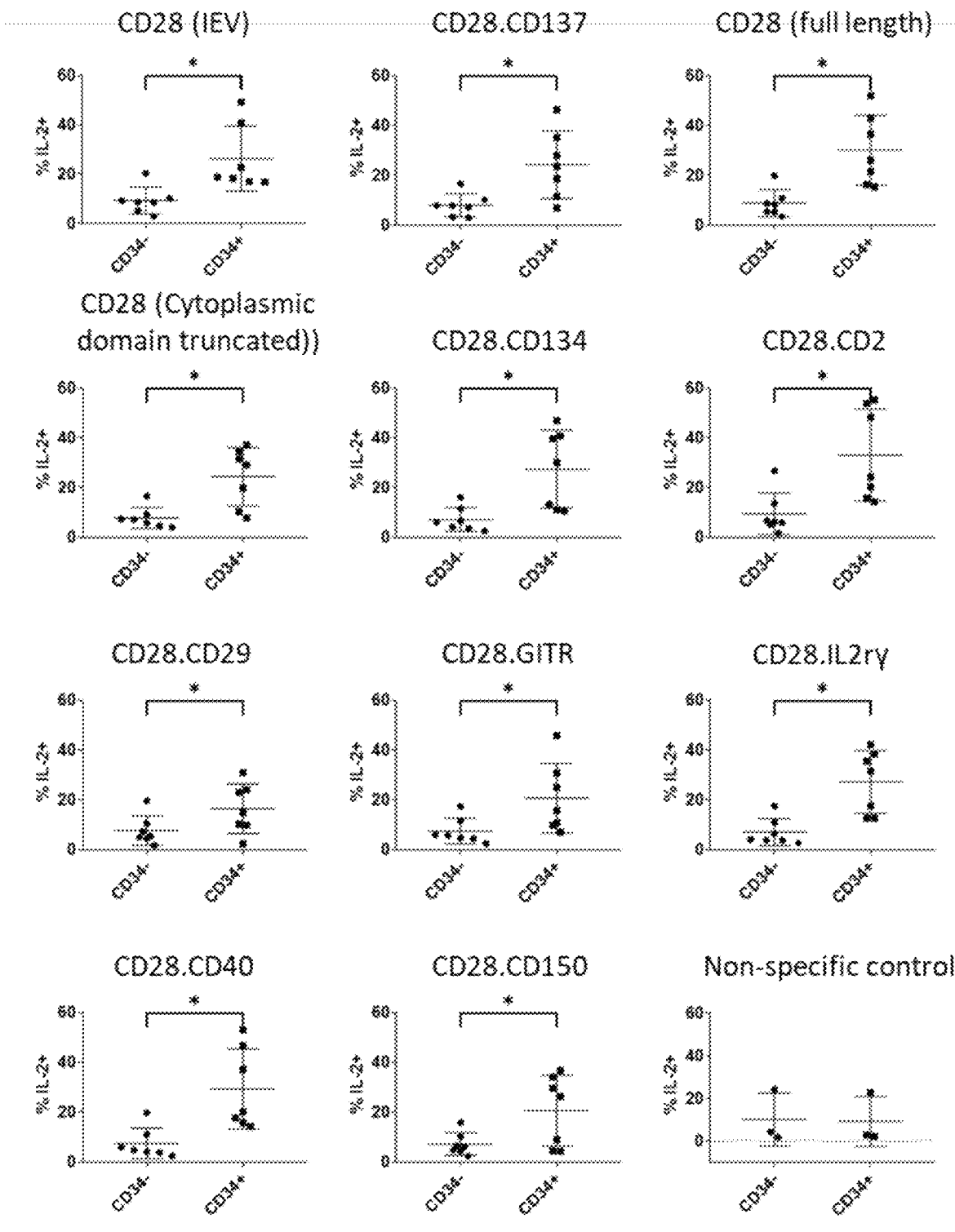
FIG. 5—IL-2 activity of CoStAR fusion receptors in primary human T-cells. Normal donor CD8+ T-cells from seven donors (except control CoStAR is three donors) were lentivirally transduced with the indicated CEA-targeting CoStARs and IL-2 production assessed after an overnight stimulation in the presence of LoVo-OKT3 cells. The proportion of IL-2 positive cells was determined using intracellular flow staining in both the CD34 negative (CoStAR non-transduced) and CD34+ (CoStAR transduced) populations. Asterisks show significant differences between the transduced and non-transduced populations using paired Wilcoxon signed rank test with *p<0.05
Figure 6A:
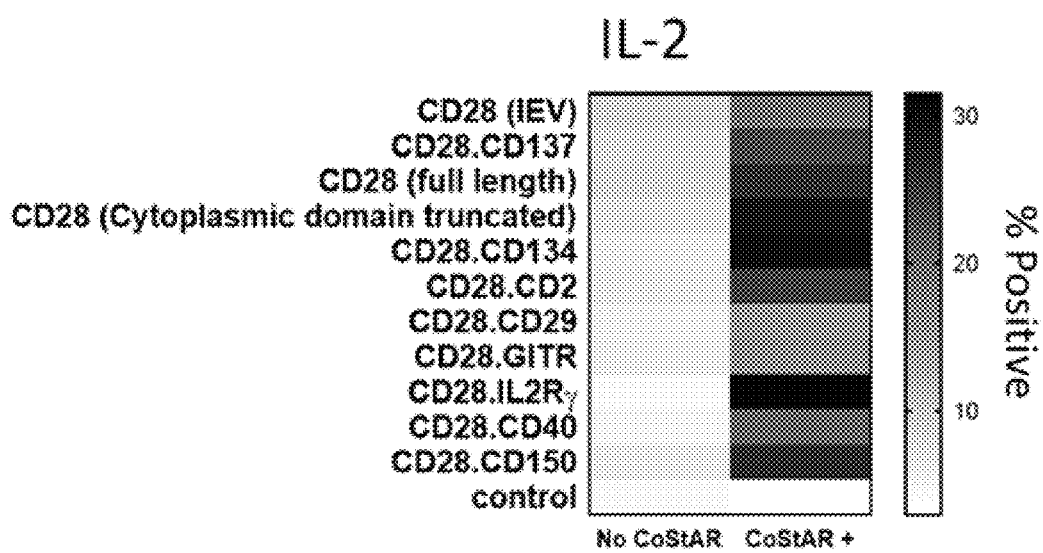
FIGS. 6A-6D—Multi parameter analysis of CoStAR activity in primary human T-cells. Normal donor CD8+ T-cells were lentivirally transduced with the indicated CEA-targeting CoStARs and IL-2 production assessed after an overnight stimulation in the presence of LoVo-OKT3 cells. The proportion of IL-2 (seven donors) (FIG. 6A), IFNγ (seven donors) (FIG. 6B), bcl-xL (five donors) (FIG. 6C) and CD107a (six donors) (FIG. 6D) positive cells was determined using intracellular flow staining in both the CD34 negative (CoStAR non-transduced) and CD34+ (CoStAR transduced) populations. Control is an irrelevant CA125 targeting CoStAR and is from three donors in all instances. Heat maps are averages of all donors with the intensity of colour related to the percentage of cells positive for a particular read out under the defined conditions.
Figure 6B:
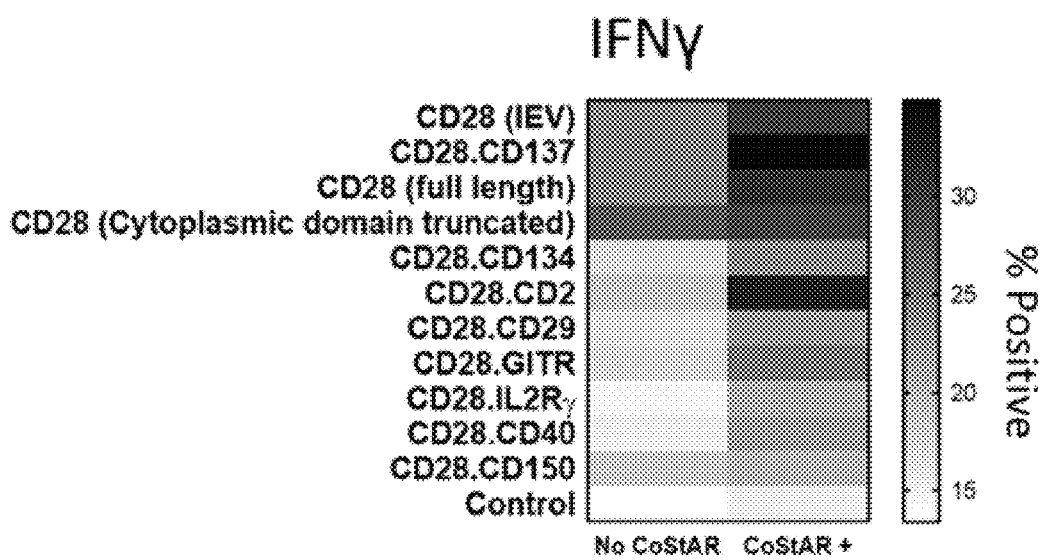
Figure 6C:
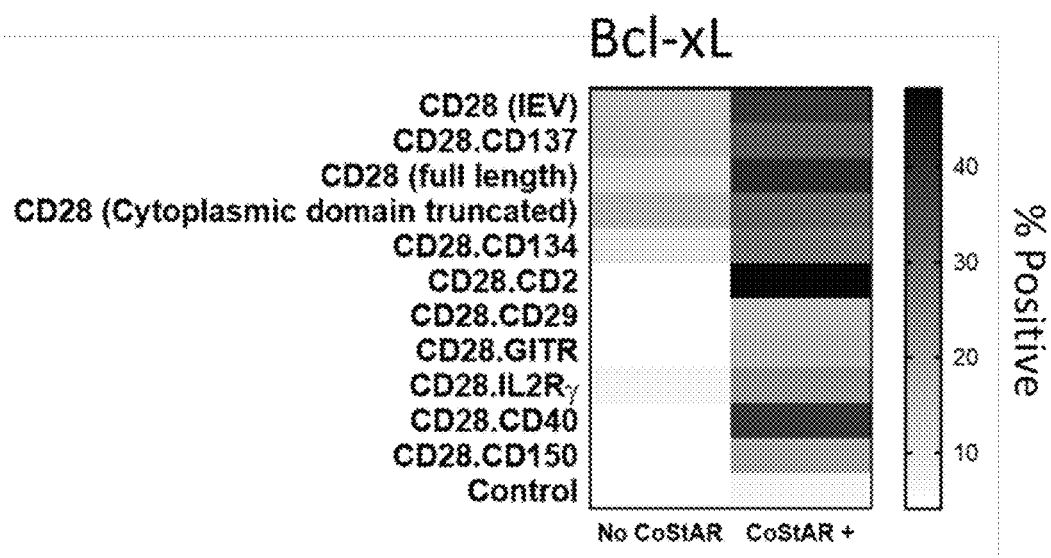
Figure 6D:
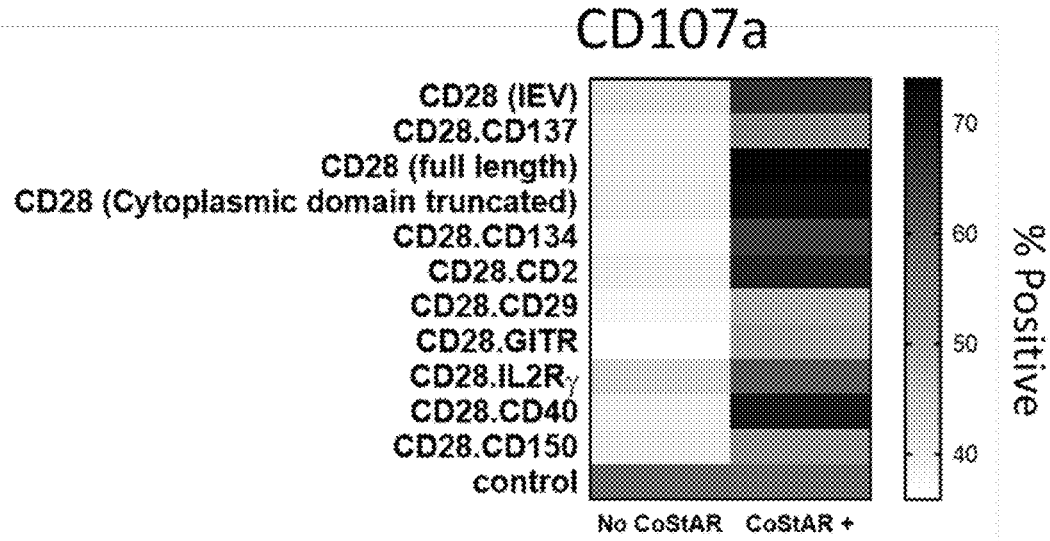

A variety of fusion receptors consisting of CD28 fused to an N-terminal additional costimulatory domain were generated. Costimulatory domains obtained from: CD137, CD2, CD29, CD134, CD150, CD40, GITR and the signalling domain from the IL-2 receptor γ-chain (IL-2Rγ) were chosen. A receptor as close to that used in previous studies of inducible costimulation was included. This receptor designated CD28(IEV) is truncated such that the C-terminal motif of CD28 is the amino acid triad 'IEV'. Sequences were generated de novo by Genewiz and cloned into a lentiviral vector under an EF1α promoter along with a CD34 marker gene separated from the fusion CoStAR by a 2A self-cleaving peptide. Primary CD8+ T-cells were isolated using EasySep beads (StemCell Technologies) and activated with anti-CD3/anti-CD28 activation/expansion Dynabeads before addition of lentiviral particles. Following a short expansion period the cells were mixed with LoVo or LoVo-OKT3 cells, with the inclusion of anti-CD107a antibodies and brefeldin and monensin, and following a 16 hour incubation were fixed and stained with antibodies to the marker gene (CD34) as well as antibodies to IL-2, IFNγ and Bcl-xL. Analysis was performed using a MACSQuant analyser and MACSQuantify software. FIG. 5 shows the IL-2 response from CD34− (CoStAR non-transduced) and CD34+ (CoStAR transduced). Statistical analysis demonstrated that all receptors tested induced a significant increase in the proportion of cells producing IL-2 when harboring the variant CoStAR receptors. Three other read outs were concurrently measured: IFNγ, a cytokine released under normal signal 1 conditions but enhanced by costimulation; CD107a, a marker of degranulation; and Bcl-xL, an antiapoptotic protein upregulated by costimulation. Engagement of CoStAR enhanced all the effector functions analysed to varying degrees. CD28.CD2 and CD28.CD40 fusions receptors appeared to elicit the most robust response of all the receptors tested (See FIGS. 6A-6D)

Example 2

Figure 7:
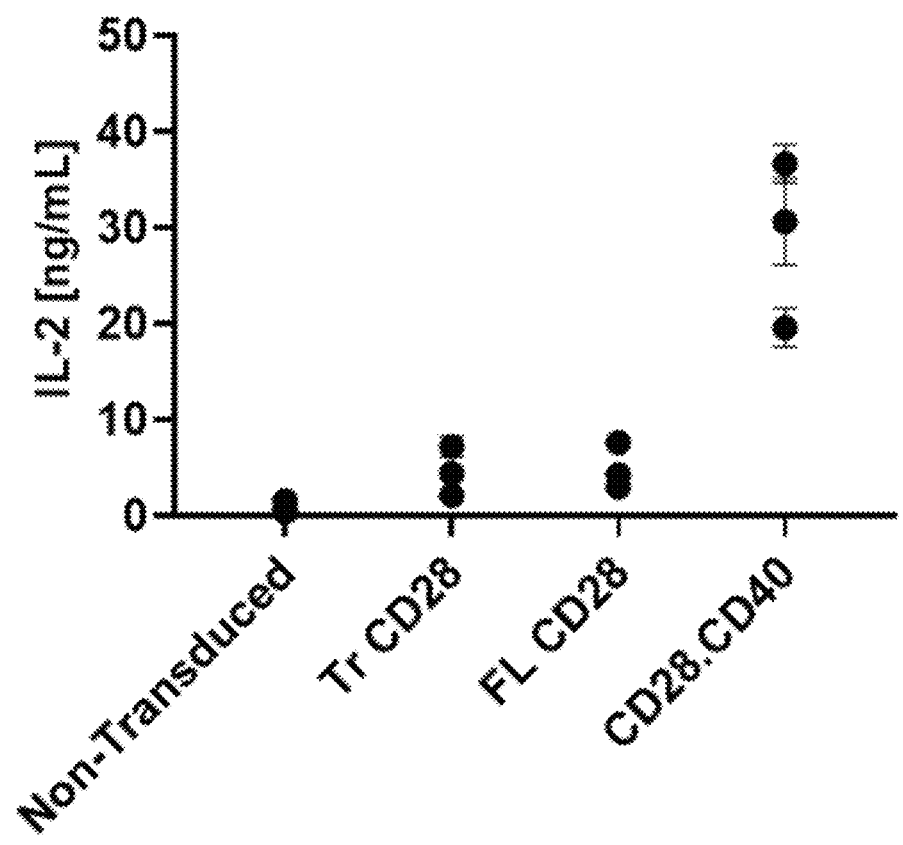
FIG. 7—CD40 enhances IL-2 production from CD28-based CoStARs. Primary human T-cells from three healthy donors were left non-transduced or transduced with either extracellular domain truncated CD28 (Tr CD28), full length CD28 (FL CD28), or CD28.CD40-based CoStARs harboring a CEA specific scFv (MFE23). Transduced cells were selected using a CD34 marker gene and expanded prior to analysis. T-cells were mixed at an 8:1 effector to target ratio with OKT3 expressing CEA+ LoVo cells for 20 hours before analysis of IL-2 production by ELISA.
Figure 8:
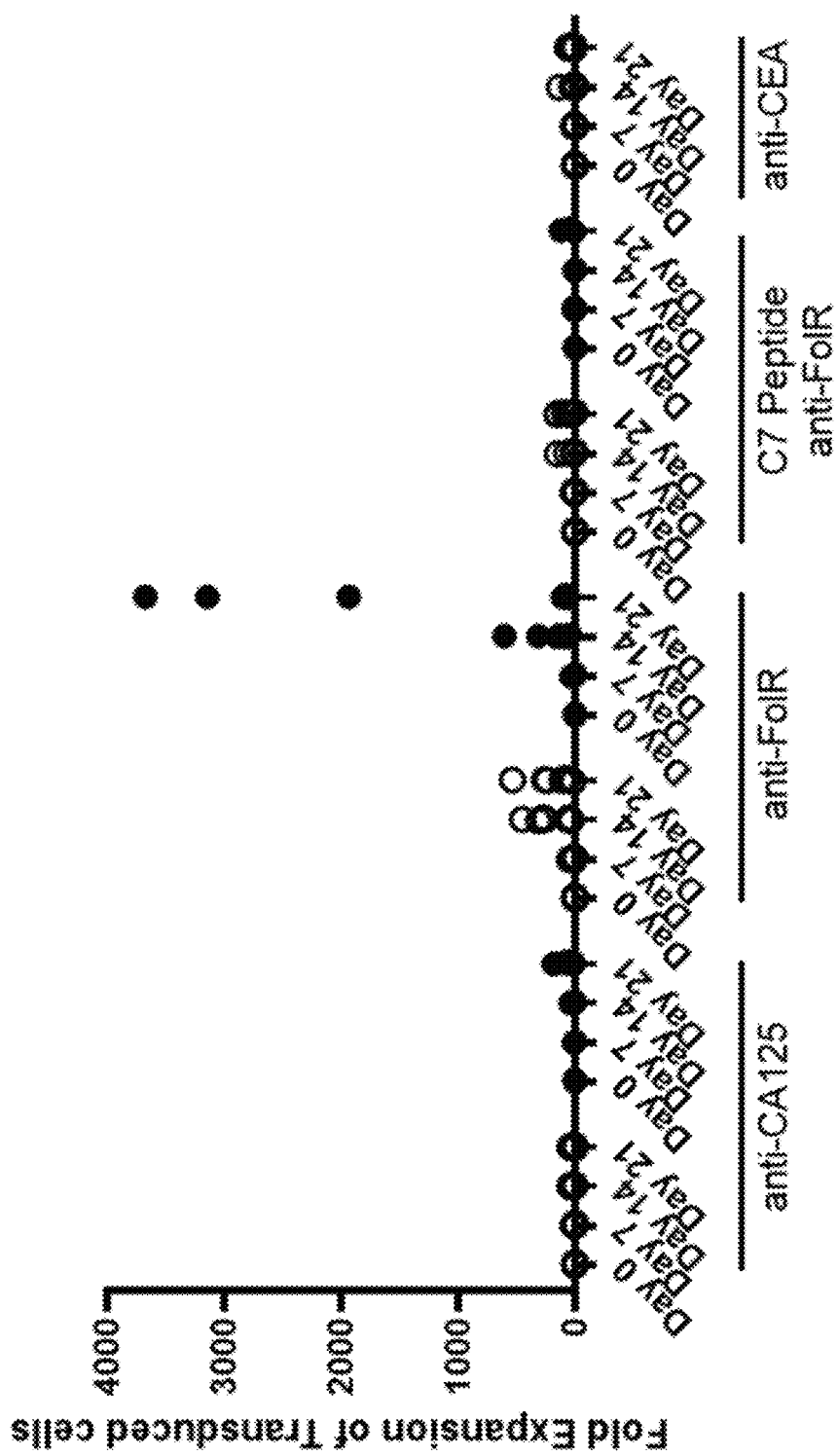
FIG. 8—Effect of signalling domain and target antigen on CoStAR-mediated T-cell expansion. T-cells were transduced with either DYKDDDDK (SEQ ID NO: 124) epitope-tagged CD28 or CD28.CD40 based CoStARs harboring CA125, FOLR1 or CEA specific scFv, or FOLR1 specific binding peptide (C7). T-cells were mixed with OKT3 expressing, CA125+/FOLR1+/CEA− cell line OVCAR3. The number of transduced cells were counted every 7 days up to 21 days, with fresh OVCAR3 cells added following each count.

The effect of CD28 and CD28.CD40 based CoStARs on population based cytokine secretion was compared. Primary T-cells from three donors were transduced with either the CD28(IEV) truncated CoStAR, full length CD28 CoStAR or CD28.CD40 CoStAR (having the full length CD28 as shown in SEQ ID NO. 10, but lacking the N terminal N and K residues) or left non-transduced. T-cells were enriched for CoStAR expression using the CD34 marker gene, and following expansion cells were mixed with LoVo-OKT3 cells and IL-2 secretion analysed by ELISA (See FIG. 7). Non-transduced cells on average produced 0.80 ng/ml IL-2, with CD28(IEV) and full length CD28 CoStAR producing 4.6 and 5.0 ng/ml IL-2 respectively. However CD28.CD40 induced 29.0 ng/ml IL-2 on average across three donors thus demonstrating a clear benefit to incorporating CD40 into the basic CD28-based CoStAR.

Next the effect of CoStAR on T-cell expansion was analysed. T-cells from seven donors were transduced with either CD28 or CD28.CD40 CoStARs with either an anti-CA125 (196-14) or anti-Folate receptor (MOV-19) scFv, or an anti-Folate receptor peptide (C7) antigen binding domain. Additional cells were transduced with a CD28 CoStAR harboring an anti-CEA scFv as a mismatched control. Cells were then mixed with CA125+/Folate receptor+/CEA− cell line OvCAR3 engineered to express a membrane bound OKT3 (OvCAR-OKT3). T-cell counts were made after 7, 14 and 21 days, and fresh OvCAR-OKT3 added at days 7, and 14. Limited expansion of cells harboring the anti-CA125 scFv was observed (mean fold expansion: CD28: 15.1; CD28.CD40: 69.1), however cells targeting Folate receptor with an scFv did expand in both the CD28 and CD28.CD40 cohorts (mean fold expansion: CD28: 186.7; CD28.CD40: 1295.0). More limited expansion was seen when the C7 peptide was used to target the Folate receptor (mean fold expansion: CD28: 71.5; CD28.CD40: 28.0). The control CEA targeting receptor demonstrated limited expansion (mean fold expansion: 28.0).

Figure 9:
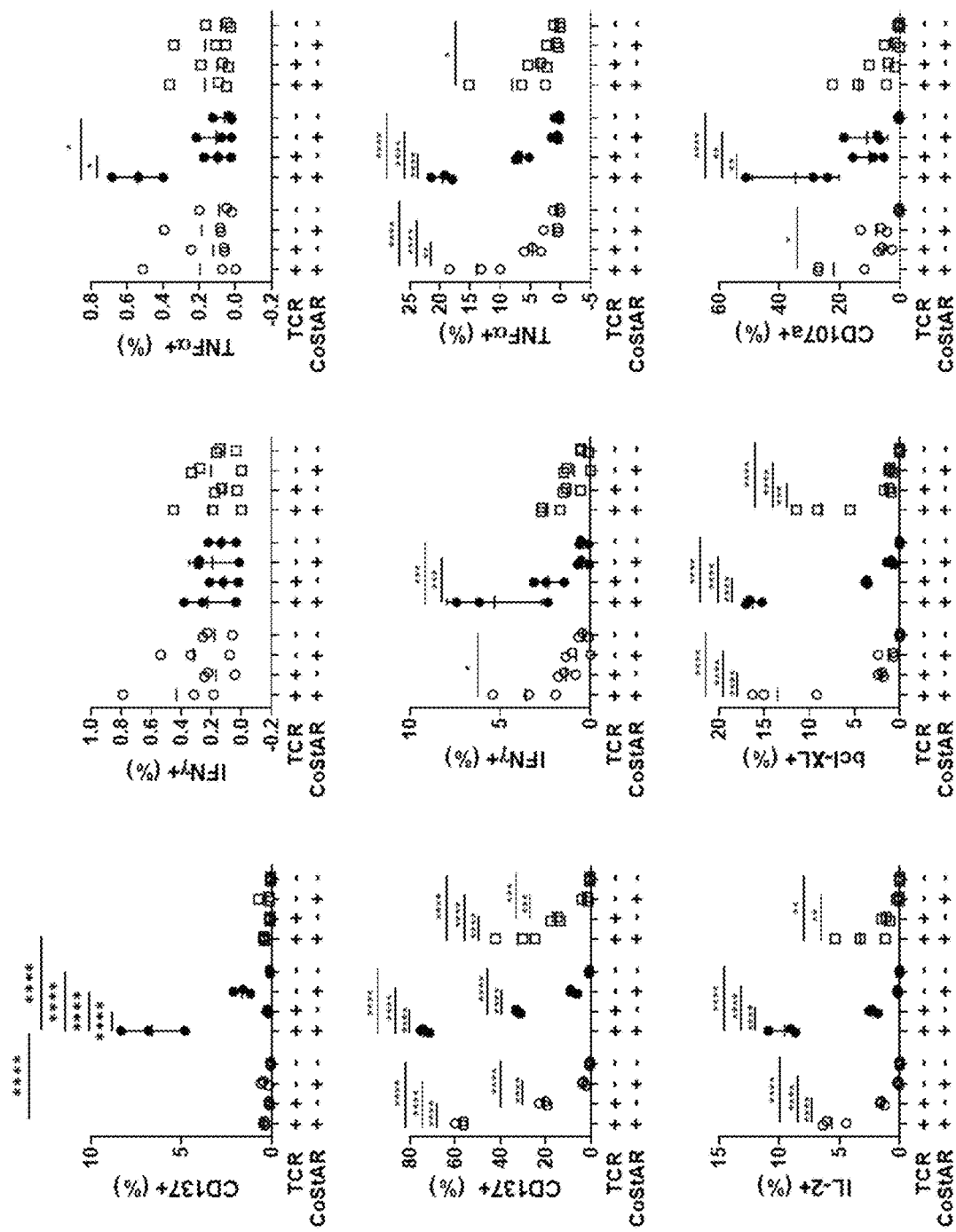
FIG. 9—CD40 based CoStARs enhance costimulation of T-cells in a model of TCR-transfer. Primary human T-cells from three healthy donors were transduced with a CEA specific TCR plus either a DYKDDDK-tagged CD28 or CD28.CD40 based CoStAR harboring either an MFE23 (open or closed circles) or CA125 (open squares) specific scFv. T-cells were mixed at a 1:1 effector:target ratio with CEA+/CA125− H508 cells and intracellular cytokine staining performed to determine the number of responding CD4+ or CD8+ T-cells in the TCR+/CoStAR+, TCR+/CoStAR−, TCR−/CoStAR+ and TCR−/CoStAR− populations. A 2-way ANOVA (Tukeys test) was performed to determine significant differences in activity: *p>0.05, p>0.01, *p>0.001, ****p>0.0001.
Figure 10A:
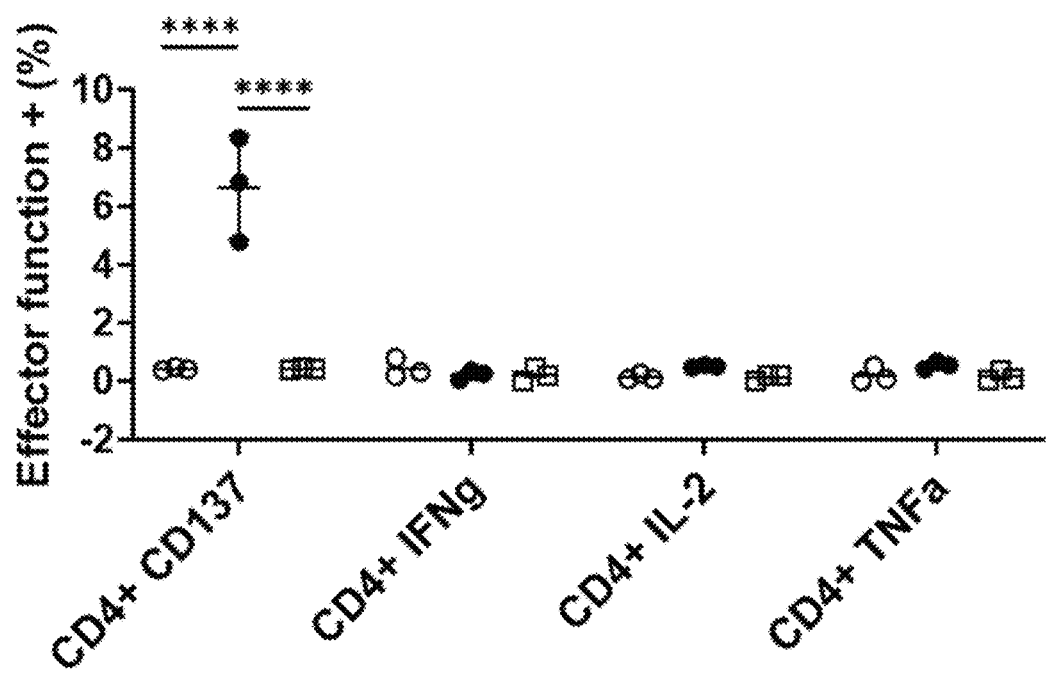
FIGS. 10A-10B—CoStAR dependent enhancement of activity in a model of TCR transfer. Primary human T-cells from three healthy donors were transduced with a CEA specific TCR plus either a DYKDDDK-tagged CD28 or CD28.CD40 based CoStAR harboring either an MFE23 (open or closed circles) or CA125 (open squares) specific scFv. T-cells were mixed at a 1:1 effector:target ratio with CEA+/CA125− H508 cells and intracellular cytokine staining performed to determine the number of responding CD4+ (FIG. 10A) or CD8+ (FIG. 10B) T-cells in the TCR+/CoStAR+, populations. A 2-way ANOVA (Tukeys test) was performed to determine significant differences in activity: p>0.01, **p>0.0001.
Figure 10B:
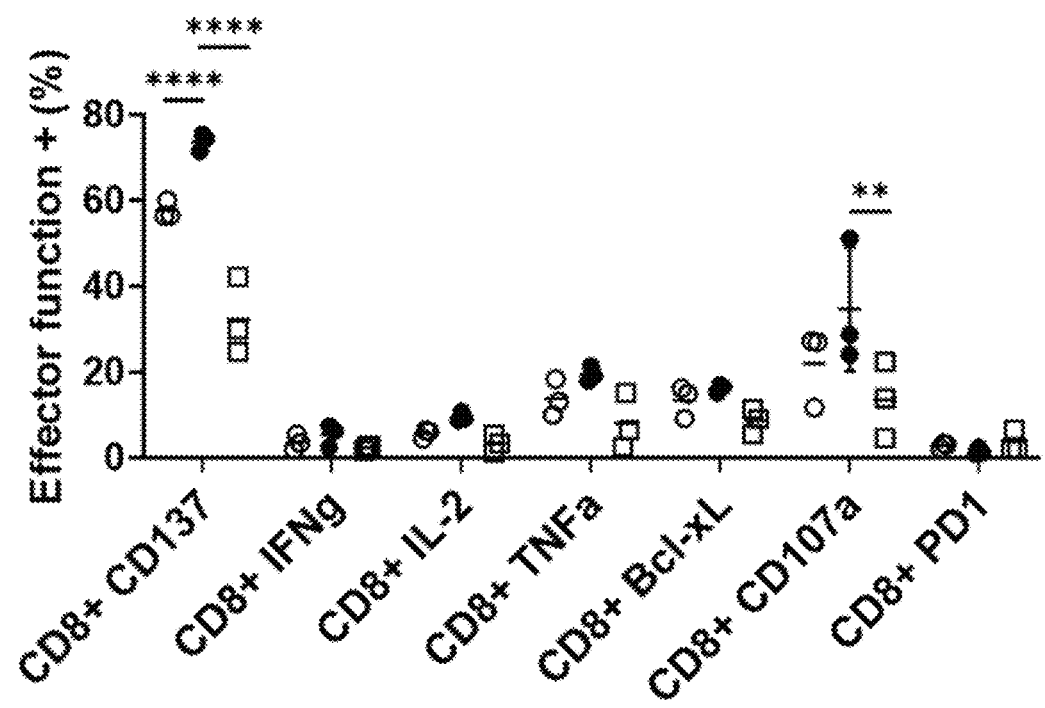

To better understand the synergy of signal 1 and signal 2 T-cells were engineered with a murine constant domain modified TCR which recognizes a CEA peptide (691-699) in the context of HLA-A*02 as well as the CD28 or CD28.CD40 CoStAR targeted towards cell surface CEA protein. As a control cells were also transduced with a CA125 specific CD28 CoStAR. The T-cells were mixed with HLA-A*02+/CEA+H508 cells and cytokine production analysed by intracellular flow cytometry staining. Flow cytometric gating was performed using antibodies directed towards the murine TCRβ constant domain (marks the TCR engineered cells) as well as the DYKDDDDK (SEQ ID NO: 124) epitope tag (marks the CoStAR engineered cells). Thus it was possible to analyse the TCR−/CoStAR−, TCR+/CoStAR−, TCR−/CoStAR+ and TCR+/CoStAR+ cells in each coculture well. Cytokine production was then plotted in each subpopulation in either the CD4+ or CD8+ T-cells (FIG. 9). In CD4+ cells CD28.CD40 CoStAR enhanced CD137 and TNFα production above TCR stimulation alone, however the TCR response in CD4+ cells was poor due to the dependency of the TCR on CD8. In CD8+ cells there was more robust effector activity with IL-2 and CD107a in particular showing a stronger induction in the CD28.CD40 CoStAR groups. To better compare the receptors the effector activity in just the TCR+/CoStAR+ groups was plotted in CD4+ and CD8+ cells (FIGS. 10A-10B). In CD4+ cells induction of CD137 was significantly enhanced by CD28.CD40 compared to either CEA or mismatched targeting CD28 CoStAR. In CD8+ cells CD137 induction was significantly increased compared to either CEA or mismatched targeting CD28 CoStAR, whereas CD107a induction was increased compared to the control CoStAR. Thus CD28.CD40 shows enhanced effector activity across a broad range of models and effector activities.

Example 3

Figure 11:
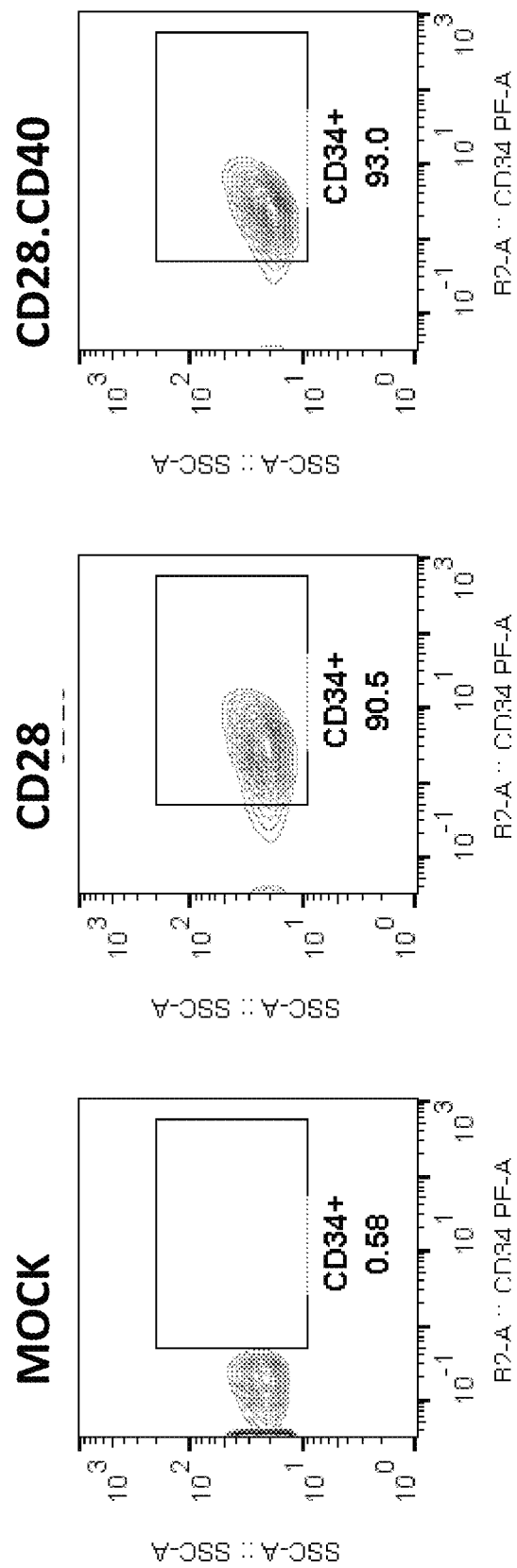
FIG. 11 depicts enrichment and expansion of primary human T-cells transduced to express costimulatory molecules of the invention. MFE23 is a single chain Fv antibody that has a high affinity for carcinoembryonic antigen (CEA). Primary human T-cells were mock transduced or transduced with MFE23.CD28 or MFE23.CD28.CD40 CoStAR, each harboring a CD34 marker gene separated by a 2A cleavage peptide. Following in vitro culture cells were enriched for CD34 using MACS™ paramagnetic selection reagents (Miltenyi Biotech) and then the cells expanded in number using irradiated feeder cells. Exemplary plots from one of three donors is shown.

To evaluate costimulation by CD40 bearing CoStARs, primary human T-cells were mock transduced or transduced with MFE23.CD28 or MFE23.CD28.CD40 CoStAR, each harboring a CD34 marker gene separated by a 2A cleavage peptide. MFE23 is a single chain Fv antibody that has a high affinity for carcinoembryonic antigen (CEA). Following in vitro culture cells were enriched for CD34 using MACS™ paramagnetic selection reagents (Miltenyi Biotech) and then the cells expanded in number using irradiated feeder cells. MFE23.CD28 CoStAR strongly mediated expansion of CD34+ T cells, and MFE23.CD28.CD40 CoStAR further enhanced expansion (FIG. 11).

Figure 12A:
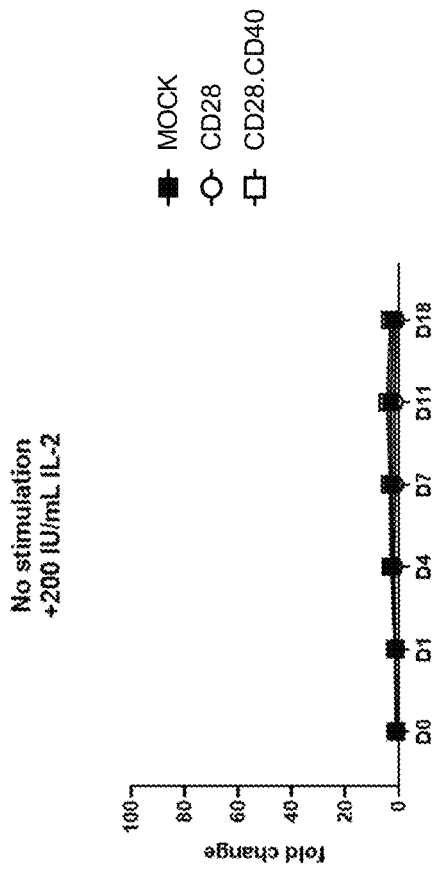
FIGS. 12A-12D depict expansion of T-cells transduced with costimulatory molecules of the invention in response to stimulation and exogenous IL-2. Cells were mock transduced or transduced with MFE23.CD28 or MFE23.CD28.CD40 CoStAR and cocultured with LoVo-OKT3 cells at an 8:1 effector:target ratio in the presence (200 IU/ml) or absence of exogenous IL-2. At days 1, 4, 7, 11 and 18 cells were taken and the number of viable T-cells enumerated by using anti-CD2 reagents on a MACSQuant flow cytometer.
Figure 12B:
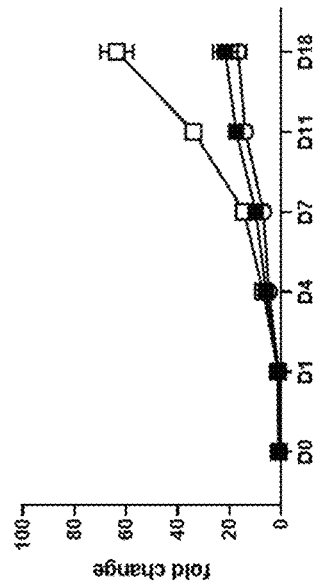
Figure 12C:
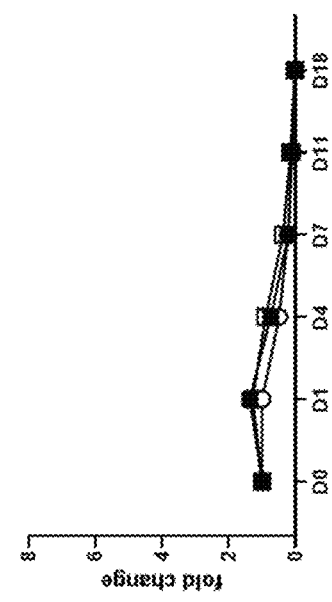
Figure 12D:
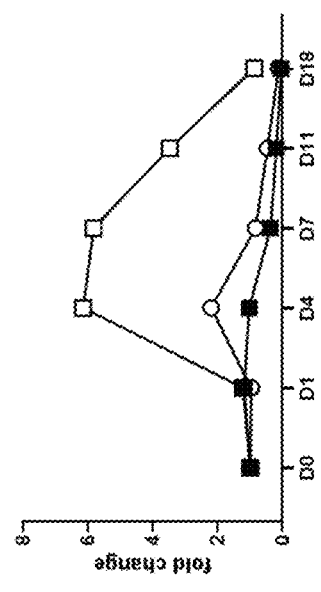

To evaluate costimulatory activity and persistence, T cells mock transduced or transfected with MFE23.CD28 or MFE23.CD28.CD40 were cocultured with LoVo-OKT3 cells at an 8:1 effector:target ratio in the presence (200 IU/ml) or absence of exogenous IL-2. At days 1, 4, 7, 11 and 18 cells were taken and the number of viable T-cells enumerated by using anti-CD2 reagents on a MACSQuant flow cytometer. In the absence of stimulation by tumor and IL-2, cells declined in number as would be expected (FIG. 12A). In the absence of stimulation but presence of IL-2 there was a more apparent survival of the cells, but no specific growth (FIG. 12B). In the presence of tumor, but absence of IL-2 mock cells did not show specific survival. MFE23.CD28 CoStAR mediated an apparent doubling in expansion over the first four days followed by decline. MFE23.CD28.CD40 mediated a greater expansion up to day 7 followed by a steady decline (FIG. 12C). Under the same conditions but in the presence of IL-2 both mock and MFE23.CD28 transduced cells demonstrated a 20-fold expansion over 18 days, whereas MFE23.CD28.CD40 cells expanded by over 60-fold (FIG. 12D). Thus CD28.CD40 based receptors demonstrated superior expansion and survival under conditions of stimulation both in the presence and absence of exogenous IL-2.

Mock transduced and T cells transduced with MFE23.CD28 or MFE23.CD28.CD40 CoStARs were then tested for cytokine production. Bead array analysis was performed on supernatants obtained from T-cell/tumor cocultures. Engineered T-cells were incubated at a 1:1 effector:target ratio with LoVo-OKT3 cells for 24 hours and supernatant collected. Conditioned supernatant was also collected from an equal number of T-cells alone, or LoVo-OKT3 cells alone. Production of IL-2, IFN-γ, TNFα, IL-4, IL-5, IL-13, IL-17A, IL-17F, IL-22, IL-6, IL-10, IL-9, and IL-21 was analysed using a Legendplex™ Human TH1/TH2 cytokine panel (Biolegend) (FIGS. 13A-13M). Cytokines were either very low or undetectable in media from T-cells or tumor alone. However when cocultured with tumor cytokine production was enhanced. MFE23.CD28 enhanced production of IL-2, IL-5, IL-17A/17F, IL-10, IL-9 and IL-21 compared to mock. However, MFE23.CD28.CD40 also enhanced production of TNFα, IL-13 and IL-22. MFE23.CD28.CD40 also enhanced the production of a number of cytokines greater than that elicited by MFE23.CD28 (IL-2, IL-9 and IL-17F), but also reduced the production of some cytokines below the levels seen with MFE23.CD28 (IL-5 and IL-10). Together this data demonstrates that addition of CD40 to CD28-based Costimulatory receptors enhances and/or modulates their specific activity with respect to cytokine production.

Mock transduced and T cells transduced with MFE23.CD28 or MFE23.CD28.CD40 CoStARs were further tested for chemokine production. Production of IL-8 (CXCL8), IP-10 (CSCL10), Eotaxin (CCL11), TARC (CCL17), MCP-1 (CCL2), RANTES (CCL5), MIP-1a (CCL3), MIG (CXCL9), ENA-78 (CXCL5), MIP-3α (CCL20), GROα (CXCL1), I-TAC (CXCL11), and MEP-1β (3 (CCL4) was analysed using a Legendplex™ Human Pro inflammatory chemokine panel. (FIGS. 14A-14M). Chemokines were either very low or undetectable in media from T-cells alone. When cocultured with tumor, chemokine production was enhanced. MFE23.CD28 enhanced production of CXCL5, CXCL10, CXCL11, CCL17 and CCL20 compared to mock. However, MFE23.CD28.CD40 enhanced production of CCL2, CXCL1 and CXCL9. MFE23.CD28.CD40 also further enhanced the production of certain cytokines to a greater amount than that elicited by MFE23.CD28 (CXCL1, CXCL9, CXCL10, CXCL11, CCL17, CCL2, CXCL9, CCL5 and CCL20), while reducing the production of some cytokines below the levels seen with MFE23.CD28 (CCL4). Together this data demonstrates that addition of CD40 to CD28-based Costimulatory receptors enhances and/or modulates their specific activity with respect to chemokine production.

Figure 15A:
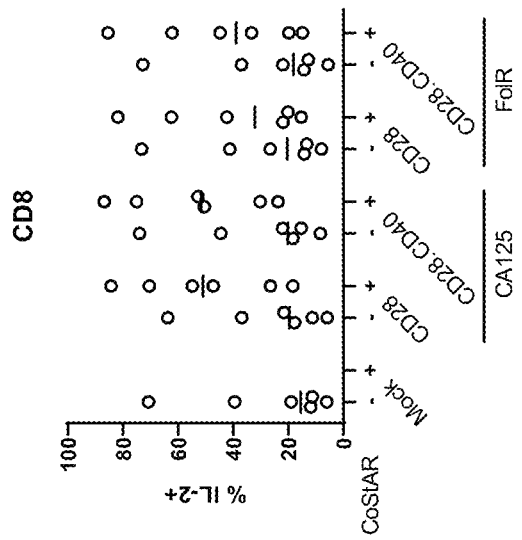
FIGS. 15A-15H depict functional activity of ovarian CoStAR engineered cells using a CoStAR harboring a FolR or CA125 reactive scFv (MOV19 & 196-14 respectively). Human folate receptor alpha (FolR) represents a suitable target for a number of tumors including ovarian, head and neck, renal and lung and CA125 represents an alternative target for ovarian cancer. Primary human T-cells from six healthy donors were engineered with either 196-14.CD28, 196-14.CD28.CD40, MOV19.CD28 or MOV19.CD28.CD40 receptors, all harboring a DYKDDDDK (SEQ ID NO: 124) epitope tag for detection. Transduced cells were mixed with FolR+/CA125+ OvCAR-OKT3 cells before analysis of effector activity using intracellular staining in the epitope tag positive and negative populations. Specific enhancement of effector activity determined by production of IL-2 (15A and 15B), TNFα (15C and 15D), CD137 (15E and 15F), and BCL-xL (15G and 15H) was observed in CD28 and CD28.CD40 engineered cells in response to both CA125 and FolR, except for specific BCL-xL induction by MOV19.CD28 which was not observed compared to MOV19.CD28.CD40.
Figure 15C:
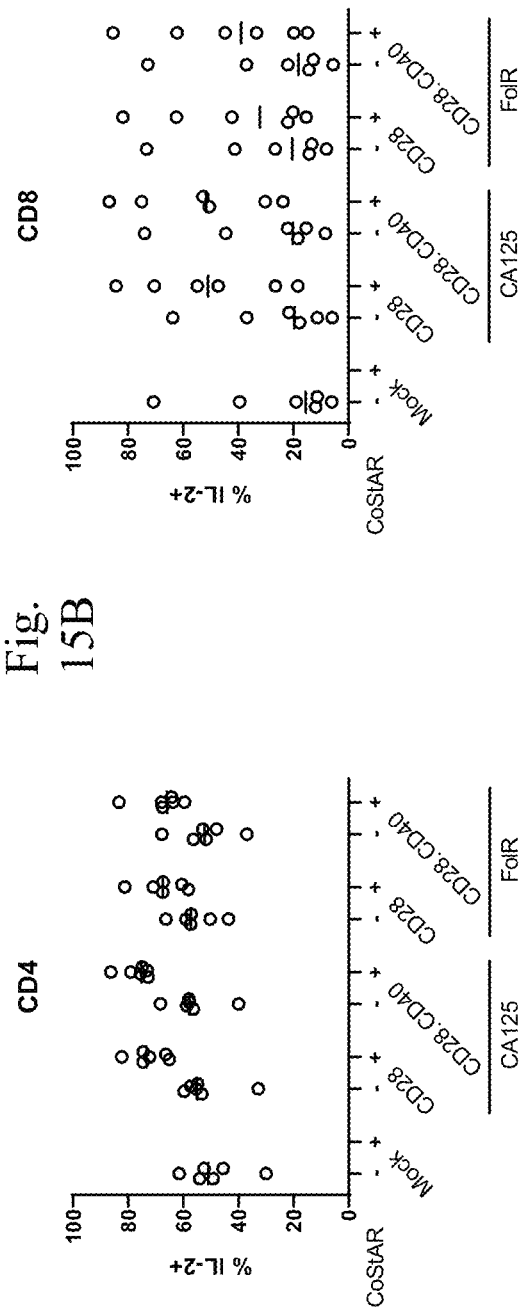
Figure 15B:
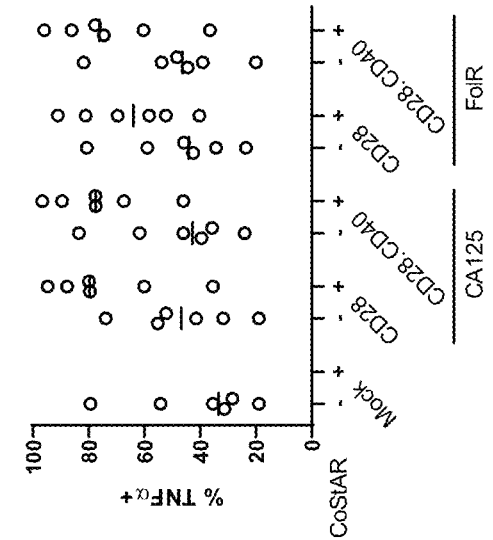
Figure 15D:
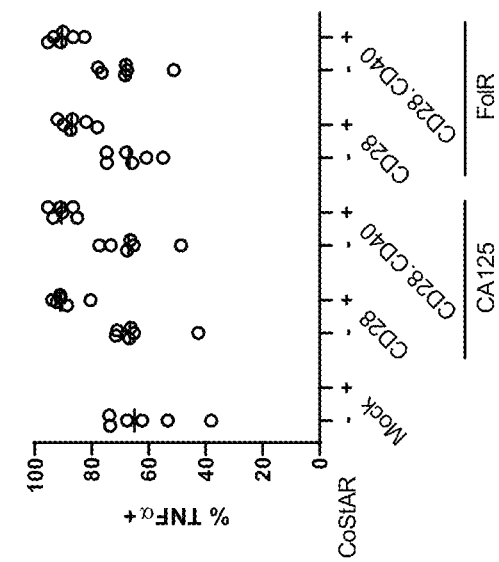
Figure 15E:
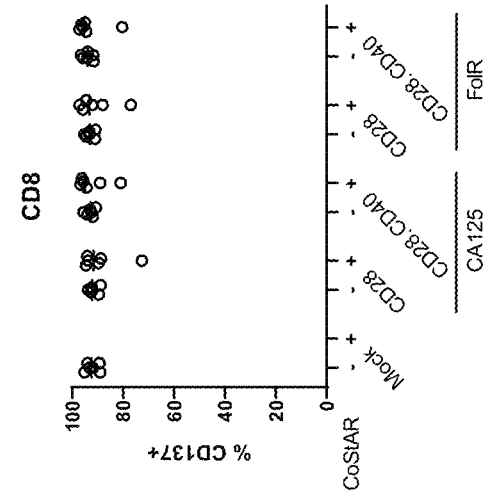
Figure 15F:
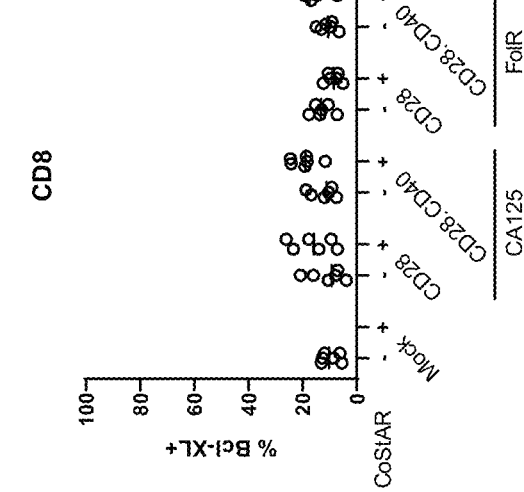
Figure 15G:
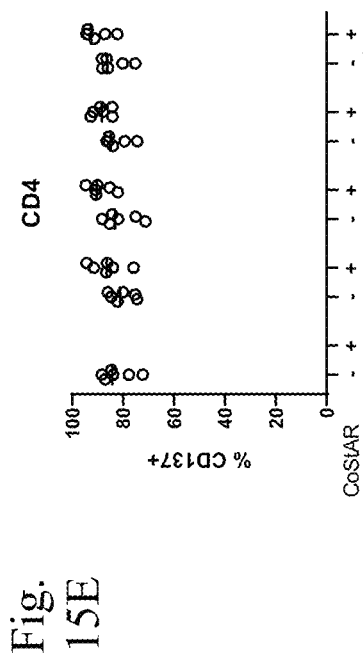
Figure 15H:
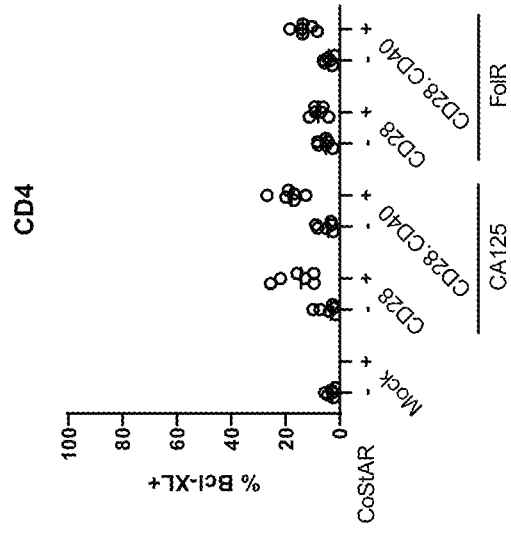

CoStARs were tested for functional activity against cancer targets. Cells were transduced with CD28 or CD28.CD40 CoStARs engineered with an scFv binding domain specific for FolR or CA125 (scFv MOV19 and scFv 196-14 respectively). Human folate receptor alpha (FolR) represents a suitable target for a number of tumors including ovarian, head and neck, renal and lung and CA125 represents an alternative target for ovarian cancer. Primary human T-cells from six healthy donors were engineered with either 196-14.CD28, 196-14.CD28.CD40, MOV19.CD28 or MOV19.CD28.CD40 receptors, all harboring a DYKDDDDK (SEQ ID NO: 124) epitope tag for detection. Transduced cells were mixed with FolR+/CA125+ OvCAR-OKT3 cells before analysis of effector activity using intracellular staining in the epitope tag positive and negative populations. Specific enhancement of effector activity determined by production of IL-2 (FIGS. 15A and 15B), TNFα (FIGS. 15C and 15D), CD137 (FIGS. 15E and 15F), and BCL-xL (FIGS. 15G and 15H) was observed in CD28 and CD28.CD40 engineered cells compared to mock transduce cells in response to both CA125 and FolR, although specific BCL-xL induction by MOV19.CD28 was not substantial as compared to MOV19.CD28.CD40.

Figure 16A:
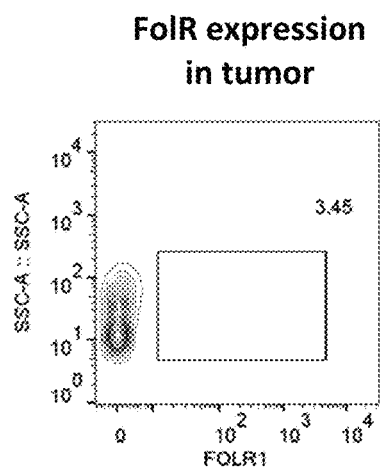
FIGS. 16A-16F depict three TIL populations mock transduced or engineered with MOV19.CD28.CD40 CoStAR and then mixed with patient matched tumor digest. The donor tumors displayed varying levels of FolR on the digest, ranging from negative (FIG. 16A), low expression (FIG. 16B) to high expression (FIG. 16C). Mock and CoStAR negative TIL in the CoStAR engineered populations of TIL matched for the FolR negative digest demonstrated similar levels of CD137 upregulation following tumor coculture which was not enhanced by the presence of CoStAR (FIG. 16D). In the TIL exposed to FolR low expressing digest there was an enhancement in activity in the CoStAR+ cells compared to CoStAR−, with CD137 expression increasing from <10% to >20% (FIG. 16E). In the TIL exposed to FolR high tumor digest there was an increase in activity from around 20% in the CoStAR− population, up to approximately 50% in the CoStAR+ population (FIG. 16F).
Figure 16B:
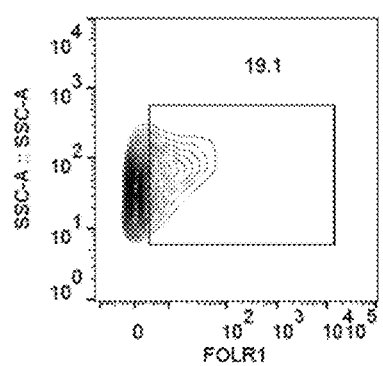
Figure 16C:
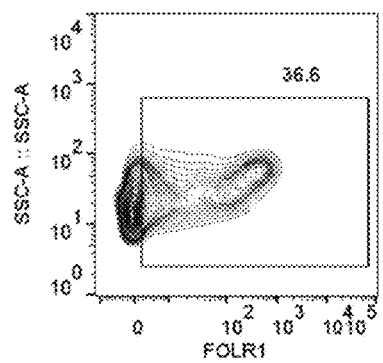
Figure 16D:
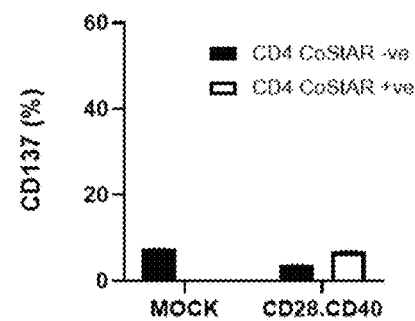
Figure 16E:
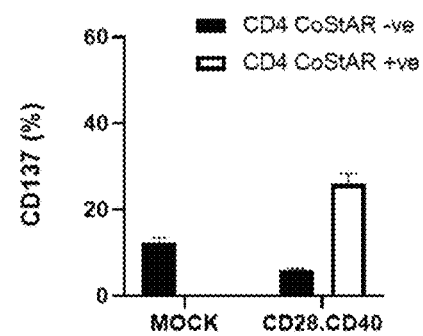
Figure 16F:
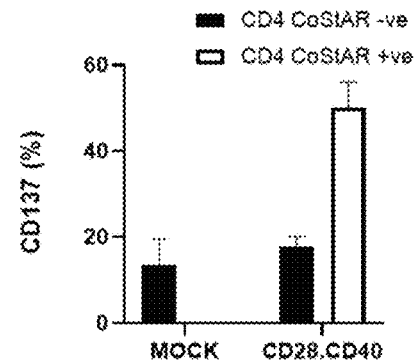

Mock transduced TILs or TILs engineered with MOV19.CD28.CD40 CoStAR were evaluated for expansion and CD137 production stimulated by patient matched tumor digest (FIGS. 16A-16F). Three donor tumors were tested which displayed varying levels of FolR on the digest, ranging from negative (FIG. 16A), low expression (FIG. 16B) to high expression (FIG. 16C). Mock and CoStAR negative TIL in the CoStAR engineered populations of TIL matched for the FolR negative digest demonstrated similar levels of CD137 upregulation following tumor coculture which was not enhanced by the presence of CoStAR (FIG. 16D). In the TIL exposed to FolR low expressing digest there was an enhancement in activity in the CoStAR+ cells compared to CoStAR−, with CD137 expression increasing from <10% to >20% (FIG. 16E). In the TIL exposed to FolR high expressing tumor digest there was an increase in activity from around 20% in the CoStAR− population, up to approximately 50% in the CoStAR+ population (FIG. 16F).

A FolR targeting CoStAR was examined for enhancement of effector functions. MOV19.CD28.CD40 enhanced CD137 expression from ~20% to ~50% (FIG. 17A), TNFα production from 10% to 15% (FIG. 17B) and IL-2 production from 2% to 5% (FIG. 17C) in response to FolR+ tumor digest.

Figure 18A:
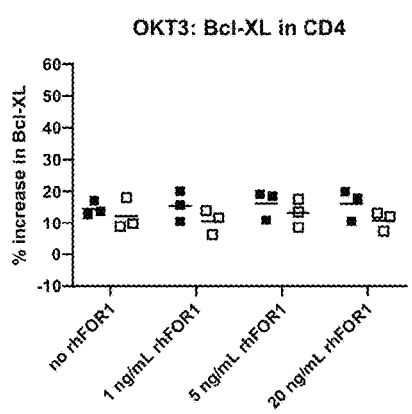
FIGS. 18A-18F depict soluble ligand does not inhibit effector functions. T-cells from three healthy donors were engineered with MOV19.CD28 or MOV19.CD28.CD40 CoStAR and activated with either immobilised OKT3, providing stimulation in the absence of FolR, or with OvCAR-OKT3, to provide TCR and CoStAR activity. Bcl-XL activity was increased from between 10 and 20% across the three donors following OKT3 stimulation (FIG. 18A) whereas IL-2 was increased between 0 and 12% (FIG. 18B) and TNFα increased between 0 and 20% (FIG. 18C). The presence of exogenous soluble FolR did not enhance any of these particular effector functions. In the presence of OvCAR-OKT3, Bcl-XL induction was enhanced by ~20% in CD28 CoStAR but by ~35% in CD28.CD40 CoStAR (FIG. 18D), IL-2 induction was enhanced by ~20% in CD28 CoStAR but 30-50% in CD28.CD40 CoStAR (FIG. 18E) and TNFα production was enhanced by 20-30% in CD28 CoStAR and 25-50% in CD28.CD40 CoStAR (FIG. 18F). Exogenous soluble FolR did not have an inhibitory effect on any of these effector functions.
Figure 18B:
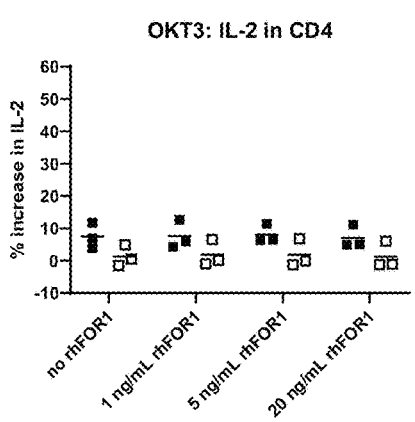
Figure 18C:
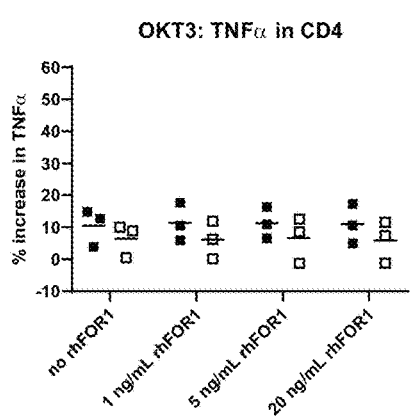
Figure 18D:
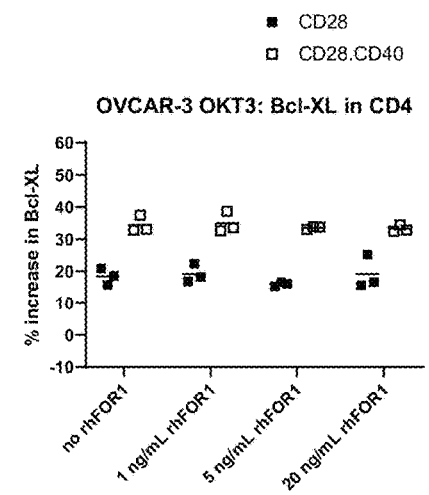
Figure 18E:
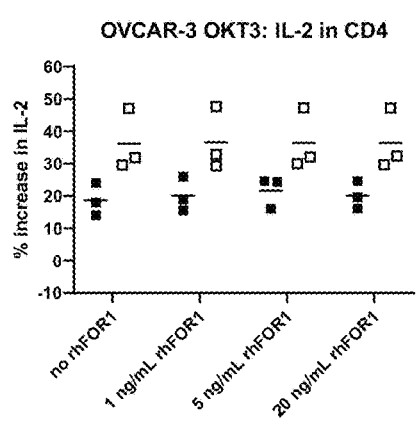
Figure 18F:
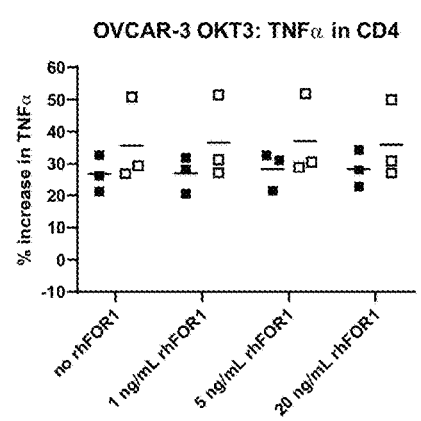
Figure 19:
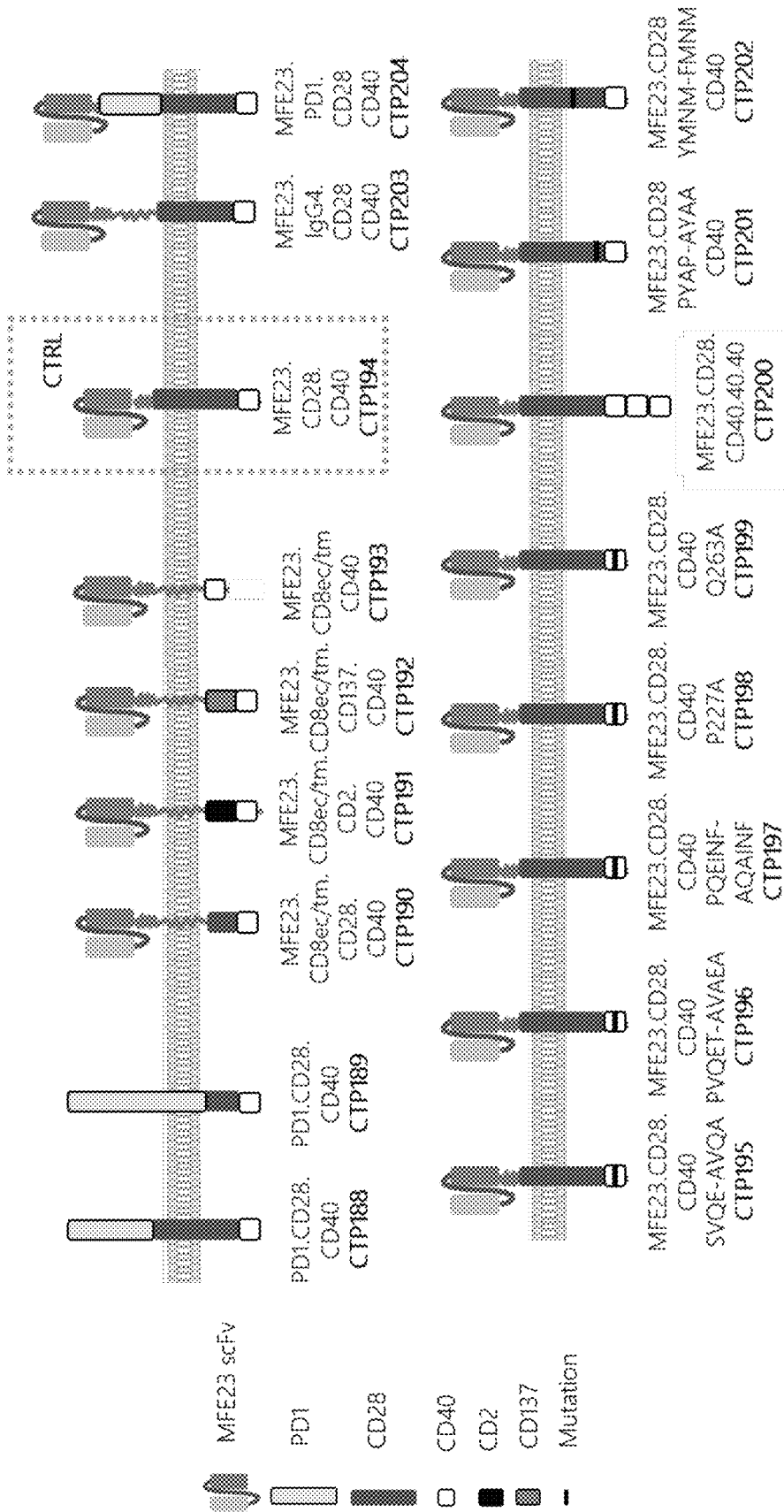
FIG. 19 depicts exemplary CoStAR constructs. MFE23: scFv specific for carcinoembryonic antigen (CEA). Costimulatory domains are identified. CTP188: SEQ ID NO:89; CTP189: SEQ ID NO:109; CTP190: SEQ ID NO:41; CTP191: SEQ ID NO:45; CTP192: SEQ ID NO:43; CTP193: SEQ ID NO:42; CTP194: SEQ ID NO: 33; CTP195: SEQ ID NO:110; CTP196: SEQ ID NO:111; CTP197 SEQ ID NO:112; CTP198: SEQ ID NO:113; CTP199: SEQ ID NO:114; CTP200: SEQ ID NO:115; CTP201: SEQ ID NO:116; CTP202: SEQ ID NO:117; CTP203: SEQ ID NO:49; CTP204: SEQ ID NO:59.

CoStAR mediated stimulation by soluble ligand was also examined. T-cells from three healthy donors were engineered with MOV19.CD28 or MOV19.CD28.CD40 CoStAR and activated with either immobilised OKT3, providing stimulation in the absence of FolR, or with OvCAR-OKT3, to provide TCR and CoStAR activity. Bcl-XL activity was increased from between 10 and 20% across the three donors following OKT3 stimulation (FIG. 18A) whereas IL-2 was increased between 0 and 12% (FIG. 18B) and TNFα increased between 0 and 20% (FIG. 18C). The presence of exogenous soluble FolR did not enhance any of these particular effector functions. In the presence of OvCAR-OKT3 Bcl-XL induction was enhanced by ~20% in CD28 CoStAR and by ~35% in CD28.CD40 CoStAR (FIG. 18D), IL-2 induction was enhanced by ~20% in CD28 CoStAR and 30-50% in CD28.CD40 CoStAR (FIG. 18E) and TNFα production was enhanced by 20-30% in CD28 CoStAR and 25-50% in CD28.CD40 CoStAR (FIG. 18F). Exogenous soluble FolR did not have an inhibitory effect on any of these effector functions.

Example 4

Materials and Methods

Construct design—The MFE23, MOV19 and 196-14 CoStAR constructs include an MFE23 (CEA specific), MOV19 (Folate receptor α specific) or 196-14 (CA125 specific) derived single chain antibody fragment nucleotide sequence with an oncostatin M1 leader sequence fused to a costimulatory domain. The costimulatory domains contain an extracellular spacer region and transmembrane domain derived from human CD8 or CD28 and a signalling domain of either CD28, CD2 or CD137 and/or wild-type or mutant CD40 variants. Some CoStARs detailed herein comprise a human PD1 extracellular domain fused to CD28 and CD40. Receptors were cloned with a P2A cleavage sequence and a truncated form of human CD34 to permit detection of transduced cells. The CoStAR nucleotide sequence was codon optimised and gene synthesised by Genewiz Inc. The constructs were cloned into a third generation lentiviral vector.

Peripheral blood mononuclear cells were isolated from normal healthy donors before activation for 24 hours with T-cell activation and expansion beads (Invitrogen) according to the manufacturer's instructions before addition of lentiviral supernatants.

Cell transduction was assessed 96 hours post infection using CEA.hFc protein (R&D Systems) and anti-hFc-PE secondary, plus anti-CD34-APC or by anti-CD34-PE antibodies alone. Cells were then expanded further using ×10 donor mismatched irradiated PBMC feeders at a 1:20-1:200 ratio in RPMI+10% FCS with the addition of 30 ng/ml OKT3 and 200 IU/ml IL-2. After 14 days the cells were stained as previous and stored ready for assay.

Functionality assays were performed by mixing CoStAR positive or negative cells with wild-type or OKT3 engineered CEA-Positive LoVo cells. Briefly, T-cells were mixed with LoVo cells at varying ratios in 96-well plates. For flow analysis cocultures were incubated with Brefeldin and monensin and anti-CD107a antibodies for 16 hours following which cells were stained with Fixable Viability Dye ef450 (eBiosciences), fixed with 4% paraformaldehyde and then permeabilised using Fix/Perm wash buffer (BD Biosciences). Cells were then stained with anti-CD34 or anti DYKDDDDK (SEQ ID NO: 124) antibodies to differentiate between the CoStAR+ and CoStAR-populations, anti-IL-2, anti-TNFα and anti-IFNγ antibodies (Biolegend). For soluble analyte analysis supernatants were collected for analysis by ELISA, cytokine bead array (LEGENDPLEX™ Human Th Cytokine Panel (12-plex)) or chemokine bead array (LEGENDPLEX™ Human Proinflammatory Chemokine Panel (13-plex).

Proliferation assays were performed by mixing T-cells and tumor cells at an 8:1 effector:target ratio in complete T-cell media (TCM: RPMI supplemented with 10% FCS, 0.01 M HEPES and 1% Penicillin/streptomycin, 50 mM β-mercaptoethanol) in the presence or absence of IL-2. Cell counts were made at indicated time points and fresh tumor cells were added in restimulation assays at a final E:T of 8:1. Cell counts for proliferation assays were performed by taking cells from the wells and staining with anti-CD2 PerCP eFluor710 antibody (eBioscience, UK) for 20 min in the dark, followed by DRAQ7 staining and counts made using a MACSQuant analyser.

Example 5

To evaluate the in vivo anti-tumor activity of T cells transduced with CD40 bearing CoStARs, primary human T-cells are mock transduced or transduced with MOV19.CD28.CD40 CoStAR construct followed by in vitro expansion and cryopreservation. MOV19 is a single chain Fv antibody that has a high affinity for Folate Receptor alpha (FOLR1). Immunocompromised mice are implanted with an established ovarian cancer cell line (A2870, OVCAR-5, OVCAR-8 or SK-OV-3), which is allowed to grow in the animal for few days. Mice are subsequently staged according to their tumor burden, and finally injected with the mock transduced T cells or MOV19.CD28.CD40 transduced T cells. Shortly after the T cell dosing, some of the mice are injected with intravenous IL-2 (5 μg IL-2, Q2Dx7) to support the engraftment and initial expansion of T cells. The final study design contains 5 groups (each one containing 5 mice): PBS (no cells dosed), mock transduced T cells, mock transduced T cells with IL-2 supplementation, MOV19.CD28.CD40 transduced T cells and MOV19.CD28.CD40 transduced T cells with IL-2 supplementation. Tumor growth and mice survival is monitored on weekly basis for a total of 40 days.

Mice administered with MOV19.CD28.CD40 transduced cells show better tumor control and prolonged survival compared to the mock transduced groups, whether or not supplemented with IL-2. This data demonstrates the ability of the CoStAR platform to improve in vivo the T cell anti-tumor response and also illustrates how this improved response is independent of the presence of exogenous IL-2.

Example 6

The example relates to identification of key components of CoStAR such as, but not limited to, PD-1, MFE23, CD40 combined with another component, a spacer, a CD40 mutant and/or a CD28 mutant.

Virus production was carried out by $CaCl_2$ transfection of HEK293T cells. CD34 (a marker gene) expression was determined by titration with JRT3 cells.

An experimental design for outgrowth in healthy donors was as follows: Day 0 was T cell isolation from frozen PBMCs. Day 0 was also activation with Dynabeads. Day 2 was transduction by spinoculation. Day 5 was bead removal. Day 8 was measuring viability and transduction rate. Day 8 was also post activation (before REP), Days 13-15 was freezing.

CD34 expression after magnetic enrichment, before REP, was measured before sort and in positive and negative fractions after sort. Healthy donors were activated with Dynabeads and transduced (spinoculation, MOI 5) with CD40 CoStAR constructs or MOCK. Cells were then magnetically enriched for their CD34 expression and analyzed by flow cytometry (Novocyte) before and after sort An experimental design in healthy donors included the outgrowth as described above as well as REP: Day −2 was transduced T cells thawing, Day −1 was magnetic CD34 enrichment, Day 0 was REP with G-Rex, Day 5-6 was changing medium, Day 11-12 was measuring viability and transduction rate and freezing.

Figure 20:
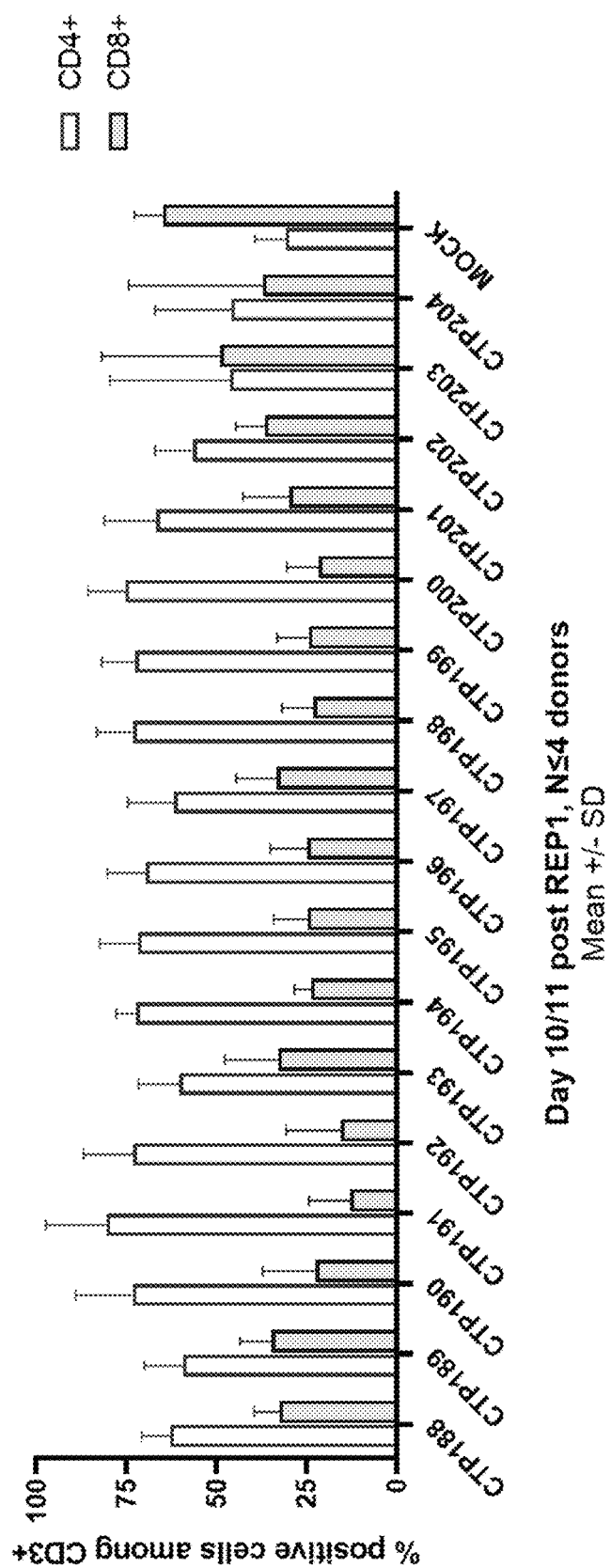
FIG. 20 depicts CD4+ and CD8+ subpopulations of CD40 CoStAR modified T cells. T cells of four healthy donors were activated and transduced with various CD40 CoStARs with a CD34 marker or mock transduced. Cells were enriched for their CD34 expression and expanded following the rapid expansion protocol (REP). CD4 (light grey) and CD8 (grey) T cell phenotypes were assessed 10-11 days after REP using anti-human CD4-PerCP-eF710, anti-human CD8-PE-Cy7, and anti-human CD3-FITC. Data shown as mean+/−SD, n=4 healthy donors

The majority of CD40 CoStAR modified T cells were enriched in CD4 after CD34 enrichment and REP (FIG. 20). CD4 and CD8 T cell phenotypes were assessed 10-11 days after REP using anti-human CD4-PerCP-eF710, anti-human CD8-PE-Cy7, and anti-human CD3-FITC. Analysis was performed by flow cytometry (Novocyte) and data were analyzed using NovoExpress 1.5.0 software with the following gating strategy: live/dead exclusion, single cells, CD3+ cells, CD4+ cells or CD8+ cells.

CoStAR modified CD4 T cells were highly transduced compared to the CD8 population. Healthy donors were activated with Dynabeads and transduced (spinoculation, MOI 5) with CD40 CoStAR constructs or MOCK. Cells were then magnetically enriched for their CD34 expression and expanded following the rapid expansion protocol (REP). Surface expression of the marker gene CD34 on CD4 and CD8 T cells, was assessed 10-11 days after REP using anti-human CD34-PE associated with anti-human CD4-PerCP-eF710, anti-human CD8-PE-Cy7, and anti-human CD3-FITC. Analysis was performed by flow cytometry (Novocyte) and data was analyzed using NovoExpress 1.5.0 software with the following gating strategy: live/dead exclusion, single cells, CD3+ cells, CD34+ cells among CD4+ cells or CD8+ cells.

Example 7

Figure 22:
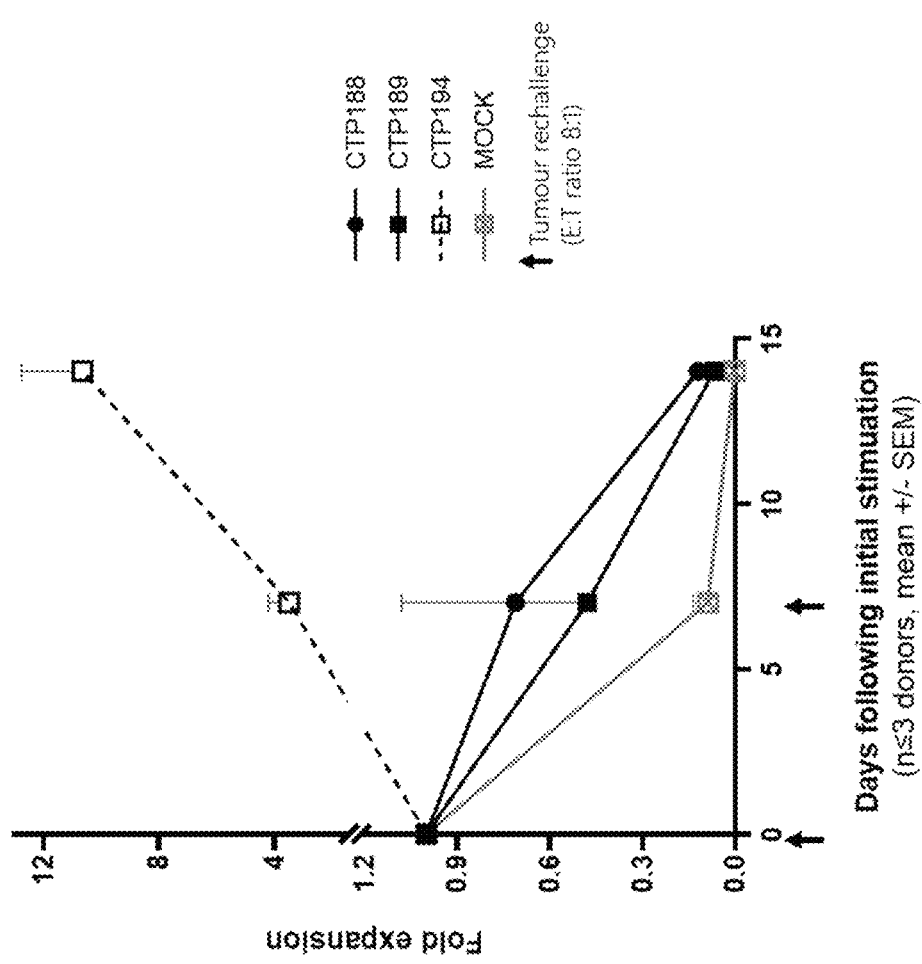
FIG. 22 depicts PD-1 extracellular domain conferring a slight proliferation advantage to CD40 CoStAR transduced T cells when cocultured with LoVo.OKT3. Healthy donor T cells activated with Dynabeads and transduced with CTP188, CTP189, CTP194 or mock-transduced were enriched for CD34 expression, expanded following the rapid expansion protocol (REP) and frozen for subsequent experiments. After thaw, cells were rested for 3-4 days in complete RPMI supplemented with IL-2 and their transduction rate was determined looking at the CD34 marker gene expression. The viability and absolute count were assessed after overnight IL-2 starvation using DRAQ-7 (1:200) by flow cytometry (Novocyte) and data were analysed using the NovoExpress 1.5.0 software. Transduced T cells were cocultured in absence of IL-2 for 6-8 days with LoVo.OKT3.GFP tumor cells at 8:1 effector to target ratio, changing half of the culture medium every 3-4 days. LoVo.OKT3.GFP naturally expresses CEA and PD-L1 on their surface, conferring both signal 2 and signal 1 (OKT3) to the transduced T cells. After 6-8 days, the viability and absolute count were assessed, and live T cells were rechallenged for an additional week with fresh LoVo.OKT3.GFP tumor cells as described above. At the end of the long-term coculture, the viability and absolute count were measured, and the fold expansion was calculated. Data shown as mean+/−SEM of n≤3 donors analysed in triplicates.
Figure 23B:
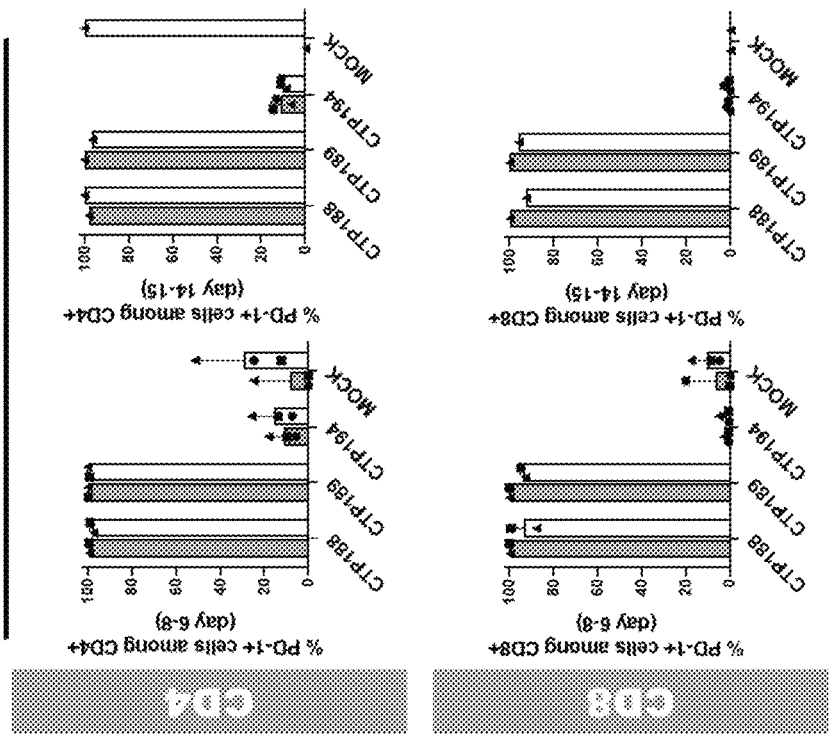
FIGS. 23A-23C depict exhaustion profiles of PD-1 fusion CD40 CoStAR transduced T cells after tumor challenge. Healthy donor T cells were activated with Dynabeads and transduced with CTP188, CTP189, CTP194 or mock transduced. Cells were enriched for CD34 marker expression, expanded following the rapid expansion protocol (REP) and frozen for subsequent experiments. After thaw, cells were rested for 3-4 days in complete RPMI supplemented with IL-2. The viability and absolute count were assessed after overnight IL-2 starvation using DRAQ-7 (1:200) by flow cytometry (Novocyte) and data were analysed using the NovoExpress 1.5.0 software. Transduced T cells were cocultured in absence of IL-2 for 6-8 days with LoVo.OKT3.GFP tumor cells at 8:1 effector to target ratio, changing half of the culture medium every 3-4 days. LoVo.OKT3.GFP naturally expresses CEA and PD-L1 on their surface, conferring both signal 2 and signal 1 (OKT3) to the transduced T cells. After 6-8 days, the viability and absolute count were assessed, and live T cells were rechallenged for an additional week with fresh LoVo.OKT3.GFP tumor cells as described above. Exhaustion profiles (LAG-3 (FIG. 23A), PD-1 (FIG. 23B), TIM-3 (FIG. 23C)) of transduced (CD34+ (grey)) or non-transduced (CD34− (white)) CD4 (upper panels) and CD8 (lower panels) T cells were assessed by flow cytometry and shown as mean+/−SD of n≤3 donors.
Figure 23A:
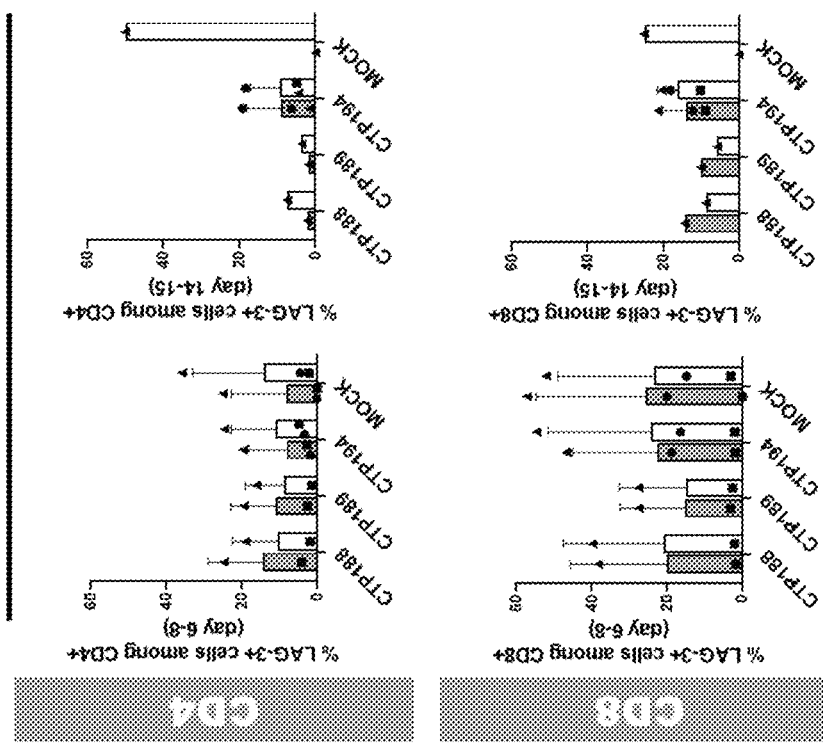
Figure 23C:
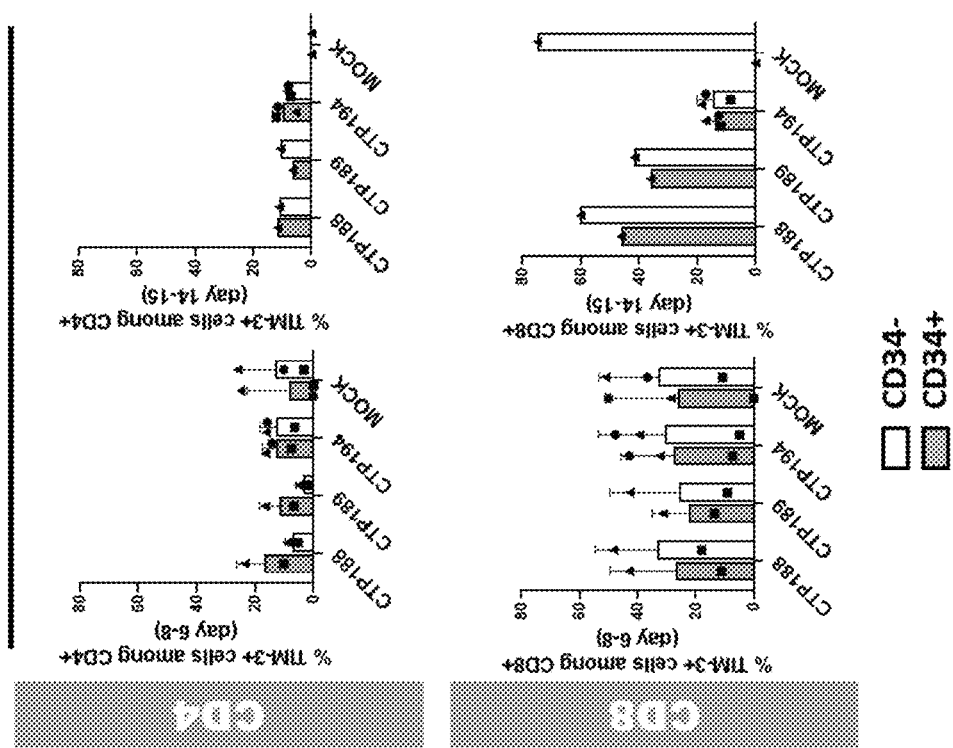

CoStARs composed of an extracellular checkpoint binding domain fused to a CD40 costimulatory domain could convert an inhibitory signal into an activating signal upon engagement of the CoStAR. To test the applicability of such receptors we generated PD1-fusion CoStARs based on the descriptions outlined in Ankri et al. J Immunol 2013; 191: 4121-4129 and Prosser et al. Molecular Immunology 51 (2012) 263-272, but with the addition of CD40 to the signalling domain (FIG. 21A). Primary human T-cells isolated from healthy donors were activated with CD3/CD28 Dynabeads and transduced with the indicated PD1 fusion CoStAR receptors at an MOI=5, or an MFE23.CD28.CD40 CoStAR (positive control) or mock transduced (negative control). Transduced T-cells were enriched using CD34 microbeads and expanded via a rapid expansion protocol using irradiated feeder cells before banking. After thaw, cells were rested for 3-4 days in complete RPMI supplemented with IL-2. The viability and absolute count were assessed after overnight IL-2 starvation using DRAQ-7 (1:200) by flow cytometry (Novocyte) and data were analysed using the NovoExpress 1.5.0 software. Transduced T cells were cocultured in the absence of IL-2 with LoVo (CCL-229TM) or LoVo.OKT3.GFP tumor cells at 8:1 effector to target ratio. After 24 hours, supernatants were collected and frozen. LoVo and LoVo.OKT3.GFP naturally express CEA and PD-L1 on their surface, conferring signal 2 through the CoStAR alone (LoVo) or associated with signal 1 (LoVo.OKT3.GFP) to the transduced T cells. Cocultures were performed in triplicate and corresponding negative (T cells alone, tumor cells alone) and positive (PMA+ionomycin) controls were included in the experiment. Secreted IL-2 and IFN-γ were detected by ELISA and the absorbance was measured using a FLUOstar Omega microplate reader and subsequently analysed with the Omega MARS 3.42 R5 software. Each symbol is the average triplicate value for each donor (FIG. 21C). MFE23.CD28.CD40 (CTP194) expressing cells produced on average approximately 4000 pg/ml IL-2 in the presence of LoVo-OKT3 cells, whereas production from PD1 fusions was <1000 pg/ml. Analysis of IFNγ secretion also demonstrated enhanced production of this cytokine from MFE23.CD28.CD40 engineered cells compared to mock, however no enhancement in production from cells harboring the PD1 fusions was observed. Next, we assessed the ability of PD1-fusion CoStARs to mediate T-cell survival in the presence of repeated tumor challenge (FIG. 22). To this end CoStAR or mock transduced T-cells were mixed at 8:1 E:T ratio with LoVo-OKT3 cells at day 0 and 7 and counts and checkpoint expression phenotyping made at day 6-8 and 14-15 (FIGS. 23A-23C). FIG. 22 shows the fold expansion of cells over the duration of the experiment, with mock transduced cells dropping in number throughout the experiment; conversely MFE23.CD28.CD40 (CTP194) engineered cells expanded upon serial stimulation with tumor up to 12-fold by day 14. Although PD1 fusion CoStARs did not demonstrate a similar degree of expansion to CTP194 engineered cells, the degree of T-cell death was not as great as mock engineered cells suggesting that the PD1 domain can mediate some degree of T-cell survival. Checkpoint expression (LAG3, PD1 and TIM3) was also assessed in the CD4+ and CD8+ cells in both CD34– and CD34+ populations and is shown at days 6-8 and 14-15 on FIGS. 23A-23C. LAG3 was found to be relatively low (typically <20%) at day 6-8 in CD4+ and CD8+ cells (albeit more variably in CD8+ cells) with no obvious difference between cells harboring the different receptors or mock transduced. However, at day 14-15 we observed lower LAG3 expression in cells harboring the PD1 or MFE23 based CoStAR compared to mock engineered cells. PD1 expression was more difficult to assess as PD1 as a component of the CoStAR could not be separated from endogenous expression. In CD4+ cells we observed lower PD1 expression in MFE23.CD28.CD40 engineered cells compared to mock transduced, an effect which was more obvious at day 14-15. Expression of TIM3 mirrored LAG3 expression in CD4+ and CD8+ cells at day 6-8, whereas at day 14-15 TIM3 expression was generally low, however we did observe a high expression of TIM3 in mock transduced cells at day 14-15 (~80% of cells), which was lower in PD1-fusion CoStAR cells, but <20% in cells harboring MFE23.CD28.CD40. In summary, CoStARs consisting of an antigen recognition domain which inverts signals, such as PD1, are functional but do not perform as well in cytokine release or expansion assays as cells harboring CoStAR with an scFv-based antigen recognition domain. PD1-fusion receptors can also modulate checkpoint expression compared to mock engineered cells as well.

Figure 24A:
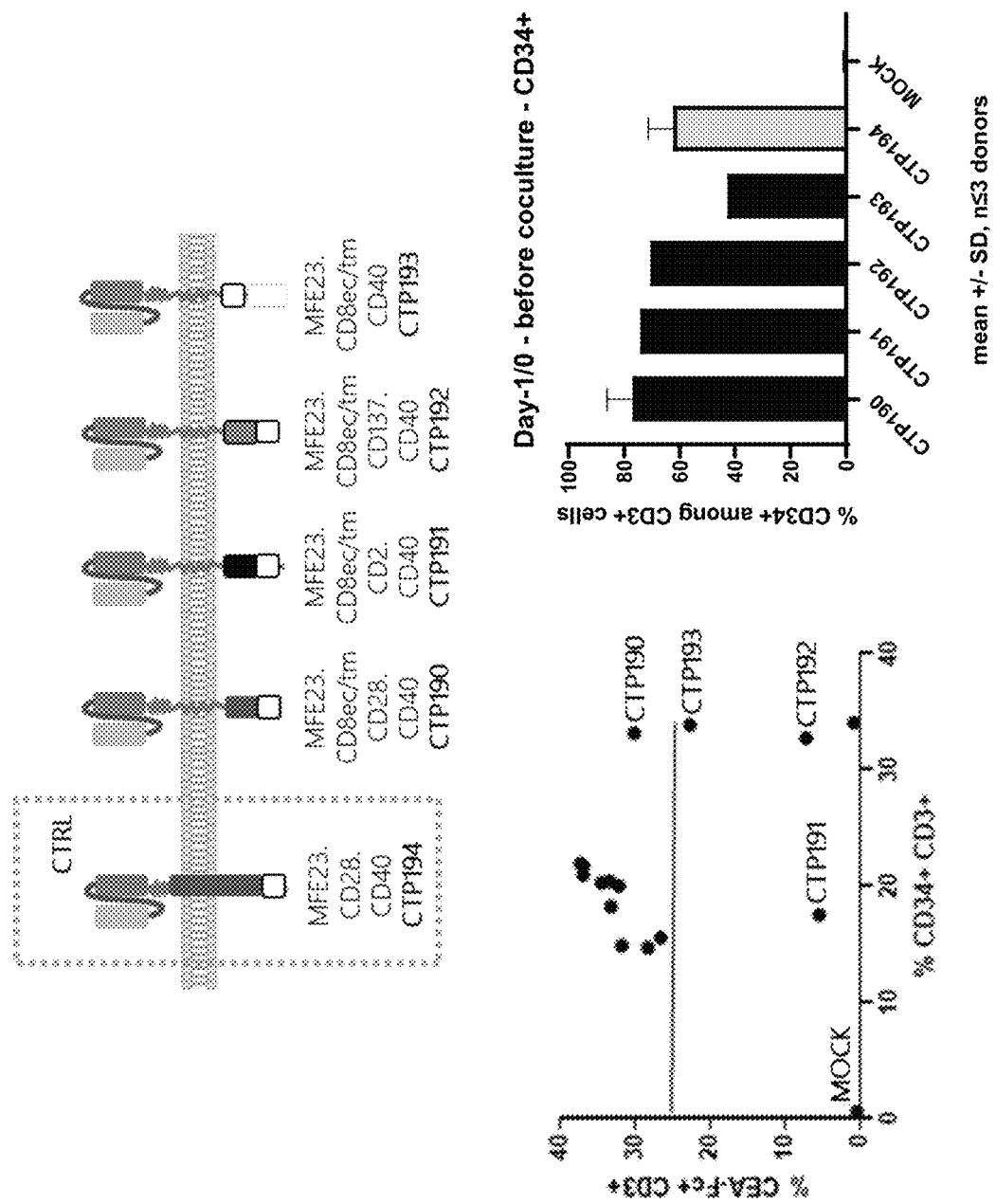
FIGS. 24A-24B depict T cells transduced with CD28, CD137 and CD40 alone CoStARs secrete higher amount of IL-2 following activation compared to mock transduced T cells.
Figure 24B:
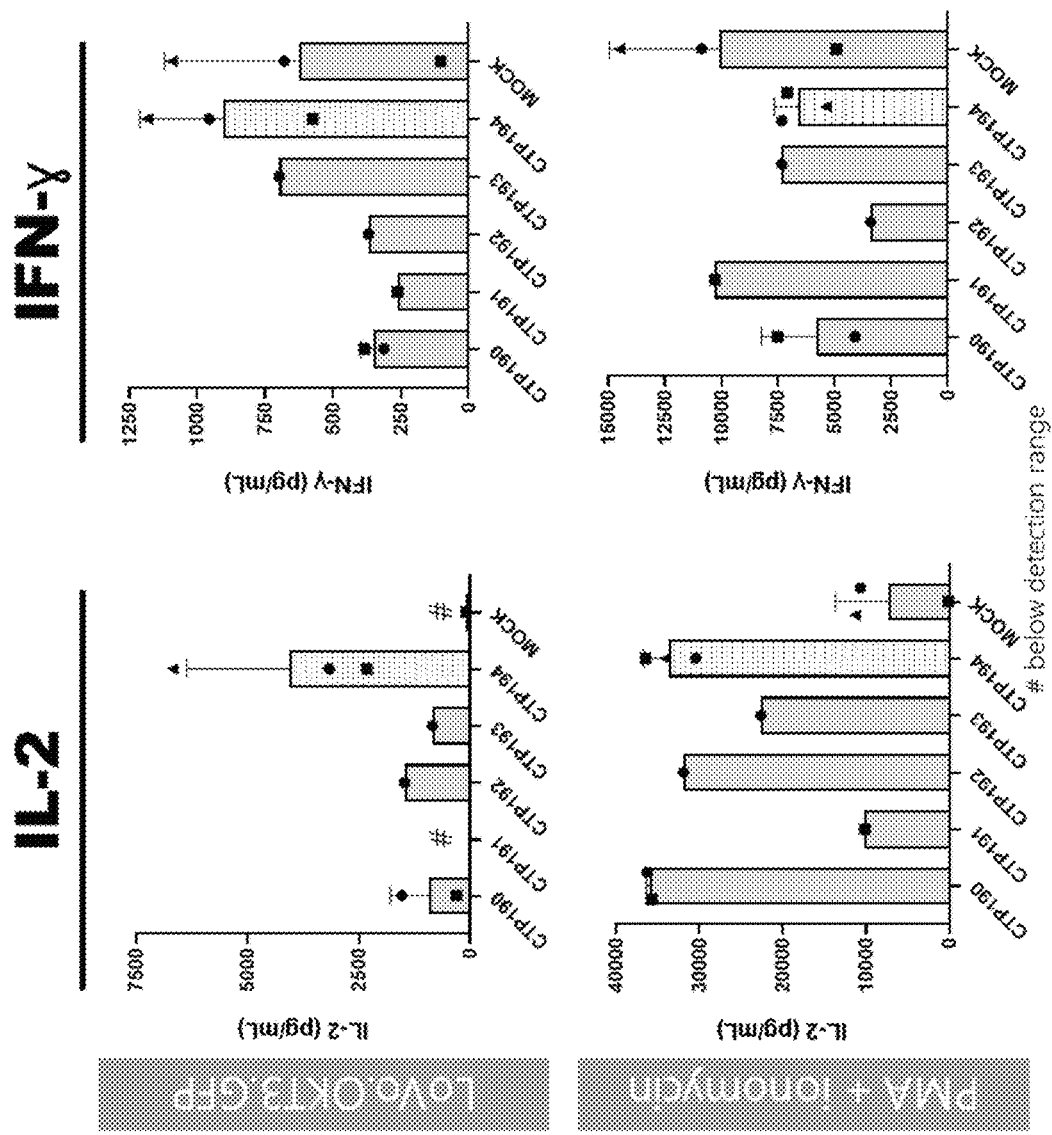
Figure 25:
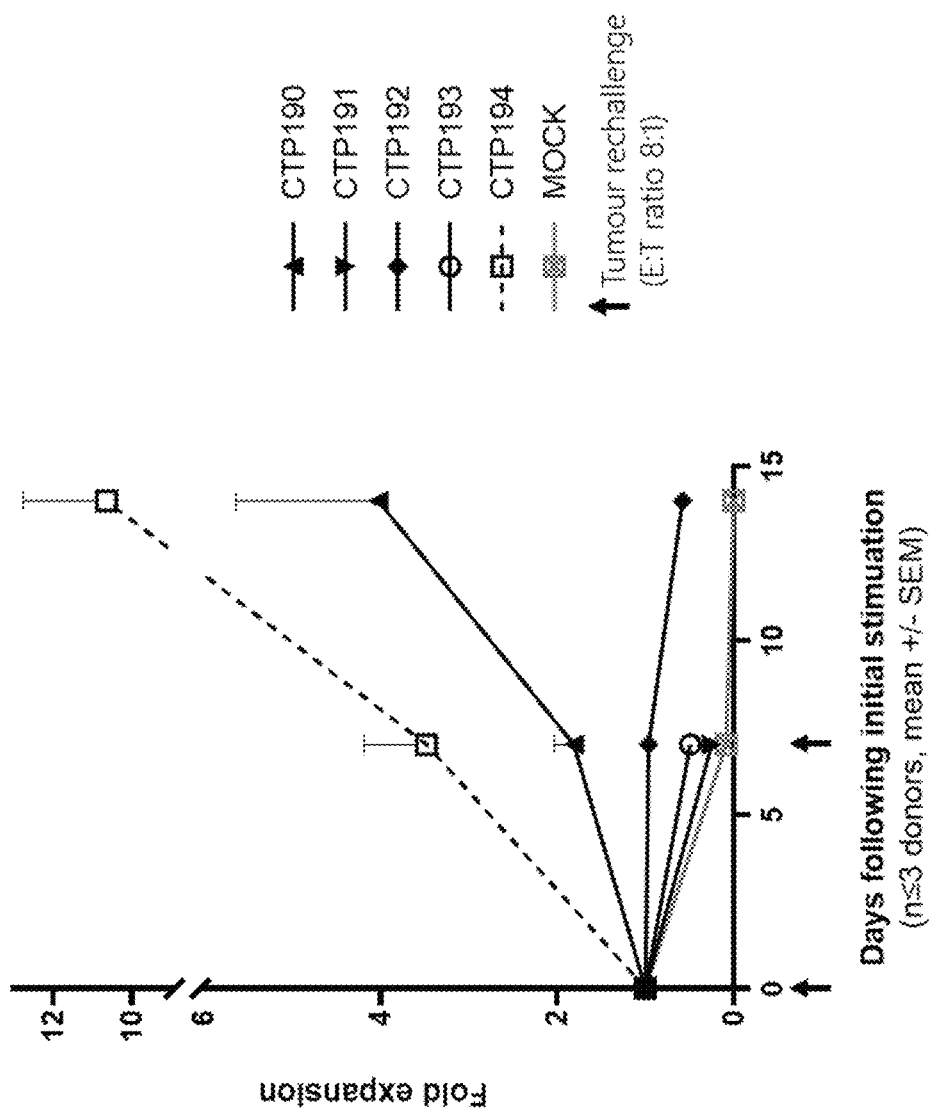
FIG. 25 depicts CD28 and CD137 endodomains conferring a proliferation advantage to CD40 CoStAR transduced T cells when cocultured with LoVo.OKT3. Healthy donor T cells were activated with Dynabeads and transduced with CTP190, CTP191, CTP192, CTP193, CTP194 or mock transduced. Cells were enriched for CD34 marker expression, expanded following the rapid expansion protocol (REP) and frozen for subsequent experiments. After thaw, cells were rested for 3-4 days in complete RPMI supplemented with IL-2. The viability and absolute count were assessed after overnight IL-2 starvation using DRAQ-7 (1:200) by flow cytometry (Novocyte) and data were analysed using the NovoExpress 1.5.0 software. Transduced T cells were cocultured in absence of IL-2 for 6-8 days with LoVo.OKT3.GFP tumor cells at 8:1 effector to target ratio, changing half of the culture medium every 3-4 days. LoVo.OKT3.GFP naturally expresses CEA and PD-L1 on their surface, conferring both signal 2 and signal 1 (OKT3) to the transduced T cells. After 6-8 days, the viability and absolute count were assessed, and live T cells were rechallenged for an additional week with fresh LoVo.OKT3.GFP tumor cells as described above. At the end of the long-term coculture, the viability and absolute count were measured, and the fold expansion was calculated. Data shown as mean+/−SEM of n≤3 donors analysed in triplicates.
Figure 26A:
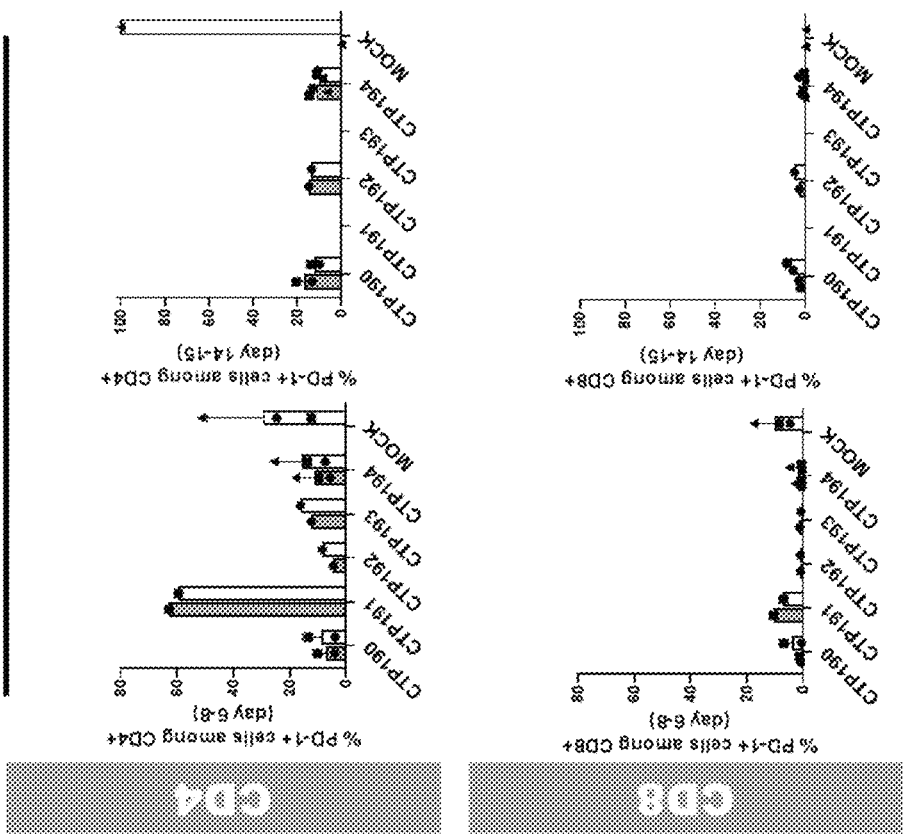
FIGS. 26A-26C depict exhaustion profiles of transduced T cells with CD28, CD2, CD137 and CD40 alone CoStARs after tumor challenge. Healthy donor T cells were activated with Dynabeads and transduced with CTP190, CTP191, CTP192, CTP193, CTP194 or mock transduced. Cells were enriched for CD34 marker expression, expanded following the rapid expansion protocol (REP) and frozen for subsequent experiments. After thaw, cells were rested for 3-4 days in complete RPMI supplemented with IL-2. The viability and absolute count were assessed after overnight IL-2 starvation using DRAQ-7 (1:200) by flow cytometry (Novocyte) and data were analysed using the NovoExpress 1.5.0 software. Transduced T cells were cocultured in absence of IL-2 for 6-8 days with LoVo.OKT3.GFP tumor cells at 8:1 effector to target ratio, changing half of the culture medium every 3-4 days. LoVo.OKT3.GFP naturally expresses CEA and PD-L1 on their surface, conferring both signal 2 and signal 1 (OKT3) to the transduced T cells. After 6-8 days, the viability and the absolute count were assessed, and live T cells were rechallenged for an additional week with fresh LoVo.OKT3.GFP tumor cells as described above. Exhaustion profiles (LAG-3 (FIG. 26A), PD-1 (FIG. 26B), TIM-3 (FIG. 26C)) of transduced (CD34+ (grey)) or non-transduced (CD34− (white)) CD4 (upper panels) and CD8 (lower panels) T cells were assessed by flow cytometry and shown as mean+/−SD of n≤3 donors.
Figure 26B:
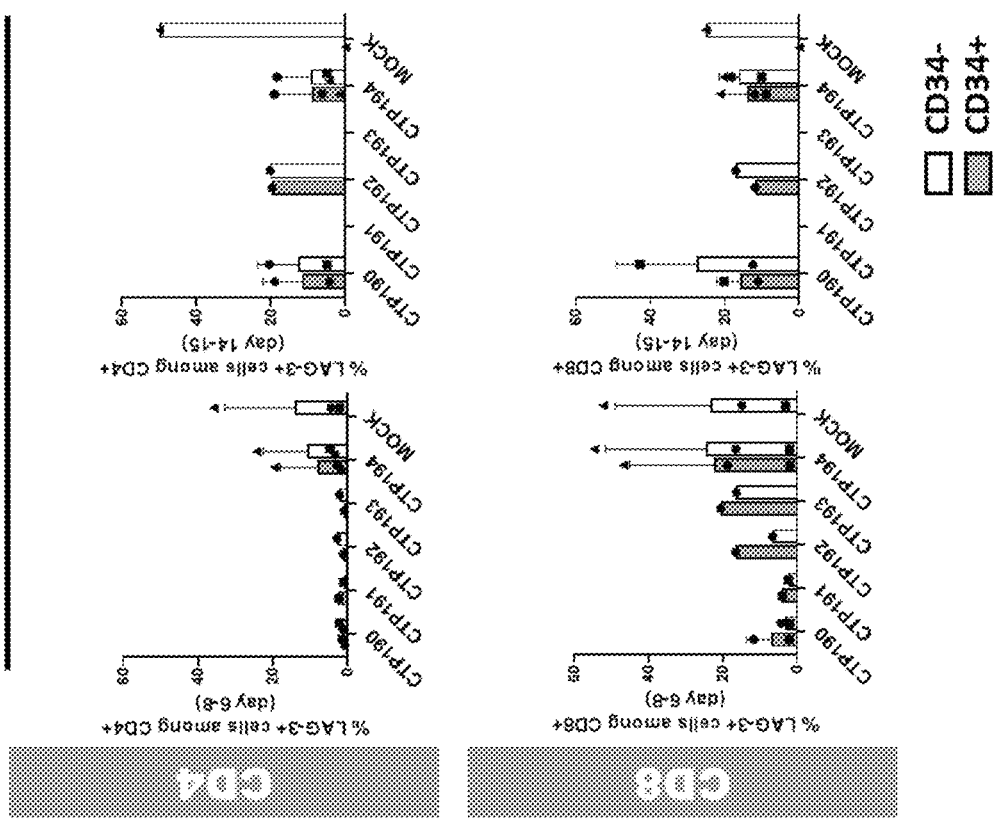
Figure 26C:
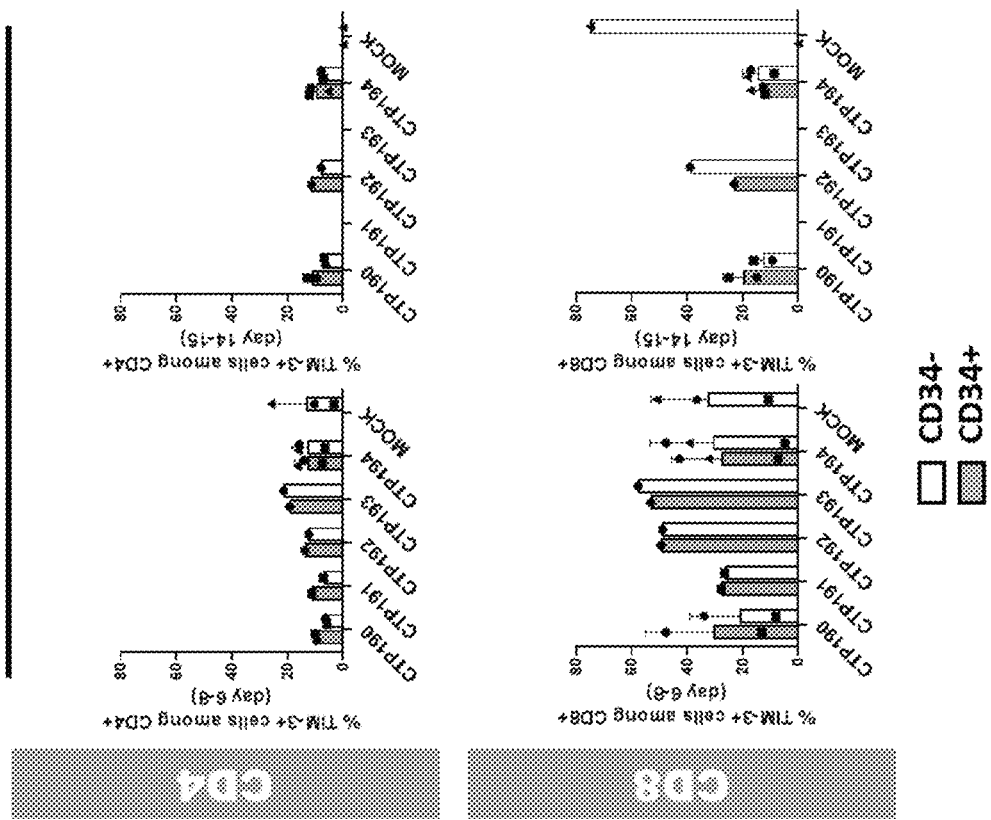

Next we sought to understand how CD40 may operate as a single component of the CoStAR, or in combination with costimulatory domains other than CD28. To control for the effect of receptor oligomerisation and stoichiometry we used a base CD8 transmembrane domain for each fusion and compared with the control MFE23.CD28.CD40 receptor (FIG. 24A). The first receptor consists of a CD28.CD40 signalling domain with CD8 extracellular and transmembrane domain (CTP190), CD2.CD40 signalling domain with CD8 extracellular and transmembrane domain (CTP191), or CD137.CD40 signalling domain with CD8 extracellular and transmembrane domain (CTP192). Additionally, a receptor consisting of CD40 alone (CTP193) was also generated. Flow cytometric analysis of transduced cells showed that expression of these receptors did not correlate well with CD34 marker gene expression, suggesting that the structural formats did not permit efficient surface expression (FIG. 24A, lower left panel). Nonetheless we conducted functionality assays and showed that the CD28.CD40, CD137.CD40 and CD40 receptors could mediate enhanced IL-2 secretion compared to mock transduced cells in LoVo-OKT3 cocultures, whereas IFNγ secretion was lower than from mock transduced cells, and MFE23.CD28.CD40 engineered cells (FIG. 24B). Analysis of expansion in the presence of LoVo-OKT3 cells (FIG. 25) demonstrated that MFE23.CD28.CD40 based receptors mediated optimal expansion with those harboring the native CD28 extracellular and transmembrane domain (CTP194) outperforming those with CD8 derived transmembrane domains (CTP190). The fusion of CD137 and CD40 maintained T-cell numbers throughout the experiment with no associated expansion, whereas receptors consisting of CD2.CD40 or CD40 alone did not support long term survival. Akin to an effect seen with mock transduced cells. Phenotypic analysis of cells at day 6-8 and 14-15 was also conducted (FIGS. 26A-26C). LAG3 was very low on CD4 cells at day 6-8, and <20% on CD8+ cells. At day 14-15 LAG3 was present on ~50% of CD4+ mock cells but <20% of engineered cells (data unavailable for some receptors due to insufficient cell numbers to analyse). PD1 expression was again <20% on CD4+ and CD8+ cells at both time points analysed except for the CD2.CD40 CTP191 engineered cells at day 6-8 and mock transduced cells at the later time point. TIM3 expression was generally low in CD4+ cells at both timepoints analysed, but higher in CD8+ cells, in particular in CD137.CD40 (CTP192) and CD40 (CTP193) engineered cells. Finally, mock transduced cells displayed >70% expression of TIM3 at day 14-15 whereas those harboring either CD28.CD40 CoStAR had ~20% expression. In summary CoStARs containing any combination of costimulatory domain tested with CD40 can modulate checkpoint expression, but this effect is most apparent in combination with CD28, and better than when CD40 is used as a sole signaling component.

Figure 27A:
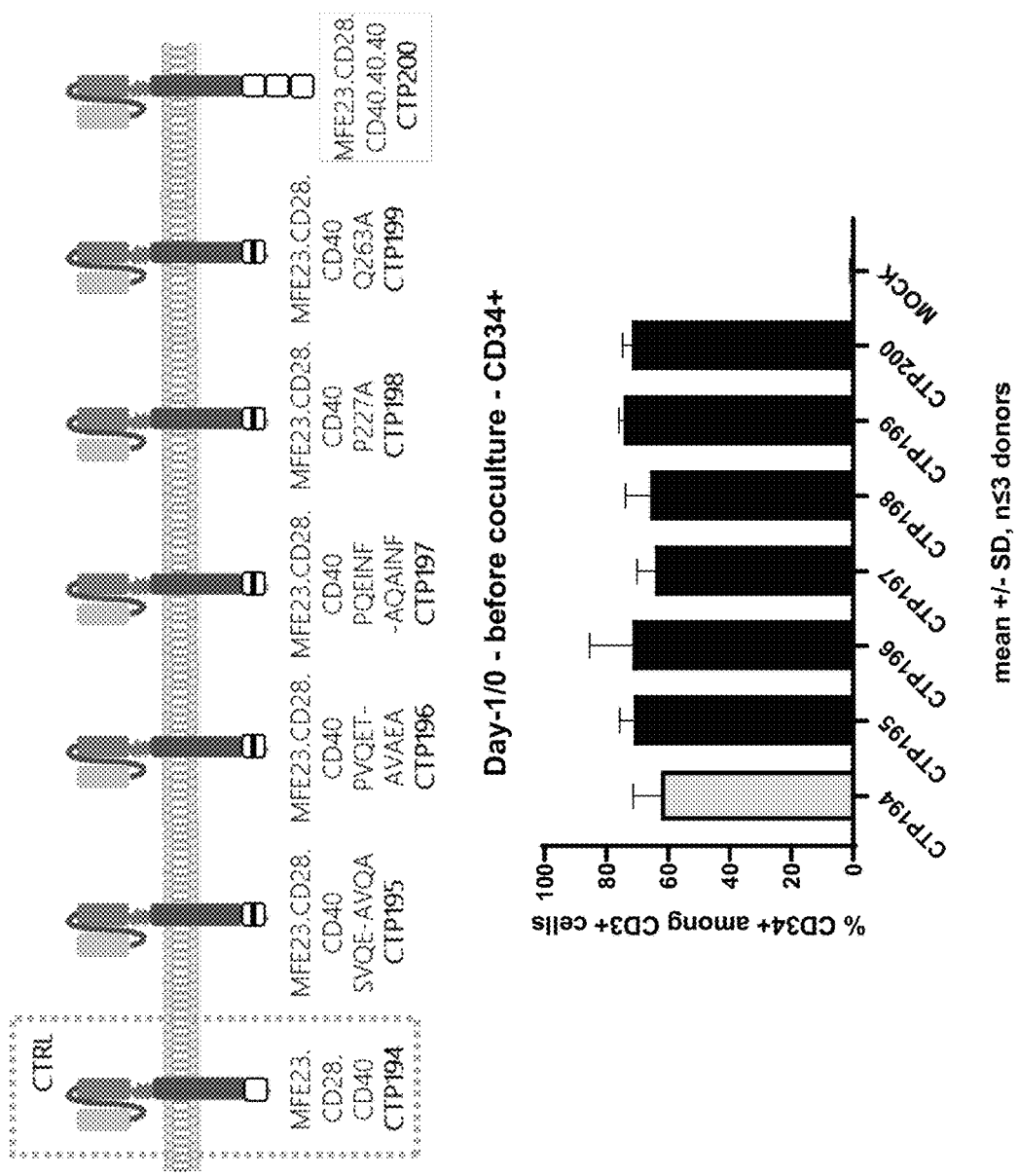
FIGS. 27A-27B depict CD40 CoStAR TRAF-binding site mutations have a direct impact on the secretion of IL-2 and IFN-γ following activation.
Figure 27B:
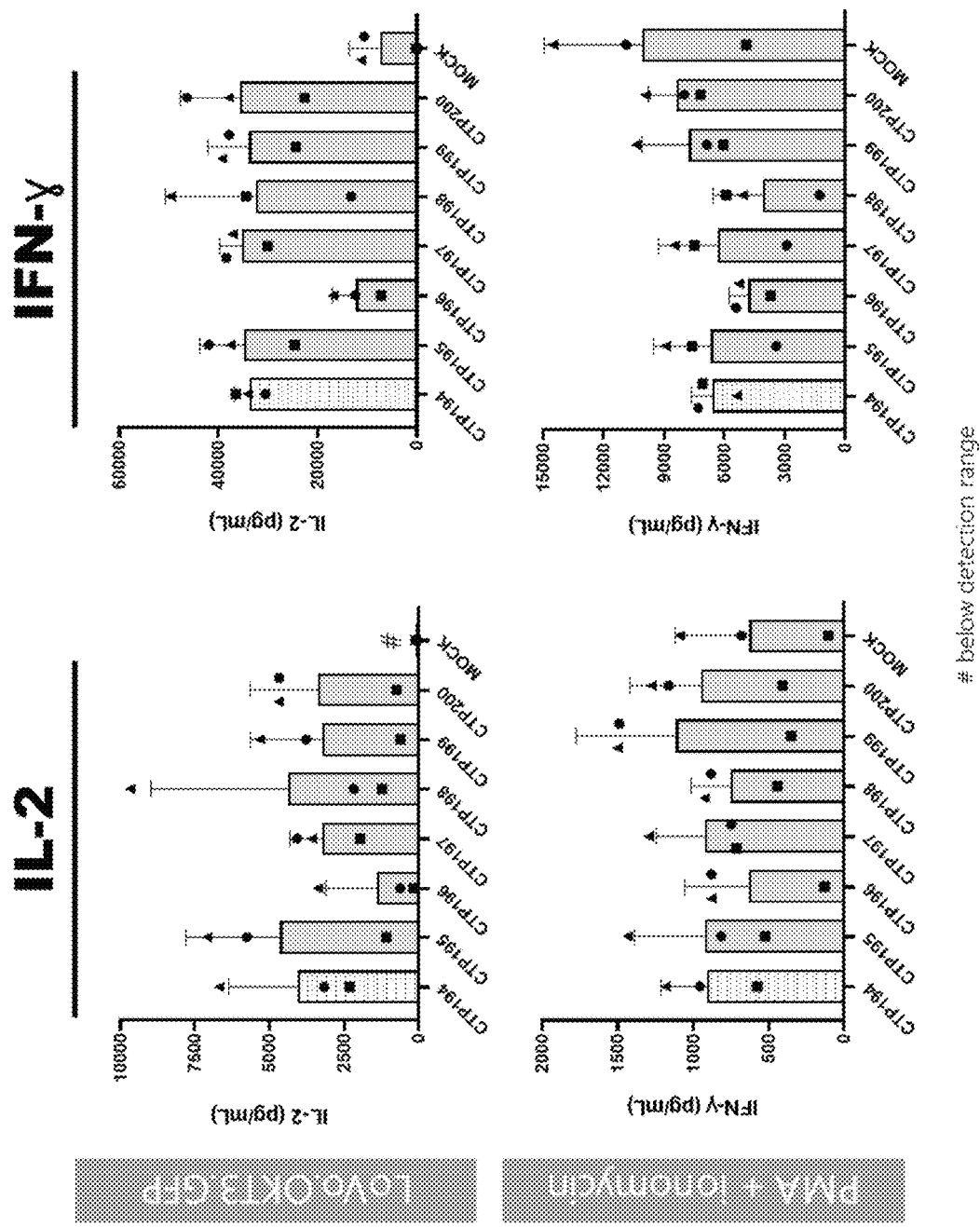
Figure 29A:
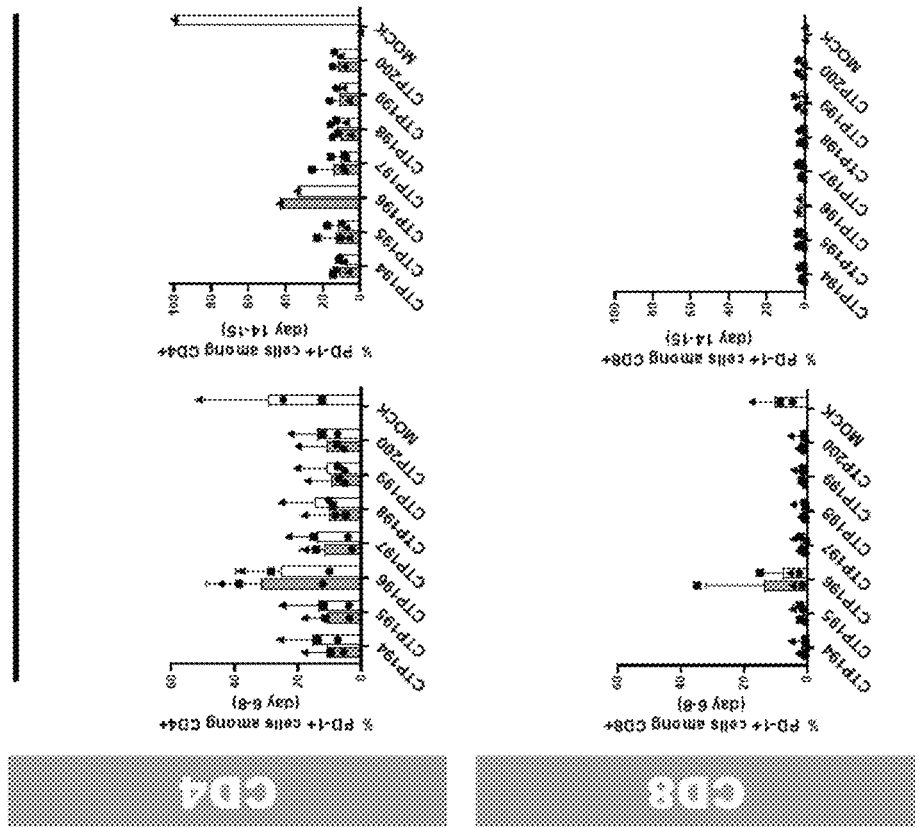
FIGS. 29A-29C depict exhaustion profiles of transduced T cells with CD28.CD40 mutants CoStAR constructs after tumor challenge. Cells of three donors were activated with Dynabeads and transduced with CTP194, CTP195, CTP196, CTP197, CTP198, CTP199, CTP200 or mock transduced. Cells were enriched for CD34 marker expression, expanded following the rapid expansion protocol (REP) and frozen for subsequent experiments. After thaw, cells were rested for 3-4 days in complete RPMI supplemented with IL-2. The viability and absolute count were assessed after overnight IL-2 starvation using DRAQ-7 (1:200) by flow cytometry (Novocyte) and data were analysed using the NovoExpress 1.5.0 software. Transduced T cells were cocultured in absence of IL-2 for 6-8 days with LoVo.OKT3.GFP tumor cells at 8:1 effector to target ratio, changing half of the culture medium every 3-4 days. LoVo.OKT3.GFP naturally expresses CEA and PD-L1 on their surface, conferring both signal 2 and signal 1 (OKT3) to the transduced T cells. After 6-8 days, the viability and the absolute count were assessed, and live T cells were rechallenged for an additional week with fresh LoVo.OKT3.GFP tumor cells as described above. Exhaustion profiles (LAG-3 (FIG. 29A), PD-1 (FIG. 29B), TIM-3 (FIG. 29C)) of transduced (CD34+ (grey)) or non-transduced (CD34− (white)) CD4 (upper panels) and CD8
Figure 29B:
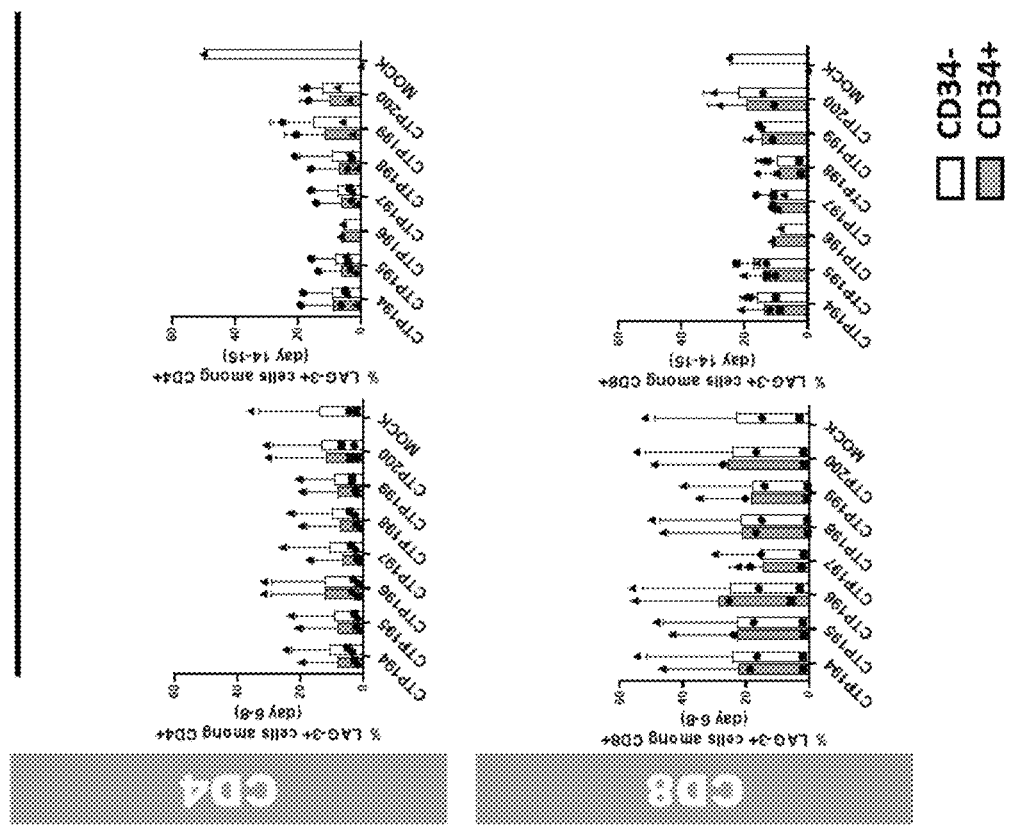
Figure 29C:
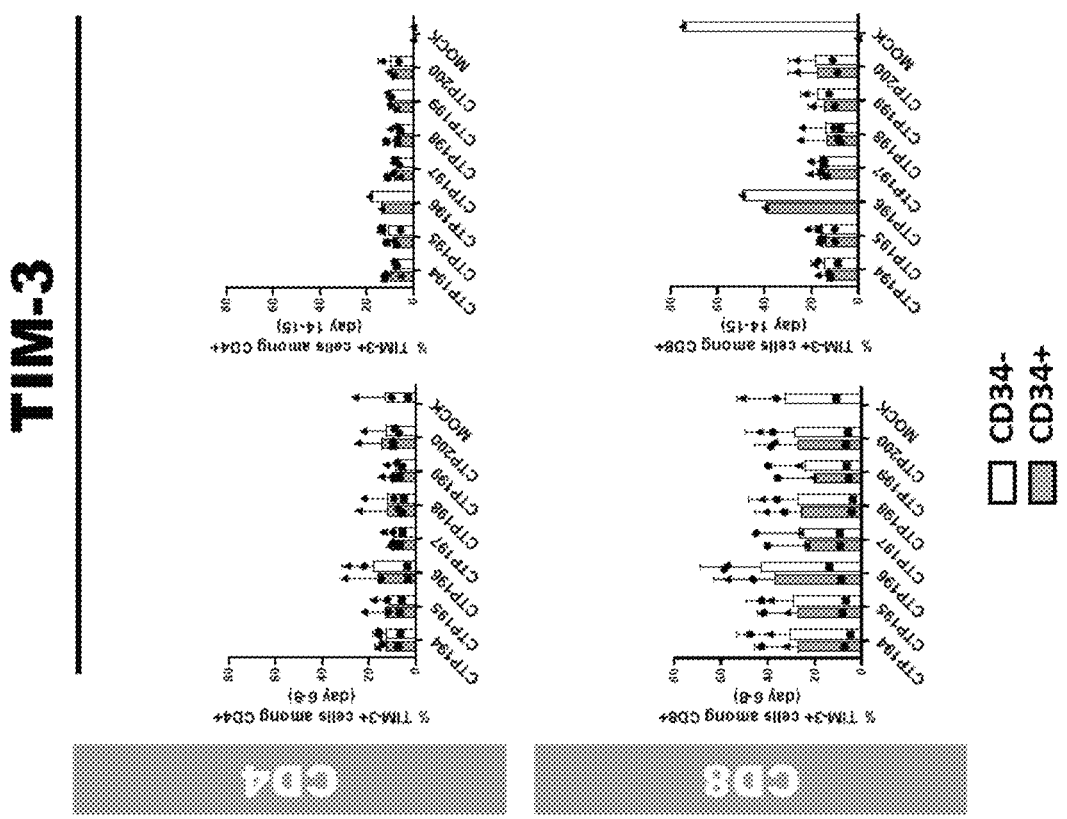

Next we sought to investigate the effect of specific mutations within the MFE23.CD28.CD40 construct, in an effort to understand how different signaling components are responsible for the optimal activity of the CTP194 MFE23.CD28.CD40 receptor. To this end we introduced mutations into a known TRAF2 binding motif (SVQE-AVQA) (CTP195), a TRAF2/3 binding domain (PVQET-AVAEA) (CTP196), and a TRAF6 binding domain (PQEINF-AQAINF) (CTP197). We also introduce point mutations to introduce a polymorphic variant of CD40 which has been shown to have enhanced activity in B-cells (P227A) (CTP198) and a Q263A mutation which has been shown to affect TRAF3 binding (Leo et al. J Biol Chem. 1999) (CTP199). Finally the cohort of receptors was completed by cloning of a CoStAR with a triplicated CD40 intracellular domain (CTP200) (FIGS. 27A-27B). As previously, primary human T-cells were transduced with lentiviral vectors encoding these receptors, enriched using CD34 microbeads and frozen prior to experimentation. Expression levels of CD34 were on average between 60 and 70% (FIG. 27A). Transduced or mock transduced cells were mixed with LoVo-OKT3 cells, and IL-2 and IFNγ measured by ELISA after 24 h (FIG. 29B). IL-2 production from mock transduced cells was below the level of detection. IL-2 production from the control CTP194 receptor was approximately 4000 pg/ml, as was production from CTP195 harboring the SVQE-AVQA mutations, and cells harboring the CTP198 receptor with the P227A polymorphism. Cells expressing the TRAF6 binding mutations PQEINF-AQAINF, or the TRAF3 binding mutation Q263A, as well as cells expressing the triplicated CD40 motif, all demonstrated moderate reductions in IL-2 production. However, cells expressing CTP196 containing the TRAF2/3 binding motif mutations PVQET-AVAEA displayed a considerable reduction in IL-2 production. This cytokine reduction was also observed when IFNγ was measured, with all receptors producing >30 ng/ml IFNγ, except CTP196 which produced approximately 10 ng/ml, similar to mock transduced cells.

Figure 28:
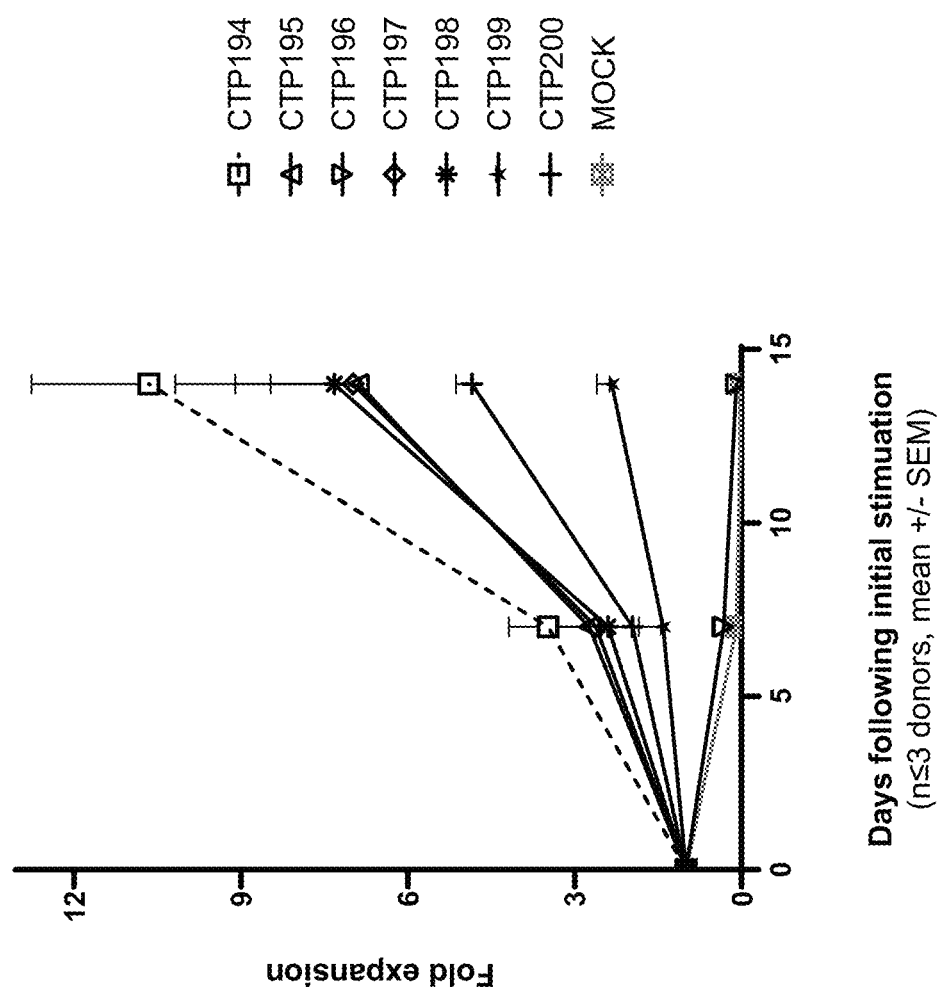
FIG. 28 depicts the critical role of the PVQET TRAF-binding motif in long term survival and proliferation of CD28.CD40 CoStAR transduced T cells when cocultured with LoVo.OKT3. Cells of three donors were activated with Dynabeads and transduced with CTP194, CTP195, CTP196, CTP197, CTP198, CTP199, CTP200 or mock transduced. Cells were enriched for CD34 marker expression, expanded following the rapid expansion protocol (REP) and frozen for subsequent experiments. After thaw, cells were rested for 3-4 days in complete RPMI supplemented with IL-2. The viability and absolute count were assessed after overnight IL-2 starvation using DRAQ-7 (1:200) by flow cytometry (Novocyte) and data were analysed using the NovoExpress 1.5.0 software. Transduced T cells were cocultured in absence of IL-2 for 6-8 days with LoVo.OKT3.GFP tumor cells at 8:1 effector to target ratio, changing half of the culture medium every 3-4 days. LoVo.OKT3.GFP naturally expresses CEA and PD-L1 on their surface, conferring both signal 2 and signal 1 (OKT3) to the transduced T cells. After 6-8 days, the viability and absolute count were assessed, and live T cells were rechallenged for an additional week with fresh LoVo.OKT3.GFP tumor cells as described above. At the end of the long-term coculture, the viability and absolute count were measured, and the fold expansion was calculated. Data shown as mean+/−SEM of n≤3 donors analysed in triplicates.

Next we assessed the impact of these different CD40 signalling domain mutations on the ability to support repeat stimulation (FIG. 28). To this end mock or transduced T-cells were mixed with LoVo-OKT3 cells at an 8:1 E:T ratio and counts made at day 6-8 and 14-15 across three different donors. CTP194 expressing cells expanded approximately four-fold by the first time point, and upon restimulation expanded to >10-fold. Cells expressing the TRAF2 binding mutation CTP195, TRAF6 binding mutation CTP197 or P227A polymorphism (CTP198), had moderate reductions in ability to support restimulation, whereas cells expressing the C263A TRAF3 binding mutant, or triplicated CD40 binding domain were further disabled in their ability to expand cells. Strikingly, cells expressing the TRAF2/3 binding mutant CTP196 were profoundly impacted in their ability to support repeat stimulation. Phenotypic analysis of cell expressing these different mutations was also conducted (FIGS. 29A-29B). No clear differences were seen in the relative expression of LAG3 in CD4+ or CD8+ cells at days 6-8 between transduced and non-transduced cells, However mock transduced cells had higher LAG3 expression at days 14-15 compared to CD4+ cells expressing any of the CoStARs. No differences were observed with regards LAG3 expression in CD8+ cells at days 14-15. PD1 expression was found to be <20% on average at days 6-8 for all receptor engineered CD4+ cells, with higher expression in mock engineered cells. Interestingly we also observed elevated PD1 expression in CD4+ and CD8+ cells expressing the TRAF2/3 motif mutant CTP196 at days 6-8, and in CD4+ cells at days 14-15. TIM3 expression was found to be lower than 20% on average in all CD4+ cell groups at both time points analysed. Expression was generally more variable in CD8+ cells at the first time point, with an average of approximately 30%, although slightly higher in cells expressing CTP196. At days 14-15 mock transduced cells had considerably higher TIM3 expression than transduced cells and cells expressing CTP196 had approximately twice as much TIM3 expression than cells from other groups.

The final group of receptors tested were those containing CD28 harboring mutations to the YMNM and PYAP cytoplasmic motifs which are critical for activating signal cascades involving PKCθ, PI3k and Lck amongst others (Esensten et al. 2016). CTP201 contains a PYAP-AYAA mutation, whereas CTP202 contains a YMNM-FMNM mutation. We also included a receptor with an extended IgG4 hinge into this cohort to establish whether CoStARs containing a longer linker domain maintain functionality (CTP203) (FIG. 30A). As previously, cells were transduced and enriched with CD34 microbeads. Expression after sort and expansion was found to be approximately 60% for the wild-type control and CTP201 and CTP202 receptor expressing cells, but lower at 30% for the CTP203 IgG4 hinge domain receptor expressing cells (FIG. 30A, lower panel). IL-2 production from mock or transduced T-cells was assessed following coculture with LoVo-OKT3 cells (FIG. 30B). IL-2 from CTP194 expressing cells was approximately 4000 pg/ml and lower for the CD28 mutant receptors, both being approximately 2500 pg/ml. However, IL-2 from IgG4 hinge receptor expressing cells was lower at approximately 1000 pg/ml. As a control IL-2 from mock transduced cells was below the lower level of detection. We also measured IFNγ from the same cells (FIG. 30B). IFNγ from CTP194 was approximately 1000 pg/ml, as was IFNγ from CTP201 cells harboring the PYAP-AYAA CD28 mutation. We observed enhanced IFNγ secretion from cells expressing the YMNM-FMNM mutation. Within this cohort of receptors, the production of IFNγ was highest from cells expressing the CTP203 IgG4 hinge receptor.

Next we analysed the ability to support expansion following tumor restimulation with this cohort of receptors (FIG. 31). Cells expressing MFE23.CD28.CD40 expanded approximately 10-fold following two rounds of stimulation with LoVo-OKT3 cells. We observed that mutations to the CD28 signalling domain had a profound effect on the ability of cells to expand over two rounds of stimulation, as did use of receptors containing the IgG4 hinge/spacer domain. Mock cells dropped in number over the two rounds of stimulation. Phenotypic analysis of cells after the first stimulation (6-8 days) revealed no obvious differences in LAG3 expression within CD4+ or CD8+ cells with the former expressing approximately 10% expression on average, and the latter 20% (FIGS. 32A-32C). However, LAG3 expression was higher in CD4+ mock cells at days 14-15 at approximately 50%+, compared to an average of 10% or lower in transduced cells, and was also higher in CD8+ mock cells compared to transduced cells. PD1 expression analysis revealed approximately 10% expression in MFE23.CD28.CD40, or CD28 mutant CD4+ cells at the first time point, whereas cells expressing the IgG4 receptor had >20% PD1 expression, as did mock transduced cells. At days 14-15 the difference was greater still with 100% of mock CD4+ cells being PD1+. CD8+ cells demonstrated low PD1 positivity at both time points. Finally, no obvious difference was seen in CD4 or CD8+ TIM3 expression at days 6-8, however at days 14-15 CD4+ cells expressing the IgG4 spacer domain receptor showed higher PD1 positivity compared to cells expressing the control or CD28 mutant receptors, with a similar effect observed in CD8+ cells.

Example 8

Coculture assay set up. Effector (ie, Non-Td and Td) T cells were thawed one day prior to coculture, resuspended at $1\times10^6$ cells/mL in TCM without IL-2, and incubated overnight at 37° C. with 5% $CO_2$. On the day of coculture, T cells and BA/F3 targets (ie, WT, OKT3, FOLR1, and OKT3-FOLR1) were collected and counted using a ViCELL BLU per manufacturer's instructions. Both Non-Td and Td T cells were preincubated for 30 minutes at room temperature with a range of solFOLR1 (ie, 0, 20, 60 and 200 ng/mL) concentrations that represent concentrations reported in ovarian cancer patient serum as well as supraphysiological levels. Following incubation, cells were cocultured with either BA/F3 WT, OKT3, FOLR1, or OKT3-FOLR1 targets at the following E:T ratios (3:1, 1:1, 1:3) overnight. Each condition was performed in duplicates. T cells stimulated with PMA/ionomycin as per manufacturer's instructions and unstimulated T cells served as positive and negative controls, respectively. Following overnight, plates were collected and centrifuged at 500×g for 3 minutes. 100 μL of supernatant was collected from each well and stored at –80° C. prior to analysis of cytokine content. The remaining cells in plates were then stained as described below.

For proliferation coculture assays, T cells were first labeled with CellTrace™ Violet Dye on the day of coculture setup, according to the manufacturer's instructions. The labeled cells were then cultured for 5 days with BA/F3 target cells (BA/F3, BA/F3-FOLR1, BA/F3-OKT3-FOLR1) at a E:T of 10:1.

Flow staining and analysis of coculture assay. After collecting supernatant, pelleted cells were washed and labeled with 100 μL Live/Dead Fixable Near IR dye (prepared by adding 1 μL reconstituted dye to 1 mL PBS) for 30 minutes at room temperature. All wash steps were performed by adding 100 μL stain buffer to each well, centrifuging at 500×g for 3 minutes and decanting the supernatant. Following incubation with the Live/Dead Dye, cells were washed and blocked with Fc block (1:50 dilution) for 15 minutes at room temperature following which 50 μL antibody cocktail was added to each well and incubated for 30 minutes at 4° C. Cells were then washed and a volume of 100 μL BD Cytofix buffer was added and cells were incubated for 20 minutes at 4° C. After fixing, cells were washed, reconstituted in 150 μL stain buffer, and stored in 4° C. until analysis using a BD LSR Fortessa X-20.

Prior to cytometric analysis, plates were centrifuged at 500×g for 3 minutes, and 25 μL counting beads (ie, 26000 beads) with 125 μL FACs stain buffer was added to each well. A total of 100 μL of the sample was acquired from each well. The gating strategy was as follows:

Lymphocytes (forward scatter [FSC]-A vs side scatter [SSC]-A)
Single cells gate 1 (FSC-H vs FSC-A)
Single cells gate 2 (SSC-H vs SSC-A)
Viable cells (FSC-H vs Near Far IR APC-Cy7 dye)
Tumor vs T cells (anti-mouse CD45 BV785 vs anti-human CD45 BV650)
Activation markers 4-1BB (FSC-H vs anti-human 4-1BB BV421) and CD69 (FSC-H vs anti-human CD69 BV711) gated specifically from T cells Bead count from each well was recorded using the following gating strategy:
FSC-A vs SSC-A
SSC-H vs FITC Analysis was performed using FlowJo (BD, version 10). Graphs were plotted using GraphPad Prism 9.

Cytokine analysis. Supernatants collected from coculture assays as described above were evaluated either neat or at 1:200 dilution with Diluent 2 from the MSD V-Plex Plus Proinflammatory Panel 1 kit from Meso scale discovery (MSD). The assay was carried out according to the manufacturer's instructions and analysis performed using MSD discovery workbench software.

Expression of activation markers (4-1BB and CD69) and cytokine production (IL-2 and IFN gamma) respectively, from non-transduced (NTD) and anti-FOLR1 CoStAR modified T cells (CoStAR) from 3 healthy donors cocultured overnight with Ba/F3 targets. 4-1BB expression was higher in the anti-FOLR1 CoStAR modified T cells than the NTD cells whereas CD69 expression was similar in both cells (FIG. 34A). IL-2 and IFN gamma expression was higher in the anti-FOLR1 coSTAR modified T cells than the NTD cells (FIG. 34B).

Tumor counts of Ba/F3 targets assessed by flow cytometry after overnight coculture with NTD and CoStAR T cells were comparable in the anti-FOLR1 CoStAR modified T cells and the NTD cells (FIG. 34C).

NTD and CoStAR T cell counts as well as proliferation assessed by flow cytometry after overnight or 5-day coculture with Ba/F3 targets indicated that total cell counts and proliferation of both CD4 and CD8 T cells were higher in the anti-FOLR1 CoStAR modified T cells than the NTD cells (FIG. 34D).

Expression of activation markers (4-1BB and CD69) from non-transduced (NTD) and anti-FOLR1 CoStAR modified T cells (CoStAR) from 3 healthy donors pre-incubated with increasing concentrations of soluble folate receptor (sFOLR) and co-cultured overnight with Ba/F3 targets was comparable in the anti-FOLR1 CoStAR modified T cells and the NTD cells, with the exception of increased expression of the anti-FOLR1 CoStAR modified T cells than the NTD cells FIGS. 25A and 25B).

Figure 35A:
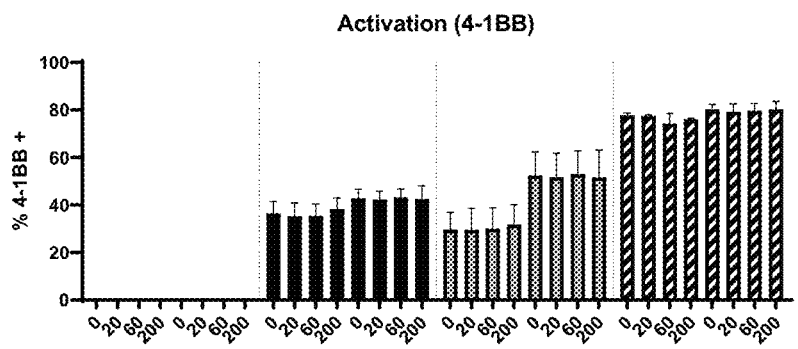
Figure 35B:
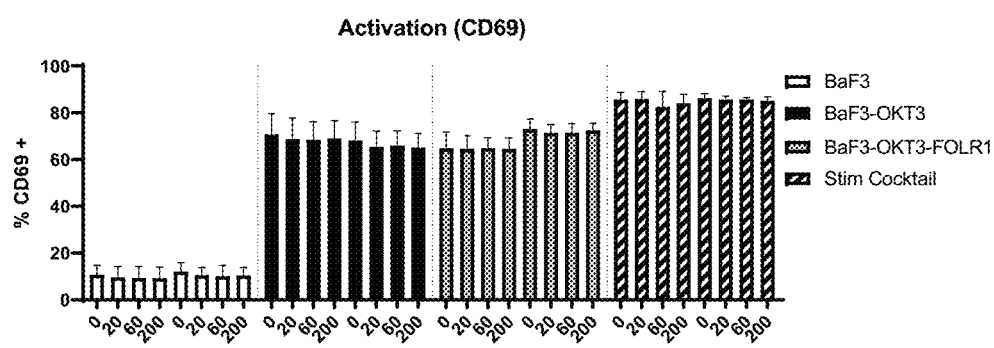
Figure 35C:
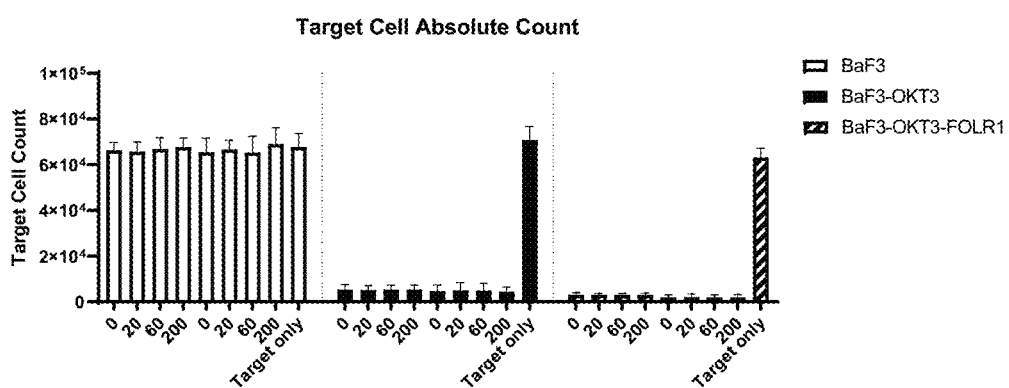
Figure 35D:
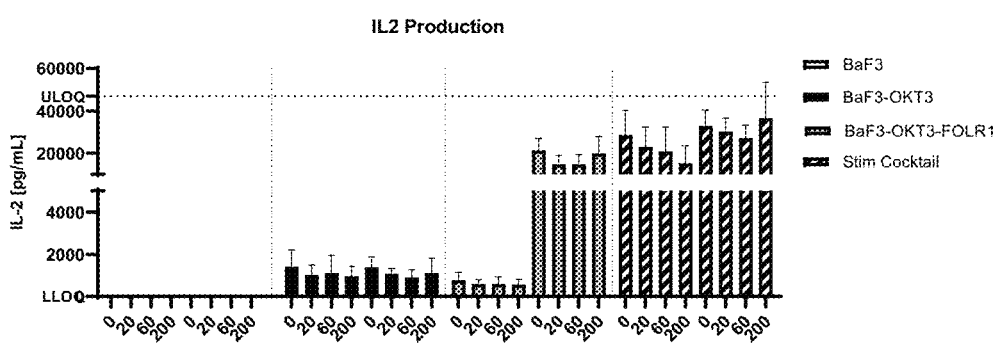

Tumor counts of Ba/F3 targets assessed by flow cytometry after overnight coculture with NTD and CoStAR T cells pre-incubated with increasing concentrations of sFOLR were comparable in the anti-FOLR1 CoStAR modified T cells and the NTD cells (FIG. 35C).

Espression of cytokine production (IL-2) of NTD and CoStAR T cells pre-incubated with increasing concentrations of sFOLR assessed by flow cytometry after overnight coculture with Ba/F3 targets were comparable in the anti-FOLR1 CoStAR modified T cells and the NTD cells.

Figure 36A:
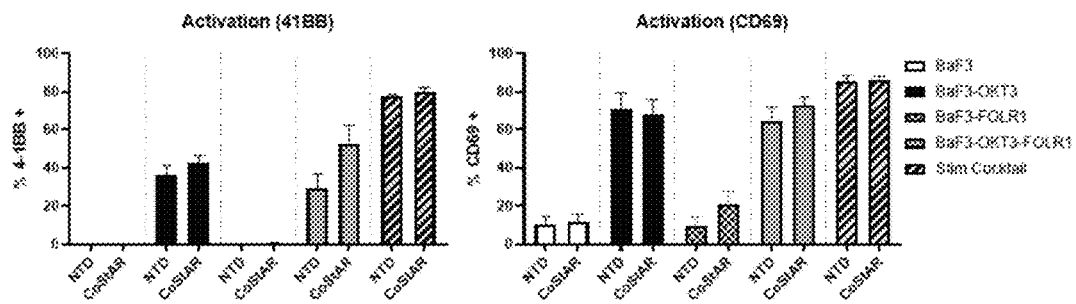

Expression of activation markers (4-1BB and CD69) from non-transduced (NTD) and anti-FOLR1 CoStAR modified T cells (CoStAR) from 3 healthy donors co-cultured overnight with Ba/F3 targets were comparable in the anti-FOLR1 CoStAR modified T cells and the NTD cells FIG. 36A).

Figure 36B:
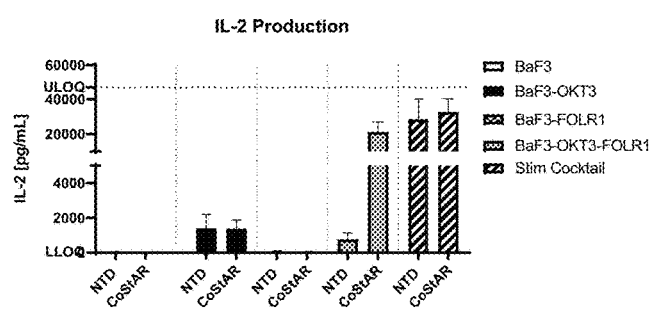

Expression of cytokine production (IL-2), from non-transduced (NTD) and anti-FOLR1 CoStAR modified T cells (CoStAR) from 3 healthy donors co-cultured overnight with Ba/F3 targets was increased in the anti-FOLR1 CoStAR modified T cells as compared to the NTD cells (FIG. 36B).

Figure 36C:
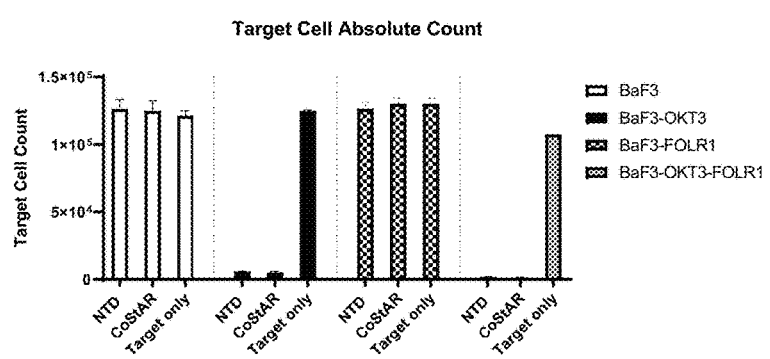

Tumor counts of Ba/F3 targets assessed by flow cytometry after overnight coculture with NTD and CoStAR T cells were comparable in the anti-FOLR1 CoStAR modified T cells and the NTD cells (FIG. 36C).

Figure 36D:
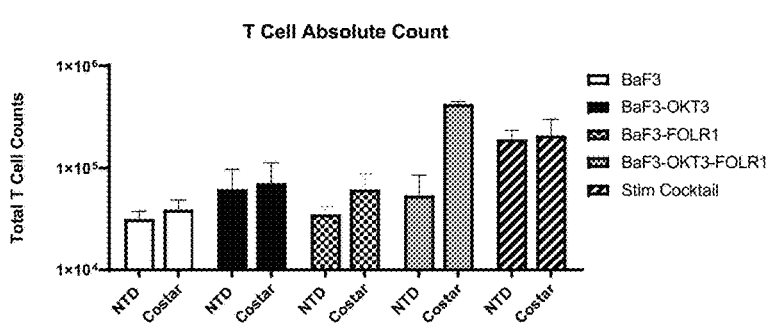

NTD and CoStAR T cell counts assessed by flow cytometry after overnight or 5-day coculture with Ba/F3 targets was increased in the anti-FOLR1 CoStAR modified T cells as compared to the NTD cells (FIG. 36D).

Example: 9

Production of CoStAR TIL

TIL from 6 ovarian tumors were liberated by digestion and cultured in 3000U IL-2. Transduction with a 3rd generation lentiviral vector encoding a CoStAR molecule with and scFv targeting human FOLR1, linker, full length CD28 fused to truncated CD40 cytoplasmic domain was carried out at an MOI of 5, both 48 h and 72 h after tumor digestion.

Flow cytometric analysis was used to determine the frequency of CD4 and CD8 T-cells expressing the CoStAR Molecule using an anti-idiotype antibody for surface detection. About 20% to 70% of CD4 and CD8 T-cells expressed the CoStAR molecule (FIG. 37A).

Flow cytometric surface staining analysis was used to determine the frequency of cells expressing TCRαβ and TCRγδ. About 100% of CD3+ cells expressed TCRαβ and considerably fewer CD3+ cells (close to zero) expressed TCRγδ (FIG. 37C).

CoStAR modified TIL from 6 ovarian tumors were co-cultured with autologous digest overnight in the presence of brefeldin A. The frequency of cells expressing IL-2 or TNFα was assessed the following day by flow cytometry. The frequency of TIL reacting to autologous digest is enhanced by the CoStAR molecule (FIG. 38A).

CoStAR modified TIL from 6 ovarian tumors were co-cultured with autologous digest and supernatant assessed for cytokine release. CoStAR modified cells had increased effector functions as demonstrated by increased IFNγ, TNFα and IL-13 release. Maximal levels of these molecules was similar in response to stimulation with PMA (Phorbol 12-myristate 13-acetate) and ionomycin (FIG. 38B).

CoStAR modified TIL from 5 ovarian tumors were co-cultured with BA/F3 cells or BA/F3 cells engineered to express OKT3, FOLR or both. Cytokine secretion of non-modified and CoStAR modified TIL was equivalent when co-cultured with non-modified BA/F3 or BA/F3 expressing OKT3 alone or FOLR1 alone. CoStAR modified TIL secreted increased levels of cytokines IL-2 and IFNγ when co-cultured with BA/F3 modified to express both FOLR1 and OKT3 (FIG. 39A)

CoStAR modified TIL from 5 ovarian tumors were co-cultured with BA/F3 cells or BA/F3 cells engineered to express OKT3, FOLR or both. Cytotoxicity towards BA/F3 target cells was assessed via cell counts, determined by flow cytometric analysis of mouse CD45. Non-modified and CoStAR modified cells killed target cells expressing OKT3 equivalently. CoStAR modified TILs do not kill BA/F3 cells expressing FOLR1 alone (FIG. 39B).

Mock or CoStAR modified TIL from 3 ovarian cancer patients were co-cultured with autologous tumor in the presence of no blocking, MHCI, MHC II or MHC I+MHC II blocking or antibodies or isotype control. Supernatant was assessed for the level of IFNγ release. Normalized to levels of release without antibody, IFNγ levels are similarly reduced in mock and CoStAR modified TIL, showing that activity is led by endogenous TCR-MHC peptide interactions (FIG. 39C).

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A chimeric costimulatory antigen receptor (CoStAR) which comprises:
an extracellular binding domain comprising a VH of antibody 196-14 and a VL of antibody 196-14, operatively linked to a transmembrane domain, an intracellular CD28 signaling domain and an intracellular CD40 signaling domain,
wherein the CD28 signaling domain comprises the amino acid sequence of SEQ ID NO: 16, and
wherein the CD40 signaling domain comprises the amino acid sequence of SEQ ID NO: 23,
wherein the CoStAR does not comprise a third intracellular signaling domain.

2. The CoStAR of claim 1, wherein the extracellular binding domain is operatively linked to the transmembrane domain by a linker or a spacer.

3. The CoStAR of claim 2, wherein the linker comprises from about 5 to about 20 amino acids.

4. The CoStAR of claim 2, wherein the linker comprises AAAGSGGSG (SEQ ID NO: 8).

5. The CoStAR of claim 2, wherein the spacer comprises from about 10 to about 250 amino acids.

6. The CoStAR of claim 2, wherein the spacer comprises one or more immunoglobulin domains or an immunoglobulin constant region.

7. The CoStAR of claim 2, wherein the spacer comprises one or more immunoglobulin domains or an immunoglobulin constant region of SEQ ID NO: 13.

8. The CoStAR of claim 1, wherein the transmembrane domain comprises the transmembrane domain of CD28 or CD8.

9. The CoStAR of claim 1, wherein the transmembrane domain comprises the transmembrane domain sequence of SEQ ID NO:11 or SEQ ID NO:12.

10. The CoStAR of claim 1, wherein the extracellular binding domain is specific for CA125.

11. A nucleic acid which encodes a chimeric costimulatory antigen receptor (CoStAR), the CoStAR comprising:
an extracellular binding domain comprising a VH of antibody 196-14 and a VL of antibody 196-14, operatively linked to a transmembrane domain, a CD28 signaling domain and a CD40 signaling domain,
wherein the CD28 signaling domain comprises the amino acid sequence of SEQ ID NO: 16, and
wherein the CD40 signaling domain comprises the amino acid sequence of SEQ ID NO: 23.

12. A cell which expresses a chimeric costimulatory antigen receptor (CoStAR), the CoStAR comprising:
an extracellular binding domain comprising a VH of antibody 196-14 and a VL of antibody 196-14, operatively linked to a transmembrane domain, a CD28 signaling domain and a CD40 signaling domain,
wherein the CD28 signaling domain comprises the amino acid sequence of SEQ ID NO: 16, and
wherein the CD40 signaling domain comprises the amino acid sequence of SEQ ID NO: 23.

13. A cell population which is enriched for cell expression of a chimeric costimulatory antigen receptor (CoStAR), the CoStAR comprising:
an extracellular binding domain comprising a VH of antibody 196-14 and a VL of antibody 196-14, operatively linked to a transmembrane domain, a CD28 signaling domain and a CD40 signaling domain,
wherein the CD28 signaling domain comprises the amino acid sequence of SEQ ID NO: 16, and
wherein the CD40 signaling domain comprises the amino acid sequence of SEQ ID NO: 23.

* * * * *